United States Patent
Joung et al.

(10) Patent No.: US 10,526,591 B2
(45) Date of Patent: *Jan. 7, 2020

(54) ENGINEERED CRISPR-CAS9 NUCLEASES

(71) Applicant: The General Hospital Corporation, Boston, MA (US)

(72) Inventors: J. Keith Joung, Winchester, MA (US); Benjamin Kleinstiver, Medford, MA (US); Vikram Pattanayak, Wellesley, MA (US)

(73) Assignee: The General Hospital Corporation, Boston, MA (US)

( * ) Notice: Subject to any disclaimer, the term of this patent is extended or adjusted under 35 U.S.C. 154(b) by 54 days.

This patent is subject to a terminal disclaimer.

(21) Appl. No.: 15/935,299

(22) Filed: Mar. 26, 2018

(65) Prior Publication Data

US 2018/0216088 A1  Aug. 2, 2018

Related U.S. Application Data

(63) Continuation of application No. 15/249,756, filed on Aug. 29, 2016, now Pat. No. 9,926,546, and a continuation-in-part of application No. 15/015,947, filed on Feb. 4, 2016, now Pat. No. 9,512,446, application No. 15/935,299, filed on Mar. 26, 2018, which is a continuation-in-part of application No. 15/369,533, filed on Dec. 5, 2016, now Pat. No. 10,093,910, which is a continuation of application No. 15/015,947, filed on Feb. 4, 2016, now Pat. No. 9,512,446.

(60) Provisional application No. 62/211,553, filed on Aug. 28, 2015, provisional application No. 62/216,033, filed on Sep. 9, 2015, provisional application No. 62/258,280, filed on Nov. 20, 2015, provisional application No. 62/271,938, filed on Dec. 28, 2015.

(51) Int. Cl.
*C12N 9/16* (2006.01)
*C12N 9/22* (2006.01)
*C12N 15/90* (2006.01)

(52) U.S. Cl.
CPC .............. *C12N 9/22* (2013.01); *C12N 9/16* (2013.01); *C12N 15/902* (2013.01); *C12N 15/907* (2013.01); *C12Y 114/11* (2013.01); *C12Y 201/01043* (2013.01); *C12Y 203/01048* (2013.01); *C12Y 301/00* (2013.01); *C12Y 305/01098* (2013.01); *C07K 2319/00* (2013.01); *C07K 2319/71* (2013.01); *C12N 15/90* (2013.01); *C12N 2800/22* (2013.01)

(58) Field of Classification Search
CPC .............. C12N 9/16; C12N 9/22; C12N 15/90
See application file for complete search history.

(56) References Cited

U.S. PATENT DOCUMENTS

| | | |
|---|---|---|
| 4,603,044 A | 7/1986 | Geho et al. |
| 4,957,773 A | 9/1990 | Spencer et al. |
| 5,436,150 A | 7/1995 | Candrasegaran |
| 6,007,988 A | 12/1999 | Choo et al. |
| 6,013,453 A | 1/2000 | Choo et al. |
| 6,503,717 B2 | 1/2003 | Case et al. |
| 6,511,808 B2 | 1/2003 | Wolffe et al. |
| 7,021,555 B2 | 4/2006 | Bagnall |
| 7,220,719 B2 | 5/2007 | Case |
| 7,914,796 B2 | 3/2011 | Miller |
| 7,919,277 B2 | 4/2011 | Russell et al. |
| 8,034,598 B2 | 10/2011 | Miller |
| 8,071,370 B2 | 12/2011 | Wolffe |
| 8,252,535 B2 | 8/2012 | Biekle et al. |
| 8,282,920 B2 | 10/2012 | Heo et al. |
| 8,361,725 B2 | 1/2013 | Russell et al. |
| 8,697,359 B1 | 4/2014 | Zhang |
| 8,771,986 B2 | 7/2014 | Miller |
| 8,865,406 B2 | 10/2014 | Zhang et al. |
| 8,962,281 B2 | 2/2015 | Doyon |
| 8,993,233 B2 | 3/2015 | Zhang et al. |
| 9,023,649 B2 | 5/2015 | Mali et al. |
| 9,074,199 B1 | 7/2015 | Chavez et al. |
| 9,322,037 B2 | 4/2016 | Liu et al. |
| 9,771,601 B2 | 9/2017 | May et al. |
| 9,926,546 B2 * | 3/2018 | Joung .................. C12N 9/16 |
| 2002/0160940 A1 | 10/2002 | Case et al. |
| 2002/0164575 A1 | 11/2002 | Case et al. |
| 2005/0214851 A1 | 9/2005 | Arts et al. |
| 2006/0199190 A1 | 9/2006 | Russell et al. |
| 2007/0020627 A1 | 1/2007 | Barbas, III |
| 2008/0124725 A1 | 5/2008 | Barrangou et al. |
| 2008/0193470 A1 | 8/2008 | Masignani et al. |
| 2010/0034924 A1 | 2/2010 | Fremaux et al. |
| 2010/0055793 A1 | 3/2010 | Chandrasegaran |
| 2010/0076057 A1 | 3/2010 | Sontheimer et al. |

(Continued)

FOREIGN PATENT DOCUMENTS

| | | |
|---|---|---|
| CN | 103224947 | 7/2013 |
| CN | 103233028 | 8/2013 |

(Continued)

OTHER PUBLICATIONS

U.S. Appl. No. 61/610,212, filed Mar. 13, 2012, Joung et al.

(Continued)

*Primary Examiner* — Karen Cochrane Carlson

(74) *Attorney, Agent, or Firm* — Fish & Richardson P.C.

(57) ABSTRACT

Engineered CRISPR-Cas9 nucleases with improved specificity and their use in genomic engineering, epigenomic engineering, genome targeting, and genome editing.

32 Claims, 25 Drawing Sheets

Specification includes a Sequence Listing.

(56) References Cited

U.S. PATENT DOCUMENTS

| | | |
|---|---|---|
| 2010/0093617 A1 | 4/2010 | Barrangou et al. |
| 2010/0104690 A1 | 4/2010 | Barrangou et al. |
| 2010/0120043 A1 | 5/2010 | Sood et al. |
| 2010/0183559 A1 | 7/2010 | Van Sinderen et al. |
| 2010/0184624 A1 | 7/2010 | Samuel et al. |
| 2010/0209998 A1 | 8/2010 | Attwood et al. |
| 2010/0209999 A1 | 8/2010 | Altermann et al. |
| 2010/0221185 A1 | 9/2010 | Altermann et al. |
| 2010/0311061 A1 | 12/2010 | Korlach et al. |
| 2010/0317116 A1 | 12/2010 | Flusberg et al. |
| 2011/0002889 A1 | 1/2011 | Barrangou et al. |
| 2011/0092381 A1 | 4/2011 | Sood et al. |
| 2011/0143348 A1 | 6/2011 | Tomigahara et al. |
| 2011/0150852 A1 | 6/2011 | Chambaud et al. |
| 2011/0171647 A1 | 7/2011 | Tomigahara et al. |
| 2011/0189674 A1 | 8/2011 | Tomigahara et al. |
| 2011/0189776 A1 | 8/2011 | Terns et al. |
| 2011/0201007 A1 | 8/2011 | Waller et al. |
| 2011/0201118 A1 | 8/2011 | Yang et al. |
| 2011/0217739 A1 | 9/2011 | Terns et al. |
| 2011/0217791 A1 | 9/2011 | Tomigahara et al. |
| 2011/0223638 A1 | 9/2011 | Wiedenheft et al. |
| 2011/0236530 A1 | 9/2011 | Manoury et al. |
| 2011/0236894 A1 | 9/2011 | Rao et al. |
| 2011/0269119 A1 | 11/2011 | Hutchison et al. |
| 2011/0300528 A1 | 12/2011 | Jassim et al. |
| 2011/0300538 A1 | 12/2011 | Barrangou et al. |
| 2012/0027786 A1 | 2/2012 | Gupta et al. |
| 2012/0088676 A1 | 4/2012 | Weill et al. |
| 2012/0151635 A1 | 6/2012 | Coruzzi et al. |
| 2012/0214160 A1 | 8/2012 | Deng et al. |
| 2013/0011516 A1 | 1/2013 | Griffin et al. |
| 2013/0011828 A1 | 1/2013 | Barrangou et al. |
| 2013/0130248 A1 | 5/2013 | Haurwitz et al. |
| 2013/0145497 A1 | 6/2013 | Choi et al. |
| 2013/0150240 A1 | 6/2013 | Newman et al. |
| 2013/0158245 A1 | 6/2013 | Russell et al. |
| 2013/0253040 A1 | 9/2013 | Miller et al. |
| 2013/0288251 A1 | 10/2013 | Horvath et al. |
| 2013/0326645 A1 | 12/2013 | Cost et al. |
| 2013/0326725 A1 | 12/2013 | Shukla et al. |
| 2013/0330778 A1 | 12/2013 | Zeiner et al. |
| 2013/0337454 A1 | 12/2013 | Duchateau |
| 2014/0068797 A1 | 3/2014 | Doudna et al. |
| 2014/0093941 A1 | 4/2014 | Terns et al. |
| 2014/0113376 A1 | 4/2014 | Sorek et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0199767 A1 | 7/2014 | Barrangou et al. |
| 2014/0201857 A1 | 7/2014 | Fahrenkrug et al. |
| 2014/0212869 A1 | 7/2014 | Sampas et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0242702 A1 | 8/2014 | Chen et al. |
| 2014/0248702 A1 | 9/2014 | Zhang et al. |
| 2014/0256046 A1 | 9/2014 | Zhang et al. |
| 2014/0271987 A1 | 9/2014 | Manoury et al. |
| 2014/0273037 A1 | 9/2014 | Wu |
| 2014/0273226 A1 | 9/2014 | Wu |
| 2014/0273230 A1 | 9/2014 | Chen et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0273235 A1 | 9/2014 | Voytas et al. |
| 2014/0287938 A1 | 9/2014 | Zhang et al. |
| 2014/0294773 A1 | 10/2014 | Brouns et al. |
| 2014/0295556 A1 | 10/2014 | Joung et al. |
| 2014/0295557 A1 | 10/2014 | Joung et al. |
| 2014/0298547 A1 | 10/2014 | Sastry-Dent et al. |
| 2014/0304853 A1 | 10/2014 | Ainley et al. |
| 2014/0309487 A1 | 10/2014 | Lee et al. |
| 2014/0310828 A1 | 10/2014 | Lee et al. |
| 2014/0310830 A1 | 10/2014 | Zhang et al. |
| 2014/0315985 A1 | 10/2014 | May et al. |
| 2014/0335063 A1 | 11/2014 | Cannon et al. |
| 2014/0335620 A1 | 11/2014 | Zhang et al. |
| 2014/0349400 A1 | 11/2014 | Jakimo et al. |
| 2014/0356867 A1 | 12/2014 | Peter et al. |
| 2014/0356958 A1 | 12/2014 | Mali et al. |
| 2014/0357530 A1 | 12/2014 | Zhang et al. |
| 2014/0377868 A1 | 12/2014 | Joung et al. |
| 2015/0020223 A1 | 1/2015 | Zhang et al. |
| 2015/0024499 A1 | 1/2015 | Brouns et al. |
| 2015/0024500 A1 | 1/2015 | Yu et al. |
| 2015/0031134 A1 | 1/2015 | Zhang et al. |
| 2015/0044772 A1 | 2/2015 | Zhao |
| 2015/0045546 A1 | 2/2015 | Siksnys et al. |
| 2015/0050699 A1 | 2/2015 | Siksnys et al. |
| 2015/0056629 A1 | 2/2015 | Guthrie-Honea |
| 2015/0067922 A1 | 3/2015 | Yang et al. |
| 2015/0071899 A1 | 3/2015 | Liu et al. |
| 2015/0079681 A1 | 3/2015 | Zhang |
| 2015/0093473 A1 | 4/2015 | Barrangou et al. |
| 2015/0159174 A1 | 6/2015 | Frendeway et al. |
| 2015/0159175 A1 | 6/2015 | Frendeway et al. |
| 2015/0166969 A1 | 6/2015 | Takeuchi et al. |
| 2015/0167000 A1 | 6/2015 | Voytas et al. |
| 2015/0176064 A1 | 6/2015 | Fach et al. |
| 2015/0184139 A1 | 7/2015 | Zhang et al. |
| 2015/0191744 A1 | 7/2015 | Wolfe et al. |
| 2015/0203872 A1 | 7/2015 | Zhang |
| 2015/0232882 A1 | 8/2015 | Zhang et al. |
| 2015/0232883 A1 | 8/2015 | Dahlman et al. |
| 2015/0247150 A1 | 9/2015 | Zhang et al. |
| 2015/0252358 A1 | 9/2015 | Maeder et al. |
| 2015/0291965 A1 | 10/2015 | Zhang et al. |
| 2015/0291966 A1 | 10/2015 | Zhang et al. |
| 2015/0315576 A1 | 11/2015 | Caliando et al. |
| 2015/0356239 A1 | 12/2015 | Zhang et al. |
| 2015/0376652 A1 | 12/2015 | Kuhn et al. |
| 2016/0010076 A1 | 1/2016 | Joung et al. |
| 2016/0010147 A1 | 1/2016 | Heron |
| 2016/0017301 A1 | 1/2016 | Khalili et al. |
| 2016/0017366 A1 | 1/2016 | Chen et al. |
| 2016/0024510 A1 | 1/2016 | Bikard et al. |
| 2016/0024523 A1 | 1/2016 | Joung et al. |
| 2016/0024524 A1 | 1/2016 | Joung et al. |
| 2016/0024529 A1 | 1/2016 | Carstens et al. |
| 2016/0312198 A1 | 10/2016 | Joung et al. |
| 2016/0362688 A1 | 12/2016 | May et al. |

FOREIGN PATENT DOCUMENTS

| | | |
|---|---|---|
| CN | 103343120 | 10/2013 |
| EP | 2325332 | 5/2011 |
| WO | WO 2003/072788 | 9/2003 |
| WO | WO 2004/099366 | 11/2004 |
| WO | WO 2007/014275 | 2/2007 |
| WO | WO 2007/025097 | 3/2007 |
| WO | WO 2008/108989 | 9/2008 |
| WO | WO 2010/054108 | 5/2010 |
| WO | WO 2011/017293 | 2/2011 |
| WO | WO 2011/143124 | 11/2011 |
| WO | WO 2012/093833 | 7/2012 |
| WO | WO 2012/164565 | 12/2012 |
| WO | WO 2013/012674 | 1/2013 |
| WO | WO 2013/098244 | 7/2013 |
| WO | WO 2013/141680 | 9/2013 |
| WO | WO 2013/142578 | 9/2013 |
| WO | WO 2013/169398 | 11/2013 |
| WO | WO 2013/176772 | 11/2013 |
| WO | WO 2014/059255 | 4/2014 |
| WO | WO 2014/089290 | 6/2014 |
| WO | WO 2014/093622 | 6/2014 |
| WO | WO 2014/093655 | 6/2014 |
| WO | WO 2014/099744 | 6/2014 |

(56) References Cited

FOREIGN PATENT DOCUMENTS

| WO | WO 2014/124284 | 8/2014 |
|---|---|---|
| WO | WO 2014/127287 | 8/2014 |
| WO | WO 2014/144288 | 9/2014 |
| WO | WO 2014/144592 | 9/2014 |
| WO | WO 2014/144761 | 9/2014 |
| WO | WO 2014/152432 | 9/2014 |
| WO | WO 2014/204578 | 12/2014 |
| WO | WO 2014/204724 | 12/2014 |
| WO | WO 2015/035162 | 3/2015 |
| WO | WO 2015/089364 | 6/2015 |
| WO | WO 2015/099850 | 7/2015 |
| WO | WO 2015/153940 | 10/2015 |
| WO | WO 2016/115355 | 6/2016 |

OTHER PUBLICATIONS

U.S. Appl. No. 61/799,647, filed Mar. 15, 2013, Joung et al.
U.S. Appl. No. 61/838,148, filed Jun. 21, 2013, Joung et al.
Al-Attar et al., "Clustered regularly interspaced short palindromic repeats (CRISPRs): the hallmark of an ingenious antiviral defense mechanism in prokaryotes," Biol Chem., Apr. 2011, 392:277-289.
Alexopoulou et al., "The CMV early enhancer/chicken β actin (CAG) promoter can be used to drive transgene expression during the differentiation of murine embryonic stem cells into vascular progenitors," BMC Cell Biology, 2008, 9:2.
Anders et al., "Structural basis of PAM-dependent target DNA recognition by the Cas9 endonuclease," Nature, 2014, 513:569-573.
Anonymous, "2013 Runners-Up. Genetic microsurgery for the masses," Science. Dec. 20, 2013;342(6165):1434-5.
Appela., "Non-natural nucleic acids for synthetic biology", Current Opinion in Chemical Biology, Dec. 2009,13(5-6): 687-696.
Arimondo et al., "Exploring the Cellular Activity of Camptothecin—Triple—Helix-Forming Oligonucleotide Conjugates," Mol. Cell. Biol., 26(1):324-33 (2006).
Arnould et al., "Engineering of large numbers of highly specific homing endonucleases that induce recombination on novel DNA targets," J Mol Biol., 355(3):443-458, Epub Nov. 15, 2005.
Arnould et al., "The I-CreI meganuclease and its engineered derivatives: applications from cell modification to gene therapy," Protein Eng Des Sel., 24(1-2):27-31, Epub Nov. 3, 2010.
Arora et al., "Residues 1-254 of anthrax toxin lethal factor are sufficient to cause cellular uptake of fused polypeptides," J. Biol. Chem., Feb. 1993, 268:3334-41.
Auer et al., "Highly efficient CRISPR/Case9-mediated known-in in zebrafish by homology-independent DNA repair," Genome Res., 2014, 24:142-153.
Bae et al., "Cas-OFFinder: a fast and versatile algorithm that searches for potential off-target sites of Cas9 RNA-guided endonucleases," Bioinformatics, 2014, 30:1473-1475.
Bae et al., "Human zinc fingers as building blocks in the construction of artificial transcription factors," Nat Biotechnol., 21(3):275-280, Epub Feb. 18, 2003.
Barker et al., "Increased DNA microarray hybridization specificity using sscDNA targets," BMC Genomics, Apr. 2005, 6:57, 8 pages.
Baron-Benhamou et al., "Using the λN Peptide to Tether Proteins to RNAs," Methods Mole Biol., Jan. 2004 257:135-153.
Barrangou & May, "Unraveling the potential of CRISPR-Cas9 for gene therapy," Expert Opin. Biol. Ther., 2015, 15:311-314.
Barrangou et al., "CRISPR Provides Acquired Resistance Against Viruses in Prokaryotes," Sci., 2007, 315:1709-1712.
Barrangou, "RNA-mediated programmable DNA cleavage," Nature Biotechnol., 2012, 30(9):836-838.
Bassett et al., "Highly efficient targeted mutagenesis of *Drosophila* with the CRISPR/Cas9 system," Cell Reports, 2013, 4:220-228.
Beerli and Barbas, "Engineering polydactyl zinc-finger transcription factors," Nat Biotechnol., 20(2):135-141, Feb. 2002.
Beerli et al., "Toward controlling gene expression at will: specific regulation of the erbB-2/HER-2 promoter by using polydactyl zinc finger proteins constructed from modular building blocks," PNAS USA, 1998, 95:14628-14633.
Belhaj et al., "Plant genome editing made easy: targeted mutagenesis in model and crop plants using the CRISPR/Cas system," Plant Methods, 2013, 9:39, 10 pages.
Bello et al., "Hypermethylation of the DNA repair gene MGMT: association with TP53 G:C to A:T transitions in a series of 469 nervous system tumors," Mutat. Res., Oct. 2004, 554:23-32.
Berg, "Proposed structure for the zinc-binding domains from transcription factor IIIA and related proteins," Proc Natl Acad Sci U S A., 85(1):99-102, Jan. 1988.
Bikard et al., "Programmable repression and activation of bacterial gene expression using an engineered CRISPR-Cas system," Nucleic Acid Res., Jun. 2013 41(15):7429-7437.
Bitinaite et al., "FokI dimerization is required for DNA cleavage," Proc. Natl. Acad. Sci. USA, 1998, 95:10570-10575.
Blackburn et al., "The CRISPR System-Keeping Zebrafish Gene Targeting Fresh," Zebrafish, 2013, 10(1):116-118.
Blaese et al., "T lymphocyte-directed gene therapy for ADA-SCID: initial trial results after 4 years," Science, Oct. 1995, 270:475-480.
Boch et al., "Breaking the code of DNA binding specificity of TAL-type III effectors," Science, Dec. 11, 2009;326(5959):1509-12.
Bogdanove & Voytas, "TAL Effectors: Customizable Proteins for DNA Targeting," Science, 333:1843-1846 (2011).
Bogdanove et al., "TAL effectors: finding plant genes for disease and defense," Curr. Opin. Plant Biol., 13:394-401 (2010).
Burgess, "A CRISPR genome-editing tool," Nature Reviews Genetics 14, 80-81 (Feb. 2013).
Burnett et al., "Conditional macrophage ablation in transgenic mice expressing a Fas-based suicide gene," J. Leukoc. Biol., Apr. 2004, 75(4):612-623.
Butler and Kadonaga, "The RNA polymerase II core promoter: a key component in the regulation of gene expression," Genes & Dev., 2002, 16:2583-2592.
Canadian Office Action in Canadian Application No. 2907198, dated Jul. 8, 2016, 4 pages.
Carbonetti et al., "Use of pertussis toxin vaccine molecule PT19K/129G to deliver peptide epitopes for stimulation of a cytotoxic T lymphocyte response," Abstr. Annu. Meet. Am. Soc. Microbiol., 1995, 95:295.
Carroll et al., "Design, construction and in vitro testing of zinc finger nucleases," Nat Protoc., 1(3):1329-1341, 2006.
Carroll, "A CRISPR Approach to Gene Targeting," Molecular Therapy, 2012, 20(9):1658-1660.
Carroll, "Progress and prospects: zinc-finger nucleases as gene therapy agents," Gene Ther., 15(22):1463-1468, Epub Sep. 11, 2008.
Carroll, "Staying on target with CRISPR-Case," Nat Biotechnol., 2013, 31(9):807-809.
Castellano et al., "Inducible recruitment of Cdc42 or WASP to a cell-surface receptor triggers actin polymerization and filopodium formation," Curr. Biol., 1999, 9(7): 351-360.
Cathomen and Joung, "Zinc-finger nucleases: the next generation emerges," Mol. Ther., 2008, 16:1200-1207.
Cermak et al., "Efficient design and assembly of custom TALEN and other TAL effector-based constructs for DNA targeting," Nucleic Acids Res., 39:e82, p. 1-11 (2011).
Chaikind et al., "Targeted DNA Methylation Using an Artificially Bisected M.HhaI Fused to Zinc Fingers," PLoS ONE, 7(9):E44852 pp. 1-11 (2012).
Chang et al., "Genome editing with RNA-guided Cas9 nuclease in zebrafish embryos," Cell Res., 2013, 23:465-472.
Chen & Zhao, "A highly sensitive selection method for directed evolution of homing endonucleases," Nucleic Acids Res., 2005, 33(18):e154.
Chen et al., "Cut Site Selection by the Two Nuclease Domains of the Cas9 RNA-guided Endonuclease," J Biol Chem. May 9, 2014; 289(19):13284-94.
Chen et al., "Dynamic imaging of genomic loci in living human cells by an optimized CRISPR/Cas system," Cell, 2013, 155(7):1479-1491.
Chen et al., "Efficient genome editing in Caenorhabditis elegans by CRISPR-targeted homologous recombination," Nucleic Acids Res., 2013, 41(20):e193, 6 pages.

(56) References Cited

OTHER PUBLICATIONS

Chen et al., "Induced DNA demethylation by targeting Ten-Eleven Translocation 2 to the human ICAM-1 promoter," Nucleic Acids Res., 42(3):1563-1574, Epub Nov. 4, 2013.
Cheng et al., "Multiplexed activation of endogenous genes by CRISPR-on, an RNA-guided transcriptional activator system," Cell Res., Oct. 2013, 23(10):1163-71.
Chim et al., "Methylation profiling in multiple myeloma," Leuk. Res., Apr. 2004, 28:379-85.
Chiu et al., "Transgene-free genome editing in Caenorhabditis elegans using CRISPR-Cas," Genetics, Nov. 2013, 195(3):1167-71.
Cho et al., "Analysis of off-target effects of CRISPR/Case-derived RNA-guided endonucleases and nickases," Genome Res., 2014, 24:132-141.
Cho et al., "Targeted genome engineering in human cells with the Cas9 RNA-guided endonuclease," Nat Biotechnol., 2013, 31:230-232.
Choo and Klug, "Toward a code for the interactions of zinc fingers with DNA: selection of randomized fingers displayed on phage," Proc Natl Acad Sci U S A., 91(23):11163-11167, Nov. 8, 1994.
Christian et al., "Targeting DNA Double-Strand Breaks with TAL Effector Nucleases," Genetics, 2010, 186:757-761 (2010).
Chylinski et al., "Classification and evolution of type II CRISPR-Cas systems," Nucleic Acids Res. 2014;42(10):6091-105.
Chylinski et al., "The tracrRNA and Cas9 families of type II CRISPR-Cas immunity systems," RNA Biol., 2013, 10(5):726-737.
Clark-Curtiss and Curtiss, "[23] Analysis of recombinant DNA using *Escherichia coli* minicells," Methods in Enzymology, 1983, 101:347-362.
Colley et al., "Conversion of a Golgi Apparatus Sialyltransferase to a Secretory Protein by Replacement of the NH2-terminall Signal Anchor with a Signal Peptide," J. Biol. Chem., 1989, 264:17619-22.
Cong et al., "Multiplex genome engineering using CRISPR/Cas systems," Science, 2013, 339:819-823 (Author Manuscript).
Conklin, "Sculpting genomes with a hammer and chisel," Nature Methods, 2013, 10(9):839-840.
Costa et al., "REELIN and schizophrenia: a disease at the interface of the genome and the epigenome," Mol. Interv., Feb. 2002, 2:47-57.
Crabtree and Schreiber, "Three-part inventions: intracellular signaling and induced proximity," Trends Biochem. Sci., Nov. 1996, 21(11):418-422.
Cradick et al., "CRISPR/Cas9 systems targeting beta-globin and CCR5 genes have substantial off-target activity," Nucleic Acids Res., 2013, 41(20):9584-92.
D'Avignon et al., "Site-specific experiments on folding/unfolding of Jun coiled coils: thermodynamic and kinetic parameters from spin inversion transfer nuclear magnetic resonance at leucine-18," Biopolymers, 83(3):255-267, Oct. 15, 2006.
De Souza, "RNA-guided gene editing," Nat Methods, Mar. 2013, 10(3):189.
De Zhu, "The altered DNA methylation pattern and its implications in liver cancer," Cell. Res., 2005, 15:272-80.
Deltcheva et al., "CRISPR RNA maturation by trans-encoded small RNA and host factor Rnase III," Nature, 2011, 471(7340):602-607 (Author Manuscript).
Deveau et al., "Phage response to CRISPR-encoded resistance in *Streptococcus thermophilus*," J Bacteriol., Feb. 2008, 190(4):1390-400.
Dicarlo et al., "Genome engineering in *Saccharomyces cerevisiae* using CRISPR-Cas systems," Nucleic Acids Res., 2013, 41(7):4336-43.
Dickinson et al., "Engineering the Caenorhabditis elegans genome using Cas9-triggered homologous recombination," Nat Methods., Oct. 2013, 10(10):1028-34.
Ding et al., "Enhanced efficiency of human pluripotent stem cell genome editing through replacing TALENs with CRISPRs," Cell Stem Cell., Apr. 4, 2013, 12(4):393-4 (Author Manuscript).

Donnelly et al., "Targeted delivery of peptide epitopes to class I major histocompatibility molecules by a modified Pseudomonas exotoxin," PNAS, Apr. 1993, 90:3530-34.
Doudna and Charpentier, "Genome editing. The new frontier of genome engineering with CRISPR-Cas9," Science, Nov. 2014, 346:1258096, 11 pages.
Doyon et al., "Directed Evolution and Substrate Specificity Profile of Homing Endonuclease I-Scel," J. Am. Chem. Soc., 2006, 128:2477-2484.
Doyon et al., "Heritable targeted gene disruption in zebrafish using designed zinc-finger nucleases," Nat Biotechnol., Jun. 2008, 26:702-708.
Dranoff et al., "A phase I study of vaccination with autologous, irradiated melanoma cells engineered to secrete human granulocyte-macrophage colony stimulating factor," Hum. Gene Ther., Jan. 1997, 8(1):111-23.
Dunbar et al., "Retrovirally Marked CD34-Enriched Peripheral Blood and Bone Marrow Cells Contribute to Long-Term Engraftment After Autologous Transplantation," Blood, Jun. 1995, 85:3048-3057.
Eisenschmidt et al., "Developing a programmed restriction endonuclease for highly specific DNA cleavage," Nucleic Acids Res., 33(22):7039-47 (2005).
Ellem et al., "A case report: immune responses and clinical course of the first human use of granulocyte/macrophage-colony-stimulating-factor-transduced autologous melanoma cells for immunotherapy," Immunol Immunother., Mar. 1997, 44:10-20.
Elrod-Erickson et al., "High-resolution structures of variant Zif268-DNA complexes: implications for understanding zinc finger-DNA recognition," Structure, 6(4):451-464, Apr. 15, 1998.
Esteller et al., "A Gene Hypermethylation Profile of Human Cancer," Cancer Res., Apr. 2001, 61:3225-9.
Esteller et al., "Promoter Hypermethylation and BRCA1 Inactivation in Sporadic Breast and Ovarian Tumors," J. Natl. Cancer Inst., Apr. 2000, 92:564-9.
Esvelt et al., "Orthogonal Cas9 proteins for RNA-guided gene regulation and editing," Nat Methods, Nov. 2013, 10(11):1116-21.
European Partial Supplementary Search Report in European Application No. 14764117.9, dated Aug. 11, 2016, 7 pages.
European Search Report in European Application No. 14763916.5, dated Jul. 27, 2016, 10 pages.
Fisher et al., "A scalable, fully automated process for construction of sequence-ready human exome targeted capture libraries," Genome Biol., 2011, 12-R1.
Fonfara et al., "Phylogeny of Cas9 determines functional exchangeability of dual-RNA and Cas9 among orthologous type II CRISPR-Cas systems." Nucleic Acids Res., Feb. 2014, 42(4):2577-90.
Freeman et al., "Inducible Prostate Intraepithelial Neoplasia with Reversible Hyperplasia in Conditional FGFR1-Expressing Mice," Cancer Res., Dec. 2003, 63(23):8256-8563.
Friedland et al., "Heritable genome editing in C. elegans via a CRISPR-Cas9 system," Nature Methods 10(8): 741-743, 2013 (Author Manuscript).
Fu et al, Targeted genome editing in human cells using CRISPR/Cas nucleases and truncated guide RNAs, Methods in Enzymology, Nov. 2014, 546: 21-45.
Fu et al., "High-frequency off-target mutagenesis induced by CRISPR-Cas nucleases in human cells," Nat Biotechnol., 2013, 31:822-826 (Author Manuscript).
Fu et al., "Improving CRISPR-Cas nuclease specificity using truncated guide RNAs," Nat. Biotechnol. Mar. 2014, 32:279-284.
Gabriel et al., "An unbiased genome-wide analysis of zinc-finger nuclease specificity," Nat Biotechnol., 2011, 29:816-823.
Gagnon et al., "Efficient mutagenesis by Cas9 protein-mediated oligonucleotide insertion and large-scale assessment of single-guide RNAs," PLoS One, May 2014, 9, e98186.
Gao et al., "Hypermethylation of the RASSF1A gene in gliomas," Clin. Chim. Acta., Nov. 2004, 349:173-9.
Garcia-Bustos et al., "Nuclear protein localization," Biochim. Biophys. Acta, Mar. 1991, 1071:83-101.
Garneau et al., "The CRISPR/Cas bacterial immune system cleaves bacteriophage and plasmid DNA," Nature, Nov. 4, 2010, 468(7320):67-71.

(56) References Cited

OTHER PUBLICATIONS

Gasiunas and Siksnys, "RNA-dependent DNA endonuclease Cas9 of the CRISPR system: Holy Grail of genome editing?" Trends Microbiol., 2013, 21(11):562-567.
Gasiunas, "Cas9-crRNA ribonucleoprotein complex mediates specific DNA cleavage for adaptive immunity in bacteria," Proc Natl Acad Sci U S A, Sep. 25, 2012, 109(39):E2579-86.
Geibler et al., "Transcriptional Activators of Human Genes with Programmable DNA-Specificity ," PLoS ONE, 6:e19509 (2011).
Gilbert et al., "CRISPR-mediated modular RNA-guided regulation of transcription in eukaryotes," Cell, 2013, 154(2):442-51.
Gossen and Bujard, "Tight control of gene expression in mammalian cells by tetracycline-responsive promoters," Proc. Natl. Acad. Sci., Jun. 1992, 89:5547-5551.
Graef et al., "Proximity and orientation underlie signaling by the non-receptor tyrosine kinase ZAP70," Embo. J., 1997, 16(18):5618-5628.
Gratz et al., "CRISPR/Cas9-mediated genome engineering and the promise of designer flies on demand," Fly (Austin), Oct.-Dec. 2013, 7(4):249-55.
Gratz et al., "Genome engineering of *Drosophila* with the CRISPR RNA-guided Cas9 nuclease," Genetics, 2013, 194(4):1029-35.
Grizot et al., "Generation of redesigned homing endonucleases comprising DNA-binding domains derived from two different scaffolds," Nucleic Acids Res., 38(6):2006-2018, Epub Dec. 21, 2009.
Gross and Garrard, "Nuclease Hypersensitive Sites in Chromatin," Annu. Rev. Biochem., Jul. 1988, 57:159-97.
Guilinger et al., "Broad specificity profiling of TALENs results in engineered nucleases with improved DNA-cleavage specificity," Nat. Methods, Apr. 2014, 11:429-435.
Guilinger et al., "Fusion of catalytically inactive Cas9 to FokI nuclease improves the specificity of genome modification," Nat Biotechnol., Apr. 2014, 32(6):577-583.
Guo et el., "Hydroxylation of 5-Methylcytosine by TET1 Promotes Active DNA Demethylation in the Adult Brain ," Cell, 145:423-434 (2011).
Haft et al., "A Guild of 45 CRISPR-Associated (Cas) Protein Families and multiple CRISPER/cas Subtypes Exist in Prokaryotic Genomes," PLOS, 2005, 1(6):0474-0483.
Hale et al., "Essential features and rational design of CRISPR RNAs that function with the Case RAMP modlule complex to cleave RNAs," Mol Cell., 2012, 45(3):292-302 (Author Manuscript).
Han et al., "CTCF Is the Master Organizer of Domain-Wide Allele-Specific Chromatin at the H19/Igf2 Imprinted Region," Mol Cell Biol., Feb. 2008, 28(3):1124-35.
Han et al., "Ligand-directed retroviral targeting of human breast cancer cells," PNAS, Oct. 1995, 92:9747-51.
Harikrishna et al., "Construction and function of fusion enzymes of the human cytochrome P450scc system," DNA Cell Biol., 12(5):371-379, Jun. 1993.
Harrison, "A structural taxonomy of DNA-binding domains," Nature, 353(6346): 715-719, Oct. 24, 1991.
Haurwitz et al., "Sequence- and Structure-Specific RNA Processing by a CRISPR Endonuclease," Science, Sep. 2010, 329(5997):1355-8.
Haurwitz, R. "The CRISPR endoribonuclease Csy4 utilizes unusual sequence and structures pecific mechanisms to recognize and process crRNAs," Thesis. May 8, 2012 (May 8, 2012), University of California, Berkeley, pp. 1-120. Retrieved from the lnternet:<http://escholarship.org/uc/item/0rh5940p> on Dec. 26, 2014 (Dec. 26, 2014). entire document.
He et al., "Tet-Mediated Formation of 5-Carboxylcytosine and Its Excision by TDG in Mammalian DNA," Science, 333:1303-1307 (2011).
Hockemeyer et al., "Genetic engineering of human ES and iPS cells using TALE nucleases," Nat Biotechnol., 2011, 29:731-734 (Author Manuscript).
Horii et al., "Generation of an ICF Syndrome Model by Efficient Genome Editing of Human Induced Pluripotent Stem Cells using the CRISPR System," Int J Mol Sci., 2013, 14:19774-19781.
Horvath and Barrangou, "CRISPR/Cas, the immune system of bacteria and archaea," Science, 2010, 327:167-170.
Horvath et al., "Diversity, activity, and evolution of CRISPR loci in *Streptococcus thermophilus*," J. Bacteriol., Feb. 2008, 190:1401-1412.
Hou et al., "Efficient genome engineering in human pluripotent stem cells using Cas9 from Neisseria meningitidis," Proc Natl Acad Sci U S A, Sep. 24, 2013, 110(39):15644-9.
Hsu et al., "Development and Applications of CRISPR-Cas9 for Genome Engineering," Cell, 2014, 157(6):1262-1278.
Hsu et al., "DNA targeting specificity of RNA-guided Cas9 nucleases," Nat Biotechnol., 2013, 31:827-832.
Huang et al., "Heritable gene targeting in zebrafish using customized TALENs," Nat. Biotechnol., 29:699-700 (2011).
Hwang et al., "Efficient In Vivo Genome Editing Using RNA-Guided Nucleases," Nat Biotechnol., 2013, 31:227-229 (Author Manuscript).
Hwang et al., "Heritable and Precise Zebrafish Genome Editing Using a CRISPR-Cas System," PLoS One, 2013, 8(7):e68708, 9 pages.
International Preliminary Report on Patentability in International Application No. PCT/US2013/043075, dated Dec. 2, 2014, 7 pages.
International Preliminary Report on Patentability in International Application No. PCT/US2014/027335, dated Sep. 15, 2015, 10 pages.
International Preliminary Report on Patentability in International Application No. PCT/US2014/028630, dated Sep. 15, 2015, 8 pages.
International Preliminary Report on Patentability in International Application No. PCT/US2014/029068, dated Sep. 15, 2015, 10 pages.
International Preliminary Report on Patentability in International Application No. PCT/US2014/029304, dated Sep. 22, 2015, 12 pages.
International Preliminary Report on Patentability in International Application No. PCT/US2014/056416, dated Jun. 28, 2016, 7 pages.
International Search Report and Written Opinion in International Application No. PCT/US2013/043075, dated Sep. 26, 2013, 10 pages.
International Search Report and Written Opinion in International Application No. PCT/US2014/027335, dated Jul. 16, 2014, 13 pages.
International Search Report and Written Opinion in International Application No. PCT/US2014/028630, dated Jul. 24, 2014, 9 pages.
International Search Report and Written Opinion in International Application No. PCT/US2014/029068, dated Nov. 5, 2014, 15 pages.
International Search Report and Written Opinion in International Application No. PCT/US2014/029304, dated Nov. 14, 2014, 17 pages.
International Search Report and Written Opinion in International Application No. PCT/US2014/035162, dated Oct. 14, 2014, 10 pages.
International Search Report and Written Opinion in International Application No. PCT/US2014/056416, dated Apr. 3, 2015, 11 pages.
Invitation to Pay Additional Fees and, Where Applicable, Protest Fee in International Application No. PCT/US2014/029068, mailed Aug. 20, 2014, 3 pages.
Invitation to Pay Additional Fees and, Where Applicable, Protest Fee in International Application No. PCT/US2014/029304, mailed Jul. 30, 2014, 3 pages.
Isalan et al., "A rapid, generally applicable method to engineer zinc fingers illustrated by targeting the HIV-1 promoter," Nat. Biotechnol., 19(7):656-660, Jul. 2001.
Ishino et al., "Nucleotide sequence of the iap gene, responsible for alkaline phosphatase isozyme conversion in *Escherichia coli*, and identification of the gene product," J Bacteriol., Dec. 1987, 169(12):5429-33.
Ito et al., "Tet proteins can convert 5-methylcytosine to 5-formylcytosine and 5-carboxylcytosine," Science, 333(6047):1300-1303, Sep. 2, 2011.

(56) References Cited

OTHER PUBLICATIONS

Iyer et al., "Prediction of novel families of enzymes involved in oxidative and other complex modifications of bases in nucleic acids," Cell Cycle, Jun. 1, 2009, 8(11):1698-710.
Iyer et al., Supplementary Material for "Prediction of novel families of enzymes involved in oxidative and other complex modifications of bases in nucleic acids," Cell Cycle, Jun. 1, 2009, 8(11):1698-710, [retrieved on Dec. 22, 2015]. Retrieved from the Internet: URL<ftp://ftp.ncbi.nih.gov/pub/aravind/DONS/supplementary_material_DONS.html>.
Jamieson et al., "In vitro selection of zinc fingers with altered DNA-binding specificity," Biochemistry, 33(19):5689-5695, May 17, 1994.
Jansen et al., "Identification of genes that are associated with DNA repeats in prokaryotes," Mol Microbiol., Mar. 2002, 43(6):1565-75.
Jiang et al., "CRISPR-assisted editing of bacterial genomes," Nat Biotechnol., 2013, 31:233-239 (Author Manuscript).
Jiang et al., "Structural Biology. A Cas9-guide RNA complex preorganized for target DNA recognition," Science, Jun. 2015, 348:1477-1481.
Jinek et al., "A programmable dual-RNA-guided DNA endonuclease in adaptive bacterial immunity," Science, 2012, 337:816-821.
Jinek et al., "RNA-programmed genome editing in human cells," Elife, 2013, 2:e00471, 9 pages.
Jinek et al., "Structures of Cas9 Endonucleases Reveal RNA-Mediated Conformational Activation," Science. Mar. 14, 2014; 343(6176):1247997.
Jinek et al., "Supplementary Materials for a Programmable Dual-RNA-Guided DNA Endonuclease in Adaptive Bacterial Immunity," Science Express, pp. 1-37 (2012).
Josephs et al., "Structure and specificity of the RNA-guided endonuclease Cas9 during DNA interrogation, target binding and cleavage," Nucleic Acids Res., Sep. 2015, 43:8924-8941.
Joung and Sander, "TALENs: a widely applicable technology for targeted genome editing," Nat Rev Mol Cell Biol., 14(1):49-55, Epub Nov. 21, 2012.
Joung et al., "Reply to "Successful genome editing with modularly assembled zinc finger nucleases"," Nat. Methods, Jan. 2010, 7:91-92.
Karkare and Bhatnagar, "Promising nucleic acid analogs and mimics: characteristic features and applications of PNA, LNA, and morpholino", Applied Microbiology and Biotechnology, May 2006, 71(5): 575-586.
Karmirantzou and Harnodrakas, "A Web-based classification system of DNA-binding protein families," Protein Eng. 14(7):465-472, Jul. 2001.
Karvelis et al., "crRNA and tracrRNA guide Cas9-mediated DNA interference in *Streptococcus thermophilus*," RNA Biol., 2013, 10(5):841-851.
Katic and Großhans, "Targeted heritable mutation and gene conversion by Cas9-CRISPR in Caenorhabditis elegans," Genetics, Nov. 2013, 195(3):1173-6.
Kearns et al., "Recombinant adeno-associated virus (AAV-CFTR) vectors do not integrate in a site-specific fashion in an immortalized epithelial cell line," Gene Ther., Sep. 1996, 9:748-55.
Keryer-Bibens et al., "Tethering of proteins to RNAs by bacteriophage proteins," Biol Cell, 2008, 100:125-138.
Kiani et al., "Cas9 gRNA engineering for genome editing, activation and repression," Nat. Methods, 2015, 12:1051-1054.
Kim and Kim, "A guide to genome engineering with programmable nucleases," Nature Rev Genetics 15, 321-334 (2014).
Kim et al., "Highly efficient RNA-guided genome editing in human cells via delivery of purified Cas9 ribonucleoproteins," Genome Res. Jun. 2014; 24(6):1012-9.
Kim et al., "Targeted genome editing in human cells with zinc finger nucleases constructed via modular assembly," Genome Res., 19(7):1279-1288, Epub May 21, 2009.
Kim et al., "Genome editing with modularly assembled zinc-finger nucleases," Nat. Methods, 7(2):91-92, Feb. 2010.
Kleinstiver et al., "A unified genetic, computational and experimental framework identifies functionally relevant residues of the homing endonuclease I-BmoI," Nucleic Acids Res., 2010, 38:2411-2427.
Kleinstiver et al., "Engineered CRISPR-Cas9 nucleases with altered PAM specificities," Nature, Jul. 2015, 523(7561):481-5.
Klimpel et al., "Anthrax toxin protective antigen is activated by a cell surface protease with the sequence specificity and catalytic properties of furin," PNAS, Nov. 1992, 89:10277-81.
Klug, "Co-chairman's remarks: protein designs for the specific recognition of DNA," Gene, 135(1-2):83-92, Dec. 15, 1993.
Koike-Yusa et al., "Genome-wide recessive genetic screening in mammalian cells with a lentiviral CRISPR-guide RNA library," Nat Biotechnol., Mar. 2014, 32(3):267-73.
Kondo and Ueda, "Highly improved gene targeting by germline-specific Cas9 expression in *Drosophila*," Genetics, Nov. 2013, 195(3):715-21.
Konermann et al., "Optical control of mammalian endogenous transcription and epigenetic states," Nature. Aug. 22, 2013; 500(7463):472-6. (Author Manuscript).
Kumar et al., "DNA-Prot: identification of DNA binding proteins from protein sequence information using random forest," J Biomol Struct Dyn., 26(6):679-686, Jun. 2009.
Kumar et al., "Identification of DNA-binding proteins using support vector machines and evolutionary profiles," BMC Bioinformatics, 8:463, Nov. 27, 2007.
Kummerfeld and Teichmann, "DBD: a transcription factor prediction database," Nucleic Acids Res., 34 (Database issue): D74-D81, Jan. 1, 2006.
Kurmasheva et al., "Upstream CpG island methylation of the PAX3 gene in human rhabdomyosarcomas," Pediatr. Blood Cancer, Apr. 2005, 44:328-37.
Lea et al., "Aberrant p16 methylation is a biomarker for tobacco exposure in cervical squamous cell carcinogenesis," Am. J. Obstet. Gynecol., 2004, 190:674-9.
Lee et al., "Three-dimensional solution structure of a single zinc finger DNA-binding domain," Science., 245(4918):635-637, Aug. 11, 1989.
Li et al., "DNA methylation in prostate cancer," Biochim. Biophys. Acta., Sep. 2004, 1704:87-102.
Li et al., "Heritable gene targeting in the mouse and rat using a CRISPR-Cas system," Nat Biotechnol, Aug. 2013, 31(8):681-3.
Li et al., "Modularly assembled designer TAL effector nucleases for targeted gene knockout and gene replacement in eukaryotes," Nucleic Acids Res., 39(14):6315-6325, Epub Mar. 31, 2011.
Li et al., "Protein trans-splicing as a means for viral vector-mediated in vivo gene therapy," Hum Gene Ther., 19(9):958-964, Sep. 2008.
Li et al., "Simultaneous generation and germline transmission of multiple gene mutations in rat using CRISPR-Cas systems," Nat Biotechnol., Aug. 2013, 31(8):684-6.
Li et al., "TAL nucleases (TALNs): hybrid proteins composed of TAL effectors and FokI DNA-cleavage domain," Nucleic Acids Res., 2011, 39(1): 359-372.
Lin et al., "CRISPR/Cas9 systems have off-target activity with insertions or deletions between target DNA and guide RNA sequences," Nucleic Acids Res., 2014, 42:7473-7485.
Lin et al., "iDNA-Prot: identification of DNA binding proteins using random forest with grey model," PLoS One., 6(9):e24756, Epub Sep. 15, 2011.
Liu et al., "Regulation of an Endogenous Locus Using a Panel of Designed Zinc Finger Proteins Targeted to Accessible Chromatin Regions," J. Biol. Chem., Apr. 2001, 276(14):11323-34.
Liu et al., "Validated zinc finger protein designs for all 16 GNN DNA triplet targets," J. Biol. Chem., 277(6):3850-3856, Epub Nov. 28, 2001.
Lo et al., "Precise and Heritable Genome Editing in Evolutionarily Diverse Nematodes Using TALENs and CRISPR/Cas9 to Engineer Insertions and Delections," Genetics, 2013, 195:331-348.
Lund et al., "DNA Methylation Polymorphisms Precede Any Histological Sign of Atherosclerosis in Mice Lacking Apolipoprotein E," J. Biol. Chem., Jul. 2004, 279:29147-54.

(56) References Cited

OTHER PUBLICATIONS

Mabaera et al., "Developmental- and differentiation-specific patterns of human γ- and β-globin promoter DNA methylation," Blood, 110(4):1343-52 (2007).
Maeder et al., "CRISPR RNA-guided activation of endogenous human genes," Nat Methods, 2013, 10:977-979 (Author Manuscript).
Maeder et al., "Rapid 'open-source' engineering of customized zinc-finger nucleases for highly efficient gene modification," Mol Cell, 2008, 31(2):294-301.
Maeder et al., "Robust, synergistic regulation of human gene expression using TALE activators," Nat. Methods, 2013, 10:243-245.
Maeder et al., "Targeted DNA demethylation and activation of endogenous genes using programmable TALE-TET1 fusion proteins," Nat Biotechnol., 31(12):1137-1142, [author manuscript] Epub Oct. 9, 2013.
Mahfouz et al., "De novo-engineered transcription activator-like effector (TALE) hybrid nuclease with novel DNA binding specificity creates double-strand breaks," Proc Natl Acad Sci U S A, 108:2623-2628 (2011).
Maiti and Drohat, "Thymine DNA glycosylase can rapidly excise 5-formylcytosine and 5-carboxylcytosine: potential implications for active demethylation of CpG sites," J Biol Chem., 286(41):35334-35338, Epub Aug. 23, 2011.
Majumdar et al., "Targeted Gene Knock in and Sequence Modulation Mediated by a Psoralen-linked Triplex-forming Oligonucleotide," J Biol Chem., 283(17):11244-52 (2008).
Makarova et al., "A putative RNA-interference-based immune system in prokaryotes: computational analysis of the predicted enzymatic machinery, functional analogies with eukaryotic RNAi, and hypothetical mechanisms of action," Biol. Direct, 2006, 1:7, 26 pages.
Makarova et al., "Evolution and classification of the CRISPR-Cas systems," Nat. Rev. Microbiol., 2011, 9(6):467-77 (Author Manuscript).
Makarova et al., "Unification of Cas protein families and a simple scenario for the origin and evolution of CRISPR-Cas systems," Biol. Direct, 2011, 6:38, 27 pages.
Malech et al., "Prolonged production of NADPH oxidase-corrected granulocytes after gene therapy of chronic granulomatous disease," PNAS, Oct. 1997, 94:12133-38.
Mali et al., "Cas9 as a versatile tool for engineering biology," Nature Methods, 2013, 10(10):957-963.
Mali et al., "CAS9 transcriptional activators for target specificity screening and paired nickases for cooperative genome engineering," Nat Biotechnol., 2013, 31:833-838.
Mali et al., "RNA-guided human genome engineering via Cas9," Science, Feb. 2013, 339:823-826 (Author Manuscript).
Mancini et al. "CpG methylation within the 5' regulatory region of the BRCA1 gene is tumor specific and includes a putative CREB binding site," Oncogene, 1998, 16:1161-9.
Mandell and Barbas et al., "Zinc Finger Tools: custom DNA-binding domains for transcription factors and nucleases," Nucleic Acids Res., 34(Web Server issue):W516-W523, Jul. 1, 2006.
Marraffini and Sontheimer, "CRISPR Interference Limits Horizontal Gene Transfer in *Staphylococci* by Targeting DNA," Sci., 2008, 322(5909):1843-1845.
Marraffini and Sontheimer, "Self vs. non-self discrimination during CRISPR RNA-directed immunity," Nature, 2010, 463(7280):568-571 (Author Manuscript).
Mashiko et al., "Generation of mutant mice by pronuclear injection of circular plasmid expressing Cas9 and single guided RNA," Sci Reports, 2013, 3(3355):1-6.
McGarty, "CRISPRs and Cancer," White Paper No. 111, Apr. 2014, 22 pages.
Mendenhall et al., "Locus-specific editing of histone modifications at endogenous enhancers," Nat Biotechnol., 31(12):1133-1136, Epub Sep. 8, 2013.
Miller et al., "A TALE nuclease architecture for efficient genome editing," Nature Biotechnology, Feb. 2011, 29:143-148.
Miller et al., "An improved zinc-finger nuclease architecture for highly specific genome editing," Nat Biotechnol., 2007, 25:778-785.
Miller et al., "Repetitive zinc-binding domains in the protein transcription factor IIIA from Xenopus oocytes," EMBO J., 4(6):1609-1614, Jun. 1985.
Miyazaki et al., "Expression vector system based on the chicken beta-actin promoter directs efficient production of interleukin-5," Gene, Jul. 1989, 79(2):269-77.
Mojica et al., "Biological significance of a family of regularly spaced repeats in the genomes of Archaea, Bacteria and mitochondria," Mol Microbiol., Apr. 2000, 36(1):244-6.
Mojica et al., "Short motif sequences determine the targets of the prokaryotic CRISPR defense system," Microbiology, 2009, 155:733-740.
Moore et al., "Design of polyzinc finger peptides with structured linkers," Proc Natl Acad Sci USA, Feb. 2001, 98:1432-1436.
Morbitzer et al., "Regulation of selected genome loci using de novo-engineered transcription activator-like effector (TALE)-type transcription factors," Proc Natl Acad Sci U S A., 107(50):21617-21622, Epub Nov. 24, 2010.
Morbitzer et al., "Assembly of custom TALE-type DNA binding domains by modular cloning," Nucl Acids Res., 39:5790-5799 (2011).
Morrison, "Transformation in *Escherichia coli*: Cryogenic Preservation of Competent Cells," J. Bacteriol., Oct. 1977, 132:349-351.
Moscou and Bogdanove, "A simple cipher governs DNA recognition by TAL effectors," Science, 326(5959):1501, Dec. 11, 2009.
Mussolino and Cathomen, "RNA guides genome engineering," Nat Biotechnol., 2013, 31(3):208-209.
Mussolino et al., "A novel TALE nuclease scaffold enables high genome editing activity in combination with low toxicity," Nucleic Acids Res., 2011, 39:9283-93.
Muthuswamy et al., "Controlled Dimerization of ErbB Receptors Provides Evidence for Differential Signaling by Homo- and Heterodimers," Mol. Cell. Biol., Oct. 1999, 19(10):6845-6857.
Needleman and Wunsch, "A General Method Applicable to the Search for Similarities in the Amino Acid Sequence of Two Proteins," J. Mol. Biol., 1970, 48:444-453.
Neering et al., "Transduction of Primitive Human Hematopoietic Cells With Recombinant Adenovirus Vectors," Blood, Aug. 1996, 88:1147-55.
Nishimasu et al., "Crystal structure of Cas9 in complex with guide RNA and target DNA," Cell, 2014, 156:935-949.
Nissim et al., "Multiplexed and Programmable Regulation of Gene Networks with an Integrated RNA and CRISPR/Cas Toolkit in Human Cells," Molecular Cell, May 2014, 54:698-710.
Niu et al., "Generation of gene-modified cynomolgus monkey via Cas9/RNA-mediated gene targeting in one-cell embryos," Cell, 2014, 156:836-843.
Niwa et al., "Efficient selection for high-expression transfectants with a novel eukaryotic vector," Gene, 1991, 108(2):193-9.
Novak et al., "Functional Characterization of Protease-treated Bacillus anthracia Protective Antigen," J. Biol. Chem., Aug. 1992, 267:17186-93.
Oligino et al., "Drug inducible transgene expression in brain using a herpes simplex virus vector," Gene Ther., 1998, 5:491-496.
Palva et al., "Secretion of interferon by Bacillus subtilis," Gene, 1983, 22:229-235.
Pattanayak et al., "High-throughput profiling of off-target DNA cleavage reveals RNA-programmed Cas9 nuclease specificity," Nat Biotechnol., 2013, 31:839-843 (Author Manuscript).
Pattanayak et al., "Revealing off-target cleavage specificities of zinc-finger nucleases by in vitro selection," Nat Methods, 2011, 8:765-770 (Author Manuscript).
Pavletich and Pabo, "Zinc finger-DNA recognition: crystal structure of a Zif268-DNA complex at 2.1 A," Science, 252(5007):809-817, May 10, 1991.
Perelle et al., "Characterization of Clostridium perfringens Iota-Toxin Genes and Expression in *Eschenichia coli*," Infect. Immun , Dec. 1993, 61:5147-56.

(56) References Cited

OTHER PUBLICATIONS

Perez et al., "Establishment of HIV-1 resistance in CD4+ T cells by genome editing using zinc-finger nucleases," Nat Biotechnol., 2008, 26:808-816 (Author Manuscript).
Perez-Pinera et al., "RNA-guided gene activation by CRISPR-Case9-based transcription factors," Nat Methods, 2013, 10(10):973-976 (Author Manuscript).
Pingoud and Silva, "Precision genome surgery," Nat Biotechnol., 25(7):743-744, Jul. 2007.
Puchta and Fauser et al., "Synthetic nucleases for genome engineering in plants: prospects for a bright future," Plant J. Jun. 2014; 78(5):727-41.
Qi et al., "Repurposing CRISPR as an RNA-Guided Platform for Sequence-Specific Control of Gene Expression," Cell, Feb. 2013, 152:1173-1183.
Ramakrishna et al., "Gene disruption by cell-penetrating peptide-mediated delivery of Cas9 protein and guide RNA," Genome Res. Jun. 2014; 24(6): 1020-1027.
Ramakrishna et al., "Surrogate reporter-based enrichment of cells containing RNA-guided Cas9 nuclease-induced mutations," Nat Commun. Feb. 26, 2014; 5:3378.
Ramalingam et al., "A CRISPR way to engineer the human genome," Genome Biol., 2013, 14:107, 4 pages.
Ramirez et al., "Unexpected failure rates for modular assembly of engineered zinc fingers," Nat Methods., 5(5):374-375, May 2008.
Ran et al., "Double nicking by RNA-guided CRISPR Cas9 for enhanced genome editing specificity," Cell, 2013, 154:1380-1389.
Ran et al., "Genome engineering using the CRISPR-Cas9 system," Nature Protocols, 2013, 8(11):2281-2308.
Ran et al., "In vivo genome editing using *Staphylococcus aureus* Cas9," Nature, 2015, 520:186-191.
Rebar and Pabo, "Zinc finger phage: affinity selection of fingers with new DNA-binding specificities," Science, 263(5147):671-673, Feb. 4, 1994.
Ren et al., "Optimized gene editing technology for *Drosophila melanogaster* using germ line-specific Cas9," Proc Natl Acad Sci U S A, Nov. 19, 2013, 110(47):19012-7.
Rendahl et al., "Regulation of gene expression in vivo following transduction by two separate rAAV vectors," Nat. Biotechnol., Aug. 1998, 16:757-761.
Reyon et al., "Flash assembly of TALENs for high-throughput genome editing," Nat Biotech, 2012, 30:460-465 (Author Manuscript).
Ro et al., "Adenovirus-based short hairpin RNA vectors containing an EGFP marker and mouse U6, human H1, or human U6 promoter," BioTechniques, 2005, 38(4):625-627.
Rodenhiser and Mann, "Epigenetics and human disease: translating basic biology into clinical applications," CMAJ, 174(3):341-348 (2006).
Rohde et al., "BISMA—Fast and accurate bisulfite sequencing data analysis of individual clones from unique and repetitive sequences," BMC Bioinformatics, 11:230 12 pages (2010).
Rothman, "Mechanisms of intracellular protein transport," Nature, 372(6501):55-63, Nov. 3, 1994.
Rusk, "CRISPRs and epigenome editing," Nature Methods, 2014, 11(1):28.
Sander and Joung et al., "CRISPR-Cas systems for editing, regulating and targeting genomes," Nat Biotechnol., Apr. 2014, 32(4):347-55.
Sander et al., "In silico abstraction of zinc finger nuclease cleavage profiles reveals an expanded landscape of off-target sites," Nucleic Acids Res., 2013, 41:e181.
Sander et al., "ZiFiT (Zinc Finger Targeter): an updated zinc finger engineering tool," Nucleic Acids Res., 2010, 38:W462-468.
Sander et al., "Zinc Finger Targeter (ZiFiT): an engineered zinc finger/target site design tool," Nucleic Acids Res., 2007, 35:W599-605.
Sander et al., "Targeted gene disruption in somatic zebrafish cells using engineered TALENs," Nat. Biotechnol., 29:697-698 (2011).
Sanjana et al., A transcription activator-like effector toolbox for genome engineering, Nature Protocols, 2012, 7:171-192.
Sapranauskas et al., "The *Streptococcus thermophilus* CRISPR/Cas system provides immunity in *Escherichia coli*," Nucleic Acids Res., 2011, 39(21):9275-9282.
Schleifman et al., "Triplex-mediated gene modification," Methods Mol. Biol., 435:175-190, 2008.
Scholze & Boch, "TAL effectors are remote controls for gene activation," J. Curr. Opin. Microbiol, 14:47-53 (2011).
Schwank et al., "Functional repair of CFTR by CRISPR/Cas9 in intestinal stem cell organoids of cystic fibrosis patients," Cell Stem Cell, Dec. 5, 2013, 13(6):653-8.
Sebo et al., "Cell-invasive activity of epitope-tagged adenylate cyclase of Bordetella pertussis allows in vitro presentation of a foreign epitope to CD8+ cytotoxic T cells," Infect. Immun Oct. 1995, 63:3851-57.
Segal et al., "Evaluation of a modular strategy for the construction of novel polydactyl zinc finger DNA-binding proteins," Biochemistry, 42(7):2137-2148, Feb. 25, 2003.
Shah et al., "Protospacer recognition motifs," RNA Biol., 2013, 10:891-899.
Sharma, "Schizophrenia, epigenetics and ligand-activated nuclear receptors: a framework for chromatin therapeutics," Schizophr. Res., Jan. 2005, 72:79-90.
Shen et al., "Efficient genome modification by CRISPR-Cas9 nickase with minimal off-target effects," Nat Methods, 2014, 11(4):399-402.
Shen et al., "Generation of gene-modified mice via Cas9/RNA-mediated gene targeting," Cell Res., 2013, 23(5):720-3.
Shmakov et al., "Discovery and Functional Characterization of Diverse Class 2 CRISPR-Cas Systems," Molecular Cell, 2015 60:385-397.
Silva et al., "Meganucleases and other tools for targeted genome engineering: perspectives and challenges for gene therapy," Curr Gene Ther., 11(1):11-27, Feb. 2011.
Silver, "How Proteins Enter the Nucleus," Cell, 64(3):489-497, Feb. 8, 1991.
Simon et al., "Sequence-specific DNA cleavage mediated by bipyridine polyamide conjugates," Nucl. Acids Res., 36(11):3531-8 (2008).
Stenmark et al., "Peptides fused to the amino-terminal end of diphtheria toxin are translocated to the cytosol," J. Cell Biol., Jun. 1991, 113:1025-32.
Sterman et al., "Adenovirus-mediated herpes simplex virus thymidine kinase/ganciclovir gene therapy in patients with localized malignancy: results of a phase I clinical trial in malignant mesothelioma," Hum. Gene Ther., May 1998, 7:1083-89.
Sternberg et al., "Conformational control of DNA target cleavage by CRISPR-Cas9" Nature, 2015, 527:110-113.
Sternberg et al., "DNA interrogation by the CRISPR RNA-guided endonuclease Cas9," Nature, 2014, 507:62-67.
Sternberg et al., "Mechanism of substrate selection by a highly specific CRISPR endoribonuclease," RNA, 2012, 18:661-672.
Stoddard, "Homing endonuclease structure and function," Q. Rev. Biophys., 38(1): 49-95, Epub Dec. 9, 2005.
Storrs, "A CRISPR Fore-Cas-t: A newcomer's guide to the hottest gene-editing tool on the block," Scientist Magazine, Mar. 2014, 4 pages.
Sugimoto et al., "Thermodynamic parameters to predict stability of RNA/DNA hybrid duplexes," Biochemistry, 1995, 34:11211-11216.
Sugimoto et al., "Thermodynamics-structure relationship of single mismatches in RNA/DNA duplexes," Biochemistry, Sep. 19, 2000, 39(37):11270-81.
Swarts el al., "CRISPR Interference Directed Strand Specific Spacer Acquisition," PLOS, 2012, 7(4):1-7.
Szczepek et al., "Structure-based redesign of the dimerization interface reduces the toxicity of zinc-finger nucleases," Nat Biotechnol., 2007, 25:786-793.
Szyf et al., "DNA methylation and breast cancer," Biochem. Pharmacol., Sep. 2004, 68:1187-97.
Tahiliani et al., "Conversion of 5-Methylcytosine to 5-Hydroxymethylcytosine in Mammalian DNA by MLL Partner TET1," Science, 324:930-935 (2009).

(56) References Cited

OTHER PUBLICATIONS

Tan et al., "Efficient nonmeiotic allele introgression in livestock using custom endonucleases," Proc Natl Acad Sci U S A, Oct. 8, 2013, 110(41):16526-31.
Tan et al., "Zinc-finger protein-targeted gene regulation: genomewide single-gene specificity," Proc Natl Acad Sci U S A., 100(21):11997-2002, Epub Sep. 26, 2003.
Terns and Terns, "CRISPR-based adaptive immune systems," Curr Opin Microbiol., 2011, 14:321-327.
Tesson et al., "Knockout rats generated by embryo microinjection of TALENs," Nat. Biotechnol., 29:695-696 (2011).
Tjong and Zhou, "DISPLAR: an accurate method for predicting DNA-binding sites on protein surfaces," Nucleic Acids Res., 35(5):1465-1477, Epub Feb. 6, 2007.
Tsai et al., "Dimeric CRISPR RNA-guided FokI nucleases for highly specific genome editing," Nat Biotechnol., Apr. 2014, 32(6):569-576.
Tsai et al., "GUIDE-Seq enables genome-wide profiling of off-target cleavage by CRISPR-Cas nucleases," Nat Biotechnol, Feb. 2015, 33:187-197.
Tzur et al., "Heritable Custom Genomic Modifications in Caenorhabditis elegans via a CRISPR-Cas9 System," Genetics, 2013, 195:1181-1185.
Uhlmann et al., "Distinct methylation profiles of glioma subtypes," Int. J. Cancer, Aug. 2003, 106:52-9.
Office Action in U.S. Appl. No. 13/838,520, dated Jul. 15, 2015, 35 pages.
Office Action in U.S. Appl. No. 14/211,117, dated Sep. 8, 2015, 20 pages.
Office Action in U.S. Appl. No. 14/213,479, dated Dec. 9, 2015, 39 pages.
Office Action in U.S. Appl. No. 14/213,723, dated Mar. 2, 2016, 39 pages.
Office Action in U.S. Appl. No. 13/838,520, dated Oct. 6, 2014, 38 pages.
Van der Oost et al., "Unravelling the Structural and Mechanistic Basis of CRISPR-Cas Systems," Nature Reviews Microbiology, 2014, 12:479-492.
Ventura et al., "Cre-lox-regulated conditional RNA interference from transgenes," PNAS, Jul. 2004, 101:10380-10385.
Waaijers et al., "CRISPR/Cas9-Targeted Mutagenesis in Caenorhabditis elegans," Genetics, 2013, 195:1187-1191.
Wagner et al., "Efficient and persistent gene transfer of AAV-CFTR in maxillary sinus," Lancet, Jun. 1998, 351:1702-1703.
Wang et al., "One-Step Generation of Mice Carrying Mutations in Multiple Genes by CRISPR/Cas-Mediated Genome Engineering," Cell, 2013, 153:910-918.
Wang et al., "Positive and negative regulation of gene expression in eukaryotic cells with an inducible transcriptional regulator," Gene Ther., May 1997, 4:432-441.
Wang et al., "The CRISPR/Cas system mediates efficient genome engineering in Bombyx mori," Cell Res., Dec. 2013, 23(12):1414-6.
Weber et al., "Assembly of Designer TAL Effectors by Golden Gate Cloning," PLoS ONE, 6:e19722 (2011).
Widschwendter and Jones, "DNA methylation and breast carcinogenesis," Oncogene, Aug. 2002, 21:5462-82.
Wiedenheft, "RNA-guided genetic silencing systems in bacteria and archaea," Nature, 2012, 482:331-338.
Wolfe et al., "DNA recognition by Cys2His2 zinc finger proteins," Annu Rev Biophys Biomol Struct. 29:183-212 (2000).
Wong et al., "Detection of aberrant p16 methylation in the plasma and serum of liver cancer patients," Cancer Res., 59(1):71-73 Jan. 1, 1999.
Wood et al., "Targeted Genome Editing Across Species Using ZFNs and TALENs," Science, 333:307 (2011).
Wright et al., "Standardized reagents and protocols for engineering zinc finger nucleases by modular assembly," Nat Protoc., 2006, 1(3):1637-1652.

Wu et al., "Building zinc fingers by selection: toward a therapeutic application," Proc Natl Acad Sci U S A., 92(2):344-348, Jan. 17, 1995.
Wu et al., "Correction of a genetic disease in mouse via use of CRISPR-Cas9," Cell Stem Cell., Dec. 5, 2013, 13(6):659-62.
Wu et al., "Custom-designed zinc finger nucleases: what is next?" Cell Mol Life Sci., 64(22):2933-2944, Nov. 2007.
Wu et al., "Genome-wide binding of the CRISPR endonuclease Cas9 in mammalian cells," Nat Biotechnol. Jul. 2014; 32(7):670-6.
Xu et al., "Optimization of transcriptional regulatory elements for constructing plasmid vectors," Gene. Jul. 2001, 272(1-2):149-56.
Xu et al., "Genome-wide regulation of 5hmC, 5mC, and gene expression by Tet1 hydroxylase in mouse embryonic stem cells," Mol Cell., 42(4):451-464, Epub Apr. 21, 2011.
Yang et al., "One-step generation of mice carrying reporter and conditional alleles by CRISPR/Cas-mediated genome engineering," Cell, Sep. 12, 2013; 154(6):1370-9.
Yang et al., "Optimization of scarless human stem cell genome editing," Nucleic Acids Res., 2013, 41:9049-9061.
Yin et al., "Genome editing with Cas9 in adult mice corrects a disease mutation and phenotype," Nature Biotechnology 32, 551-553 (2014).
Zetsche et al., "Cpf1 Is a Single RNA-Guided Endonuclease of a Class 2 CRISPR-Cas System," Cell, 2015, 163:759-771.
Zhang et al., "Efficient construction of sequence-specific TAL effectors for modulating mammalian transcription," Nat Biotechnol., 29(2):149-153, Epub Jan. 19, 2011.
Zhang et al., "TET1 is a DNA-binding protein that modulates DNA methylation and gene transcription via hydroxylation of 5-methylcytosine," Cell Res., 20(12):1390-1393, Epub Nov. 16, 2010.
Zhou et al., "High-throughput screening of a CRISPR/Cas9 library for functional genomics in human cells," Nature. May 22, 2014; 509(7501):487-91.
Zitzewitz et al., "Probing the folding mechanism of a leucine zipper peptide by stopped-flA4:A48ism spectroscopy," Biochemistry, 34(39):12812-12819, Oct. 3, 1995.
U.S. Final Office Action in U.S. Appl. No. 14/211,117, dated Jun. 30, 2016, 26 pages.
Extended European Search Report in European Application No. 14768877.4, dated Aug. 10, 2016.
Extended European Search Report in European Application No. 14764159.1, dated Aug. 10, 2016, 7 pages.
International Search Report and Written Opinion in International Application No. PCT/US2013/074736, dated Sep. 17, 2014, 4 pages.
Gaj et al., ZFN, TALEN, and CRISPR/Cas-based methods for genome engineering, Trends in Biotechnology, Jul. 2013, 31(7): 397-405.
International Search Report in International Application No. PCT/US2014/054291, dated Mar. 27, 2015, 6 pages.
Slaymaker et al. 2016; Rationally engineered Cas9 nucleases with improved specificity. Science 351(6268): 84-88.
Addgene.org [Online]. CRISPR/Cas9 Guide on the web, Jan. 2016, [retrieved on Sep. 13, 2016]. Retrieved from the internet: URL<http://www.addgene.org/CRISPR/guide>/. 146 pages.
Invitation to Pay Additional Fees and, Where Applicable, Protest Fee in International application No. PCT/US2016/49147, mailed on Oct. 31, 2016, 2 pages.
Office Action in Australian Application No. 2014227653, dated Nov. 18, 2016, 3 pages.
International Search Report and Written Opinion in International Application No. PCT/US16/49147, dated Dec. 23, 2016, 12 pages.
Kleinstiver et al., "High-fidelity CRISPR-Cas9 nucleases with no detectable genome-wide offtarget effects," Nature, Jan. 2016, 529: 490-495.
Office Action in U.S. Appl. No. 14/775,930, dated Feb. 27, 2017, 55 pages.
Office Action in U.S. Appl. No. 14/776,620, dated Mar. 31, 2017, 45 pages.
Office Action in European Application No. 14/763916.5, dated Mar. 27, 2017, 6 pages.

(56) References Cited

OTHER PUBLICATIONS

Office Action in Chinese Application No. 2014800261133.4, dated May 31, 2017, 21 pages (with English translation).
Extended European Search Report in Application No. 14875819.6, dated Jun. 8, 2017, 11 pages.
Office Action in Canadian Application No. 2907198, dated Aug. 24, 2017, 10 pages.
Office Action in Chinese Application No. 201480026133.4, dated Feb. 12, 2018, 22 pages (with English translation).
Office Action in European Application No. 14763916.5, dated Oct. 26, 2017, 5 pages.
Office Action in European Application No. 14764117.9, dated Jan. 4, 2018, 4 pages.
Office Action in European Application No. 14764117.9, dated Jul. 6, 2017, 4 pages.
Office Action in European Application No. 14764159.1, dated Jun. 16, 2017, 4 pages.
Office Action in European Application No. 14764159.1, dated Nov. 21, 2017.
Office Action in European Application No. 14768877.4, dated Jan. 8, 2018, 4 pages.
Office Action in European Application No. 14768877.4, dated Jul. 14, 2017, 4 pages.
Office Action in U.S. Appl. No. 14/211,117, dated Jan. 9, 2017, 12 pages.
Office Action in U.S. Appl. No. 14/211,117, dated Nov. 3, 2017, 11 pages.
Office Action in U.S. Appl. No. 14/775,869, dated Sep. 11, 2017, 43 pages.
Office Action in U.S. Appl. No. 14/775,930, dated Sep. 21, 2017, 23 pages.
Office Action in U.S. Appl. No. 14/776,620, dated Sep. 28, 2017, 8 pages.
BLAST sequence alignment: Query = Applicants SEQ ID No. 26 and Sbjct = Jinek et al.'s SEQ ID No. 8 from WO2013176772 (Retrieved from the Internet <https://blast.nchi.nlm.nih.gov/Blast.cgi>, retrieved on Feb. 1, 2018, 3 pages.
Office Action in U.S. Appl. No. 15/107,550, dated Mar. 9, 2018, 21 pages.
Sequence Alignment of SEQ ID No. 1 of U.S. Appl. No. 15/107,550 with SEQ ID No. 103 of US2013/0130248A1. Search conducted on Feb. 15, 2018, 1 page as part of Office Action in U.S. Appl. No. 15/107,550.
International Preliminary Report on Patentability in International Application No. PCT/US2016/49147, dated Mar. 6, 2018, 8 pages.
Office Action in Chinese Application No. 201480027950.1, dated Mar. 23, 2018, 13 pages (with English translation).
Ma et al., "A Guide RNA Sequence Design Platform for the CRISPR/Cas9 System for Model Organism Genomes," BioMed Research International, 2013, 2013: 270805, 4 pages.
Farboud and Meyer, "Dramatic Enhancement of Genome Editing by CRISPR/Cas9 Through Improved Guide RNA Design," Genetics, 2015, 199:959-971.
Office Action in Chinese Application No. 201480026276.5, dated Apr. 17, 2018, 12 pages (with English translation).
Office Action in Japanese Application No. 2016-502976, dated May 8, 2018, 16 pages (with English translation).
Jiang et al., "RNA-guided editing of bacterial genomes using CRISPR-Cas systems," Nature Biotechnology, Mar. 2013, 31: 233-239.
Office Action in Canadian Application No. 2907198, dated May 14, 2018, 3 pages.
Office Action in Japanese Application No. 2016-502853, dated Jun. 12, 2018, 15 pages (with English translation).
Mino et al., "Efficient double-strand DNA cleavage by artificial zinc-finger nucleases composed of one zinc-finger protein and a single-chain FokI dimer," Journal of biotechnology, 2009, 140: 156-161.
Kim et al., Hybrid restriction enzymes: zinc finger fusions to Fok I cleavage domain, PNAS, Feb. 1996, 93: 1156-1160.
Office Action in Japanese Application No. 2016-502406, dated Jun. 12, 2018, 23 pages (with English translation).
Nielsen et al., "Interaction with members of the heterochromatin protein 1 (HP1) family and histone deacetylation are differentially involved in transcriptional silencing by members of the TIF1 family," EMBO J., 1999, 18: 6385-6395.
Melo et al., "eRNAs Are Required for p53-Dependent Enhancer Activity and Gene Transcription," Mol Cell, Feb. 2013, 49: 524-535.
Williams et al., Tet1 and hydroxymethylcytosine in transcription and DNA methylation fidelity, Nature, May 2011, 473: 343-349.
Qi et al., "Repurposing CRISPR as an RNA-Guided Platform for Sequence-Specific Control of Gene Expression," Supplemental Information, Cell, Feb. 2013, 152.
Office Action in Australian Application No. 2017204909, dated Aug. 8, 2018, 8 pages.
Office Action in Chinese Application No. 201480027950.1, dated Oct. 18, 2018, 6 pages.
Office Action in European Application No. 14764117.9, dated Oct. 5, 2018, 6 pages.
Office Action in European Application No. 14875819.6, dated Jun. 19, 2018.
Office Action in Israeli Application No. 241671, dated Sep. 13, 2018, 8 pages (with English translation).
Office Action in Japanese Application No. 2016-542968, dated Sep. 18, 2018 (with English translation).
Ui-Tei et al., "Functional dissection of siRNA sequence by systematic DNA substitution: modified siRNA with a DNA seed arm is a powerful tool for mammalian gene silencing with significantly reduced off-target effect," Nucleic Acids Research, 2008, 36: 2136-2151.
Lino et al, "Delivering CRISPR: a review of the challenges and approaches," Drug Delivery, 2018, 25: 1234-1257.
Liu et al, "Delivery strategies of the CRISPR-Cas9 gene-editing system for therapeutic applications," Journal of Controlled Release, 2017, 266: 17-26.
Australian Office Action in Australian Application No. 2014239665, dated Sep. 5, 2019, 4 pages.
Brazilian Office Action in Brazilian Application No. BR112015023489-5, dated Oct. 3, 2019, 6 pages (with English abstract).
Chinese Office Action in Chinese Application No. 201480076396.6, dated Feb. 19, 2019, 14 pages (with English translation).
Extended European Search Report in Application No. 18208105.9, dated Jan. 15, 2019, 5 pages.
Extended European Search Report in European Application No. 16842722.7, dated Jun. 7, 2019, 14 pages.
Israeli Office Action in Israeli Application No. 241671, dated Aug. 1, 2019, 10 pages (with English translation).
Japanese Office Action in Japanese Application No. 2016-502406, dated May 28, 2019, 14 pages (with English translation).
Japanese Office Action in Japanese Application No. 2016-502853, dated May 28, 2019, 4 pages (with English translation).
Japanese Office Action in Japanese Application No. 2016-502976, dated Apr. 2, 2019, 15 pages (with English translation).
Japanese Office Action in Japanese Application No. 2016-542968, dated Jul. 30, 2019, 8 pages (with English translation).
Partial Supplementary Search Report in European Application No. 16842722.7, dated Mar. 7, 2019, 13 pages.

\* cited by examiner

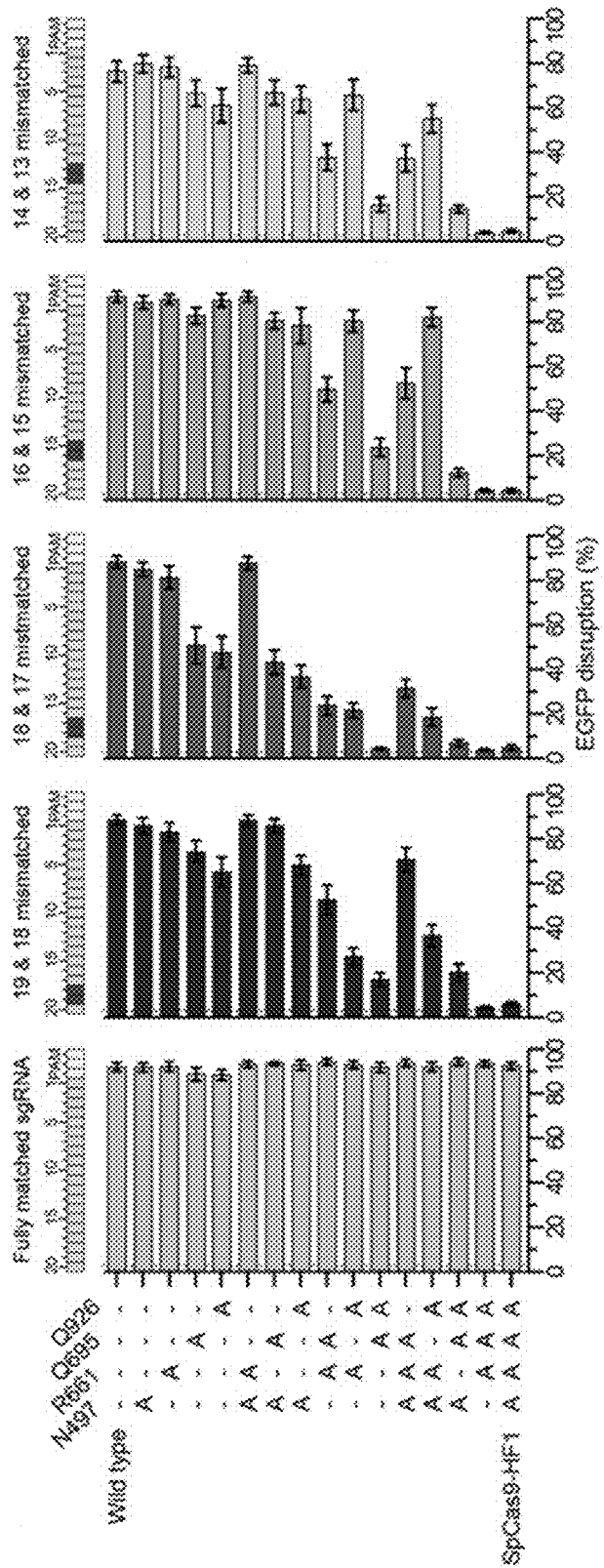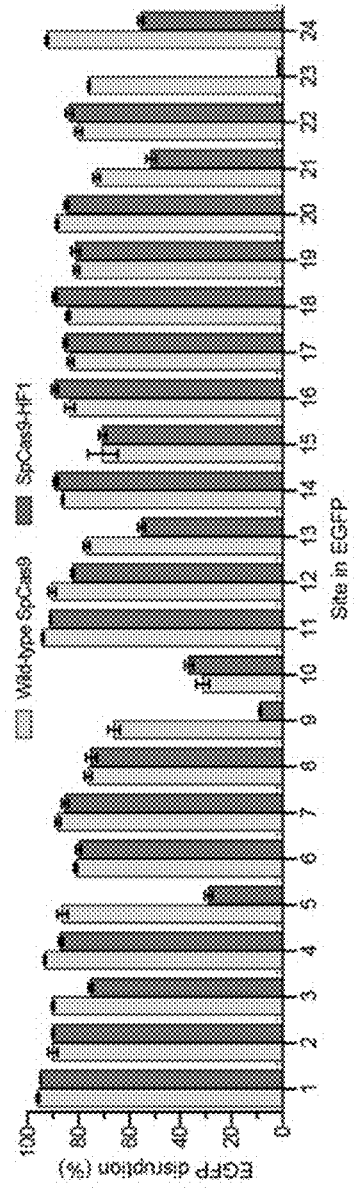
FIG. 1B
FIG. 1C

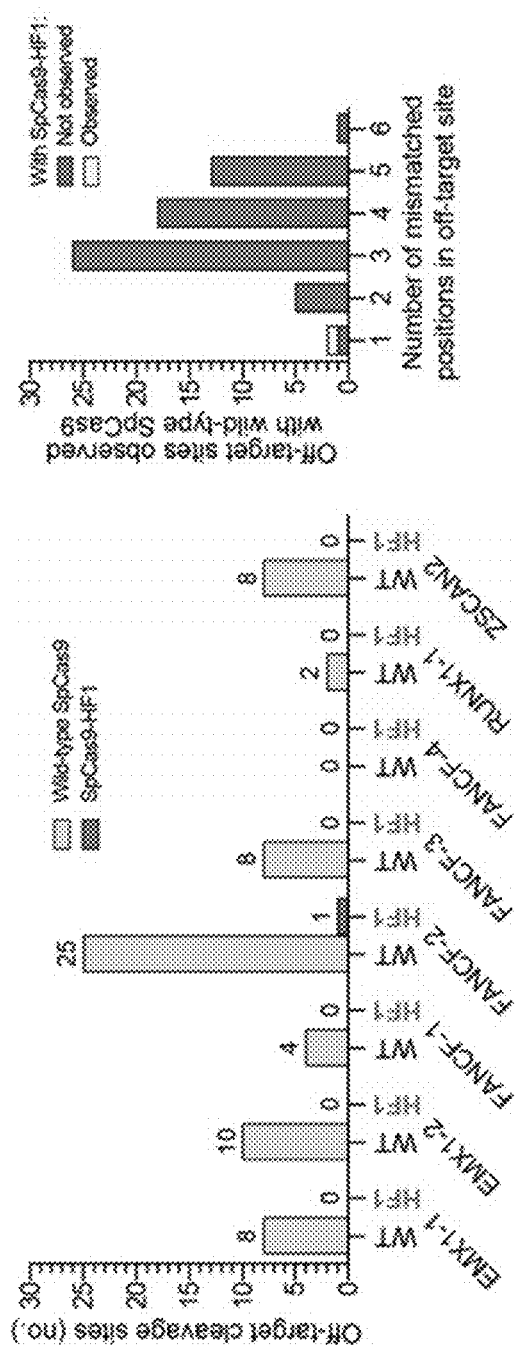
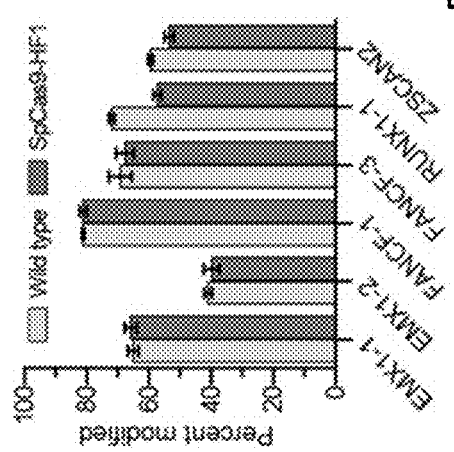
FIG. 2C
FIG. 2B
FIG. 3A

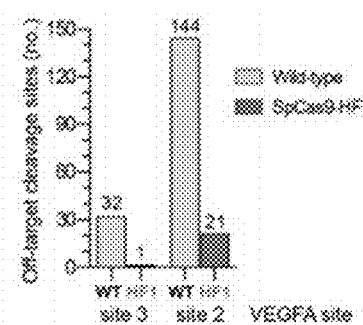
FIG. 4B
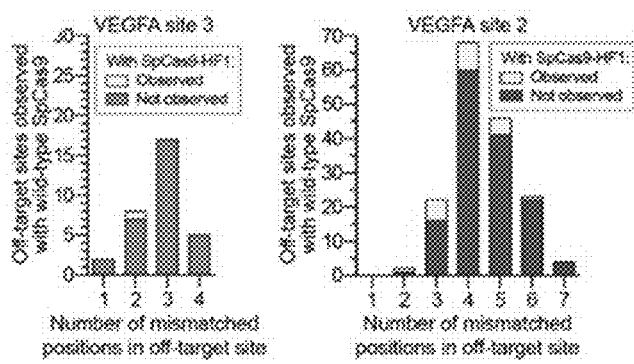
FIG. 4C
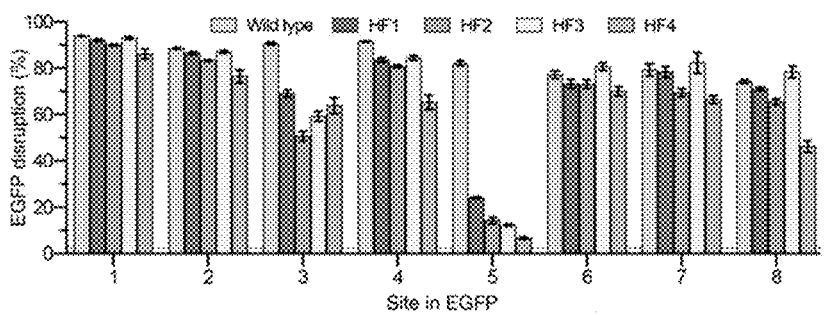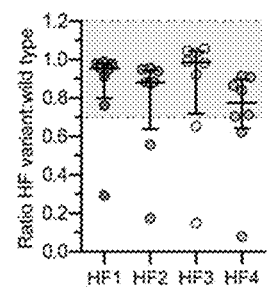
FIG. 5A                    FIG. 5B
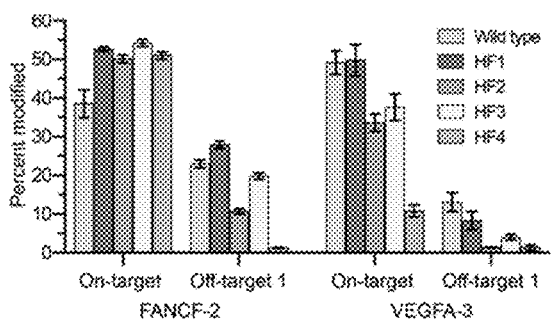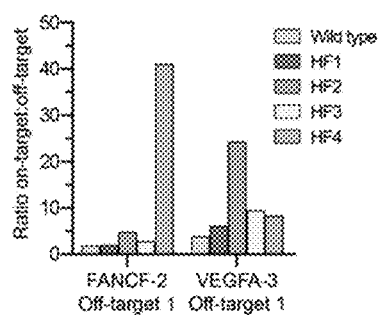
FIG. 5C                    FIG. 5D

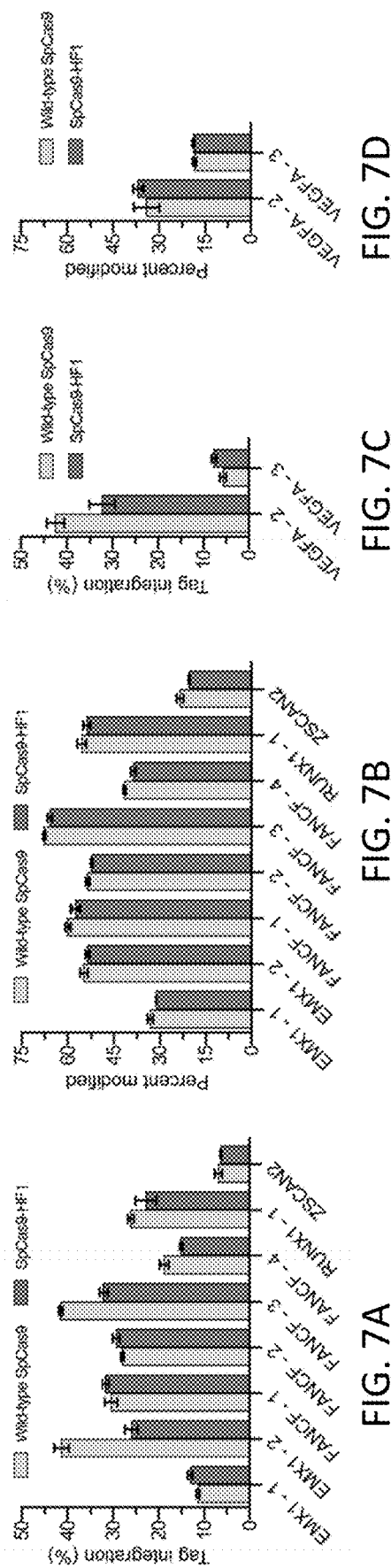

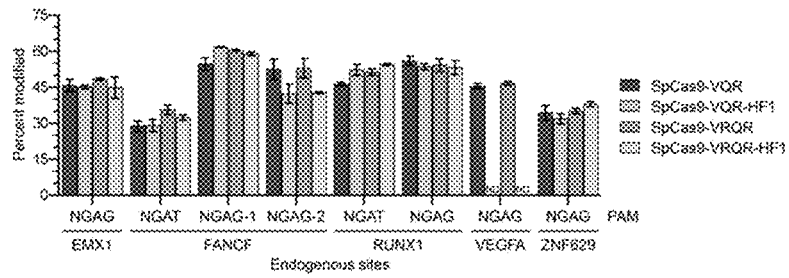
FIG. 12C
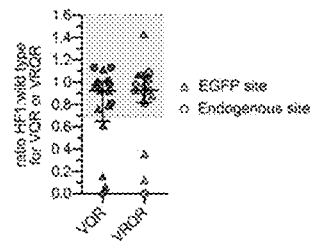
FIG. 12D
FIG. 13A
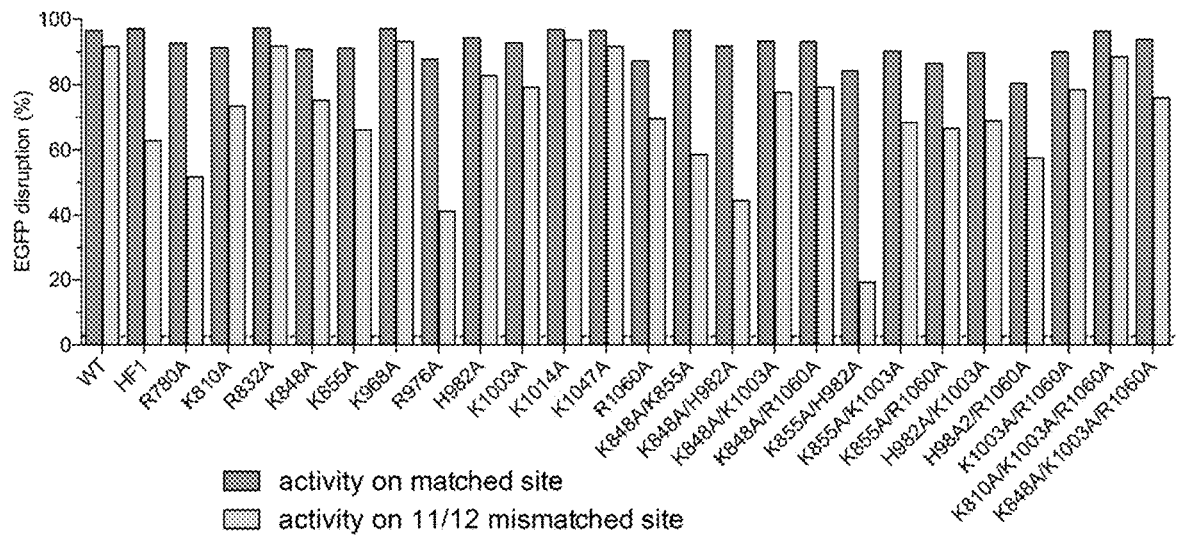
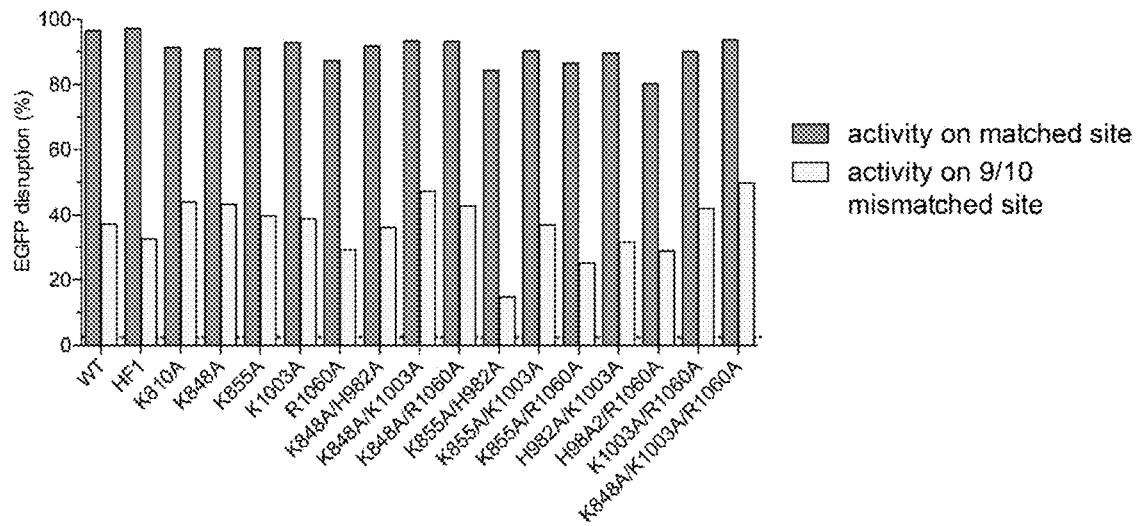
FIG. 13B

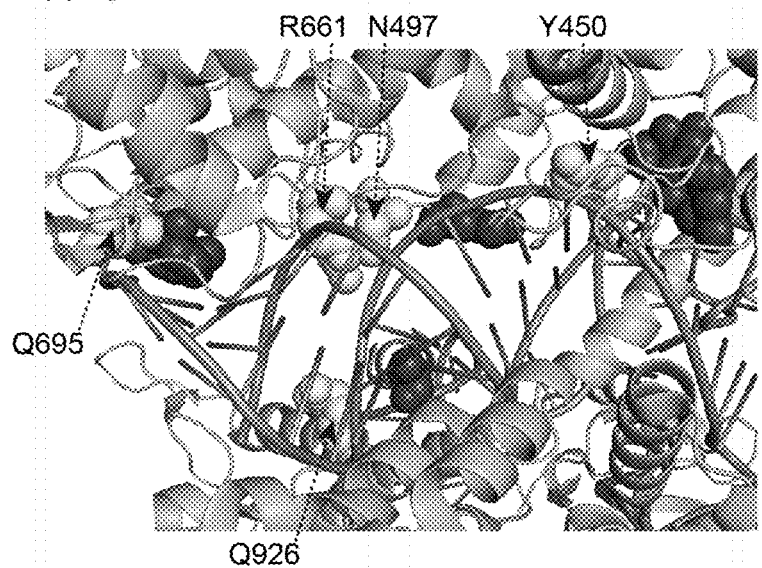
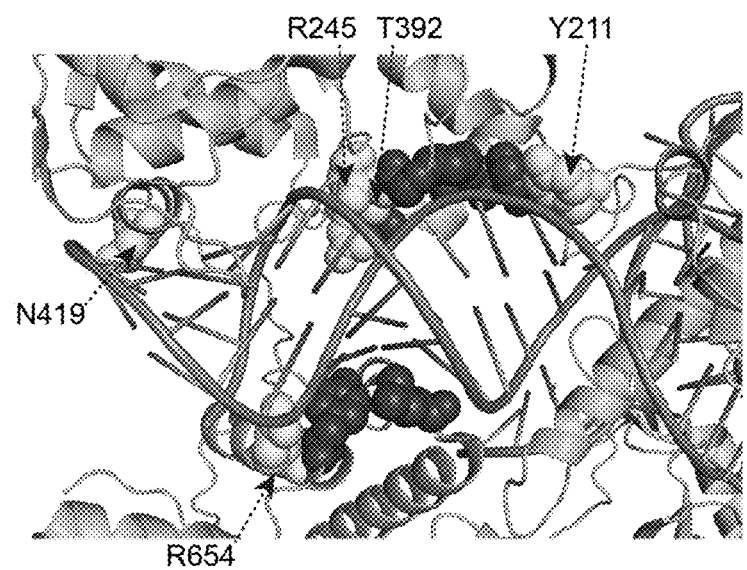
FIG. 20

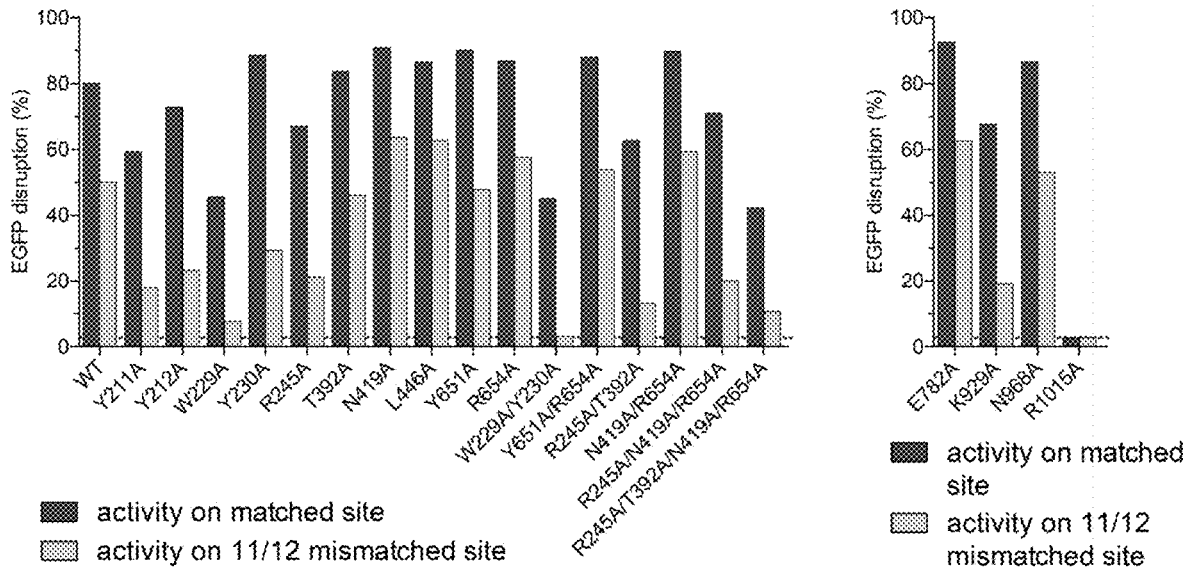
FIG. 21A
FIG. 21B
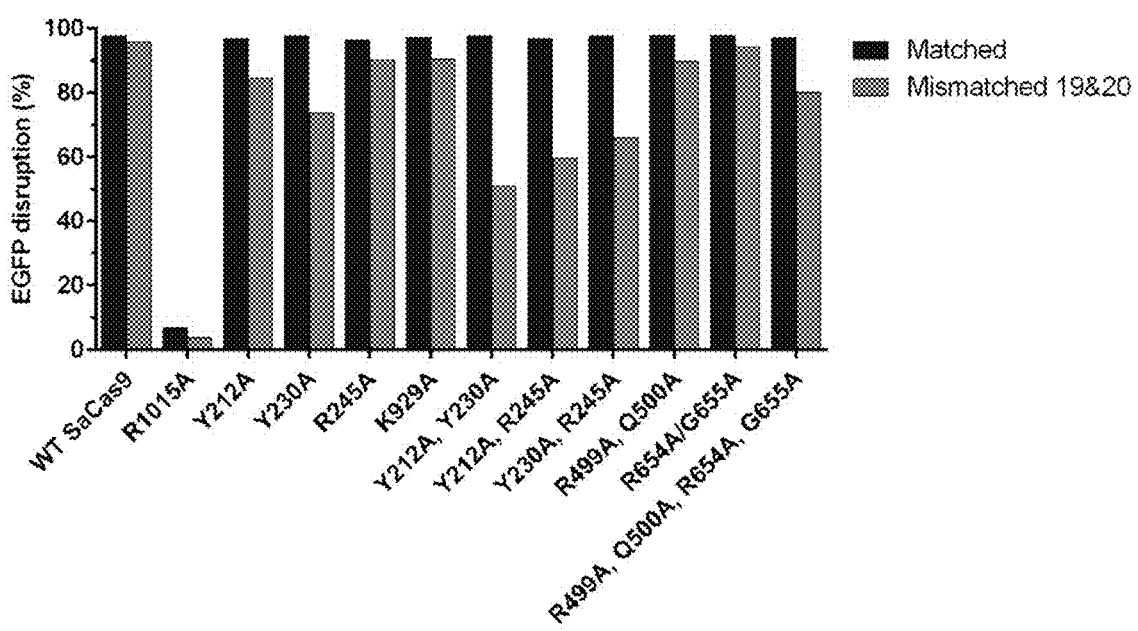
FIG. 22A

SEQUENCE LISTING

<160> NUMBER OF SEQ ID NOS: 289

<210> SEQ ID NO 1
<211> LENGTH: 1368
<212> TYPE: PRT
<213> ORGANISM: Streptococcus pyogenes

<400> SEQUENCE: 1

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

-continued

Gly Ala Leu Leu Phe Asp Ser Gly Glu Thr Ala Glu Ala Thr Arg Leu
 50                  55                  60

Lys Arg Thr Ala Arg Arg Tyr Thr Arg Arg Lys Asn Arg Ile Cys
 65                  70                  75                  80

Tyr Leu Gln Glu Ile Phe Ser Asn Glu Met Ala Lys Val Asp Asp Ser
                     85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu

```
                465                 470                 475                 480
Val Val Asp Lys Gly Ala Ser Ala Gln Ser Phe Ile Glu Arg Met Thr
                    485                 490                 495

Asn Phe Asp Lys Asn Leu Pro Asn Glu Lys Val Leu Pro Lys His Ser
                    500                 505                 510

Leu Leu Tyr Glu Tyr Phe Thr Val Tyr Asn Glu Leu Thr Lys Val Lys
                    515                 520                 525

Tyr Val Thr Glu Gly Met Arg Lys Pro Ala Phe Leu Ser Gly Glu Gln
                    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                    565                 570                 575

Ser Val Glu Ile Ser Gly Val Glu Asp Arg Phe Asn Ala Ser Leu Gly
                    580                 585                 590

Thr Tyr His Asp Leu Leu Lys Ile Ile Lys Asp Lys Asp Phe Leu Asp
                    595                 600                 605

Asn Glu Glu Asn Glu Asp Ile Leu Glu Asp Ile Val Leu Thr Leu Thr
                    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                    645                 650                 655

Thr Gly Trp Gly Arg Leu Ser Arg Lys Leu Ile Asn Gly Ile Arg Asp
                    660                 665                 670

Lys Gln Ser Gly Lys Thr Ile Leu Asp Phe Leu Lys Ser Asp Gly Phe
                    675                 680                 685

Ala Asn Arg Asn Phe Met Gln Leu Ile His Asp Asp Ser Leu Thr Phe
                    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                    725                 730                 735

Ile Leu Gln Thr Val Lys Val Val Asp Glu Leu Val Lys Val Met Gly
                    740                 745                 750

Arg His Lys Pro Glu Asn Ile Val Ile Glu Met Ala Arg Glu Asn Gln
                    755                 760                 765

Thr Thr Gln Lys Gly Gln Lys Asn Ser Arg Glu Arg Met Lys Arg Ile
                    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                    805                 810                 815

Gln Asn Gly Arg Asp Met Tyr Val Asp Gln Glu Leu Asp Ile Asn Arg
                    820                 825                 830

Leu Ser Asp Tyr Asp Val Asp His Ile Val Pro Gln Ser Phe Leu Lys
                    835                 840                 845

Asp Asp Ser Ile Asp Asn Lys Val Leu Thr Arg Ser Asp Lys Asn Arg
                    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                    885                 890                 895
```

-continued

```
Phe Asp Asn Leu Thr Lys Ala Glu Arg Gly Gly Leu Ser Glu Leu Asp
            900                 905                 910
Lys Ala Gly Phe Ile Lys Arg Gln Leu Val Glu Thr Arg Gln Ile Thr
        915                 920                 925
Lys His Val Ala Gln Ile Leu Asp Ser Arg Met Asn Thr Lys Tyr Asp
        930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
            980                 985                 990
Val Gly Thr Ala Leu Ile Lys Lys Tyr Pro Lys Leu Glu Ser Glu Phe
        995                 1000                1005
Val Tyr Gly Asp Tyr Lys Val Tyr Asp Val Arg Lys Met Ile Ala
   1010                1015                1020
Lys Ser Glu Gln Glu Ile Gly Lys Ala Thr Ala Lys Tyr Phe Phe
   1025                1030                1035
Tyr Ser Asn Ile Met Asn Phe Phe Lys Thr Glu Ile Thr Leu Ala
   1040                1045                1050
Asn Gly Glu Ile Arg Lys Arg Pro Leu Ile Glu Thr Asn Gly Glu
   1055                1060                1065
Thr Gly Glu Ile Val Trp Asp Lys Gly Arg Asp Phe Ala Thr Val
   1070                1075                1080
Arg Lys Val Leu Ser Met Pro Gln Val Asn Ile Val Lys Lys Thr
   1085                1090                1095
Glu Val Gln Thr Gly Gly Phe Ser Lys Glu Ser Ile Leu Pro Lys
   1100                1105                1110
Arg Asn Ser Asp Lys Leu Ile Ala Arg Lys Lys Asp Trp Asp Pro
   1115                1120                1125
Lys Lys Tyr Gly Gly Phe Asp Ser Pro Thr Val Ala Tyr Ser Val
   1130                1135                1140
Leu Val Val Ala Lys Val Glu Lys Gly Lys Ser Lys Lys Leu Lys
   1145                1150                1155
Ser Val Lys Glu Leu Leu Gly Ile Thr Ile Met Glu Arg Ser Ser
   1160                1165                1170
Phe Glu Lys Asn Pro Ile Asp Phe Leu Glu Ala Lys Gly Tyr Lys
   1175                1180                1185
Glu Val Lys Lys Asp Leu Ile Ile Lys Leu Pro Lys Tyr Ser Leu
   1190                1195                1200
Phe Glu Leu Glu Asn Gly Arg Lys Arg Met Leu Ala Ser Ala Gly
   1205                1210                1215
Glu Leu Gln Lys Gly Asn Glu Leu Ala Leu Pro Ser Lys Tyr Val
   1220                1225                1230
Asn Phe Leu Tyr Leu Ala Ser His Tyr Glu Lys Leu Lys Gly Ser
   1235                1240                1245
Pro Glu Asp Asn Glu Gln Lys Gln Leu Phe Val Glu Gln His Lys
   1250                1255                1260
His Tyr Leu Asp Glu Ile Ile Glu Gln Ile Ser Glu Phe Ser Lys
   1265                1270                1275
Arg Val Ile Leu Ala Asp Ala Asn Leu Asp Lys Val Leu Ser Ala
   1280                1285                1290
```

```
Tyr Asn Lys His Arg Asp Lys Pro Ile Arg Glu Gln Ala Glu Asn
    1295            1300            1305

Ile Ile His Leu Phe Thr Leu Thr Asn Leu Gly Ala Pro Ala Ala
    1310            1315            1320

Phe Lys Tyr Phe Asp Thr Thr Ile Asp Arg Lys Arg Tyr Thr Ser
    1325            1330            1335

Thr Lys Glu Val Leu Asp Ala Thr Leu Ile His Gln Ser Ile Thr
    1340            1345            1350

Gly Leu Tyr Glu Thr Arg Ile Asp Leu Ser Gln Leu Gly Gly Asp
    1355            1360            1365

<210> SEQ ID NO 2
<211> LENGTH: 1053
<212> TYPE: PRT
<213> ORGANISM: Staphylococcus aureus

<400> SEQUENCE: 2

Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
                20                  25                  30

Val Arg Leu Phe Lys Glu Ala Asn Val Glu Asn Asn Glu Gly Arg Arg
            35                  40                  45

Ser Lys Arg Gly Ala Arg Arg Leu Lys Arg Arg Arg Arg His Arg Ile
        50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Phe Ser Ala Ala Leu Leu His Leu
                100                 105                 110

Ala Lys Arg Arg Gly Val His Asn Val Asn Glu Val Glu Glu Asp Thr
            115                 120                 125

Gly Asn Glu Leu Ser Thr Lys Glu Gln Ile Ser Arg Asn Ser Lys Ala
        130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
                180                 185                 190

Leu Asp Gln Ser Phe Ile Asp Thr Tyr Ile Asp Leu Leu Glu Thr Arg
            195                 200                 205

Arg Thr Tyr Tyr Glu Gly Pro Gly Glu Gly Ser Pro Phe Gly Trp Lys
        210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
                260                 265                 270

Glu Lys Leu Glu Tyr Tyr Glu Lys Phe Gln Ile Ile Glu Asn Val Phe
            275                 280                 285

Lys Gln Lys Lys Lys Pro Thr Leu Lys Gln Ile Ala Lys Glu Ile Leu
        290                 295                 300
```

```
Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
                340                 345                 350

Lys Ile Leu Thr Ile Tyr Gln Ser Ser Glu Asp Ile Gln Glu Glu Leu
                355                 360                 365

Thr Asn Leu Asn Ser Glu Leu Thr Gln Glu Glu Ile Glu Gln Ile Ser
370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
                420                 425                 430

Gln Lys Glu Ile Pro Thr Thr Leu Val Asp Asp Phe Ile Leu Ser Pro
                435                 440                 445

Val Val Lys Arg Ser Phe Ile Gln Ser Ile Lys Val Ile Asn Ala Ile
                450                 455                 460

Ile Lys Lys Tyr Gly Leu Pro Asn Asp Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
                500                 505                 510

Gly Lys Glu Asn Ala Lys Tyr Leu Ile Glu Lys Ile Lys Leu His Asp
                515                 520                 525

Met Gln Glu Gly Lys Cys Leu Tyr Ser Leu Glu Ala Ile Pro Leu Glu
                530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
                580                 585                 590

Ser Ser Ser Asp Ser Lys Ile Ser Tyr Glu Thr Phe Lys Lys His Ile
                595                 600                 605

Leu Asn Leu Ala Lys Gly Lys Gly Arg Ile Ser Lys Thr Lys Lys Glu
                610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
                660                 665                 670

Val Lys Ser Ile Asn Gly Gly Phe Thr Ser Phe Leu Arg Arg Lys Trp
                675                 680                 685

Lys Phe Lys Lys Glu Arg Asn Lys Gly Tyr Lys His His Ala Glu Asp
                690                 695                 700

Ala Leu Ile Ile Ala Asn Ala Asp Phe Ile Phe Lys Glu Trp Lys Lys
705                 710                 715                 720
```

Leu Asp Lys Ala Lys Lys Val Met Glu Asn Gln Met Phe Glu Glu Lys
            725                 730                 735

Gln Ala Glu Ser Met Pro Glu Ile Glu Thr Glu Gln Glu Tyr Lys Glu
            740                 745                 750

Ile Phe Ile Thr Pro His Gln Ile Lys His Ile Lys Asp Phe Lys Asp
            755                 760                 765

Tyr Lys Tyr Ser His Arg Val Asp Lys Lys Pro Asn Arg Glu Leu Ile
            770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
            805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
            835                 840                 845

Asp Glu Lys Asn Pro Leu Tyr Lys Tyr Tyr Glu Glu Thr Gly Asn Tyr
            850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
            885                 890                 895

Tyr Pro Asn Ser Arg Asn Lys Val Val Lys Leu Ser Leu Lys Pro Tyr
            900                 905                 910

Arg Phe Asp Val Tyr Leu Asp Asn Gly Val Tyr Lys Phe Val Thr Val
            915                 920                 925

Lys Asn Leu Asp Val Ile Lys Lys Glu Asn Tyr Tyr Glu Val Asn Ser
            930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
            965                 970                 975

Glu Leu Tyr Arg Val Ile Gly Val Asn Asn Asp Leu Leu Asn Arg Ile
            980                 985                 990

Glu Val Asn Met Ile Asp Ile Thr Tyr Arg Glu Tyr Leu Glu Asn Met
            995                 1000                1005

Asn Asp Lys Arg Pro Pro Arg Ile Ile Lys Thr Ile Ala Ser Lys
            1010                1015                1020

Thr Gln Ser Ile Lys Lys Tyr Ser Thr Asp Ile Leu Gly Asn Leu
            1025                1030                1035

Tyr Glu Val Lys Ser Lys Lys His Pro Gln Ile Ile Lys Lys Gly
            1040                1045                1050

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Gly Ser
1

<210> SEQ ID NO 4

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Gly Gly Ser
1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Gly Ser
1

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Gly Gly Ser
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Pro Lys Lys Lys Arg Arg Val
1               5

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Arg Pro Ala Ala Thr Lys Lys Ala Gly Gln Ala Lys Lys Lys Lys
1               5                   10                  15

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
```
gggcacgggc agcttgccgg                                              20

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gggcacgggc agcttgccgg tggt                                         24

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gcacgggcag cttgccgg                                                18

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gcacgggcag cttgccggtg gt                                           22

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gggcacccgc agcttgccgg                                              20

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gggcacccgc agcttgccgg tggt                                         24

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gggctggggc agcttgccgg                                              20

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gggctggggc agcttgccgg tggt                                           24

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ggcgacgggc agcttgccgg                                                20

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ggcgacgggc agcttgccgg tggt                                           24

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gcccacgggc agcttgccgg                                                20

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gcccacgggc agcttgccgg tggt                                           24

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gtcgccctcg aacttcacct                                                20

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gtcgccctcg aacttcacct cggc                                          24

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gtaggtcagg gtggtcacga                                               20

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gtaggtcagg gtggtcacga gggt                                          24

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ggcgagggcg atgccaccta                                               20

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ggcgagggcg atgccaccta cggc                                          24

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ggtcgccacc atggtgagca                                               20

```
<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ggtcgccacc atggtgagca aggg                                              24

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ggtcagggtg gtcacgaggg                                                   20

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ggtcagggtg gtcacgaggg tggg                                              24

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ggtggtgcag atgaacttca                                                   20

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ggtggtgcag atgaacttca gggt                                              24

<210> SEQ ID NO 33
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ggtgcagatg aacttca                                                      17

<210> SEQ ID NO 34
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ggtgcagatg aacttcaggg t                                              21

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gttggggtct ttgctcaggg                                                20

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gttggggtct ttgctcaggg cgga                                           24

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ggtggtcacg agggtgggcc                                                20

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ggtggtcacg agggtgggcc aggg                                           24

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gatgccgttc ttctgcttgt                                                20

<210> SEQ ID NO 40
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gatgccgttc ttctgcttgt cggc                                            24

<210> SEQ ID NO 41
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gccgttcttc tgcttgt                                                    17

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gccgttcttc tgcttgtcgg c                                               21

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gtcgccacca tggtgagcaa                                                 20

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gtcgccacca tggtgagcaa gggc                                            24

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gcactgcacg ccgtaggtca                                                 20

<210> SEQ ID NO 46
<211> LENGTH: 24
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 46
gcactgcacg ccgtaggtca gggt                                          24

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gtgaaccgca tcgagctgaa                                               20

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gtgaaccgca tcgagctgaa gggc                                          24

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gaagggcatc gacttcaagg                                               20

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gaagggcatc gacttcaagg agga                                          24

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gcttcatgtg gtcggggtag                                               20

<210> SEQ ID NO 52
<211> LENGTH: 24
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 52
gcttcatgtg gtcggggtag cggc                                              24

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gctgaagcac tgcacgccgt                                                   20

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gctgaagcac tgcacgccgt aggt                                              24

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gccgtcgtcc ttgaagaaga                                                   20

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gccgtcgtcc ttgaagaaga tggt                                              24

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gaccaggatg ggcaccaccc                                                   20

<210> SEQ ID NO 58
<211> LENGTH: 24
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 58
gaccaggatg ggcaccaccc cggt                                          24

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gacgtagcct tcgggcatgg                                               20

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gacgtagcct tcgggcatgg cgga                                          24

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gaagttcgag ggcgacaccc                                               20

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gaagttcgag ggcgacaccc tggt                                          24

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gagctggacg gcgacgtaaa                                               20

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 64
gagctggacg gcgacgtaaa cggc                                      24

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
ggcatcgccc tcgccctcgc                                           20

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
ggcatcgccc tcgccctcgc cgga                                      24

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ggccacaagt tcagcgtgtc                                           20

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ggccacaagt tcagcgtgtc cggc                                      24

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gggcgaggag ctgttcaccg                                           20

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gggcgaggag ctgttcaccg gggt                                    24

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gcgaggagct gttcaccg                                           18

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
gcgaggagct gttcaccggg gt                                      22

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
cctcgaactt cacctcggcg                                         20

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
cctcgaactt cacctcggcg cggg                                    24

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gctcgaactt cacctcggcg                                         20

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gctcgaactt cacctcggcg cggg                                          24

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
caactacaag acccgcgccg                                               20

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
caactacaag acccgcgccg aggt                                          24

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gaactacaag acccgcgccg                                               20

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gaactacaag acccgcgccg aggt                                          24

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
cgctcctgga cgtagccttc                                               20

<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82

```
cgctcctgga cgtagccttc gggc                                          24
```

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83

```
ggctcctgga cgtagccttc                                               20
```

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84

```
cgctcctgga cgtagccttc gggc                                          24
```

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85

```
agggcgagga gctgttcacc                                               20
```

<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86

```
agggcgagga gctgttcacc gggg                                          24
```

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87

```
ggggcgagga gctgttcacc                                               20
```

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
ggggcgagga gctgttcacc gggg                           24

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gttcgagggc gacaccctgg                                20

<210> SEQ ID NO 90
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gttcgagggc gacaccctgg tgaa                           24

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gttcaccagg gtgtcgccct                                20

<210> SEQ ID NO 92
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
gttcaccagg gtgtcgccct cgaa                           24

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
gcccaccctc gtgaccaccc                                20

<210> SEQ ID NO 94
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gcccaccctc gtgaccaccc tgac                           24

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
gcccttgctc accatggtgg                                                    20

<210> SEQ ID NO 96
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
gcccttgctc accatggtgg cgac                                               24

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gtcgccgtcc agctcgacca                                                    20

<210> SEQ ID NO 98
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
gtcgccgtcc agctcgacca ggat                                               24

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gtgtccggcg agggcgaggg                                                    20

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
gtgtccggcg agggcgaggg cgat                                               24

```
<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
ggggtggtgc ccatcctggt                                                    20

<210> SEQ ID NO 102
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
ggggtggtgc ccatcctggt cgag                                               24

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gccaccatgg tgagcaaggg                                                    20

<210> SEQ ID NO 104
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gccaccatgg tgagcaaggg cgag                                               24

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
gagtccgagc agaagaagaa                                                    20

<210> SEQ ID NO 106
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gagtccgagc agaagaagaa gggc                                               24
```

```
<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gtcacctcca atgactaggg                                              20

<210> SEQ ID NO 108
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
gtcacctcca atgactaggg tggg                                         24

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
gggaagactg aggctacata                                              20

<210> SEQ ID NO 110
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
gggaagactg aggctacata gggt                                         24

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
gccacgaagc aggccaatgg                                              20

<210> SEQ ID NO 112
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
gccacgaagc aggccaatgg ggag                                         24

<210> SEQ ID NO 113
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
ggaatccctt ctgcagcacc                                              20

<210> SEQ ID NO 114
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ggaatccctt ctgcagcacc tgga                                         24

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
gctgcagaag ggattccatg                                              20

<210> SEQ ID NO 116
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
gctgcagaag ggattccatg aggt                                         24

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
ggcggctgca caaccagtgg                                              20

<210> SEQ ID NO 118
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
ggcggctgca caaccagtgg aggc                                         24

<210> SEQ ID NO 119
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
gctccagagc cgtgcgaatg                                              20

<210> SEQ ID NO 120
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
gctccagagc cgtgcgaatg gggc                                         24

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
gaatcccttc tgcagcacct                                              20

<210> SEQ ID NO 122
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
gaatcccttc tgcagcacct ggat                                         24

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
gcggcggctg cacaaccagt                                              20

<210> SEQ ID NO 124
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
gcggcggctg cacaaccagt ggag                                         24

<210> SEQ ID NO 125
<211> LENGTH: 20
<212> TYPE: DNA
```

<213> ORGANISM: Artificial Sequence
<220> FEATURE:
<223> OTHER INFORMATION: Description of Artificial Sequence: Synthetic oligonucleotide

<400> SEQUENCE: 125
ggttgtgcag ccgccgctcc                                                    20

<210> SEQ ID NO 126
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 126
ggttgtgcag ccgccgctcc agag                                               24

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 127
gcattttcag gaggaagcga                                                    20

<210> SEQ ID NO 128
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 128
gcattttcag gaggaagcga tggc                                               24

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 129
gggagaagaa agagagatgt                                                    20

<210> SEQ ID NO 130
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 130
gggagaagaa agagagatgt aggg                                               24

<210> SEQ ID NO 131
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 131
ggtgcatttt caggaggaag                                                     20

<210> SEQ ID NO 132
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
ggtgcatttt caggaggaag cgat                                                24

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
gagatgtagg gctagagggg                                                     20

<210> SEQ ID NO 134
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
gagatgtagg gctagagggg tgag                                                24

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
ggtatccagc agagggaga                                                      20

<210> SEQ ID NO 136
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
ggtatccagc agagggaga agaa                                                 24

<210> SEQ ID NO 137
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 137
gaggcatctc tgcaccgagg                                                    20

<210> SEQ ID NO 138
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
gaggcatctc tgcaccgagg tgaa                                               24

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
gaggggtgag gctgaaacag                                                    20

<210> SEQ ID NO 140
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
gaggggtgag gctgaaacag tgac                                               24

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
gagcaaaagt agatattaca                                                    20

<210> SEQ ID NO 142
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
gagcaaaagt agatattaca agac                                               24

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 143
ggaattcaaa ctgaggcata                                          20

<210> SEQ ID NO 144
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
ggaattcaaa ctgaggcata tgat                                     24

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
gcagagggga gaagaaagag                                          20

<210> SEQ ID NO 146
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
gcagagggga gaagaaagag agat                                     24

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
gcaccgaggc atctctgcac                                          20

<210> SEQ ID NO 148
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
gcaccgaggc atctctgcac cgag                                     24

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
gagatgtagg gctagagggg                                           20

<210> SEQ ID NO 150
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
gagatgtagg gctagagggg tgag                                      24

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
gtgcggcaag agcttcagcc                                           20

<210> SEQ ID NO 152
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
gtgcggcaag agcttcagcc gggg                                      24

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153 gggtggggggg agtttgctcc                                          20

<210> SEQ ID NO 154
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154 gggtggggggg agtttgctcc tgga                                     24

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
gaccccctcc accccgcctc                                               20

<210> SEQ ID NO 156
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
gaccccctcc accccgcctc cggg                                          24

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
ggtgagtgag tgtgtgcgtg                                               20

<210> SEQ ID NO 158
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
ggtgagtgag tgtgtgcgtg tggg                                          24

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
gcgagcagcg tcttcgagag                                               20

<210> SEQ ID NO 160
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
gcgagcagcg tcttcgagag tgag                                          24

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161

```
gtgcggcaag agcttcagcc                                               20
```

<210> SEQ ID NO 162
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162

```
gtgcggcaag agcttcagcc agag                                          24
```

<210> SEQ ID NO 163
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163

```
gagtccgagc agaagaagaa ggg                                           23
```

<210> SEQ ID NO 164
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164

```
gtcacctcca atgactaggg tgg                                           23
```

<210> SEQ ID NO 165
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165

```
ggaatccctt ctgcagcacc tgg                                           23
```

<210> SEQ ID NO 166
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166

```
gctgcagaag ggattccatg agg                                           23
```

<210> SEQ ID NO 167
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
ggcggctgca caaccagtgg agg                                           23

<210> SEQ ID NO 168
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
gctccagagc cgtgcgaatg ggg                                           23

<210> SEQ ID NO 169
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
gcattttcag gaggaagcga tgg                                           23

<210> SEQ ID NO 170
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
gtgcggcaag agcttcagcc ggg                                           23

<210> SEQ ID NO 171
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
gaccccctcc accccgcctc cgg                                           23

<210> SEQ ID NO 172
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
ggtgagtgag tgtgtgcgtg tgg                                           23

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
ggagcagctg gtcagagggg                                               20

<210> SEQ ID NO 174
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
ccatagggaa gggggacact gg                                              22

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
gggccgggaa agagttgctg                                                 20

<210> SEQ ID NO 176
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
gccctacatc tgctctccct cc                                              22

<210> SEQ ID NO 177
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
ccagcacaac ttactcgcac ttgac                                           25

<210> SEQ ID NO 178
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
catcaccaac ccacagccaa gg                                              22

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
tccagatggc acattgtcag                                                 20

```
<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
agggagcagg aaagtgaggt                                                    20

<210> SEQ ID NO 181
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
cgaggaagag agagacgggg tc                                                 22

<210> SEQ ID NO 182
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
ctccaatgca cccaagacag cag                                                23

<210> SEQ ID NO 183
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
agtgtggggt gtgtgggaag                                                    20

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184 gcaagggaa gactctggca                                                     20

<210> SEQ ID NO 185
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
tacgagtgcc tagagtgcg                                                     19
```

-continued

```
<210> SEQ ID NO 186
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
gcagatgtag gtcttggagg ac                                            22

<210> SEQ ID NO 187
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
ggagcagctg gtcagagggg                                               20

<210> SEQ ID NO 188
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
cgatgtcctc cccattggcc tg                                            22

<210> SEQ ID NO 189
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
gtggggagat ttgcatctgt ggagg                                         25

<210> SEQ ID NO 190
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
gcttttatac catcttgggg ttacag                                        26

<210> SEQ ID NO 191
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
caatgtgctt caacccatca cggc                                          24

<210> SEQ ID NO 192
```

```
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
ccatgaattt gtgatggatg cagtctg                                        27

<210> SEQ ID NO 193
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
gagaaggagg tgcaggagct agac                                           24

<210> SEQ ID NO 194
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
catcccgacc ttcatccctc ctgg                                           24

<210> SEQ ID NO 195
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
gtagttctga cattcctcct gaggg                                          25

<210> SEQ ID NO 196
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
tcaaacaagg tgcagataca gca                                            23

<210> SEQ ID NO 197
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
cagggtcgct cagtctgtgt gg                                             22

<210> SEQ ID NO 198
<211> LENGTH: 24
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
ccagcgcacc attcactcca cctg                                          24

<210> SEQ ID NO 199
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
ggctgaagag gaagaccaga ctcag                                         25

<210> SEQ ID NO 200
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
ggcccctctg aattcaattc tctgc                                         25

<210> SEQ ID NO 201
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
ccacagcgag gagtgacagc c                                             21

<210> SEQ ID NO 202
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
ccaagtcttt cctaactcga ccttgg                                        26

<210> SEQ ID NO 203
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
ccctaggccc acaccagcaa tg                                            22

<210> SEQ ID NO 204
<211> LENGTH: 24
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 204
gggatgggaa tgggaatgtg aggc                                            24

<210> SEQ ID NO 205
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
gcccaggtga aggtgtggtt cc                                              22

<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
ccaaagcctg gccagggagt g                                               21

<210> SEQ ID NO 207
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
aggcaaagat ctaggacctg gatgg                                           25

<210> SEQ ID NO 208
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
ccatctgagt cagccagcct tgtc                                            24

<210> SEQ ID NO 209
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
ggttccctcc cttctgagcc c                                               21

<210> SEQ ID NO 210
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 210
ggataggaat gaagaccccc tctcc                                              25

<210> SEQ ID NO 211
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
ggactggctg gctgtgtgtt ttgag                                              25

<210> SEQ ID NO 212
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
cttatccagg gctacctcat tgcc                                               24

<210> SEQ ID NO 213
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
gctgctgctg ctttgatcac tcctg                                              25

<210> SEQ ID NO 214
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
ctccttaaac cctcagaagc tggc                                               24

<210> SEQ ID NO 215
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
gcactgtcag ctgatcctac agg                                                23

<210> SEQ ID NO 216
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 216
acgttggaac agtcgagctg tagc                                          24

<210> SEQ ID NO 217
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
tgtgcataac tcatgttggc aaact                                         25

<210> SEQ ID NO 218
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
tccacaacta ccctcagctg gag                                           23

<210> SEQ ID NO 219
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
ccactgacaa ttcactcaac cctgc                                         25

<210> SEQ ID NO 220
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
aggcagacca gttatttggc agtc                                          24

<210> SEQ ID NO 221
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
acaggcgcag ttcactgaga ag                                            22

<210> SEQ ID NO 222
<211> LENGTH: 22
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 222
gggtaggctg actttgggct cc                                              22

<210> SEQ ID NO 223
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
gccctcttgc ctccactggt tg                                              22

<210> SEQ ID NO 224
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
cgcggatgtt ccaatcagta cgc                                             23

<210> SEQ ID NO 225
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
gcgggcagtg gcgtcttagt cg                                              22

<210> SEQ ID NO 226
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
ccctgggttt ggttggctgc tc                                              22

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
ctccttgccg cccagccggt c                                               21

<210> SEQ ID NO 228
<211> LENGTH: 23
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 228
cactggggaa gaggcgagga cac                                              23

<210> SEQ ID NO 229
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
ccagtgtttc ccatccccaa cac                                              23

<210> SEQ ID NO 230
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
gaatggatcc cccctagag ctc                                               23

<210> SEQ ID NO 231
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
caggcccaca ggtccttctg ga                                               22

<210> SEQ ID NO 232
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
ccacacggaa ggctgaccac g                                                21

<210> SEQ ID NO 233
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
gcgcagagag agcaggacgt c                                                21

<210> SEQ ID NO 234
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 234
gcacctcatg gaatcccttc tgc                                            23

<210> SEQ ID NO 235
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
caagtgatgc gacttccaac ctc                                            23

<210> SEQ ID NO 236
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
ccctcagagt tcagcttaaa aagacc                                         26

<210> SEQ ID NO 237
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
tgcttctcat ccactctaga ctgct                                          25

<210> SEQ ID NO 238
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
caccaaccag ccatgtgcca tg                                             22

<210> SEQ ID NO 239
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
ctgcctgtgc tcctcgatgg tg                                             22

<210> SEQ ID NO 240
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
```

```
gggttcaaag ctcatctgcc cc                                           22
```

<210> SEQ ID NO 241
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241

```
gcatgtgcct tgagattgcc tgg                                          23
```

<210> SEQ ID NO 242
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242

```
gacattcaga gaagcgacca tgtgg                                        25
```

<210> SEQ ID NO 243
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243

```
ccatcttccc ctttggccca cag                                          23
```

<210> SEQ ID NO 244
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244

```
ccccaaaagt ggccaagagc ctgag                                        25
```

<210> SEQ ID NO 245
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245

```
gttctccaaa ggaagagagg ggaatg                                       26
```

<210> SEQ ID NO 246
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
ggtgctgtgt cctcatgcat cc                                              22

<210> SEQ ID NO 247
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
cggcttgcct agggtcgttg ag                                              22

<210> SEQ ID NO 248
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
ccttcagggg ctcttccagg tc                                              22

<210> SEQ ID NO 249
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
gggaactggc aggcaccgag g                                               21

<210> SEQ ID NO 250
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
gggtgaggct gaaacagtga cc                                              22

<210> SEQ ID NO 251
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
gggaggatgt tggttttagg gaactg                                          26

<210> SEQ ID NO 252
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
tccaatcact acatgccatt ttgaaga                                         27

<210> SEQ ID NO 253
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
ccaccctctt cctttgatcc tccc                                        24

<210> SEQ ID NO 254
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
tcctccctac tccttcaccc agg                                         23

<210> SEQ ID NO 255
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
gagtgcctga catgtgggga gag                                         23

<210> SEQ ID NO 256
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
tccagctaaa gcctttccca cac                                         23

<210> SEQ ID NO 257
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
gaactctctg atgcacctga aggctg                                      26

<210> SEQ ID NO 258
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
accgtatcag tgtgatgcat gtggt                                       25

<210> SEQ ID NO 259
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
tgggtttaat catgtgttct gcactatg                                         28

<210> SEQ ID NO 260
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
cccatcttcc attctgccct ccac                                             24

<210> SEQ ID NO 261
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 261
cagctagtcc atttgttctc agactgtg                                         28

<210> SEQ ID NO 262
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 262
ggccaacatt gtgaaaccct gtctc                                            25

<210> SEQ ID NO 263
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
ccagggacct gtgcttgggt tc                                               22

<210> SEQ ID NO 264
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264
caccccatga cctggcacaa gtg                                              23

-continued

```
<210> SEQ ID NO 265
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265
aagtgttcct cagaatgcca gccc                                              24

<210> SEQ ID NO 266
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
caggagtgca gttgtgttgg gag                                               23

<210> SEQ ID NO 267
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 267
ctgatgaagc accagagaac ccacc                                             25

<210> SEQ ID NO 268
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
cacacctggc acccatatgg c                                                 21

<210> SEQ ID NO 269
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
gatccacact ggtgagaagc cttac                                             25

<210> SEQ ID NO 270
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
cttcccacac tcacagcaga tgtagg                                            26

<210> SEQ ID NO 271
```

<211> LENGTH: 4206
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 271

| | | | | | |
|---|---|---|---|---|---|
| atggataaaa | agtattctat | tggtttagac | atcggcacta | attccgttgg | atgggctgtc | 60 |
| ataaccgatg | aatacaaagt | accttcaaag | aaatttaagg | tgttggggaa | cacagaccgt | 120 |
| cattcgatta | aaaagaatct | tatcggtgcc | ctcctattcg | atagtggcga | aacggcagag | 180 |
| gcgactcgcc | tgaaacgaac | cgctcggaga | aggtatacac | gtcgcaagaa | ccgaatatgt | 240 |
| tacttacaag | aaattttttag | caatgagatg | gccaaagttg | acgattcttt | ctttcaccgt | 300 |
| ttggaagagt | ccttccttgt | cgaagaggac | aagaaacatg | aacggcaccc | catctttgga | 360 |
| aacatagtag | atgaggtggc | atatcatgaa | agtacccaa | cgatttatca | cctcagaaaa | 420 |
| aagctagttg | actcaactga | taaagcggac | ctgaggttaa | tctacttggc | tcttgcccat | 480 |
| atgataaagt | tccgtgggca | ctttctcatt | gagggtgatc | taaatccgga | caactcggat | 540 |
| gtcgacaaac | tgttcatcca | gttagtacaa | acctataatc | agttgtttga | agagaaccct | 600 |
| ataaatgcaa | gtggcgtgga | tgcgaaggct | attcttagcg | cccgcctctc | taaatcccga | 660 |
| cggctagaaa | acctgatcgc | acaattaccc | ggagagaaga | aaatgggtt | gttcggtaac | 720 |
| cttatagcgc | tctcactagg | cctgacacca | aatttttaagt | cgaacttcga | cttagctgaa | 780 |
| gatgccaaat | tgcagcttag | taaggacacg | tacgatgacg | atctcgacaa | tctactggca | 840 |
| caaattggag | atcagtatgc | ggacttattt | ttggctgcca | aaaaccttag | cgatgcaatc | 900 |
| ctcctatctg | acatactgag | agttaatact | gagattacca | aggcgccgtt | atccgcttca | 960 |
| atgatcaaaa | ggtacgatga | acatcaccaa | gacttgacac | ttctcaaggc | cctagtccgt | 1020 |
| cagcaactgc | ctgagaaata | taaggaaata | ttctttgatc | agtcgaaaaa | cgggtacgca | 1080 |
| ggttatattg | acggcggagc | gagtcaagag | gaattctaca | agtttatcaa | acccatatta | 1140 |
| gagaagatgg | atgggacgga | agagttgctt | gtaaaactca | atcgcgaaga | tctactgcga | 1200 |
| aagcagcgga | ctttcgacaa | cggtagcatt | ccacatcaaa | tccacttagg | cgaattgcat | 1260 |
| gctatactta | gaaggcagga | ggatttttat | ccgttcctca | aagacaatcg | tgaaaagatt | 1320 |
| gagaaaatcc | taaccttcg | cataccttac | tatgtggac | ccctggcccg | agggaactct | 1380 |
| cggttcgcat | ggatgacaag | aaagtccgaa | gaaacgatta | ctccatggaa | ttttgaggaa | 1440 |
| gttgtcgata | aggtgcgtc | agctcaatcg | ttcatcgaga | ggatgaccaa | ctttgacaag | 1500 |
| aatttaccga | acgaaaaagt | attgcctaag | cacagtttac | tttacgagta | tttcacagtg | 1560 |
| tacaatgaac | tcacgaaagt | taagtatgtc | actgagggca | tgcgtaaacc | cgcctttcta | 1620 |
| agcggagaac | agaagaaagc | aatagtagat | ctgttattca | agaccaaccg | caaagtgaca | 1680 |
| gttaagcaat | tgaaagagga | ctactttaag | aaaattgaat | gcttcgattc | tgtcgagatc | 1740 |
| tccggggtag | aagatcgatt | taatgcgtca | cttggtacgt | atcatgaccct | cctaaagata | 1800 |
| attaaagata | aggacttcct | ggataacgaa | gagaatgaag | atatcttaga | agatatagtg | 1860 |
| ttgactctta | ccctctttga | agatcgggaa | atgattgagg | aaagactaaa | acatacgct | 1920 |
| cacctgttcg | acgataaggt | tatgaaacag | ttaaagaggc | gtcgctatac | gggctgggga | 1980 |
| cgattgtcgc | ggaaacttat | caacgggata | agagacaagc | aaagtggtaa | aactattctc | 2040 |
| gattttctaa | agagcgacgg | cttcgccaat | aggaacttta | tgcagctgat | ccatgatgac | 2100 |

```
tctttaacct tcaaagagga tatacaaaag gcacaggttt ccggacaagg ggactcattg    2160
cacgaacata ttgcgaatct tgctggttcg ccagccatca aaaagggcat actccagaca    2220
gtcaaagtag tggatgagct agttaaggtc atgggacgtc acaaaccgga aaacattgta    2280
atcgagatgg cacgcgaaaa tcaaacgact cagaaggggc aaaaaaacag tcgagagcgg    2340
atgaagagaa tagaagaggg tattaaagaa ctgggcagcc agatcttaaa ggagcatcct    2400
gtggaaaata cccaattgca gaacgagaaa ctttacctct attacctaca aaatggaagg    2460
gacatgtatg ttgatcagga actggacata aaccgtttat ctgattacga cgtcgatcac    2520
attgtacccc aatccttttt gaaggacgat tcaatcgaca ataaagtgct tacacgctcg    2580
gataagaacc gagggaaaag tgacaatgtt ccaagcgagg aagtcgtaaa gaaaatgaag    2640
aactattggc ggcagctcct aaatgcgaaa ctgataacgc aaagaaagtt cgataactta    2700
actaaagctg agaggggtgg cttgtctgaa cttgacaagg ccggatttat taaacgtcag    2760
ctcgtggaaa cccgccaaat cacaaagcat gttgcacaga tactagattc ccgaatgaat    2820
acgaaatacg acgagaacga taagctgatt cgggaagtca aagtaatcac tttaaagtca    2880
aaattggtgt cggacttcag aaaggatttt caattctata agttaggga gataaataac     2940 taccaccatg cgcacgacgc ttatcttaat gccgtcgtag ggaccgcact cattaagaaa    3000
tacccgaagc tagaaagtga gtttgtgtat ggtgattaca agtttatga cgtccgtaag     3060 atgatcgcga aaagcgaaca ggagataggc aaggctacag ccaaatactt cttttattct    3120
aacattatga atttctttaa gacggaaatc actctggcaa acggagagat acgcaaacga    3180
cctttaattg aaaccaatgg ggagacaggt gaaatcgtat gggataaggg ccgggacttc    3240
gcgacggtga gaaagttttt gtccatgccc caagtcaaca tagtaaagaa aactgaggtg    3300
cagaccggag ggttttcaaa ggaatcgatt cttccaaaaa ggaatagtga taagctcatc    3360
gctcgtaaaa aggactggga cccgaaaaag tacggtggct tcgatagccc tacagttgcc    3420
tattctgtcc tagtagtggc aaaagttgag aaggagaaat ccaagaaact gaagtcagtc    3480
aaagaattat tggggataac gattatggag cgctcgtctt ttgaaaagaa ccccatcgac    3540
ttccttgagg cgaaaggtta caggaagta aaaaaggatc tcataattaa actaccaaag     3600
tatagtctgt ttgagttaga aaatggccga aaacggatgt tggctagcgc cggagagctt    3660
caaaagggga acgaactcgc actaccgtct aaatacgtga atttcctgta tttagcgtcc    3720
cattacgaga agttgaaagg ttcacctgaa gataacgaac agaagcaact ttttgttgag    3780
cagcacaaac attatctcga cgaaatcata gagcaaattt cggaattcag taagagagtc    3840
atcctagctg atgccaatct ggacaaagta ttaagcgcat acaacaagca cagggataaa    3900
cccatacgtg agcaggcgga aaatattatc catttgttta ctcttaccaa cctcggcgct    3960
ccagccgcat tcaagtattt tgacacaacg atagatcgca acgatacac ttctaccaag      4020 gaggtgctag acgcgacact gattcaccaa tccatcacgg gattatatga aactcggata    4080
gatttgtcac agcttggggg tgacggatcc cccaagaaga agaggaaagt ctcgagcgac    4140
tacaaagacc atgacggtga ttataaagat catgacatcg attacaagga tgacgatgac    4200
aagtga                                                               4206
```

<210> SEQ ID NO 272
<211> LENGTH: 4206
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 272

| | |
|---|---|
| atggataaaa agtattctat tggtttagac atcggcacta attccgttgg atgggctgtc | 60 |
| ataaccgatg aatacaaagt accttcaaag aaatttaagg tgttgggaa cacagaccgt | 120 |
| cattcgatta aaaagaatct tatcggtgcc ctcctattcg atagtggcga aacggcagag | 180 |
| gcgactcgcc tgaaacgaac cgctcggaga aggtatacac gtcgcaagaa ccgaatatgt | 240 |
| tacttacaag aaattttag caatgagatg gccaaagttg acgattcttt ctttcaccgt | 300 |
| ttggaagagt ccttccttgt cgaagaggac aagaaacatg aacggcaccc catctttgga | 360 |
| aacatagtag atgaggtggc atatcatgaa aagtacccaa cgatttatca cctcagaaaa | 420 |
| aagctagttg actcaactga taaagcggac ctgaggttaa tctacttggc tcttgcccat | 480 |
| atgataaagt tccgtgggca ctttctcatt gagggtgatc taaatccgga caactcggat | 540 |
| gtcgacaaac tgttcatcca gttagtacaa acctataatc agttgtttga agagaaccct | 600 |
| ataaatgcaa gtggcgtgga tgcgaaggct attcttagcg cccgcctctc taatcccga | 660 |
| cggctagaaa acctgatcgc acaattaccc ggagagaaga aaatgggtt gttcggtaac | 720 |
| cttatagcgc tctcactagg cctgacacca aattttaagt cgaacttcga cttagctgaa | 780 |
| gatgccaaat tgcagcttag taaggacacg tacgatgacg atctcgacaa tctactggca | 840 |
| caaattggag atcagtatgc ggacttattt ttggctgcca aaaaccttag cgatgcaatc | 900 |
| ctcctatctg acatactgag agttaatact gagattacca aggcgccgtt atccgcttca | 960 |
| atgatcaaaa ggtacgatga acatcaccaa gacttgacac ttctcaaggc cctagtccgt | 1020 |
| cagcaactgc ctgagaaata taggaaata ttctttgatc agtcgaaaaa cgggtacgca | 1080 |
| ggttatattg acgcggagc gagtcaagag gaattctaca agtttatcaa acccatatta | 1140 |
| gagaagatgg atgggacgga agagttgctt gtaaaactca atcgcgaaga tctactgcga | 1200 |
| aagcagcgga ctttcgacaa cggtagcatt ccacatcaaa tccacttagg cgaattgcat | 1260 |
| gctatactta gaaggcagga ggattttat ccgttcctca agacaatcg tgaaaagatt | 1320 |
| gagaaaatcc taacctttcg cataccttac tatgtgggac ccctggcccg agggaactct | 1380 |
| cggttcgcat ggatgacaag aaagtccgaa gaaacgatta ctccctggaa ttttgaggaa | 1440 |
| gttgtcgata aggtgcgtc agctcaatcg ttcatcgaga ggatgaccgc ctttgacaag | 1500 |
| aatttaccga acgaaaagt attgcctaag cacagtttac tttacgagta tttcacagtg | 1560 |
| tacaatgaac tcacgaaagt taagtatgtc actgagggca tgcgtaaacc cgcctttcta | 1620 |
| agcggagaac agaagaaagc aatagtagat ctgttattca agaccaaccg caaagtgaca | 1680 |
| gttaagcaat tgaaagagga ctactttaag aaaattgaat gcttcgattc tgtcgagatc | 1740 |
| tccggggtag aagatcgatt taatgcgtca cttggtacgt atcatgacct cctaaagata | 1800 |
| attaaagata aggacttcct ggataacgaa gagaatgaag atatcttaga agatatagtg | 1860 |
| ttgactctta ccctctttga agatcgggaa atgattgagg aaagactaaa acatacgct | 1920 |
| cacctgttcg acgataaggt tatgaaacag ttaaagaggc gtcgctatac gggctgggga | 1980 |
| gccttgtcgc ggaaacttat caacgggata agagacaagc aaagtggtaa aactattctc | 2040 |
| gattttctaa agagcgacgg cttcgccaat aggaacttta tggccctgat ccatgatgac | 2100 |
| tctttaacct tcaaagagga tatacaaaag gcacaggttt ccggacaagg ggactcattg | 2160 |
| cacgaacata ttgcgaatct tgctggttcg ccagccatca aaagggcat actccagaca | 2220 |
| gtcaaagtag tggatgagct agttaaggtc atgggacgtc acaaaccgga aaacattgta | 2280 |

```
atcgagatgg cacgcgaaaa tcaaacgact cagaaggggc aaaaaaacag tcgagagcgg    2340
atgaagagaa tagaagaggg tattaaagaa ctgggcagcc agatcttaaa ggagcatcct    2400
gtggaaaata cccaattgca gaacgagaaa ctttacctct attacctaca aaatggaagg    2460
gacatgtatg ttgatcagga actggacata aaccgtttat ctgattacga cgtcgatcac    2520
attgtacccc aatccttttt gaaggacgat tcaatcgaca ataaagtgct tacacgctcg    2580
gataagaacc gagggaaaag tgacaatgtt ccaagcgagg aagtcgtaaa gaaaatgaag    2640
aactattggc ggcagctcct aaatgcgaaa ctgataacgc aaagaaagtt cgataactta    2700
actaaagctg agagggggtgg cttgtctgaa cttgacaagg ccggatttat taaacgtcag    2760
ctcgtggaaa cccgcgccat cacaaagcat gttgcgcaga tactagattc cgaatgaat    2820
acgaaatacg acgagaacga taagctgatt cgggaagtca agtaatcac tttaaagtca    2880
aaattggtgt cggacttcag aaaggatttt caattctata agttaggga gataaataac    2940
taccaccatg cgcacgacgc ttatcttaat gccgtcgtag ggaccgcact cattaagaaa    3000
tacccgaagc tagaaagtga gtttgtgtat ggtgattaca agtttatga cgtccgtaag    3060
atgatcgcga aaagcgaaca ggagataggc aaggctacag ccaaatactt ctttttattct    3120
aacattatga atttctttaa gacggaaatc actctggcaa acggagagat acgcaaacga    3180
cctttaattg aaaccaatgg ggagacaggt gaaatcgtat gggataaggg ccgggacttc    3240
gcgacggtga gaaaagttttt gtccatgccc caagtcaaca tagtaaagaa aactgaggtg    3300
cagaccggag ggttttcaaa ggaatcgatt cttccaaaaa ggaatagtga taagctcatc    3360
gctcgtaaaa aggactggga cccgaaaaag tacggtggct tcgatagccc tacagttgcc    3420
tattctgtcc tagtagtggc aaaagttgag aagggaaaat ccaagaaact gaagtcagtc    3480
aaagaattat tggggataac gattatggag cgctcgtctt ttgaaaagaa ccccatcgac    3540
ttccttgagg cgaaaggtta caggaagta aaaaaggatc tcataattaa actaccaaag    3600
tatagtctgt ttgagttaga aaatggccga aaacggatgt tggctagcgc cggagagctt    3660
caaaagggga acgaactcgc actaccgtct aaatacgtga atttcctgta tttagcgtcc    3720
cattacgaga agttgaaagg ttcacctgaa gataacgaac agaagcaact ttttgttgag    3780
cagcacaaac attatctcga cgaaatcata gagcaaattt cggaattcag taagagagtc    3840
atcctagctg atgccaatct ggacaaagta ttaagcgcat acaacaagca cagggataaa    3900
cccatacgtg agcaggcgga aaatattatc catttgttta ctcttaccaa cctcggcgct    3960
ccagccgcat tcaagtattt tgacacaacg atagatcgca aacgatacac ttctaccaag    4020
gaggtgctag acgcgacact gattcaccaa tccatcacgg gattatatga aactcggata    4080
gatttgtcac agcttggggg tgacggatcc cccaagaaga agaggaaagt ctcgagcgac    4140
tacaaagacc atgacggtga ttataaagat catgacatcg attacaagga tgacgatgac    4200
aagtga                                                                4206
```

<210> SEQ ID NO 273
<211> LENGTH: 4206
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 273

```
atggataaaa agtattctat tggtttagac atcggcacta attccgttgg atgggctgtc    60
```

```
ataaccgatg aatacaaagt accttcaaag aaatttaagg tgttgggaa cacagaccgt      120 cattcgatta aaaagaatct tatcggtgcc ctcctattcg atagtggcga aacggcagag      180
gcgactcgcc tgaaacgaac cgctcggaga aggtatacac gtcgcaagaa ccgaatatgt      240
tacttacaag aaatttttag caatgagatg gccaaagttg acgattcttt ctttcaccgt      300
ttggaagagt ccttccttgt cgaagaggac aagaaacatg aacggcaccc catctttgga      360
aacatagtag atgaggtggc atatcatgaa aagtacccaa cgatttatca cctcagaaaa      420
aagctagttg actcaactga taaagcggac ctgaggttaa tctacttggc tcttgcccat      480
atgataaagt tccgtgggca ctttctcatt gagggtgatc taaatccgga caactcggat      540
gtcgacaaac tgttcatcca gttagtacaa acctataatc agttgtttga agagaaccct      600
ataaatgcaa gtggcgtgga tgcgaaggct attcttagcg cccgcctctc taaatcccga      660
cggctagaaa acctgatcgc acaattaccc ggagagaaga aaaatgggtt gttcggtaac      720
cttatagcgc tctcactagg cctgacacca aatttaagt cgaacttcga cttagctgaa      780
gatgccaaat tgcagcttag taaggacacg tacgatgacg atctcgacaa tctactggca      840
caaattggag atcagtatgc ggacttattt ttggctgcca aaaaccttag cgatgcaatc      900
ctcctatctg acatactgag agttaatact gagattacca aggcgccgtt atccgcttca      960
atgatcaaaa ggtacgatga acatcaccaa gacttgacac ttctcaaggc cctagtccgt     1020
cagcaactgc ctgagaaata taaggaaata ttctttgatc agtcgaaaaa cgggtacgca     1080
ggttatattg acggcggagc gagtcaagag gaattctaca agtttatcaa acccatatta     1140
gagaagatgg atgggacgga agagttgctt gtaaaactca atcgcgaaga tctactgcga     1200
aagcagcgga ctttcgacaa cggtagcatt ccacatcaaa tccacttagg cgaattgcat     1260
gctatactta gaaggcagga ggattttat ccgttcctca aagacaatcg tgaaaagatt     1320
gagaaaatcc taacctttcg catacccttac tatgtgggac ccctggcccg agggaactct     1380
cggttcgcat ggatgacaag aaagtccgaa gaaacgatta ctccctggaa ttttgaggaa     1440
gttgtcgata aagtgcgtc agctcaatcg ttcatcgaga ggatgaccgc ctttgacaag     1500
aatttaccga acgaaaaagt attgcctaag cacagtttac tttacgagta tttcacagtg     1560
tacaatgaac tcacgaaagt taagtatgtc actgagggca tgcgtaaacc cgccttttcta    1620 agcggagaac agaagaaagc aatagtagat ctgttattca agaccaaccg caaagtgaca     1680
gttaagcaat tgaaagagga ctactttaag aaaattgaat gcttcgattc tgtcgagatc     1740
tccggggtag aagatcgatt taatgcgtca cttggtacgt atcatgacct cctaaagata     1800
attaaagata aggacttcct ggataacgaa gagaatgaag atatcttaga agatatagtg     1860
ttgactctta ccctctttga agatcggaa atgattgagg aaagactaaa acatacgct     1920 cacctgttcg acgataaggt tatgaaacag ttaaagaggc gtcgctatac gggctgggga     1980
gccttgtcgc ggaaacttat caacgggata agagacaagc aaagtggtaa aactattctc     2040
gattttctaa agagcgacgg cttcgccaat aggaacttta tggcccctgat ccatgatgac     2100 tctttaaccct tcaaagagga tatacaaaag gcacaggttt ccggacaagg ggactcattg     2160
cacgaacata ttgcgaatct tgctggttcg ccagccatca aaaagggcat actccagaca     2220
gtcaaagtag tggatgagct agttaaggtc atgggacgtc acaaaccgga aacattgta     2280 atcgagatgg cacgcgaaaa tcaaacgact cagaaggggc aaaaaaacag tcgagagcgg     2340
atgaagagaa tagaagaggg tattaaagaa ctgggcagcc agatcttaaa ggagcatcct     2400
```

```
gtggaaaata cccaattgca gaacgagaaa ctttacctct attacctaca aaatggaagg    2460
gacatgtatg ttgatcagga actggacata aaccgtttat ctgattacga cgtcgatcac    2520
attgtacccc aatccttttt gaaggacgat tcaatcgaca ataaagtgct tacacgctcg    2580
gataagaacc gagggaaaag tgacaatgtt ccaagcgagg aagtcgtaaa gaaaatgaag    2640
aactattggc ggcagctcct aaatgcgaaa ctgataacgc aaagaaagtt cgataactta    2700
actaaagctg agaggggtgg cttgtctgaa cttgacaagg ccggatttat taaacgtcag    2760
ctcgtggaaa cccgcgccat cacaaagcat gttgcgcaga tactagattc ccgaatgaat    2820
acgaaatacg acgagaacga taagctgatt cgggaagtca agtaatcac tttaaagtca     2880 aaattggtgt cggacttcag aaaggatttt caattctata aagttaggga gataaataac    2940
taccaccatg cgcacgacgc ttatcttaat gccgtcgtag ggaccgcact cattaagaaa    3000
tacccgaagc tagaaagtga gtttgtgtat ggtgattaca agtttatga cgtccgtaag     3060 atgatcgcga aaagcgaaca ggagataggc aaggctacag ccaaatactt ctttttattct   3120 aacattatga atttctttaa gacgaaatc actctggcaa acgagagat acgcaaacga     3180 cctttaattg aaaccaatgg ggagacaggt gaaatcgtat gggataaggg ccgggacttc    3240
gcgacggtga gaaagttttt gtccatgccc caagtcaaca tagtaaagaa aactgaggtg    3300
cagaccggag ggttttcaaa ggaatcgatt cttccaaaaa ggaatagtga taagctcatc    3360
gctcgtaaaa aggactggga cccgaaaaag tacggtggct tcgagagccc tacagttgcc    3420
tattctgtcc tagtagtggc aaaagttgag aagggaaaat ccaagaaact gaagtcagtc    3480
aaagaattat tggggataac gattatggag cgctcgtctt ttgaaaagaa ccccatcgac    3540
ttccttgagg cgaaaggtta caaggaagta aaaaaggatc tcataattaa actaccaaag    3600
tatagtctgt ttgagttaga aaatggccga aaacggatgt tggctagcgc cggagagctt    3660
caaaagggga acgaactcgc actaccgtct aaatacgtga atttcctgta tttagcgtcc    3720
cattacgaga gttgaaagg ttcacctgaa gataacgaac agaagcaact ttttgttgag    3780
cagcacaaac attatctcga cgaaatcata gagcaaattt cggaattcag taagagagtc    3840
atcctagctg atgccaatct ggacaaagta ttaagcgcat acaacaagca cagggataaa    3900
cccatacgtg agcaggcgga aaatattatc catttgttta ctcttaccaa cctcggcgct    3960
ccagccgcat tcaagtattt tgacacaacg atagatcgca aacgatacac ttctaccaag    4020
gaggtgctag acgcgacact gattcaccaa tccatcacgg gattatatga aactcggata    4080
gatttgtcac agcttggggg tgacggatcc cccaagaaga agaggaaagt ctcgagcgac    4140
tacaaagacc atgacggtga ttataaagat catgacatcg attacaagga tgacgatgac    4200
aagtga                                                               4206
```

<210> SEQ ID NO 274
<211> LENGTH: 4206
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 274

```
atggataaaa agtattctat tggtttagac atcggcacta attccgttgg atgggctgtc      60
ataaccgatg aatacaaagt accttcaaag aaatttaagg tgttggggaa cacagaccgt    120
cattcgatta aaaagaatct tatcggtgcc ctcctattcg atagtggcga aacggcagag    180
```

-continued

```
gcgactcgcc tgaaacgaac cgctcggaga aggtatacac gtcgcaagaa ccgaatatgt      240
tacttacaag aaattttag caatgagatg gccaaagttg acgattcttt ctttcaccgt       300
ttggaagagt ccttccttgt cgaagaggac aagaaacatg aacggcaccc catctttgga     360
aacatagtag atgaggtggc atatcatgaa aagtacccaa cgatttatca cctcagaaaa     420
aagctagttg actcaactga taaagcggac ctgaggttaa tctacttggc tcttgcccat    480
atgataaagt tccgtgggca ctttctcatt gagggtgatc taaatccgga caactcggat   540
gtcgacaaac tgttcatcca gttagtacaa acctataatc agttgtttga agagaacccat  600 ataaatgcaa gtggcgtgga tgcgaaggct attcttagcg cccgcctctc taaatcccga    660
cggctagaaa acctgatcgc acaattaccc ggagagaaga aaaatgggtt gttcggtaac     720
cttatagcgc tctcactagg cctgacacca aattttaagt cgaacttcga cttagctgaa     780
gatgccaaat tgcagcttag taaggacacg tacgatgacg atctcgacaa tctactggca    840
caaattggag atcagtatgc ggacttattt ttggctgcca aaaaccttag cgatgcaatc    900
ctcctatctg acatactgag agttaatact gagattacca aggcgccgtt atccgcttca    960
atgatcaaaa ggtacgatga acatcaccaa gacttgacac ttctcaaggc cctagtccgt   1020
cagcaactgc ctgagaaata taaggaaata ttctttgatc agtcgaaaaa cgggtacgca   1080
ggttatattg acggcggagc gagtcaagag gaattctaca agtttatcaa acccatatta   1140
gagaagatgg atgggacgga agagttgctt gtaaaactca atcgcgaaga tctactgcga  1200
aagcagcgga ctttcgacaa cggtagcatt ccacatcaaa tccacttagg cgaattgcat   1260
gctatactta gaaggcagga ggattttat ccgttcctca aagacaatcg tgaaaagatt    1320
gagaaaatcc taacctttcg catacctgcc tatgtgggac ccctggcccg agggaactct   1380
cggttcgcat ggatgacaag aaagtccgaa gaaacgatta ctccctggaa ttttgaggaa    1440
gttgtcgata aggtgcgtc agctcaatcg ttcatcgaga ggatgaccgc cttttgacaag    1500 aatttaccga acgaaaaagt attgcctaag cacagtttac tttacgagta tttcacagtg    1560
tacaatgaac tcacgaaagt taagtatgtc actgagggca tgcgtaaacc cgcctttcta   1620
agcggagaac agaagaaagc aatagtagat ctgttattca agaccaaccg caaagtgaca   1680
gttaagcaat tgaaagagga ctactttaag aaaattgaat gcttcgattc tgtcgagatc   1740
tccggggtag aagatcgatt taatgcgtca cttggtacgt atcatgacct cctaaagata    1800
attaaagata aggacttcct ggataacgaa gagaatgaag atatcttaga agatatagtg    1860
ttgactctta ccctctttga agatcggaa atgattgagg aaagactaaa aacatacgct   1920
cacctgttcg acgataaggt tatgaaacag ttaaagaggc gtcgctatac gggctgggga   1980
gccttgtcgc ggaaacttat caacgggata agagacaagc aaagtggtaa aactattctc   2040
gattttctaa agagcgacgg cttcgccaat aggaacttta tggccctgat ccatgatgac   2100 tctttaaccct tcaaagagga tatacaaaag gcacaggttt ccggacaagg ggactcattg   2160
cacgaacata ttgcgaatct tgctggttcg ccagccatca aaaagggcat actccagaca   2220
gtcaaagtag tggatgagct agttaaggtc atgggacgtc acaaaccgga aacattgta    2280 atcgagatgg cacgcgaaaa tcaaacgact cagaagggc aaaaaaacag tcgagagcgg   2340
atgaagagaa tagaagaggg tattaaagaa ctgggcagcc agatcttaaa ggagcatcct   2400
gtggaaaata cccaattgca gaacgagaaa ctttacctct attacctaca aaatggaagg   2460
gacatgtatg ttgatcagga actggacata aaccgtttat ctgattacga cgtcgatcac   2520
attgtacccc aatccttttt gaaggacgat tcaatcgaca ataaagtgct tacacgctcg   2580
```

```
gataagaacc gagggaaaag tgacaatgtt ccaagcgagg aagtcgtaaa gaaaatgaag    2640
aactattggc ggcagctcct aaatgcgaaa ctgataacgc aaagaaagtt cgataactta    2700
actaaagctg agaggggtgg cttgtctgaa cttgacaagg ccggatttat taaacgtcag    2760
ctcgtggaaa cccgcgccat cacaaagcat gttgcgcaga tactagattc cgaatgaat    2820 acgaaatacg acgagaacga taagctgatt cgggaagtca agtaatcac tttaaagtca    2880 aaattggtgt cggacttcag aaaggatttt caattctata aagttaggga gataaataac    2940
taccaccatg cgcacgacgc ttatcttaat gccgtcgtag ggaccgcact cattaagaaa    3000
tacccgaagc tagaaagtga gtttgtgtat ggtgattaca aagtttatga cgtccgtaag    3060
atgatcgcga aaagcgaaca ggagataggc aaggctacag ccaaatactt cttttattct    3120
aacattatga atttctttaa gacggaaatc actctggcaa acggagagat acgcaaacga    3180
cctttaattg aaaccaatgg ggagacaggt gaaatcgtat gggataaggg ccgggacttc    3240
gcgacggtga gaaaagtttt gtccatgccc caagtcaaca tagtaaagaa aactgaggtg    3300
cagaccggag ggttttcaaa ggaatcgatt cttccaaaaa ggaatagtga taagctcatc    3360
gctcgtaaaa aggactggga cccgaaaaag tacggtggct cgatagccc tacagttgcc    3420 tattctgtcc tagtagtggc aaaagttgag aagggaaaat ccaagaaact gaagtcagtc    3480
aaagaattat tggggataac gattatggag cgctcgtctt ttgaaaagaa ccccatcgac    3540
ttccttgagg cgaaaggtta caaggaagta aaaaggatc tcataattaa actaccaaag    3600
tatagtctgt ttgagttaga aaatggccga aaacggatgt tggctagcgc cggagagctt    3660
caaaagggga acgaactcgc actaccgtct aaatacgtga atttcctgta tttagcgtcc    3720
cattacgaga agttgaaagg ttcacctgaa gataacgaac agaagcaact ttttgttgag    3780
cagcacaaac attatctcga cgaaatcata gagcaaattt cggaattcag taagagagtc    3840
atcctagctg atgccaatct ggacaaagta ttaagcgcat acaacaagca cagggataaa    3900
cccatacgtg agcaggcgga aaatattatc catttgttta ctcttaccaa cctcggcgct    3960
ccagccgcat tcaagtattt tgacacaacg atagatcgca aacgatacac ttctaccaag    4020
gaggtgctag acgcgacact gattcaccaa tccatcacgg gattatatga aactcggata    4080
gatttgtcac agcttggggg tgacggatcc cccaagaaga gaggaaagt ctcgagcgac    4140 tacaaagacc atgacggtga ttataaagat catgacatcg attacaagga tgacgatgac    4200
aagtga                                                               4206
```

<210> SEQ ID NO 275
<211> LENGTH: 4206
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 275

```
atggataaaa agtattctat tggtttagac atcggcacta attccgttgg atgggctgtc      60
ataaccgatg aatacaaagt accttcaaag aaatttaagg tgttgggaa cacagaccgt     120 cattcgatta aaaagaatct tatcggtgcc ctcctattcg atagtggcga acggcagag     180 gcgactcgcc tgaaacgaac cgctcggaga aggtatacac gtcgcaagaa ccgaatatgt     240
tacttacaag aaatttttag caatgagatg gccaaagttg acgattcttt ctttcaccgt     300
ttggaagagt ccttccttgt cgaagaggac aagaaacatg aacggcaccc catctttgga     360
```

```
aacatagtag atgaggtggc atatcatgaa aagtacccaa cgatttatca cctcagaaaa    420
aagctagttg actcaactga taaagcggac ctgaggttaa tctacttggc tcttgcccat    480
atgataaagt tccgtgggca ctttctcatt gagggtgatc taaatccgga caactcggat    540
gtcgacaaac tgttcatcca gttagtacaa acctataatc agttgtttga agagaaccct    600
ataaatgcaa gtggcgtgga tgcgaaggct attcttagcg cccgcctctc taaatcccga    660
cggctagaaa acctgatcgc acaattaccc ggagagaaga aaaatgggtt gttcggtaac    720
cttatagcgc tctcactagg cctgacacca aattttaagt cgaacttcga cttagctgaa    780
gatgccaaat tgcagcttag taaggacacg tacgatgacg atctcgacaa tctactggca    840
caaattggag atcagtatgc ggacttattt ttggctgcca aaaaccttag cgatgcaatc    900
ctcctatctg acatactgag agttaatact gagattacca aggcgccgtt atccgcttca    960
atgatcaaaa ggtacgatga acatcaccaa gacttgacac ttctcaaggc cctagtccgt   1020
cagcaactgc ctgagaaata taaggaaata ttctttgatc agtcgaaaaa cgggtacgca   1080
ggttatattg acggcggagc gagtcaagag gaattctaca agtttatcaa acccatatta   1140
gagaagatgg atgggacgga agagttgctt gtaaaactca atcgcgaaga tctactgcga   1200
aagcagcgga ctttcgacaa cggtagcatt ccacatcaaa tccacttagg cgaattgcat   1260
gctatactta gaaggcagga ggattttat ccgttcctca aagacaatcg tgaaaagatt   1320
gagaaaatcc taacctttcg cataccttac tatgtgggac ccctggcccg agggaactct   1380
cggttcgcat ggatgacaag aaagtccgaa gaaacgatta ctccatggaa ttttgaggaa   1440
gttgtcgata aggtgcgtc agctcaatcg ttcatcgaga ggatgaccaa ctttgacaag   1500
aatttaccga cgaaaaagt attgcctaag cacagtttac tttacgagta tttcacagtg   1560
tacaatgaac tcacgaaagt taagtatgtc actgagggca tgcgtaaacc cgccttttcta   1620 agcggagaac agaagaaagc aatagtagat ctgttattca agaccaaccg caaagtgaca   1680
gttaagcaat tgaaagagga ctactttaag aaaattgaat gcttcgattc tgtcgagatc   1740
tccggggtag aagatcgatt taatgcgtca cttggtacgt atcatgacct cctaaagata   1800
attaaagata aggacttcct ggataacgaa gagaatgaag atatcttaga agatatagtg   1860
ttgactctta ccctctttga agatcgggaa atgattgagg aaagactaaa aacatacgct   1920 caccgttcg acgataaggt tatgaaacag ttaaagaggc gtcgctatac gggctgggga   1980
cgattgtcgc ggaaacttat caacgggata agagacaagc aaagtggtaa aactattctc   2040
gattttctaa agagcgacgg cttcgccaat aggaacttta tgcagctgat ccatgatgac   2100 tcttaacct tcaaagagga tatacaaaag gcacaggttt ccggacaagg ggactcattg   2160
cacgaacata ttgcgaatct tgctggttcg ccagccatca aaaagggcat actccagaca   2220
gtcaaagtag tggatgagct agttaaggtc atgggacgtc acaaaccgga aacattgta   2280 atcgagatgg cacgcgaaaa tcaaacgact cagaaggggc aaaaaaacag tcgagagcgg   2340
atgaagagaa tagaagaggg tattaaagaa ctgggcagcc agatcttaaa ggagcatcct   2400
gtggaaaata cccaattgca gaacgagaaa ctttacctct attacctaca aaatggaagg   2460
gacatgtatg ttgatcagga actggacata aaccgtttat ctgattacga cgtcgatcac   2520 attgtaccc aatccttttt gaaggacgat tcaatcgaca ataaagtgct tacacgctcg   2580
gataagaacc gagggaaaag tgacaatgtt ccaagcgagg aagtcgtaaa gaaaatgaag   2640
aactattggc ggcagctcct aaatgcgaaa ctgataacgc aaagaaagtt cgataactta   2700
```

```
actaaagctg agaggggtgg cttgtctgaa cttgacaagg ccggatttat taaacgtcag    2760
ctcgtggaaa cccgccaaat cacaaagcat gttgcacaga tactagattc ccgaatgaat    2820
acgaaatacg acgagaacga taagctgatt cgggaagtca aagtaatcac tttaaagtca    2880
aaattggtgt cggacttcag aaaggatttt caattctata agttaggga gataaataac     2940 taccaccatg cgcacgacgc ttatcttaat gccgtcgtag ggaccgcact cattaagaaa    3000
tacccgaagc tagaaagtga gtttgtgtat ggtgattaca agtttatga cgtccgtaag     3060 atgatcgcga aaagcgaaca ggagataggc aaggctacag ccaaatactt ctttttattct  3120 aacattatga atttctttaa gacggaaatc actctggcaa acggagagat acgcaaacga    3180
cctttaattg aaaccaatgg ggagacaggt gaaatcgtat gggataaggg ccgggacttc    3240
gcgacggtga gaaaagttttt gtccatgccc caagtcaaca tagtaaagaa aactgaggtg   3300
cagaccggag ggttttcaaa ggaatcgatt cttccaaaaa ggaatagtga taagctcatc    3360
gctcgtaaaa aggactggga cccgaaaaag tacggtggct tcgtgagccc tacagttgcc   3420
tattctgtcc tagtagtggc aaaagttgag aagggaaaat ccaagaaact gaagtcagtc   3480
aaagaattat tggggataac gattatggag cgctcgtctt ttgaaaagaa ccccatcgac   3540
ttccttgagg cgaaaggtta caaggaagta aaaaaggatc tcataattaa actaccaaag    3600
tatagtctgt ttgagttaga aaatggccga aaacggatgt tggctagcgc cggagagctt    3660
caaaagggga acgaactcgc actaccgtct aaatacgtga atttcctgta tttagcgtcc   3720
cattacgaga agttgaaagg ttcacctgaa gataacgaac agaagcaact ttttgttgag   3780
cagcacaaac attatctcga cgaaatcata gagcaaattt cggaattcag taagagagtc  3840
atcctagctg atgccaatct ggacaaagta ttaagcgcat acaacaagca cagggataaa   3900
cccatacgtg agcaggcgga aaatattatc catttgttta ctcttaccaa cctcggcgct   3960
ccagccgcat tcaagtattt tgacacaacg atagatcgca aacagtacag atctaccaag   4020
gaggtgctag acgcgacact gattcaccaa tccatcacgg gattatatga aactcggata    4080
gatttgtcac agcttggggg tgacggatcc cccaagaaga agaggaaagt ctcgagcgac    4140
tacaaagacc atgacggtga ttataaagat catgacatcg attacaagga tgacgatgac    4200
aagtga                                                              4206
```

<210> SEQ ID NO 276
<211> LENGTH: 4206
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 276

```
atggataaaa agtattctat tggtttagac atcggcacta attccgttgg atgggctgtc     60
ataaccgatg aatacaaagt accttcaaag aaatttaagg tgttggggaa cacagaccgt   120
cattcgatta aaagaatct tatcggtgcc ctcctattcg atagtggcga aacggcagag    180
gcgactcgcc tgaaacgaac cgctcggaga aggtatacac gtcgcaagaa ccgaatatgt   240
tacttacaag aaattttag caatgagatg gccaaagttg acgattcttt ctttcaccgt    300
ttggaagagt ccttccttgt cgaagaggac aagaaacatg aacggcaccc catctttgga   360
aacatagtag atgaggtggc atatcatgaa agtacccaa cgatttatca cctcagaaaa   420
aagctagttg actcaactga taaagcggac ctgaggttaa tctacttggc tcttgcccat   480
```

```
atgataaagt tccgtgggca ctttctcatt gagggtgatc taaatccgga caactcggat    540
gtcgacaaac tgttcatcca gttagtacaa acctataatc agttgtttga agagaaccct    600
ataaatgcaa gtggcgtgga tgcgaaggct attcttagcg cccgcctctc taaatcccga    660
cggctagaaa acctgatcgc acaattaccc ggagagaaga aaaatgggtt gttcggtaac    720
cttatagcgc tctcactagg cctgacacca aattttaagt cgaacttcga cttagctgaa    780
gatgccaaat tgcagcttag taaggacacg tacgatgacg atctcgacaa tctactggca    840
caaattggag atcagtatgc ggacttattt ttggctgcca aaaaccttag cgatgcaatc    900
ctcctatctg acatactgag agttaatact gagattacca aggcgccgtt atccgcttca    960
atgatcaaaa ggtacgatga acatcaccaa gacttgacac ttctcaaggc cctagtccgt   1020
cagcaactgc ctgagaaata taggaaaata ttctttgatc agtcgaaaaa cgggtacgca   1080
ggttatattg acggcggagc gagtcaagag gaattctaca agtttatcaa acccatatta   1140
gagaagatgg atgggacgga agagttgctt gtaaaactca atcgcgaaga tctactgcga   1200
aagcagcgga ctttcgacaa cggtagcatt ccacatcaaa tccacttagg cgaattgcat   1260
gctatactta gaaggcagga ggattttttat ccgttcctca agacaatcg tgaaaagatt   1320
gagaaaatcc taacctttcg catacccttac tatgtgggac ccctggcccg agggaactct   1380
cggttcgcat ggatgacaag aaagtccgaa gaaacgatta ctccctggaa ttttgaggaa   1440
gttgtcgata aggtgcgtc agctcaatcg ttcatcgaga ggatgaccgc ctttgacaag   1500
aatttaccga acgaaaaagt attgcctaag cacagtttac tttacgagta tttcacagtg   1560
tacaatgaac tcacgaaagt taagtatgtc actgagggca tgcgtaaacc cgcctttcta   1620
agcggagaac agaagaaagc aatagtagat ctgttattca agaccaaccg caaagtgaca   1680
gttaagcaat tgaaagagga ctactttaag aaaattgaat gcttcgattc tgtcgagatc   1740
tccggggtag aagatcgatt taatgcgtca cttggtacgt atcatgacct cctaaagata   1800
attaaagata aggacttcct ggataacgaa gagaatgaag atatcttaga agatatagtg   1860
ttgactctta ccctctttga agatcgggaa atgattgagg aaagactaaa acatacgct   1920
cacctgttcg acgataaggt tatgaaacag ttaaagaggc gtcgctatac gggctgggga   1980
gccttgtcgc ggaaacttat caacgggata agagacaagc aaagtggtaa aactattctc   2040
gattttctaa agagcgacgg cttcgccaat aggaacttta tggccctgat ccatgatgac   2100
tctttaacct tcaaagagga tatacaaaag gcacaggttt ccggacaagg ggactcattg   2160
cacgaacata ttgcgaatct tgctggttcg ccagccatca aaagggcat actccagaca   2220
gtcaaagtag tggatgagct agttaaggtc atgggacgtc acaaaccgga aaacattgta   2280
atcgagatgg cacgcgaaaa tcaaacgact cagaaggggc aaaaaaacag tcgagagcgg   2340
atgaagagaa tagaagaggg tattaaagaa ctgggcagcc agatcttaaa ggagcatcct   2400
gtggaaaata cccaattgca gaacgagaaa ctttacctct attacctaca aaatggaagg   2460
gacatgtatg ttgatcagga actggacata aaccgtttat ctgattacga cgtcgatcac   2520
attgtacccc aatccttttt gaaggacgat tcaatcgaca ataaagtgct tacacgctcg   2580
gataagaacc gagggaaaag tgacaatgtt ccaagcgagg aagtcgtaaa gaaaatgaag   2640
aactattggc ggcagctcct aaatgcgaaa ctgataacgc aaagaaagtt cgataactta   2700
actaaagctg agaggggtgg cttgtctgaa cttgacaagg ccggatttat taacgtcag   2760
ctcgtggaaa cccgcgccat cacaaagcat gttgcgcaga tactagattc ccgaatgaat   2820
acgaaatacg acgagaacga taagctgatt cgggaagtca agtaatcac tttaaagtca   2880
```

```
aaattggtgt cggacttcag aaaggatttt caattctata agttaggga gataaataac    2940 taccaccatg cgcacgacgc ttatcttaat gccgtcgtag ggaccgcact cattaagaaa   3000
tacccgaagc tagaaagtga gtttgtgtat ggtgattaca agtttatga cgtccgtaag    3060 atgatcgcga aaagcgaaca ggagataggc aaggctacag ccaaatactt cttttattct   3120
aacattatga atttctttaa gacggaaatc actctggcaa acggagagat acgcaaacga   3180
cctttaattg aaaccaatgg ggagacaggt gaaatcgtat gggataaggg ccgggacttc   3240
gcgacggtga gaaaagtttt gtccatgccc caagtcaaca tagtaaagaa aactgaggtg   3300
cagaccggag ggttttcaaa ggaatcgatt cttccaaaaa ggaatagtga taagctcatc   3360
gctcgtaaaa aggactggga cccgaaaaag tacggtggct tcgtgagccc tacagttgcc   3420
tattctgtcc tagtagtggc aaaagttgag aagggaaaat ccaagaaact gaagtcagtc   3480
aaagaattat tggggataac gattatggag cgctcgtctt ttgaaaagaa ccccatcgac   3540
ttccttgagg cgaaaggtta caaggaagta aaaaaggatc tcataattaa actaccaaag   3600
tatagtctgt ttgagttaga aaatggccga aaacggatgt tggctagcgc cggagagctt   3660
caaaagggga cgaactcgc actaccgtct aaatacgtga atttcctgta tttagcgtcc     3720
cattacgaga agttgaaagg ttcacctgaa gataacgaac agaagcaact ttttgttgag   3780
cagcacaaac attatctcga cgaaatcata gagcaaattt cggaattcag taagagagtc   3840
atcctagctg atgccaatct ggacaaagta ttaagcgcat acaacaagca cagggataaa   3900
cccatacgtg agcaggcgga aaatattatc catttgttta ctcttaccaa cctcggcgct   3960
ccagccgcat tcaagtattt tgacacaacg atagatcgca aacagtacag atctaccaag   4020
gaggtgctag acgcgacact gattcaccaa tccatcacgg gattatatga aactcggata   4080
gatttgtcac agcttggggg tgacggatcc cccaagaaga gaggaaagt ctcgagcgac     4140 tacaaagacc atgacggtga ttataaagat catgacatcg attacaagga tgacgatgac   4200
aagtga                                                              4206
```

<210> SEQ ID NO 277
<211> LENGTH: 4206
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 277

```
atggataaaa agtattctat tggtttagac atcggcacta attccgttgg atgggctgtc     60
ataaccgatg aatacaaagt accttcaaag aaatttaagg tgttggggaa cacagaccgt    120
cattcgatta aaaagaatct tatcggtgcc ctcctattcg atagtggcga acggcagag     180 gcgactcgcc tgaaacgaac cgctcggaga aggtatacac gtcgcaagaa ccgaatatgt    240
tacttacaag aaattttag caatgagatg gccaaagttg acgattcttt ctttcaccgt     300
ttggaagagt ccttccttgt cgaagaggac aagaaacatg aacggcaccc catctttgga   360
aacatagtag atgaggtggc atatcatgaa agtacccaa cgatttatca cctcagaaaa     420
aagctagttg actcaactga taaagcggac ctgaggttaa tctacttggc tcttgcccat    480
atgataaagt tccgtgggca ctttctcatt gagggtgatc taaatccgga caactcggat   540
gtcgacaaac tgttcatcca gttagtacaa acctataatc agttgtttga agagaaccct   600
ataaatgcaa gtggcgtgga tgcgaaggct attcttagcg cccgcctctc taaatcccga   660
```

```
cggctagaaa acctgatcgc acaattaccc ggagagaaga aaaatgggtt gttcggtaac    720
cttatagcgc tctcactagg cctgacacca aattttaagt cgaacttcga cttagctgaa    780
gatgccaaat tgcagcttag taaggacacg tacgatgacg atctcgacaa tctactggca    840
caaattggag atcagtatgc ggacttattt ttggctgcca aaaacttag cgatgcaatc     900
ctcctatctg acatactgag agttaatact gagattacca aggcgccgtt atccgcttca    960
atgatcaaaa ggtacgatga acatcaccaa gacttgacac ttctcaaggc cctagtccgt   1020
cagcaactgc ctgagaaata taaggaaata ttctttgatc agtcgaaaaa cgggtacgca   1080
ggttatattg acgcggagc gagtcaagag gaattctaca agtttatcaa acccatatta    1140
gagaagatgg atgggacgga agagttgctt gtaaaactca atcgcgaaga tctactgcga   1200
aagcagcgga ctttcgacaa cggtagcatt ccacatcaaa tccacttagg cgaattgcat   1260
gctatactta gaaggcagga ggattttat ccgttcctca aagacaatcg tgaaaagatt    1320
gagaaaatcc taacctttcg cataccttac tatgtgggac ccctggcccg agggaactct   1380
cggttcgcat ggatgacaag aaagtccgaa gaaacgatta ctccatggaa ttttgaggaa   1440
gttgtcgata aggtgcgtc agctcaatcg ttcatcgaga ggatgaccaa ctttgacaag    1500
aatttaccga acgaaaaagt attgcctaag cacagtttac tttacgagta tttcacagtg   1560
tacaatgaac tcacgaaagt taagtatgtc actgagggca tgcgtaaacc cgcctttcta   1620
agcggagaac agaagaaagc aatagtagat ctgttattca agaccaaccg caaagtgaca   1680
gttaagcaat tgaaagagga ctactttaag aaaattgaat gcttcgattc tgtcgagatc   1740
tccggggtag aagatcgatt taatgcgtca cttggtacgt atcatgacct cctaaagata   1800
attaaagata aggacttcct ggataacgaa gagaatgaag atatcttaga agatatagtg   1860
ttgactctta ccctctttga agatcgggaa atgattgagg aaagactaaa aacatacgct   1920
cacctgttcg acgataaggt tatgaaacag ttaagagagc gtcgctatac gggctgggga   1980
cgattgtcgc ggaaacttat caacgggata agagacaagc aaagtggtaa aactattctc   2040
gatttttctaa agagcgacgg cttcgccaat aggaacttta tgcagctgat ccatgatgac   2100
tcttaacct tcaaagagga tatacaaaag gcacaggttt ccggacaagg ggactcattg    2160
cacgaacata ttgcgaatct tgctggttcg ccagccatca aaaagggcat actccagaca   2220
gtcaaagtag tggatgagct agttaaggtc atgggacgtc acaaaccgga aaacattgta   2280
atcgagatgg cacgcgaaaa tcaaacgact cagaagggc aaaaaaacag tcgagagcgg    2340
atgaagagaa tagaagaggg tattaaagaa ctgggcagcc agatcttaaa ggagcatcct   2400
gtggaaaata cccaattgca gaacgagaaa ctttacctct attacctaca aaatggaagg   2460
gacatgtatg ttgatcagga actggacata aaccgtttat ctgattacga cgtcgatcac   2520
attgtacccc aatccttttt gaaggacgat tcaatcgaca ataaagtgct tacacgctcg   2580
gataagaacc gagggaaaag tgacaatgtt ccaagcgagg aagtcgtaaa gaaaatgaag   2640
aactattggc ggcagctcct aaatgcgaaa ctgataacgc aaagaaagtt cgataactta   2700
actaaagctg agagggtgg cttgtctgaa cttgacaagg ccggatttat taaacgtcag   2760
ctcgtggaaa cccgccaaat cacaaagcat gttgcacaga tactagattc ccgaatgaat   2820
acgaaatacg acgagaacga taagctgatt cgggaagtca agtaatcac tttaaagtca    2880
aaattggtgt cggacttcag aaaggatttt caattctata aagttaggga gataaataac   2940
taccaccatg cgcacgacgc ttatcttaat gccgtcgtag ggaccgcact cattaagaaa   3000
```

| | |
|---|---|
| tacccgaagc tagaaagtga gtttgtgtat ggtgattaca aagtttatga cgtccgtaag | 3060 |
| atgatcgcga aaagcgaaca ggagataggc aaggctacag ccaaatactt cttttattct | 3120 |
| aacattatga atttctttaa gacggaaatc actctggcaa acggagagat acgcaaacga | 3180 |
| cctttaattg aaaccaatgg ggagacaggt gaaatcgtat gggataaggg ccgggacttc | 3240 |
| gcgacggtga gaaaagttttt gtccatgccc caagtcaaca tagtaaagaa aactgaggtg | 3300 |
| cagaccggag ggttttcaaa ggaatcgatt cttccaaaaa ggaatagtga taagctcatc | 3360 |
| gctcgtaaaa aggactggga cccgaaaaag tacggtggct cgtgagccc tacagttgcc | 3420 |
| tattctgtcc tagtagtggc aaaagttgag aagggaaaat ccaagaaact gaagtcagtc | 3480 |
| aaagaattat tggggataac gattatggag cgctcgtctt ttgaaaagaa ccccatcgac | 3540 |
| ttccttgagg cgaaaggtta caggaagta aaaaaggatc tcataattaa actaccaaag | 3600 |
| tatagtctgt ttgagttaga aaatggccga aaacggatgt tggctagcgc cagagagctt | 3660 |
| caaaagggga acgaactcgc actaccgtct aaatacgtga atttcctgta tttagcgtcc | 3720 |
| cattacgaga agttgaaagg ttcacctgaa gataacgaac agaagcaact ttttgttgag | 3780 |
| cagcacaaac attatctcga cgaaatcata gagcaaattt cggaattcag taagagagtc | 3840 |
| atcctagctg atgccaatct ggacaaagta ttaagcgcat acaacaagca cagggataaa | 3900 |
| cccatacgtg agcaggcgga aaatattatc catttgttta ctcttaccaa cctcggcgct | 3960 |
| ccagccgcat tcaagtattt tgacacaacg atagatcgca aacagtacag atctaccaag | 4020 |
| gaggtgctag acgcgacact gattcaccaa tccatcacgg gattatatga aactcggata | 4080 |
| gatttgtcac agcttggggg tgacggatcc cccaagaaga agaggaaagt ctcgagcgac | 4140 |
| tacaaagacc atgacggtga ttataaagat catgacatcg attacaagga tgacgatgac | 4200 |
| aagtga | 4206 |

<210> SEQ ID NO 278
<211> LENGTH: 4206
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 278

| | |
|---|---|
| atggataaaa agtattctat tggtttagac atcggcacta attccgttgg atgggctgtc | 60 |
| ataaccgatg aatacaaagt accttcaaag aaatttaagg tgttggggaa cacagaccgt | 120 |
| cattcgatta aaaagaatct tatcggtgcc ctcctattcg atagtggcga acggcagag | 180 |
| gcgactcgcc tgaaacgaac cgctcggaga aggtatacac gtcgcaagaa ccgaatatgt | 240 |
| tacttacaag aaatttttag caatgagatg gccaaagttg acgattcttt cttcaccgt | 300 |
| ttggaagagt ccttccttgt cgaagaggac aagaaacatg aacggcaccc catctttgga | 360 |
| aacatagtag atgaggtggc atatcatgaa agtacccaa cgatttatca cctcagaaaa | 420 |
| aagctagttg actcaactga taaagcggac ctgaggttaa tctacttggc tcttgcccat | 480 |
| atgataaagt tccgtgggca ctttctcatt gagggtgatc taaatccgga caactcggat | 540 |
| gtcgacaaac tgttcatcca gttagtacaa acctataatc agttgtttga agagaaccct | 600 |
| ataaatgcaa gtggcgtgga tgcgaaggct attcttagcg cccgcctctc taaatcccga | 660 |
| cggctagaaa acctgatcgc acaattaccc ggagagaaga aaatgggtt gttcggtaac | 720 |
| cttatagcgc tctcactagg cctgacacca aattttaagt cgaacttcga cttagctgaa | 780 |

```
gatgccaaat tgcagcttag taaggacacg tacgatgacg atctcgacaa tctactggca      840
caaattggag atcagtatgc ggacttattt ttggctgcca aaaaccttag cgatgcaatc      900
ctcctatctg acatactgag agttaatact gagattacca aggcgccgtt atccgcttca      960
atgatcaaaa ggtacgatga acatcaccaa gacttgacac ttctcaaggc cctagtccgt     1020
cagcaactgc ctgagaaata taaggaaata ttctttgatc agtcgaaaaa cgggtacgca     1080
ggttatattg acggcggagc gagtcaagag gaattctaca agtttatcaa acccatatta     1140
gagaagatgg atgggacgga agagttgctt gtaaaactca atcgcgaaga tctactgcga     1200
aagcagcgga ctttcgacaa cggtagcatt ccacatcaaa tccacttagg cgaattgcat     1260
gctatactta gaaggcagga ggattttat ccgttcctca aagacaatcg tgaaaagatt      1320
gagaaaatcc taacctttcg catacccttac tatgtgggac ccctggcccg agggaactct    1380
cggttcgcat ggatgacaag aaagtccgaa gaaacgatta ctccctggaa ttttgaggaa    1440
gttgtcgata aggtgcgtc agctcaatcg ttcatcgaga ggatgaccgc ctttgacaag      1500
aatttaccga acgaaaaagt attgcctaag cacagtttac tttacgagta tttcacagtg     1560
tacaatgaac tcacgaaagt taagtatgtc actgagggca tgcgtaaacc cgccttctta     1620
agcggagaac agaagaaagc aatagtagat ctgttattca agaccaaccg caaagtgaca    1680
gttaagcaat tgaaagagga ctactttaag aaaattgaat gcttcgattc tgtcgagatc     1740
tccggggtag aagatcgatt taatgcgtca cttggtacgt atcatgacct cctaaagata     1800
attaaagata aggacttcct ggataacgaa gagaatgaag atatcttaga agatatagtg     1860
ttgactctta ccctctttga agatcggaa atgattgagg aaagactaaa aacatacgct      1920
cacctgttcg acgataaggt tatgaaacag ttaagaggc gtcgctatac gggctgggga      1980
gccttgtcgc ggaaacttat caacgggata agagacaagc aaagtggtaa aactattctc     2040
gattttctaa agagcgacgg cttcgccaat aggaacttta tggcccctgat ccatgatgac   2100 tctttaacct tcaaagagga tatacaaaag gcacaggttt ccggacaagg ggactcattg     2160
cacgaacata ttgcgaatct tgctggttcg ccagccatca aaagggcat actccagaca      2220 gtcaaagtag tggatgagct agttaaggtc atgggacgtc acaaaccgga aaacattgta     2280
atcgagatgg cacgcgaaaa tcaaacgact cagaaggggc aaaaaaacag tcgagagcgg     2340
atgaagagaa tagaagaggg tattaaagaa ctgggcagcc agatcttaaa ggagcatcct     2400
gtggaaaata cccaattgca gaacgagaaa ctttacctct attacctaca aaatggaagg     2460
gacatgtatg ttgatcagga actggacata aaccgtttat ctgattacga cgtcgatcac     2520 attgtaccc aatccttttt gaaggacgat tcaatcgaca ataaagtgct tacacgctcg      2580
gataagaacc gagggaaaag tgacaatgtt ccaagcgagg aagtcgtaaa gaaaatgaag     2640
aactattggc ggcagctcct aaatgcgaaa ctgataacgc aaagaaagtt cgataactta     2700
actaaagctg agaggggtgg cttgtctgaa cttgacaagg ccggatttat taaacgtcag     2760
ctcgtggaaa cccgcgccat cacaaagcat gttgcgcaga tactagattc ccgaatgaat     2820
acgaaatacg acgagaacga taagctgatt cgggaagtca agtaatcac tttaaagtca     2880 aaattggtgt cggacttcag aaaggatttt caattctata agttaggga gataaataac     2940 taccaccatg cgcacgacgc ttatcttaat gccgtcgtag ggaccgcact cattaagaaa     3000
tacccgaagc tagaaagtga gtttgtgtat ggtgattaca agtttatga cgtccgtaag     3060 atgatcgcga aaagcgaaca ggagataggc aaggctacag ccaaatactt cttttattct     3120
aacattatga atttctttaa gacggaaatc actctggcaa acggagagat acgcaaacga     3180
```

```
cctttaattg aaaccaatgg ggagacaggt gaaatcgtat gggataaggg ccgggacttc   3240
gcgacggtga gaaagttttt gtccatgccc caagtcaaca tagtaaagaa aactgaggtg   3300
cagaccggag ggttttcaaa ggaatcgatt cttccaaaaa ggaatagtga taagctcatc   3360
gctcgtaaaa aggactggga cccgaaaaag tacggtggct tcgtgagccc tacagttgcc   3420
tattctgtcc tagtagtggc aaaagttgag aagggaaaat ccaagaaact gaagtcagtc   3480
aaagaattat tggggataac gattatgag cgctcgtctt ttgaaaagaa ccccatcgac   3540
ttccttgagg cgaaaggtta caaggaagta aaaaaggatc tcataattaa actaccaaag   3600
tatagtctgt ttgagttaga aaatggccga aacggatgt tggctagcgc cagagagctt   3660
caaaagggga acgaactcgc actaccgtct aaatacgtga atttcctgta tttagcgtcc   3720
cattacgaga agttgaaagg ttcacctgaa gataacgaac agaagcaact ttttgttgag   3780
cagcacaaac attatctcga cgaaatcata gagcaaattt cggaattcag taagagagtc   3840
atcctagctg atgccaatct ggacaaagta ttaagcgcat acaacaagca cagggataaa   3900
cccatacgtg agcaggcgga aaatattatc catttgttta ctcttaccaa cctcggcgct   3960
ccagccgcat tcaagtattt tgacacaacg atagatcgca aacagtacag atctaccaag   4020
gaggtgctag acgcgacact gattcaccaa tccatcacgg gattatatga aactcggata   4080
gatttgtcac agcttggggg tgacggatcc cccaagaaga gaggaaagt ctcgagcgac   4140 tacaaagacc atgacggtga ttataaagat catgacatcg attacaagga tgacgatgac   4200
aagtga                                                              4206

<210> SEQ ID NO 279
<211> LENGTH: 422
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 279
tgtacaaaaa agcaggcttt aaaggaacca attcagtcga ctggatccgg taccaaggtc     60
gggcaggaag agggcctatt tcccatgatt ccttcatatt tgcatatacg atacaaggct    120
gttagagaga taattagaat taatttgact gtaaacacaa agatattagt acaaaatacg    180
tgacgtagaa agtaataatt tcttgggtag tttgcagttt taaaattatg ttttaaaatg    240
gactatcata tgcttaccgt aacttgaaag tatttcgatt tcttggcttt atatatcttg    300
tggaaaggac gaaacaccgg agacgattaa tgcgtctccg ttttagagct agaaatagca    360
agttaaaata aggctagtcc gttatcaact tgaaaaagtg gcaccgagtc ggtgcttttt    420
tt                                                                   422

<210> SEQ ID NO 280
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(21)
<223> OTHER INFORMATION: n is a, c, g, or t

<400> SEQUENCE: 280
gagtccgagc agaagaagaa ngg                                             23
```

<210> SEQ ID NO 281
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(21)
<223> OTHER INFORMATION: n is a, c, g, or t

<400> SEQUENCE: 281
gtcacctcca atgactaggg ngg                                            23

<210> SEQ ID NO 282
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(21)
<223> OTHER INFORMATION: n is a, c, g, or t

<400> SEQUENCE: 282
ggaatccctt ctgcagcacc ngg                                            23

<210> SEQ ID NO 283
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(21)
<223> OTHER INFORMATION: n is a, c, g, or t

<400> SEQUENCE: 283
gctgcagaag ggattccatg ngg                                            23

<210> SEQ ID NO 284
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(21)
<223> OTHER INFORMATION: n is a, c, g, or t

<400> SEQUENCE: 284
ggcggctgca caaccagtgg ngg                                            23

<210> SEQ ID NO 285
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(21)
<223> OTHER INFORMATION: n is a, c, g, or t

<400> SEQUENCE: 285

```
gctccagagc cgtgcgaatg ngg                                         23

<210> SEQ ID NO 286
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(21)
<223> OTHER INFORMATION: n is a, c, g, or t

<400> SEQUENCE: 286
gcattttcag gaggaagcga ngg                                         23

<210> SEQ ID NO 287
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(21)
<223> OTHER INFORMATION: n is a, c, g, or t

<400> SEQUENCE: 287
gtgcggcaag agcttcagcc ngg                                         23

<210> SEQ ID NO 288
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(21)
<223> OTHER INFORMATION: n is a, c, g, or t

<400> SEQUENCE: 288
ggtgagtgag tgtgtgcgtg ngg                                         23

<210> SEQ ID NO 289
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(21)
<223> OTHER INFORMATION: n is a, c, g, or t

<400> SEQUENCE: 289
gaccccctcc accccgcctc ngg                                         23
```

ENGINEERED CRISPR-CAS9 NUCLEASES

CLAIM OF PRIORITY

This application is a continuation of U.S. patent application Ser. No. 15/249,756, filed Aug. 29, 2016, which claims priority under 35 USC § 119(e) to U.S. patent application Ser. No. 62/211,553, filed on Aug. 28, 2015; Ser. No. 62/216,033, filed on Sep. 9, 2015; Ser. No. 62/258,280, filed on Nov. 20, 2015; and Ser. No. 62/271,938, filed on Dec. 28, 2015. U.S. patent application Ser. No. 15/249,756 is a continuation in part of U.S. patent application Ser. No. 15/015,947, filed on Feb. 4, 2016, now U.S. Pat. No. 9,512,446, which claims the benefit of U.S. patent application Ser. No. 62/211,553, filed on Aug. 28, 2015; Ser. No. 62/216,033, filed on Sep. 9, 2015; and Ser. No. 62/258,280, filed on Nov. 20, 2015. This application is also a continuation in part of U.S. patent application Ser. No. 15/369,533, filed Dec. 5, 2016, which is a continuation of U.S. patent application Ser. No. 15/015,947, filed on Feb. 4, 2016, now U.S. Pat. No. 9,512,446, which claims the benefit of U.S. patent application Ser. No. 62/211,553, filed on Aug. 28, 2015; Ser. No. 62/216,033, filed on Sep. 9, 2015; and Ser. No. 62/258,280, filed on Nov. 20, 2015. The entire contents of the foregoing are hereby incorporated by reference.

FEDERALLY SPONSORED RESEARCH OR DEVELOPMENT

This invention was made with Government support under Grant Nos. DP1 GM105378 and R01 GM088040 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Feb. 27, 2018, is named SEQUENCE LISTING.txt and is 129,955 bytes in size.

TECHNICAL FIELD

The invention relates, at least in part, to engineered Clustered Regularly Interspaced Short Palindromic Repeats (CRISPRs)/CRISPR-associated protein 9 (Cas9) nucleases with altered and improved target specificity and their use in genomic engineering, epigenomic engineering, genome targeting, genome editing, and in vitro diagnostics.

BACKGROUND

CRISPR-Cas9 nucleases enable efficient genome editing in a wide variety of organisms and cell types (Sander & Joung, Nat Biotechnol 32, 347-355 (2014); Hsu et al., Cell 157, 1262-1278 (2014); Doudna & Charpentier, Science 346, 1258096 (2014); Barrangou & May, Expert Opin Biol Ther 15, 311-314 (2015)). Target site recognition by Cas9 is programmed by a chimeric single guide RNA (sgRNA) that encodes a sequence complementary to a target protospacer (Jinek et al., Science 337, 816-821 (2012)), but also requires recognition of a short neighboring PAM (Mojica et al., Microbiology 155, 733-740 (2009); Shah et al., RNA Biol 10, 891-899 (2013); Jiang et al., Nat Biotechnol 31, 233-239 (2013); Jinek et al., Science 337, 816-821 (2012); Sternberg et al., Nature 507, 62-67 (2014)).

SUMMARY

As described herein, Cas9 Proteins can be engineered to show increased specificity, theoretically by reducing the binding affinity of Cas9 for DNA. Thus, described herein are a number of Cas9 variants that have increased specificity (i.e., induce substantially fewer off target effects at imperfectly matched or mismatched DNA sites) as compared to the wild type protein, as well as methods of using them.

In a first aspect, the invention provides isolated *Streptococcus pyogenes* Cas9 (SpCas9) proteins with mutations at one, two, three, four, five, six or all seven of the following positions: L169A, Y450, N497, R661, Q695, Q926, and/or D1135E e.g., comprising a sequence that is at least 80% identical to the amino acid sequence of SEQ ID NO:1 with mutations at one, two, three, four, five, six, or seven of the following positions: L169, Y450, N497, R661, Q695, Q926, D1135E, and optionally one or more of a nuclear localization sequence, cell penetrating peptide sequence, and/or affinity tag. A mutation alters the amino acid to an amino acid other than the native amino acid (e.g., 497 is anything but N). In preferred embodiments the mutation changes the amino acid to any amino acid other than the native one, arginine or lysine; in some embodiments, the amino acid is alanine.

In some embodiments, the variant SpCas9 proteins comprise mutations at one, two, three, or all four of the following: N497, R661, Q695, and Q926, e.g., one, two, three, or all four of the following mutations: N497A, R661A, Q695A, and Q926A.

In some embodiments, the variant SpCas9 proteins comprise mutations at Q695 and/or Q926, and optionally one, two, three, four or all five of L169, Y450, N497, R661 and D1135E, e.g., including but not limited to Y450A/Q695A, L169A/Q695A, Q695A/Q926A, Q695A/D1135E, Q926A/D1135E, Y450A/D1135E, L169A/Y450A/Q695A, L169A/Q695A/Q926A, Y450A/Q695A/Q926A, R661A/Q695A/Q926A, N497A/Q695A/Q926A, Y450A/Q695A/D1135E, Y450A/Q926A/D1135E, Q695A/Q926A/D1135E, L169A/Y450A/Q695A/Q926A, L169A/R661A/Q695A/Q926A, Y450A/R661A/Q695A/Q926A, N497A/Q695A/Q926A/D1135E, R661A/Q695A/Q926A/D1135E, and Y450A/Q695A/Q926A/D1135E.

In some embodiments, the variant SpCas9 proteins comprise mutations at N14; S15; S55; R63; R78; H160; K163; R165; L169; R403; N407; Y450; M495; N497; K510; Y515; W659; R661; M694; Q695; H698; A728; S730; K775; S777; R778; R780; K782; K783; K789; K797; Q805; N808; K810; R832; Q844; S845; K848; S851; K855; R859; K862; K890; Q920; Q926; K961; S964; K968; K974; R976; N980; H982; K1003; K1014; S1040; N1041; N1044; K1047; K1059; R1060; K1107; E1108; S1109; K1113; R1114; S1116; K1118; D1135; S1136; K1153; K1155; K1158; K1200; Q1221; H1241; Q1254; Q1256; K1289; K1296; K1297; R1298; K1300; H1311; K1325; K1334; T1337 and/or S1216.

In some embodiments, the variant SpCas9 proteins also comprise one or more of the following mutations: N14A; S15A; S55A; R63A; R78A; R165A; R403A; N407A; N497A; Y450A; K510A; Y515A; R661A; Q695A; S730A; K775A; S777A; R778A; R780A; K782A; K783A; K789A; K797A; Q805A; N808A; K810A; R832A; Q844A; S845A; K848A; S851A; K855A; R859A; K862A; K890A; Q920A; Q926A; K961A; S964A; K968A; K974A; R976A; N980A;

H982A; K1003A; K1014A; S1040A; N1041A; N1044A; K1047A; K1059A; R1060A; K1107A; E1108A; S1109A; K1113A; R1114A; S1116A; K1118A; D1135A; S1136A; K1153A; K1155A; K1158A; K1200A; Q1221A; H1241A; Q1254A; Q1256A; K1289A; K1296A; K1297A; R1298A; K1300A; H1311A; K1325A; K1334A; T1337A and/or S1216A. In some embodiments, the variant proteins include HF1(N497A/R661A/Q695/Q926A)+K810A, HF1+K848A, HF1+K855A, HF1+H982A, HF1+K848A/K1003A, HF1+K848A/R1060A, HF1+K855A/K1003A, HF1+K855A/R1060A, HF1+H982A/K1003A, HF1+H982A/R1060A, HF1+K1003A/R1060A, HF1+K810A/K1003A/R1060A, HF1+K848A/K1003A/R1060A. In some embodiments, the variant proteins include HF1+K848A/K1003A, HF1+K848A/R1060A, HF1+K855A/K1003A, HF1+K855A/R1060A, HF1+K1003A/R1060A, HF1+K848A/K1003A/R1060A. In some embodiments, the variant proteins include Q695A/Q926A/R780A, Q695A/Q926A/R976A, Q695A/Q926A/H982A, Q695A/Q926A/K855A, Q695A/Q926A/K848A/K1003A, Q695A/Q926A/K848A/K855A, Q695A/Q926A/K848A/H982A, Q695A/Q926A/K1003A/R1060A, Q695A/Q926A/K848A/R1060A, Q695A/Q926A/K855A/H982A, Q695A/Q926A/K855A/K1003A, Q695A/Q926A/K855A/R1060A, Q695A/Q926A/H982A/K1003A, Q695A/Q926A/H982A/R1060A, Q695A/Q926A/K1003A/R1060A, Q695A/Q926A/K810A/K1003A/R1060A, Q695A/Q926A/K848A/K1003A/R1060A. In some embodiments, the variants include N497A/R661A/Q695A/Q926A/K810A, N497A/R661A/Q695A/Q926A/K848A, N497A/R661A/Q695A/Q926A/K855A, N497A/R661A/Q695A/Q926A/R780A, N497A/R661A/Q695A/Q926A/K968A, N497A/R661A/Q695A/Q926A/H982A, N497A/R661A/Q695A/Q926A/K1003A, N497A/R661A/Q695A/Q926A/K1014A, N497A/R661A/Q695A/Q926A/K1047A, N497A/R661A/Q695A/Q926A/R1060A, N497A/R661A/Q695A/Q926A/K810A/K968A, N497A/R661A/Q695A/Q926A/K810A/K848A, N497A/R661A/Q695A/Q926A/K810A/K1003A, N497A/R661A/Q695A/Q926A/K810A/R1060A, N497A/R661A/Q695A/Q926A/K848A/K1003A, N497A/R661A/Q695A/Q926A/K848A/R1060A, N497A/R661A/Q695A/Q926A/K855A/K1003A, N497A/R661A/Q695A/Q926A/K855A/R1060A, N497A/R661A/Q695A/Q926A/K968A/K1003A, N497A/R661A/Q695A/Q926A/H982A/K1003A, N497A/R661A/Q695A/Q926A/H982A/R1060A, N497A/R661A/Q695A/Q926A/K1003A/R1060A, N497A/R661A/Q695A/Q926A/K810A/K1003A/R1060A, N497A/R661A/Q695A/Q926A/K848A/K1003A/R1060A, Q695A/Q926A/R780A, Q695A/Q926A/K810A, Q695A/Q926A/R832A, Q695A/Q926A/K848A, Q695A/Q926A/K855A, Q695A/Q926A/K968A, Q695A/Q926A/R976A, Q695A/Q926A/H982A, Q695A/Q926A/K1003A, Q695A/Q926A/K1014A, Q695A/Q926A/K1047A, Q695A/Q926A/R1060A, Q695A/Q926A/K848A/K968A, Q695A/Q926A/R976A, Q695A/Q926A/H982A, Q695A/Q926A/K855A, Q695A/Q926A/K848A/K1003A, Q695A/Q926A/K848A/K855A, Q695A/Q926A/K848A/H982A, Q695A/Q926A/K1003A/R1060A, Q695A/Q926A/R832A/R1060A, Q695A/Q926A/K968A/K1003A, Q695A/Q926A/K968A/R1060A, Q695A/Q926A/K848A/R1060A, Q695A/Q926A/K855A/H982A, Q695A/Q926A/K855A/K1003A, Q695A/Q926A/K855A/R1060A, Q695A/Q926A/H982A/K1003A, Q695A/Q926A/H982A/R1060A, Q695A/Q926A/K1003A/R1060A, Q695A/Q926A/K810A/K1003A/R1060A, Q695A/Q926A/K1003A/K1047A/R1060A, Q695A/Q926A/K968A/K1003A/R1060A, Q695A/Q926A/R832A/K1003A/R1060A, or Q695A/Q926A/K848A/K1003A/R1060A Mutations to amino acids other than alanine are also included, and can be made and used in the present methods and compositions.

In some embodiments, variant SpCas9 proteins comprise one or more of the following additional mutations: R63A, R66A, R69A, R70A, R71A, Y72A, R74A, R75A, K76A, N77A, R78A, R115A, H160A, K163A, R165A, L169A, R403A, T404A, F405A, N407A, R447A, N497A, I448A, Y450A, S460A, M495A, K510A, Y515A, R661A, M694A, Q695A, H698A, Y1013A, V1015A, R1122A, K1123A, K1124A, K1158A, K1185A, K1200A, S1216A, Q1221A, K1289A, R1298A, K1300A, K1325A, R1333A, K1334A, R1335A, and T1337A.

In some embodiments, the variant SpCas9 proteins comprise multiple substitution mutations: N497/R661/Q695/Q926 (quadruple variant mutants); Q695/Q926 (double mutant); R661/Q695/Q926 and N497/Q695/Q926 (triple mutants). In some embodiments, additional substitution mutations at L169, Y450 and/or D1135 might be added to these double-, triple-, and quadruple mutants or added to single mutants bearing substitutions at Q695 or Q926. In some embodiments, the mutants have alanine in place of the wild type amino acid. In some embodiments, the mutants have any amino acid other than arginine or lysine (or the native amino acid).

In some embodiments, the variant SpCas9 proteins also comprise one or more mutations that decrease nuclease activity selected from the group consisting of mutations at D10, E762, D839, H983, or D986; and at H840 or N863. In some embodiments, the mutations are: (i) D10A or D10N, and (ii) H840A, H840N, or H840Y.

In some embodiments, the SpCas9 variants can also include one of the following sets of mutations: D1135V/R1335Q/T1337R (VQR variant); D1135E/R1335Q/T1337R (EQR variant); D1135V/G1218R/R1335Q/T1337R (VRQR variant); or D1135V/G1218R/R1335E/T1337R (VRER variant).

Also provided herein are isolated *Staphylococcus aureus* Cas9 (SaCas9) protein, with mutations at one, two, three, four, five, six, or more of the following positions: Y211, Y212, W229, Y230, R245, T392, N419, Y651, or R654, e.g., comprising a sequence that is at least 80% identical to the amino acid sequence of SEQ ID NO:2 with mutations at one, two, three, four, five, or six of the following positions: Y211, Y212, W229, Y230, R245, T392, N419, Y651, or R654, and optionally one or more of a nuclear localization sequence, cell penetrating peptide sequence, and/or affinity tag. In some embodiments, the SaCas9 variants described herein include the amino acid sequence of SEQ ID NO:2, with mutations at one, two, three, four, five, six, or more of the following positions: Y211, Y212, W229, Y230, R245, T392, N419, Y651 and/or R654. In some embodiments the variants include one or more of the following mutations: Y211A, Y212A, W229, Y230A, R245A, T392A, N419, Y651, and/or R654A.

In some embodiments, the variant SaCas9 proteins comprise mutations at N419 and/or R654, and optionally one, two, three, four or more of the additional mutations Y211, Y212, W229, Y230, R245 and T392, preferably N419A/R654A, Y211A/R654A, Y211A/Y212A, Y211A/Y230A, Y211A/R245A, Y212A/Y230A, Y212A/R245A, Y230A/R245A, W229A/R654A, Y211A/Y212A/Y230A, Y211A/Y212A/R245A, Y211A/Y212A/Y651A, Y211A/Y230A/R245A, Y211A/Y230A/Y651A, Y211A/R245A/Y651A, Y211A/R245A/R654A, Y211A/R245A/N419A, Y211A/N419A/R654A, Y212A/Y230A/R245A, Y212A/Y230A/Y651A, Y212A/R245A/Y651A, Y230A/R245A/Y651A, R245A/N419A/R654A, T392A/N419A/R654A, R245A/T392A/N419A/R654A, Y211A/R245A/N419A/R654A, W229A/R245A/N419A/R654A, Y211A/R245A/T392A/N419A/R654A, or Y211A/W229A/R245A/N419A/R654A.

In some embodiments, the variant SaCas9 proteins comprise mutations at Y211; Y212; W229; Y230; R245; T392; N419; L446; Q488; N492; Q495; R497; N498; R499; Q500; K518; K523; K525; H557; R561; K572; R634; Y651; R654; G655; N658; S662; N667; R686; K692; R694; H700; K751; D786; T787; Y789; T882; K886; N888; 889; L909; N985; N986; R991; R1015; N44; R45; R51; R55; R59; R60; R116; R165; N169; R208; R209; Y211; T238; Y239; K248; Y256; R314; N394; Q414; K57; R61; H111; K114; V164; R165; L788; S790; R792; N804; Y868; K870; K878; K879; K881; Y897; R901; and/or K906.

In some embodiments, the variant SaCas9 proteins comprise one or more of the following mutations: Y211A; Y212A; W229A; Y230A; R245A; T392A; N419A; L446A; Q488A; N492A; Q495A; R497A; N498A; R499A; Q500A; K518A; K523A; K525A; H557A; R561A; K572A; R634A; Y651A; R654A; G655A; N658A; S662A; N667A; R686A; K692A; R694A; H700A; K751A; D786A; T787A; Y789A; T882A; K886A; N888A; A889A; L909A; N985A; N986A; R991A; R1015A; N44A; R45A; R51A; R55A; R59A; R60A; R116A; R165A; N169A; R208A; R209A; T238A; Y239A; K248A; Y256A; R314A; N394A; Q414A; K57A; R61A; H111A; K114A; V164A; R165A; L788A; S790A; R792A; N804A; Y868A; K870A; K878A; K879A; K881A; Y897A; R901A; K906A.

In some embodiments, variant SaCas9 proteins comprise one or more of the following additional mutations: Y211A, W229A, Y230A, R245A, T392A, N419A, L446A, Y651A, R654A, D786A, T787A, Y789A, T882A, K886A, N888A, A889A, L909A, N985A, N986A, R991A, R1015A, N44A, R45A, R51A, R55A, R59A, R60A, R116A, R165A, N169A, R208A, R209A, T238A, Y239A, K248A, Y256A, R314A, N394A, Q414A, K57A, R61A, H111A, K114A, V164A, R165A, L788A, S790A, R792A, N804A, Y868A, K870A, K878A, K879A, K881A, Y897A, R901A, K906A.

In some embodiments, the variant SaCas9 proteins comprise multiple substitution mutations: R245/T392/N419/R654 and Y221/R245/N419/R654 (quadruple variant mutants); N419/R654, R245/R654, Y221/R654, and Y221/N419 (double mutants); R245/N419/R654, Y211/N419/R654, and T392/N419/R654 (triple mutants). In some embodiments the mutants contain alanine in place of the wild type amino acid.

In some embodiments, the variant SaCas9 proteins also comprise one or more mutations that decrease nuclease activity selected from the group consisting of mutations at D10, E477, D556, H701, or D704; and at H557 or N580. In some embodiments, the mutations are: (i) D10A or D10N, (ii) H557A, H557N, or H557Y, (iii) N580A, and/or (iv) D556A.

In some embodiments, the variant SaCas9 proteins comprise one or more of the following mutations: E782K, K929R, N968K, or R1015H. Specifically, E782K/N968K/R1015H (KKH variant); E782K/K929R/R1015H (KRH variant); or E782K/K929R/N968K/R1015H (KRKH variant).

In some embodiments, the variant Cas9 proteins include mutations to one or more of the following regions to increase specificity:

| Functional Region | SpCas9 | SaCas9 |
|---|---|---|
| Residues contacting the DNA of the spacer region | L169; Y450; M495; N497; W659; R661; M694; Q695; H698; A728; Q926; E1108; V1015 | Y211; W229; Y230; R245; T392; N419; L446; Y651; R654 |
| Residues that potentially contact the DNA of the non-target strand | N14; S15; S55; S730; K775; S777; R778; R780; K782; R783; K789; K797; Q805; N808; K810; R832; Q844; S845; K848; S851; K855; R859; K862; K890; Q920; K961; S964; K968; K974; R976; N980; H982; K1003; K1014; S1040; N1041; N1044; K1047; K1059; R1060; K1200; H1241; Q1254; Q1256; K1289; K1296; K1297; K1300; H1311; K1325 | Q488A; N492A; Q495A; R497A; N498A; R499; Q500; K518; K523; K525; H557; R561; K572; R634; R654; G655; N658; S662; N667; R686; K692; R694; H700; K751 |
| Residues contacting the DNA of the PAM region (including direct PAM contacts) | R71; Y72; R78; R165; R403; T404; F405; K1107; S1109; R1114; S1116; K1118; D1135; S1136; K1200; S1216; E1219; R1333; R1335; T1337 | D786; T787; Y789; T882; K886; N888; A889; L909; N985; N986; R991; R1015 |
| Residues contacting the RNA of the spacer region | Y72; R75; K76; L101; S104; F105; R115; H116; I135; H160; K163; Y325; H328; R340; F351; D364; Q402; R403; I1110; K1113; R1122; Y1131 | N44; R45; R51; R55; R59; R60; R116; R165; N169; R208; R209; Y211; T238; Y239; K248; Y256; R314; N394; Q414 |
| Residues contacting the RNA of the repeat/anti-repeat region | R63; R66; R70; R71; R74; R78; R403; T404; N407; R447; I448; Y450; K510; Y515; R661; V1009; Y1013 | K57; R61; H111; K114; V164; R165; L788; S790; R792; N804; Y868; K870; K878; K879; K881; Y897; R901; K906 |

-continued

| Functional Region | SpCas9 | SaCas9 |
|---|---|---|
| Residues contacting the RNA stem loops | K30; K33; N46; R40; K44; E57; T62; R69; N77; L455; S460; R467; T472; I473; H721; K742; K1097; V1100; T1102; F1105; K1123; K1124; E1225; Q1272; H1349; S1351; Y1356 | R47; K50; R54; R58; H62; R209; E213; S219; R452; K459; R774; N780; R781; L783 |

Also provided herein are fusion proteins comprising the isolated variant Cas9 proteins described herein fused to a heterologous functional domain, with an optional intervening linker, wherein the linker does not interfere with activity of the fusion protein. In some embodiments, the heterologous functional domain acts on DNA or protein, e.g., on chromatin. In some embodiments, the heterologous functional domain is a transcriptional activation domain. In some embodiments, the transcriptional activation domain is from VP64 or NF-κB p65. In some embodiments, the heterologous functional domain is a transcriptional silencer or transcriptional repression domain. In some embodiments, the transcriptional repression domain is a Kruppel-associated box (KRAB) domain, ERF repressor domain (ERD), or mSin3A interaction domain (SID). In some embodiments, the transcriptional silencer is Heterochromatin Protein 1 (HP1), e.g., HP1α or HP1β. In some embodiments, the heterologous functional domain is an enzyme that modifies the methylation state of DNA. In some embodiments, the enzyme that modifies the methylation state of DNA is a DNA methyltransferase (DNMT) or the entirety or the dioxygenase domain of a TET protein, e.g., a catalytic module comprising the cysteine-rich extension and the 2OGFeDO domain encoded by 7 highly conserved exons, e.g., the Tet1 catalytic domain comprising amino acids 1580-2052, Tet2 comprising amino acids 1290-1905 and Tet3 comprising amino acids 966-1678. In some embodiments, the TET protein or TET-derived dioxygenase domain is from TET1. In some embodiments, the heterologous functional domain is an enzyme that modifies a histone subunit. In some embodiments, the enzyme that modifies a histone subunit is a histone acetyltransferase (HAT), histone deacetylase (HDAC), histone methyltransferase (HMT), or histone demethylase. In some embodiments, the heterologous functional domain is a biological tether. In some embodiments, the biological tether is MS2, Csy4 or lambda N protein. In some embodiments, the heterologous functional domain is FokI.

Also provided herein are nucleic acids, isolated nucleic acids encoding the variant Cas9 proteins described herein, as well as vectors comprising the isolated nucleic acids, optionally operably linked to one or more regulatory domains for expressing the variant Cas9 proteins described herein. Also provided herein are host cells, e.g., bacterial, yeast, insect, or mammalian host cells or transgenic animals (e.g., mice), comprising the nucleic acids described herein, and optionally expressing the variant Cas9 proteins described herein.

Also provided herein are isolated nucleic acids encoding the Cas9 variants, as well as vectors comprising the isolated nucleic acids, optionally operably linked to one or more regulatory domains for expressing the variants, and host cells, e.g., mammalian host cells, comprising the nucleic acids, and optionally expressing the variant proteins.

Also provided herein are methods of altering the genome or epigenome of a cell, by expressing in the cell or contacting the cell with variant Cas9 proteins or fusion proteins as described herein, and at least one guide RNA having a region complementary to a selected portion of the genome of the cell with optimal nucleotide spacing at the genomic target site. The methods can include contacting the cell with a nucleic acid encoding the Cas9 protein and the guide RNA, e.g., in a single vector; contacting the cell with a nucleic acid encoding the Cas9 protein and a nucleic acid encoding the guide RNA, e.g., in multiple vectors; and contacting the cell with a complex of purified Cas9 protein and synthetic or purified gRNA, inter alia. In some embodiments, the cell stably expresses one or both of the gRNA or the variant protein/fusion protein, and the other element is transfected or introduced into the cell. For example, the cell may stably express a variant protein or fusion protein as described herein, and the methods can include contacting the cell with a synthetic gRNA, a purified recombinantly produced gRNA, or a nucleic acid encoding the gRNA. In some embodiments, the variant protein or fusion protein comprises one or more of a nuclear localization sequence, cell penetrating peptide sequence, and/or affinity tag.

Also provided herein are methods for altering, e.g., selectively altering, an isolated dsDNA molecule in vitro by contacting the dsDNA with a purified variant protein or fusion protein as described herein, and a guide RNA having a region complementary to a selected portion of the dsDNA molecule.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-E|Identification and characterization of SpCas9 variants bearing mutations in residues that form non-specific DNA contacts. A, Schematic depicting wild-type SpCas9 recognition of the target DNA:sgRNA duplex, based on PDB 4OOG and 4UN3 (adapted from refs. 31 and 32, respectively). B, Characterization of SpCas9 variants that contain alanine substitutions in positions that form hydrogen bonds to the DNA backbone. Wild-type SpCas9 and variants were assessed using the human cell EGFP disruption assay when programmed with a perfectly matched sgRNA or four other sgRNAs that encode mismatches to the target site. Error bars represent s.e.m. for n=3; mean level of background EGFP loss represented by red dashed line (for this panel and panel C). C and D, On-target activities of wild-type SpCas9 and SpCas9-HF1 across 24 sites assessed by EGFP disruption assay (panel C) and 13 endogenous sites by T7E1 assay (panel D). Error bars represent s.e.m. for n=3. E, Ratio of on-target activity of SpCas9-HF1 to wild-type SpCas9 (from panels C and D).

FIG. 2A-C|Genome-wide specificities of wild-type SpCas9 and SpCas9-HF1 with sgRNAs for standard target sites. A, Off-target sites of wild-type SpCas9 and SpCas9-HF1 with eight sgRNAs targeted to endogenous human genes (EMX1 site 1, SEQ ID NO: 280; EMX1 site 2, SEQ ID No: 281; FANCF site 1, SEQ ID NO: 282; FANCF site 2, SEQ ID NO: 283; FANCF site 3, SEQ ID NO: 284; FANCF site 4, SEQ ID NO: 285; RUNX1 site 1, SEQ ID NO: 286; and ZSCAN2 site, SEQ ID NO: 287), as determined by GUIDE-seq. Read counts represent a measure of cleavage frequency at a given site; mismatched positions within the spacer or PAM are highlighted in color. B, Summary of the total number of genome-wide off-target sites identified by GUIDE-seq for wild-type SpCas9 and SpCas9-HF1 from the eight sgRNAs used in panel A. C, Off-target sites identified for wild-type SpCas9 and SpCas9-HF1 for the eight sgRNAs, binned according to the total number of mismatches (within the protospacer and PAM) relative to the on-target site.

FIG. 3A-C|Validation of SpCas9-HF1 specificity improvements by targeted deep sequencing of off-target sites identified by GUIDE-seq. A, Mean on-target percent modification determined by deep sequencing for wild-type SpCas9 and SpCas9-HF1 with six sgRNAs from FIG. 2. Error bars represent s.e.m. for n=3. B, Percentage of deep sequenced on-target sites (EMX1 site 1, SEQ ID NO: 163; EMX1 site 2, SEQ ID NO: 164; FANCF site 1, SEQ ID No: 165; FANCF site 3, SEQ ID No: 167; RUNX1 site 1, SEQ ID No: 169; and ZSCAN2 site, SEQ ID NO: 170) and GUIDE-seq detected off-target sites that contain indel mutations. Triplicate experiments are plotted for wild-type SpCas9, SpCas9-HF1, and control conditions. Filled circles below the x-axis represent replicates for which no insertion or deletion mutations were observed. Off-target sites that could not be amplified by PCR are shown in red text with an asterisk. Hypothesis testing using a one-sided Fisher exact test with pooled read counts found significant differences (p<0.05 after adjusting for multiple comparisons using the Benjamini-Hochberg method) for comparisons between SpCas9-HF1 and the control condition only at EMX1-1 off-target 1 and FANCF-3 off-target 1. Significant differences were also found between wild-type SpCas9 and SpCas9-HF1 at all off-target sites, and between wild-type SpCas9 and the control condition at all off-target sites except RUNX1-1 off-target 2. C, Scatter plot of the correlation between GUIDE-seq read counts (from FIG. 2A) and mean percent modification determined by deep sequencing at on- and off-target cleavage sites with wild-type SpCas9.

FIG. 4A-C|Genome-wide specificities of wild-type SpCas9 and SpCas9-HF1 with sgRNAs for non-standard, repetitive sites. A, GUIDE-seq specificity profiles of wild-type SpCas9 and SpCas9-HF1 using two sgRNAs (VEGFA site 3, SEQ ID No: 288; and VEGFA site 2, SEQ ID NO: 289) known to cleave large numbers of off-target sites (Fu et al., Nat Biotechnol 31, 822-826 (2013); Tsai et al., Nat Biotechnol 33, 187-197 (2015)). GUIDE-seq read counts represent a measure of cleavage efficiency at a given site; mismatched positions within the spacer or PAM are highlighted in color; red circles indicate sites likely to have the indicated bulge (Lin et al., Nucleic Acids Res 42, 7473-7485 (2014)) at the sgRNA-DNA interface; blue circles indicate sites that may have an alternative gapped alignment relative to the one shown (see FIG. 8). B, Summary of the total number of genome-wide off-target sites identified by GUIDE-seq for wild-type SpCas9 and SpCas9-HF1 from the two sgRNAs used in panel A. C, Off-target sites identified with wild-type SpCas9 or SpCas9-HF1 for VEGFA sites 2 and 3, binned according to the total number of mismatches (within the protospacer and PAM) relative to the on-target site. Off-target sites marked with red circles in panel A are not included in these counts; sites marked with blue circles in panel A are counted with the number of mismatches in the non-gapped alignment.

FIG. 5A-D|Activities of SpCas9-HF1 derivatives bearing additional substitutions. A, Human cell EGFP disruption activities of wild-type SpCas9, SpCas9-HF1, and SpCas9-HF1-derivative variants with eight sgRNAs. SpCas9-HF1 harbors N497A, R661A, Q695, and Q926A mutations; HF2=HF1+D1135E; HF3=HF1+L169A; HF4=HF1+Y450A. Error bars represent s.e.m. for n=3; mean level of background EGFP loss represented by the red dashed line. B, Summary of the on-target activity when using SpCas9-HF variants compared to wild-type SpCas9 with the eight sgRNAs from panel a. The median and interquartile range are shown; the interval showing >70% of wild-type activity is highlighted in green. C, Mean percent modification by SpCas9 and HF variants at the FANCF site 2 and VEGFA site 3 on-target sites, as well as off-target sites from FIGS. 2A and 4A resistant to the effects of SpCas9-HF1. Percent modification determined by T7E1 assay; background indel percentages were subtracted for all experiments. Error bars represent s.e.m. for n=3. D, Specificity ratios of wild-type SpCas9 and HF variants with the FANCF site 2 or VEGFA site 3 sgRNAs, plotted as the ratio of on-target to off-target activity (from panel C).

FIG. 7A-D|On-target activity comparisons of wild-type and SpCas9-HF1 with various sgRNAs used for GUIDE-seq experiments. A and C, Mean GUIDE-seq tag integration at the intended on-target site for GUIDE-seq experiments shown in FIGS. 2A and 4A (panels 7A and 7C, respectively), quantified by restriction fragment length polymorphism assay. Error bars represent s.e.m. for n=3. b and d, Mean percent modification at the intended on-target site for GUIDE-seq experiments shown in FIGS. 2A and 4A (panels 7B and 7D, respectively), detected by T7E1 assay. Error bars represent s.e.m. for n=3.

FIG. 12A-D|Altering the PAM recognition specificity of SpCas9-HF1. A, Comparison of the mean percent modification of on-target endogenous human sites by SpCas9-VQR (ref 15) and an improved SpCas9-VRQR using 8 sgRNAs, quantified by T7E1 assay. Both variants are engineered to recognize an NGAN PAM. Error bars represent s.e.m. for n=2 or 3. B, On-target EGFP disruption activities of SpCas9-VQR and SpCas9-VRQR compared to their -HF1 counterparts using eight sgRNAs. Error bars represent s.e.m. for n=3; mean level of background EGFP loss in negative controls represented by the red dashed line. C, Comparison of the mean on-target percent modification by SpCas9-VQR and SpCas9-VRQR compared to their -HF1 variants at eight endogenous human gene sites, quantified by T7E1 assay. Error bars represent s.e.m. for n=3; ND, not detectable. D, Summary of the fold-change in on-target activity when using SpCas9-VQR or SpCas9-VRQR compared to their corresponding -HF1 variants (from panels B and C). The median and interquartile range are shown; the interval showing >70% of wild-type activity is highlighted in green.

FIGS. 13A-B|Activities of wild-type SpCas9, SpCas9-HF1, and wild-type SpCas9 derivatives bearing one or more alanine substitutions at positions that can potentially contact the non-target DNA strand. A and B, Nucleases were assessed using the EGFP disruption assay, with an sgRNA that is perfectly matched to a site in the EGFP gene as well as an sgRNA that is intentionally mismatched at positions 11 and 12 (panel A) or positions 9 and 10 (panel B). Mismatched positions are numbered with position 20 being the most PAM-distal position; the red dashed line represents background levels of EGFP disruption; HF1=SpCas9 with N497A/R661A/Q695A/Q926A substitutions.

FIG. 20|Structural comparison of SpCas9 (top) and SaCas9 (bottom) illustrating the similarity between the positions of the mutations in the quadruple mutant constructs (shown in yellow sphere representation). Also, shown in pink sphere representation are other residues that contact the DNA backbone.

FIGS. 21A-B|Activity of wild-type SaCas9 and SaCas9 derivatives bearing one or more alanine substitutions. A and B, SaCas9 substitutions were directed to positions that may potentially contact the target DNA strand (panel A) or have previously been shown to influence PAM specificity (panel B). Nucleases were assessed using the EGFP disruption assay, with an sgRNA that is perfectly matched to a site in the EGFP gene as well as an sgRNA that is intentionally mismatched at positions 11 and 12. Mismatched positions are numbered with position 20 being the most PAM-distal position; the red dashed line represents background levels of EGFP disruption.

FIGS. 22A-B|Activities of wild-type (WT) SaCas9 and SaCas9 derivatives bearing one or more alanine substitutions at residues that may potentially contact the target DNA strand. A and B, Nucleases were assessed using the EGFP disruption assay, with an sgRNA that is perfectly matched to a site in the EGFP gene ("matched") and with an sgRNA that is intentionally mismatched at positions 19 and 20. Mismatched positions are numbered with position 20 being the most PAM-distal position.

DETAILED DESCRIPTION

A limitation of the CRISPR-Cas9 nucleases is their potential to induce undesired "off-target" mutations at imperfectly matched target sites (see, for example, Tsai et al., Nat Biotechnol. 2015), in some cases with frequencies rivaling those observed at the intended on-target site (Fu et al., Nat Biotechnol. 2013). Previous work with CRISPR-Cas9 nucleases has suggested that reducing the number of sequence-specific interactions between the guide RNA (gRNA) and the spacer region of a target site can reduce mutagenic effects at off-target sites of cleavage in human cells (Fu et al., Nat Biotechnol. 2014).

This was earlier accomplished by truncating gRNAs at their 5' ends by 2 or 3 nts and it was hypothesized that the mechanism of this increased specificity was a decrease in the interaction energy of the gRNA/Cas9 complex so that it was poised with just enough energy to cleave the on-target site, making it less likely to have enough energy to cleave off-target sites where there would presumably be an energetic penalty due to mismatches in the target DNA site (WO2015/099850).

Figure 1A:
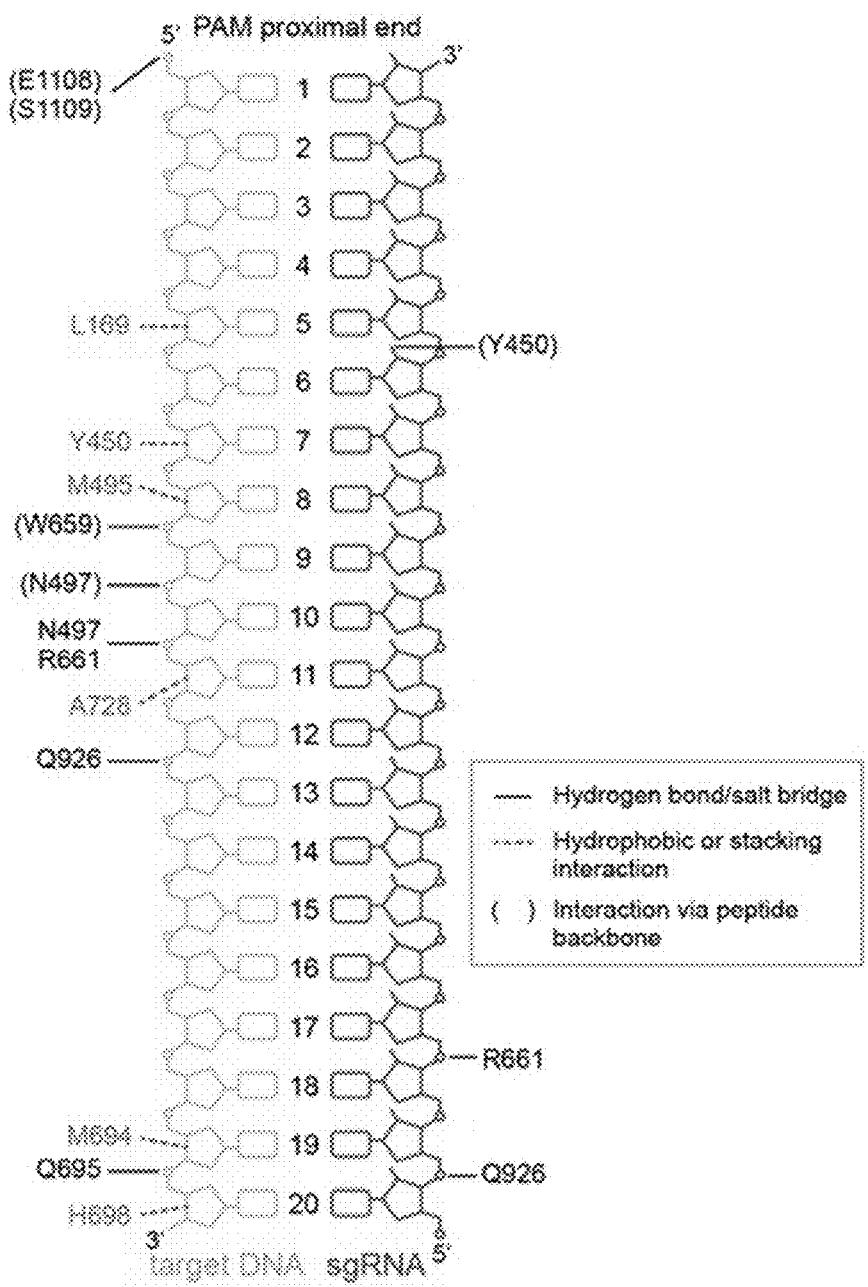
Figure 6A:
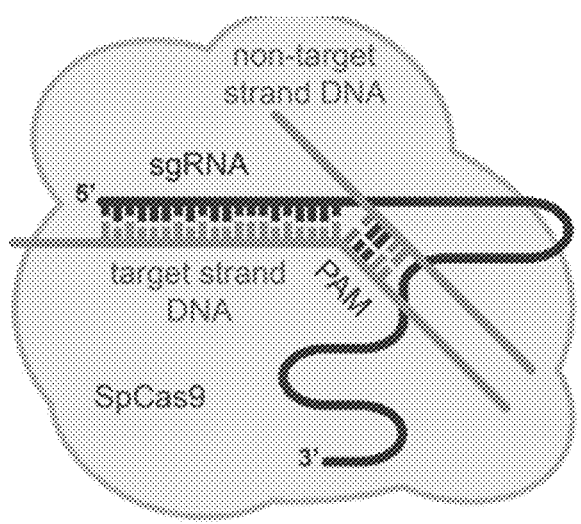
FIG. 6A-B|SpCas9 interaction with the sgRNA and target DNA. A, Schematic illustrating the SpCas9:sgRNA complex, with base pairing between the sgRNA and target DNA. B, Structural representation of the SpCas9:sgRNA complex bound to the target DNA, from PDB: 4UN3 (ref 32). The four residues that form hydrogen bond contacts to the target-strand DNA backbone are highlighted in blue; the HNH domain is hidden for visualization purposes.
Figure 6B:
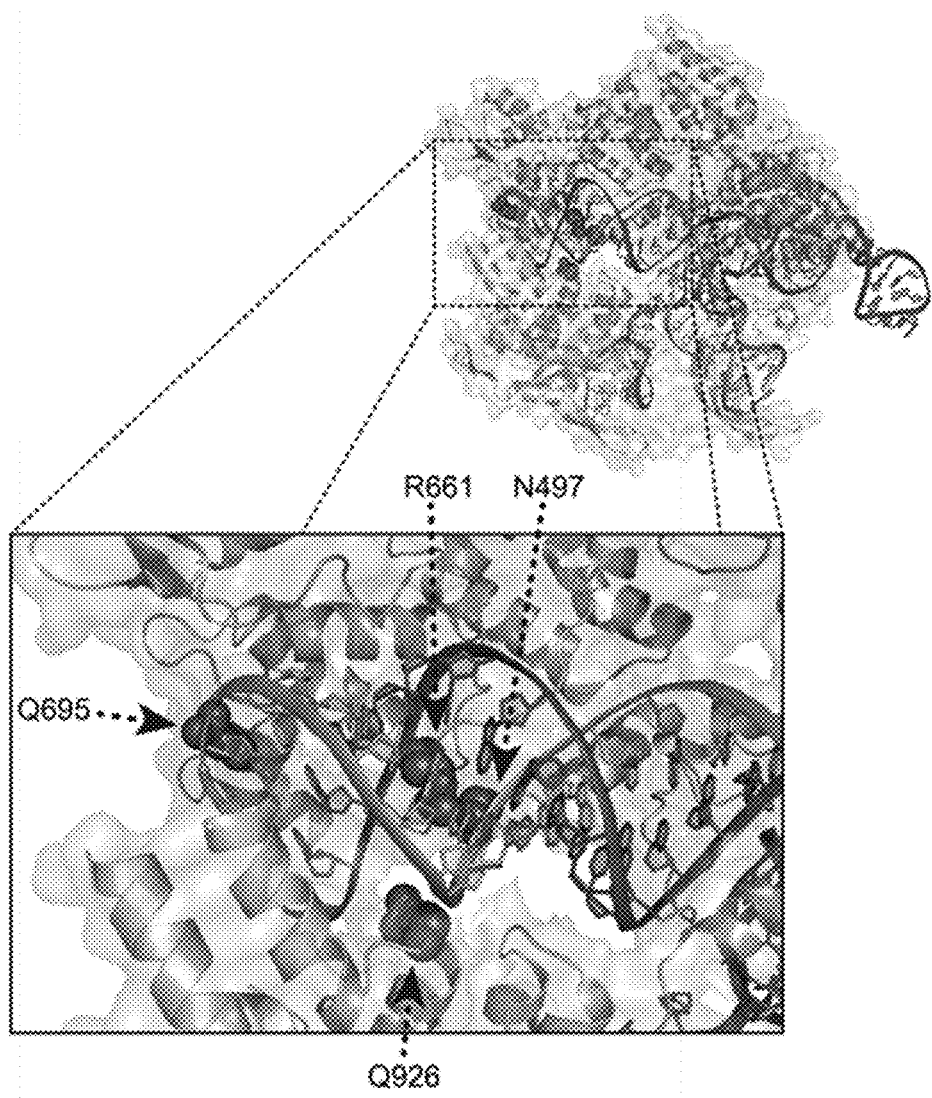

It was hypothesized that off-target effects (at DNA sites that are imperfect matches or mismatches with the intended target site for the guide RNA) of SpCas9 might be minimized by decreasing non-specific interactions with its target DNA site. SpCas9-sgRNA complexes cleave target sites composed of an NGG PAM sequence (recognized by SpCas9) (Deltcheva, E. et al. Nature 471, 602-607 (2011); Jinek, M. et al. Science 337, 816-821 (2012); Jiang, W., et al., Nat Biotechnol 31, 233-239 (2013); Sternberg, S. H., et al., Nature 507, 62-67 (2014)) and an adjacent 20 bp protospacer sequence (which is complementary to the 5' end of the sgRNA) (Jinek, M. et al. Science 337, 816-821 (2012); Jinek, M. et al. Elife 2, e00471 (2013); Mali, P. et al., Science 339, 823-826 (2013); Cong, L. et al., Science 339, 819-823 (2013)). It was previously theorized that the SpCas9-sgRNA complex may possess more energy than is needed for recognizing its intended target DNA site, thereby enabling cleavage of mismatched off-target sites (Fu, Y., et al., Nat Biotechnol 32, 279-284 (2014)). One can envision that this property might be advantageous for the intended role of Cas9 in adaptive bacterial immunity, giving it the capability to cleave foreign sequences that may become mutated. This excess energy model is also supported by previous studies demonstrating that off-target effects can be reduced (but not eliminated) by decreasing SpCas9 concentration (Hsu, P. D. et al. Nat Biotechnol 31, 827-832 (2013); Pattanayak, V. et al. Nat Biotechnol 31, 839-843 (2013)) or by reducing the complementarity length of the sgRNA (Fu, Y., et al., Nat Biotechnol 32, 279-284 (2014), although other interpretations for this effect have also been proposed (Josephs, E. A. et al. Nucleic Acids Res 43, 8924-8941 (2015); Sternberg, S. H., et al. Nature 527, 110-113 (2015); Kiani, S. et al. Nat Methods 12, 1051-1054 (2015))). Structural data suggests that the SpCas9-sgRNA-target DNA complex may be stabilized by several SpCas9-mediated DNA contacts, including direct hydrogen bonds made by four SpCas9 residues (N497, R661, Q695, Q926) to the phosphate backbone of the target DNA strand (Nishimasu, H. et al. Cell 156, 935-949 (2014); Anders, C., et al. Nature 513, 569-573 (2014)) (FIG. 1a and FIGS. 6a and 6b). The present inventors envisioned that disruption of one or more of these contacts might energetically poise the SpCas9-sgRNA complex at a level just sufficient to retain robust on-target activity but with a diminished ability to cleave mismatched off-target sites.

As described herein, Cas9 proteins can be engineered to show increased specificity, theoretically by reducing the binding affinity of Cas9 for DNA. Several variants of the widely used *Streptococcus pyogenes* Cas9 (SpCas9) were engineered by introducing individual alanine substitutions into various residues in SpCas9 that might be expected to interact with phosphates on the DNA backbone using structural information, bacterial selection-based directed evolution, and combinatorial design. The variants were further tested for cellular activity using a robust *E. coli*-based screening assay to assess the cellular activities of these variants; in this bacterial system, cell survival depended on cleavage and subsequent destruction of a selection plasmid containing a gene for the toxic gyrase poison ccdB and a 23 base pair sequence targeted by a gRNA and SpCas9, and led to identification of residues that were associated with retained or lost activity. In addition, another SpCas9 variant was identified and characterized, which exhibited improved target specificity in human cells.

Furthermore, activities of single alanine substitution mutants of SpCas9 as assessed in the bacterial cell-based system indicated that survival percentages between 50-100% usually indicated robust cleavage, whereas 0% survival indicated that the enzyme had been functionally compromised. Additional mutations of SpCas9 were then assayed in bacteria to include: R63A, R66A, R69A, R70A, R71A, Y72A, R74A, R75A, K76A, N77A, R78A, R115A, H160A, K163A, R165A, L169A, R403A, T404A, F405A, N407A, R447A, N497A, I448A, Y450A, S460A, M495A, K510A, Y515A, R661A, M694A, Q695A, H698A, Y1013A, V1015A, R1122A, K1123A, K1124A, K1158A, K1185A, K1200A, S1216A, Q1221A, K1289A, R1298A, K1300A, K1325A, R1333A, K1334A, R1335A, and T1337A. With the exception of 2 mutants (R69A and F405A) that had <5% survival in bacteria, all of these additional single mutations appeared to have little effect on the on-target activity of SpCas9 (>70% survival in the bacterial screen).

To further determine whether the variants of Cas9 identified in the bacterial screen functioned efficiently in human cells, various alanine substitution Cas9 mutants were tested using a human U2OS cell-based EGFP-disruption assay. In this assay, successful cleavage of a target site in the coding sequence of a single integrated, constitutively expressed EGFP gene led to the induction of indel mutations and disruption of EGFP activity, which was quantitatively assessed by flow cytometry (see, for example, Reyon et al., Nat Biotechnol. 2012 May; 30(5):460-5).

These experiments show that the results obtained in the bacterial cell-based assay correlate well with nuclease activities in human cells, suggesting that these engineering strategies could be extended to Cas9s from other species and different cells. Thus these findings provide support for SpCas9 and SaCas9 variants, referred to collectively herein as "variants" or "the variants".

All of the variants described herein can be rapidly incorporated into existing and widely used vectors, e.g., by simple site-directed mutagenesis, and because they require only a small number of mutations, the variants should also work with other previously described improvements to the SpCas9 platform (e.g., truncated sgRNAs (Tsai et al., Nat Biotechnol 33, 187-197 (2015); Fu et al., Nat Biotechnol 32, 279-284 (2014)), nickase mutations (Mali et al., Nat Biotechnol 31, 833-838 (2013); Ran et al., Cell 154, 1380-1389 (2013)), FokI-dCas9 fusions (Guilinger et al., Nat Biotechnol 32, 577-582 (2014); Tsai et al., Nat Biotechnol 32, 569-576 (2014); WO2014144288); and engineered CRISPR-Cas9 nucleases with altered PAM specificities (Kleinstiver et al., Nature. 2015 Jul. 23; 523(7561):481-5).

Thus, provided herein are Cas9 variants, including SpCas9 variants. The SpCas9 wild type sequence is as follows:

(SEQ ID NO: 1)

```
          10         20         30         40
  MDKKYSIGLD IGTNSVGWAV ITDEYKVPSK KFKVLGNTDR 50         60         70         80
  HSIKKNLIGA LLFDSGETAE ATRLKRTARR RYTRRKNRIC 90        100        110        120
  YLQEIFSNEM AKVDDSFFHR LEESFLVEED KKHERHPIFG 130        140        150        160
  NIVDEVAYHE KYPTIYHLRK KLVDSTDKAD LRLIYLALAH 170        180        190        200
  MIKFRGHFLI EGDLNPDNSD VDKLFIQLVQ TYNQLFEENP 210        220        230        240
  INASGVDAKA ILSARLSKSR RLENLIAQLP GEKKNGLFGN 250        260        270        280
  LIALSLGLTP NFKSNFDLAE DAKLQLSKDT YDDDLDNLLA 290        300        310        320
  QIGDQYADLF LAAKNLSDAI LLSDILRVNT EITKAPLSAS 330        340        350        360
  MIKRYDEHHQ DLTLLKALVR QQLPEKYKEI FFDQSKNGYA 370        380        390        400
  GYIDGGASQE EFYKFIKPIL EKMDGTEELL VKLNREDLLR 410        420        430        440
  KQRTFDNGSI PHQIHLGELH AILRRQEDFY PFLKDNREKI 450        460        470        480
  EKILTFRIPY YVGPLARGNS RFAWMTRKSE ETITPWNFEE 490        500        510        520
  VVDKGASAQS FIERMTNFDK NLPNEKVLPK HSLLYEYFTV 530        540        550        560
  YNELTKVKYV TEGMRKPAFL SGEQKKAIVD LLFKTNRKVT 570        580        590        600
  VKQLKEDYFK KIECFDSVEI SGVEDRFNAS LGTYHDLLKI 610        620        630        640
  IKDKDFLDNE ENEDILEDIV LTLTLFEDRE MIEERLKTYA 650        660        670        680
  HLFDDKVMKQ LKRRRYTGWG RLSRKLINGI RDKQSGKTIL 690        700        710        720
  DFLKSDGFAN RNFMQLIHDD SLTFKEDIQK AQVSGQGDSL 730        740        750        760
  HEHIANLAGS PAIKKGILQT VKVVDELVKV MGRHKPENIV 770        780        790        800
  IEMARENQTT QKGQKNSRER MKRIEEGIKE LGSQILKEHP 810        820        830        840
  VENTQLQNEK LYLYYLQNGR DMYVDQELDI NRLSDYDVDH 850        860        870        880
  IVPQSFLKDD SIDNKVLTRS DKNRGKSDNV PSEEVVKKMK 890        900        910        920
  NYWRQLLNAK LITQRKFDNL TKAERGGLSE LDKAGFIKRQ 930        940        950        960
  LVETRQITKH VAQILDSRMN TKYDENDKLI REVKVITLKS 970        980        990       1000
  KLVSDFRKDF QFYKVREINN YHHAHDAYLN AVVGTALIKK 1010       1020       1030       1040
  YPKLESEFVY GDYKVYDVRK MIAKSEQEIG KATAKYFFYS 1050       1060       1070       1080
  NIMNFFKTEI TLANGEIRKR PLIETNGETG EIVWDKGRDF
```

```
              1090       1100       1110       1120
         ATVRKVLSMP QVNIVKKTEV QTGGFSKESI LPKRNSDKLI 1130       1140       1150       1160
         ARKKDWDPKK YGGFDSPTVA YSVLVVAKVE KGKSKKLKSV 1170       1180       1190       1200
         KELLGITIME RSSFEKNPID FLEAKGYKEV KKDLIIKLPK 1210       1220       1230       1240
         YSLFELENGR KRMLASAGEL QKGNELALPS KYVNFLYLAS 1250       1260       1270       1280
         HYEKLKGSPE DNEQKQLFVE QHKHYLDEII EQISEFSKRV 1290       1300       1310       1320
         ILADANLDKV LSAYNKHRDK PIREQAENII HLFTLTNLGA 1330       1340       1350       1360
         PAAFKYFDTT IDRKRYTSTK EVLDATLIHQ SITGLYETRI

DLSQLGGD
```

The SpCas9 variants described herein can include the amino acid sequence of SEQ ID NO:1, with mutations (i.e., replacement of the native amino acid with a different amino acid, e.g., alanine, glycine, or serine), at one or more of the following positions: N497, R661, Q695, Q926 (or at positions analogous thereto). In some embodiments, the SpCas9 variants are at least 80%, e.g., at least 85%, 90%, or 95% identical to the amino acid sequence of SEQ ID NO:1, e.g., have differences at up to 5%, 10%, 15%, or 20% of the residues of SEQ ID NO:1 replaced, e.g., with conservative mutations, in addition to the mutations described herein. In preferred embodiments, the variant retains desired activity of the parent, e.g., the nuclease activity (except where the parent is a nickase or a dead Cas9), and/or the ability to interact with a guide RNA and target DNA).

To determine the percent identity of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90% or 100%. The nucleotides at corresponding amino acid positions or nucleotide positions are then compared. When a position in the first sequence is occupied by the same nucleotide as the corresponding position in the second sequence, then the molecules are identical at that position (as used herein nucleic acid "identity" is equivalent to nucleic acid "homology"). The percent identity between the two sequences is a function of the number of identical positions shared by the sequences, taking into account the number of gaps, and the length of each gap, which need to be introduced for optimal alignment of the two sequences. Percent identity between two polypeptides or nucleic acid sequences is determined in various ways that are within the skill in the art, for instance, using publicly available computer software such as Smith Waterman Alignment (Smith, T. F. and M. S. Waterman (1981) J Mol Biol 147:195-7); "BestFit" (Smith and Waterman, Advances in Applied Mathematics, 482-489 (1981)) as incorporated into GeneMatcher Plus™, Schwarz and Dayhof (1979) Atlas of Protein Sequence and Structure, Dayhof, M. O., Ed, pp 353-358; BLAST program (Basic Local Alignment Search Tool; (Altschul, S. F., W. Gish, et al. (1990) J Mol Biol 215: 403-10), BLAST-2, BLAST-P, BLAST-N, BLAST-X, WU-BLAST-2, ALIGN, ALIGN-2, CLUSTAL, or Megalign (DNASTAR) software. In addition, those skilled in the art can determine appropriate parameters for measuring alignment, including any algorithms needed to achieve maximal alignment over the length of the sequences being compared. In general, for proteins or nucleic acids, the length of comparison can be any length, up to and including full length (e.g., 5%, 10%, 20%, 30%, 40%, 50%, 60%, 70%, 80%, 90%, 95%, or 100%). For purposes of the present compositions and methods, at least 80% of the full length of the sequence is aligned.

For purposes of the present invention, the comparison of sequences and determination of percent identity between two sequences can be accomplished using a Blossum 62 scoring matrix with a gap penalty of 12, a gap extend penalty of 4, and a frameshift gap penalty of 5.

Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

In some embodiments, the SpCas9 variants include one of the following sets of mutations: N497A/R661A/Q695/Q926A (quadruple alanine mutant); Q695A/Q926A (double alanine mutant); R661A/Q695A/Q926A and N497A/Q695A/Q926A (triple alanine mutants). In some embodiments, the additional substitution mutations at L169 and/or Y450 might be added to these double-, triple-, and quadruple mutants or added to single mutants bearing substitutions at Q695 or Q926. In some embodiments, the mutants have alanine in place of the wild type amino acid. In some embodiments, the mutants have any amino acid other than arginine or lysine (or the native amino acid).

In some embodiments, the SpCas9 variants also include one of the following mutations, which reduce or destroy the nuclease activity of the Cas9: D10, E762, D839, H983, or D986 and H840 or N863, e.g., D10A/D10N and H840A/H840N/H840Y, to render the nuclease portion of the protein catalytically inactive; substitutions at these positions could be alanine (as they are in Nishimasu al., Cell 156, 935-949 (2014)), or other residues, e.g., glutamine, asparagine, tyrosine, serine, or aspartate, e.g., E762Q, H983N, H983Y, D986N, N863D, N863S, or N863H (see WO 2014/152432). In some embodiments, the variant includes mutations at D10A or H840A (which creates a single-strand nickase), or mutations at D10A and H840A (which abrogates nuclease activity; this mutant is known as dead Cas9 or dCas9).

The SpCas9 N497A/R661A/Q695A/R926A mutations have analogous residues in *Staphylococcus aureus* Cas9 (SaCas9); see FIG. 20. Mutations to the residues contacting the DNA or RNA backbone are expected to increase the specificity of SaCas9 as we've observed for SpCas9. Thus, also provided herein are SaCas9 variants.

The SaCas9 wild type sequence is as follows:

```
                                            (SEQ ID NO: 2)
              10         20         30         40
         MKRNYILGLD IGITSVGYGI IDYETRDVID AGVRLFKEAN 50         60         70         80
         VENNEGRRSK RGARRLKRRR RHRIQRVKKL LFDYNLLTDH 90        100        110        120
         SELSGINPYE ARVKGLSQKL SEEEFSAALL HLAKRRGVHN 130        140        150        160
         VNEVEEDTGN ELSTKEQISR NSKALEEKYV AELQLERLKK
```

```
         170        180        190        200
DGEVRGSINR FKTSDYVKEA KQLLKVQKAY HQLDQSFIDT 210        220        230        240
YIDLLETRRT YYEGPGEGSP FGWKDIKEWY EMLMGHCTYF 250        260        270        280
PEELRSVKYA YNADLYNALN DLNNLVITRD ENEKLEYYEK 290        300        310        320
FQIIENVFKQ KKKPTLKQIA KEILVNEEDI KGYRVTSTGK 330        340        350        360
PEFTNLKVYH DIKDITARKE IIENAELLDQ IAKILTIYQS 370        380        390        400
SEDIQEELTN LNSELTQEEI EQISNLKGYT GTHNLSLKAI 410        420        430        440
NLILDELWHT NDNQIAIFNR LKLVPKKVDL SQQKEIPTTL 450        460        470        480
VDDFILSPVV KRSFIQSIKV INAIIKKYGL PNDIIIELAR 490        500        510        520
EKNSKDAQKM INEMQKRNRQ TNERIEEIIR TTGKENAKYL 530        540        550        560
IEKIKLHDMQ EGKCLYSLEA IPLEDLLNNP FNYEVDHIIP 570        580        590        600
RSVSFDNSFN NKVLVKQEEN SKKGNRTPFQ YLSSSDSKIS 610        620        630        640
YETFKKHILN LAKGKGRISK TKKEYLLEER DINRFSVQKD 650        660        670        680
FINRNLVDTR YATRGLMNLL RSYFRVNNLD VKVKSINGGF 690        700        710        720
TSFLRRKWKF KKERNKGYKH HAEDALIIAN ADFIFKEWKK 730        740        750        760
LDKAKKVMEN QMFEEKQAES MPEIETEQEY KEIFITPHQI 770        780        790        800
KHIKDFKDYK YSHRVDKKPN RELINDTLYS TRKDDKGNTL 810        820        830        840
IVNNLNGLYD KDNDKLKKLI NKSPEKLLMY HHDPQTYQKL 850        860        870        880
KLIMEQYGDE KNPLYKYYEE TGNYLTKYSK KDNGPVIKKI 890        900        910        920
KYYGNKLNAH LDITDDYPNS RNKVVKLSLK PYRFDVYLDN 930        940        950        960
GVYKFVTVKN LDVIKKENYY EVNSKCYEEA KKLKKISNQA 970        980        990       1000
EFIASFYNND LIKINGELYR VIGVNNDLLN RIEVNMIDIT 1010       1020       1030       1040
YREYLENMND KRPPRIIKTI ASKTQSIKKY STDILGNLYE

1050
VKSKKHPQII KKG
```

SaCas9 variants described herein include the amino acid sequence of SEQ ID NO:2, with mutations at one, two, three, four, five, or all six of the following positions: Y211, W229, R245, T392, N419, and/or R654, e.g., comprising a sequence that is at least 80% identical to the amino acid sequence of SEQ ID NO:2 with mutations at one, two, three, four five or six of the following positions: Y211, W229, R245, T392, N419, and/or R654.

In some embodiments, the variant SaCas9 proteins also comprise one or more of the following mutations: Y211A; W229A; Y230A; R245A; T392A; N419A; L446A; Y651A; R654A; D786A; T787A; Y789A; T882A; K886A; N888A; A889A; L909A; N985A; N986A; R991A; R1015A; N44A; R45A; R51A; R55A; R59A; R60A; R116A; R165A; N169A; R208A; R209A; Y211A; T238A; Y239A; K248A; Y256A; R314A; N394A; Q414A; K57A; R61A; H111A; K114A; V164A; R165A; L788A; S790A; R792A; N804A; Y868A; K870A; K878A; K879A; K881A; Y897A; R901A; K906A.

In some embodiments, variant SaCas9 proteins comprise one or more of the following additional mutations: Y211A, W229A, Y230A, R245A, T392A, N419A, L446A, Y651A, R654A, D786A, T787A, Y789A, T882A, K886A, N888A, A889A, L909A, N985A, N986A, R991A, R1015A, N44A, R45A, R51A, R55A, R59A, R60A, R116A, R165A, N169A, R208A, R209A, Y211A, T238A, Y239A, K248A, Y256A, R314A, N394A, Q414A, K57A, R61A, H111A, K114A, V164A, R165A, L788A, S790A, R792A, N804A, Y868A, K870A, K878A, K879A, K881A, Y897A, R901A, K906A.

In some embodiments, the variant SaCas9 proteins comprise multiple substitution mutations: R245/T392/N419/R654 and Y221/R245/N419/R654 (quadruple variant mutants); N419/R654, R245/R654, Y221/R654, and Y221/N419 (double mutants); R245/N419/R654, Y211/N419/R654, and T392/N419/R654 (triple mutants). In some embodiments the mutants contain alanine in place of the wild type amino acid.

In some embodiments, the variant SaCas9 proteins also comprise mutations at E782K, K929R, N968K, and/or R1015H. For example, the KKH variant (E782K/N968K/R1015H), the KRH variant (E782K/K929R/R1015H), or the KRKH variant (E782K/K929R/N968K/R1015H)]

In some embodiments, the variant SaCas9 proteins also comprise one or more mutations that decrease nuclease activity selected from the group consisting of mutations at D10, E477, D556, H701, or D704; and at H557 or N580.

In some embodiments, the mutations are: (i) D10A or D10N, (ii) H557A, H557N, or H557Y, (iii) N580A, and/or (iv) D556A.

Also provided herein are isolated nucleic acids encoding the Cas9 variants, vectors comprising the isolated nucleic acids, optionally operably linked to one or more regulatory domains for expressing the variant proteins, and host cells, e.g., mammalian host cells, comprising the nucleic acids, and optionally expressing the variant proteins.

The variants described herein can be used for altering the genome of a cell; the methods generally include expressing the variant proteins in the cells, along with a guide RNA having a region complementary to a selected portion of the genome of the cell. Methods for selectively altering the genome of a cell are known in the art, see, e.g., U.S. Pat. No. 8,993,233; US 20140186958; U.S. Pat. No. 9,023,649; WO/2014/099744; WO 2014/089290; WO2014/144592; WO144288; WO2014/204578; WO2014/152432; WO2115/099850; U.S. Pat. No. 8,697,359; US20160024529; US20160024524; US20160024523; US20160024510; US20160017366; US20160017301; US20150376652; US20150356239; US20150315576; US20150291965; US20150252358; US20150247150; US20150232883; US20150232882; US20150203872; US20150191744; US20150184139; US20150176064; US20150167000; US20150166969; US20150159175; US20150159174; US20150093473; US20150079681; US20150067922; US20150056629; US20150044772; US20150024500; US20150024499; US20150020223; US20140356867; US20140295557; US20140273235; US20140273226;

US20140273037; US20140189896; US20140113376; US20140093941; US20130330778; US20130288251; US20120088676; US20110300538; US20110236530; US20110217739; US20110002889; US20100076057; US20110189776; US20110223638; US20130130248; US20150050699; US20150071899; US20150050699; US20150045546; US20150031134; US20150024500; US20140377868; US20140357530; US20140349400; US20140335620; US20140335063; US20140315985; US20140310830; US20140310828; US20140309487; US20140304853; US20140298547; US20140295556; US20140294773; US20140287938; US20140273234; US20140273232; US20140273231; US20140273230; US20140271987; US20140256046; US20140248702; US20140242702; US20140242700; US20140242699; US20140242664; US20140234972; US20140227787; US20140212869; US20140201857; US20140199767; US20140189896; US20140186958; US20140186919; US20140186843; US20140179770; US20140179006; US20140170753; WO/2008/108989; WO/2010/054108; WO/2012/164565; WO/2013/098244; WO/2013/176772; US 20150071899; Makarova et al., "Evolution and classification of the CRISPR-Cas systems" 9(6) Nature Reviews Microbiology 467-477 (1-23) (June 2011); Wiedenheft et al., "RNA-guided genetic silencing systems in bacteria and archaea" 482 Nature 331-338 (Feb. 16, 2012); Gasiunas et al., "Cas9-crRNA ribonucleoprotein complex mediates specific DNA cleavage for adaptive immunity in bacteria" 109(39) Proceedings of the National Academy of Sciences USA E2579-E2586 (Sep. 4, 2012); Jinek et al., "A Programmable Dual-RNA-Guided DNA Endonuclease in Adaptive Bacterial Immunity" 337 Science 816-821 (Aug. 17, 2012); Carroll, "A CRISPR Approach to Gene Targeting" 20(9) Molecular Therapy 1658-1660 (September 2012); U.S. Appl. No. 61/652,086, filed May 25, 2012; Al-Attar et al., Clustered Regularly Interspaced Short Palindromic Repeats (CRISPRs): The Hallmark of an Ingenious Antiviral Defense Mechanism in Prokaryotes, Biol Chem. (2011) vol. 392, Issue 4, pp. 277-289; Hale et al., Essential Features and Rational Design of CRISPR RNAs That Function With the Cas RAMP Module Complex to Cleave RNAs, Molecular Cell, (2012) vol. 45, Issue 3, 292-302.

The variant proteins described herein can be used in place of or in addition to any of the Cas9 proteins described in the foregoing references, or in combination with mutations described therein. In addition, the variants described herein can be used in fusion proteins in place of the wild-type Cas9 or other Cas9 mutations (such as the dCas9 or Cas9 nickase described above) as known in the art, e.g., a fusion protein with a heterologous functional domains as described in U.S. Pat. No. 8,993,233; US 20140186958; U.S. Pat. No. 9,023,649; WO/2014/099744; WO 2014/089290; WO2014/144592; WO144288; WO2014/204578; WO2014/152432; WO2115/099850; U.S. Pat. No. 8,697,359; US2010/0076057; US2011/0189776; US2011/0223638; US2013/0130248; WO/2008/108989; WO/2010/054108; WO/2012/164565; WO/2013/098244; WO/2013/176772; US20150050699; US 20150071899 and WO 2014/124284. For example, the variants, preferably comprising one or more nuclease-reducing, -altering, or -killing mutation, can be fused on the N or C terminus of the Cas9 to a transcriptional activation domain or other heterologous functional domains (e.g., transcriptional repressors (e.g., KRAB, ERD, SID, and others, e.g., amino acids 473-530 of the ets2 repressor factor (ERF) repressor domain (ERD), amino acids 1-97 of the KRAB domain of KOX1, or amino acids 1-36 of the Mad mSIN3 interaction domain (SID); see Beerli et al., PNAS USA 95:14628-14633 (1998)) or silencers such as Heterochromatin Protein 1 (HP1, also known as swi6), e.g., HP1α or HP1β; proteins or peptides that could recruit long non-coding RNAs (lncRNAs) fused to a fixed RNA binding sequence such as those bound by the MS2 coat protein, endoribonuclease Csy4, or the lambda N protein; enzymes that modify the methylation state of DNA (e.g., DNA methyltransferase (DNMT) or TET proteins); or enzymes that modify histone subunits (e.g., histone acetyltransferases (HAT), histone deacetylases (HDAC), histone methyltransferases (e.g., for methylation of lysine or arginine residues) or histone demethylases (e.g., for demethylation of lysine or arginine residues)) as are known in the art can also be used. A number of sequences for such domains are known in the art, e.g., a domain that catalyzes hydroxylation of methylated cytosines in DNA. Exemplary proteins include the Ten-Eleven-Translocation (TET)1-3 family, enzymes that converts 5-methylcytosine (5-mC) to 5-hydroxymethylcytosine (5-hmC) in DNA.

Sequences for human TET1-3 are known in the art and are shown in the following table:

| | GenBank Accession Nos. | |
|---|---|---|
| Gene | Amino Acid | Nucleic Acid |
| TET1 | NP_085128.2 | NM_030625.2 |
| TET2* | NP_001120680.1 (var 1) | NM_001127208.2 |
| | NP_060098.3 (var 2) | NM_017628.4 |
| TET3 | NP_659430.1 | NM_144993.1 |

*Variant (1) represents the longer transcript and encodes the longer isoform (a). Variant (2) differs in the 5' UTR and in the 3' UTR and coding sequence compared to variant 1. The resulting isoform (b) is shorter and has a distinct C- terminus compared to isoform a.

In some embodiments, all or part of the full-length sequence of the catalytic domain can be included, e.g., a catalytic module comprising the cysteine-rich extension and the 2OGFeDO domain encoded by 7 highly conserved exons, e.g., the Tet1 catalytic domain comprising amino acids 1580-2052, Tet2 comprising amino acids 1290-1905 and Tet3 comprising amino acids 966-1678. See, e.g., FIG. 1 of Iyer et al., Cell Cycle. 2009 Jun. 1; 8(11):1698-710. Epub 2009 Jun. 27, for an alignment illustrating the key catalytic residues in all three Tet proteins, and the supplementary materials thereof (available at ftp site ftp.ncbi.nih-.gov/pub/aravind/DONS/supplementary_material_DON-S.html) for full length sequences (see, e.g., seq 2c); in some embodiments, the sequence includes amino acids 1418-2136 of Tet1 or the corresponding region in Tet2/3.

Other catalytic modules can be from the proteins identified in Iyer et al., 2009.

In some embodiments, the heterologous functional domain is a biological tether, and comprises all or part of (e.g., DNA binding domain from) the MS2 coat protein, endoribonuclease Csy4, or the lambda N protein. These proteins can be used to recruit RNA molecules containing a specific stem-loop structure to a locale specified by the dCas9 gRNA targeting sequences. For example, a dCas9 variant fused to MS2 coat protein, endoribonuclease Csy4, or lambda N can be used to recruit a long non-coding RNA (lncRNA) such as XIST or HOTAIR; see, e.g., Keryer-Bibens et al., Biol. Cell 100:125-138 (2008), that is linked to the Csy4, MS2 or lambda N binding sequence. Alternatively, the Csy4, MS2 or lambda N protein binding sequence can be linked to another protein, e.g., as described in Keryer-Bibens et al., supra, and the protein can be targeted to the dCas9 variant binding site using the methods and compositions described herein. In some embodiments, the Csy4 is catalytically inactive. In some embodiments, the Cas9 variant, preferably a dCas9 variant, is fused to FokI as described in U.S. Pat. No. 8,993,233; US 20140186958; U.S. Pat. No. 9,023,649; WO/2014/099744; WO 2014/089290; WO2014/144592; WO144288; WO2014/204578; WO2014/152432; WO2115/099850; U.S. Pat. No. 8,697,359; US2010/0076057; US2011/0189776; US2011/0223638; US2013/0130248; WO/2008/108989; WO/2010/054108; WO/2012/164565; WO/2013/098244; WO/2013/176772; US20150050699; US 20150071899 and WO 2014/204578.

In some embodiments, the fusion proteins include a linker between the dCas9 variant and the heterologous functional domains. Linkers that can be used in these fusion proteins (or between fusion proteins in a concatenated structure) can include any sequence that does not interfere with the function of the fusion proteins. In preferred embodiments, the linkers are short, e.g., 2-20 amino acids, and are typically flexible (i.e., comprising amino acids with a high degree of freedom such as glycine, alanine, and serine). In some embodiments, the linker comprises one or more units consisting of GGGS (SEQ ID NO:3) or GGGGS (SEQ ID NO:4), e.g., two, three, four, or more repeats of the GGGS (SEQ ID NO:5) or GGGGS (SEQ ID NO:6) unit. Other linker sequences can also be used.

In some embodiments, the variant protein includes a cell-penetrating peptide sequence that facilitates delivery to the intracellular space, e.g., HIV-derived TAT peptide, penetratins, transportans, or hCT derived cell-penetrating peptides, see, e.g., Caron et al., (2001) Mol Ther. 3(3):310-8; Langel, Cell-Penetrating Peptides: Processes and Applications (CRC Press, Boca Raton Fla. 2002); El-Andaloussi et al., (2005) Curr Pharm Des. 11(28):3597-611; and Deshayes et al., (2005) Cell Mol Life Sci. 62(16):1839-49.

Cell penetrating peptides (CPPs) are short peptides that facilitate the movement of a wide range of biomolecules across the cell membrane into the cytoplasm or other organelles, e.g. the mitochondria and the nucleus. Examples of molecules that can be delivered by CPPs include therapeutic drugs, plasmid DNA, oligonucleotides, siRNA, peptide-nucleic acid (PNA), proteins, peptides, nanoparticles, and liposomes. CPPs are generally 30 amino acids or less, are derived from naturally or non-naturally occurring protein or chimeric sequences, and contain either a high relative abundance of positively charged amino acids, e.g. lysine or arginine, or an alternating pattern of polar and non-polar amino acids. CPPs that are commonly used in the art include Tat (Frankel et al., (1988) Cell. 55:1189-1193, Vives et al., (1997) J. Biol. Chem. 272:16010-16017), penetratin (Derossi et al., (1994) J. Biol. Chem. 269:10444-10450), polyarginine peptide sequences (Wender et al., (2000) Proc. Natl. Acad. Sci. USA 97:13003-13008, Futaki et al., (2001) J. Biol. Chem. 276:5836-5840), and transportan (Pooga et al., (1998) Nat. Biotechnol. 16:857-861).

CPPs can be linked with their cargo through covalent or non-covalent strategies. Methods for covalently joining a CPP and its cargo are known in the art, e.g. chemical cross-linking (Stetsenko et al., (2000) J. Org. Chem. 65:4900-4909, Gait et al. (2003) Cell. Mol. Life. Sci. 60:844-853) or cloning a fusion protein (Nagahara et al., (1998) Nat. Med. 4:1449-1453). Non-covalent coupling between the cargo and short amphipathic CPPs comprising polar and non-polar domains is established through electrostatic and hydrophobic interactions.

CPPs have been utilized in the art to deliver potentially therapeutic biomolecules into cells. Examples include cyclosporine linked to polyarginine for immunosuppression (Rothbard et al., (2000) Nature Medicine 6(11):1253-1257), siRNA against cyclin B1 linked to a CPP called MPG for inhibiting tumorigenesis (Crombez et al., (2007) Biochem Soc. Trans. 35:44-46), tumor suppressor p53 peptides linked to CPPs to reduce cancer cell growth (Takenobu et al., (2002) Mol. Cancer Ther. 1(12):1043-1049, Snyder et al., (2004) PLoS Biol. 2:E36), and dominant negative forms of Ras or phosphoinositol 3 kinase (PI3K) fused to Tat to treat asthma (Myou et al., (2003) J. Immunol. 171:4399-4405).

CPPs have been utilized in the art to transport contrast agents into cells for imaging and biosensing applications. For example, green fluorescent protein (GFP) attached to Tat has been used to label cancer cells (Shokolenko et al., (2005) DNA Repair 4(4):511-518). Tat conjugated to quantum dots have been used to successfully cross the blood-brain barrier for visualization of the rat brain (Santra et al., (2005) Chem. Commun. 3144-3146). CPPs have also been combined with magnetic resonance imaging techniques for cell imaging (Liu et al., (2006) Biochem. and Biophys. Res. Comm. 347(1):133-140). See also Ramsey and Flynn, Pharmacol Ther. 2015 Jul. 22. pii: 50163-7258(15)00141-2.

Alternatively, or in addition, the variant proteins can include a nuclear localization sequence, e.g., SV40 large T antigen NLS (PKKKRRV (SEQ ID NO:7)) and nucleoplasmin NLS (KRPAATKKAGQAKKKK (SEQ ID NO:8)). Other NLSs are known in the art; see, e.g., Cokol et al., EMBO Rep. 2000 Nov. 15; 1(5): 411-415; Freitas and Cunha, Curr Genomics. 2009 December; 10(8): 550-557.

In some embodiments, the variants include a moiety that has a high affinity for a ligand, for example GST, FLAG or hexahistidine sequences. Such affinity tags can facilitate the purification of recombinant variant proteins.

For methods in which the variant proteins are delivered to cells, the proteins can be produced using any method known in the art, e.g., by in vitro translation, or expression in a suitable host cell from nucleic acid encoding the variant protein; a number of methods are known in the art for producing proteins. For example, the proteins can be produced in and purified from yeast, E. coli, insect cell lines, plants, transgenic animals, or cultured mammalian cells; see, e.g., Palomares et al., "Production of Recombinant Proteins: Challenges and Solutions," Methods Mol Biol. 2004; 267: 15-52. In addition, the variant proteins can be linked to a moiety that facilitates transfer into a cell, e.g., a lipid nanoparticle, optionally with a linker that is cleaved once the protein is inside the cell. See, e.g., LaFountaine et al., Int J Pharm. 2015 Aug. 13; 494(1):180-194.

Expression Systems

To use the Cas9 variants described herein, it may be desirable to express them from a nucleic acid that encodes them. This can be performed in a variety of ways. For example, the nucleic acid encoding the Cas9 variant can be cloned into an intermediate vector for transformation into prokaryotic or eukaryotic cells for replication and/or expression. Intermediate vectors are typically prokaryote vectors, e.g., plasmids, or shuttle vectors, or insect vectors, for storage or manipulation of the nucleic acid encoding the Cas9 variant for production of the Cas9 variant. The nucleic acid encoding the Cas9 variant can also be cloned into an expression vector, for administration to a plant cell, animal cell, preferably a mammalian cell or a human cell, fungal cell, bacterial cell, or protozoan cell.

To obtain expression, a sequence encoding a Cas9 variant is typically subcloned into an expression vector that contains a promoter to direct transcription. Suitable bacterial and eukaryotic promoters are well known in the art and described, e.g., in Sambrook et al., Molecular Cloning, A Laboratory Manual (3d ed. 2001); Kriegler, Gene Transfer and Expression: A Laboratory Manual (1990); and Current Protocols in Molecular Biology (Ausubel et al., eds., 2010). Bacterial expression systems for expressing the engineered protein are available in, e.g., *E. coli, Bacillus* sp., and *Salmonella* (Palva et al., 1983, Gene 22:229-235). Kits for such expression systems are commercially available. Eukaryotic expression systems for mammalian cells, yeast, and insect cells are well known in the art and are also commercially available.

The promoter used to direct expression of a nucleic acid depends on the particular application. For example, a strong constitutive promoter is typically used for expression and purification of fusion proteins. In contrast, when the Cas9 variant is to be administered in vivo for gene regulation, either a constitutive or an inducible promoter can be used, depending on the particular use of the Cas9 variant. In addition, a preferred promoter for administration of the Cas9 variant can be a weak promoter, such as HSV TK or a promoter having similar activity. The promoter can also include elements that are responsive to transactivation, e.g., hypoxia response elements, Gal4 response elements, lac repressor response element, and small molecule control systems such as tetracycline-regulated systems and the RU-486 system (see, e.g., Gossen & Bujard, 1992, Proc. Natl. Acad. Sci. USA, 89:5547; Oligino et al., 1998, Gene Ther., 5:491-496; Wang et al., 1997, Gene Ther., 4:432-441; Neering et al., 1996, Blood, 88:1147-55; and Rendahl et al., 1998, Nat. Biotechnol., 16:757-761).

In addition to the promoter, the expression vector typically contains a transcription unit or expression cassette that contains all the additional elements required for the expression of the nucleic acid in host cells, either prokaryotic or eukaryotic. Atypical expression cassette thus contains a promoter operably linked, e.g., to the nucleic acid sequence encoding the Cas9 variant, and any signals required, e.g., for efficient polyadenylation of the transcript, transcriptional termination, ribosome binding sites, or translation termination. Additional elements of the cassette may include, e.g., enhancers, and heterologous spliced intronic signals.

The particular expression vector used to transport the genetic information into the cell is selected with regard to the intended use of the Cas9 variant, e.g., expression in plants, animals, bacteria, fungus, protozoa, etc. Standard bacterial expression vectors include plasmids such as pBR322 based plasmids, pSKF, pET23D, and commercially available tag-fusion expression systems such as GST and LacZ.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

The vectors for expressing the Cas9 variants can include RNA Pol III promoters to drive expression of the guide RNAs, e.g., the H1, U6 or 7SK promoters. These human promoters allow for expression of Cas9 variants in mammalian cells following plasmid transfection.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with the gRNA encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., 1989, J. Biol. Chem., 264:17619-22; Guide to Protein Purification, in Methods in Enzymology, vol. 182 (Deutscher, ed., 1990)). Transformation of eukaryotic and prokaryotic cells are performed according to standard techniques (see, e.g., Morrison, 1977, J. Bacteriol. 132:349-351; Clark-Curtiss & Curtiss, Methods in Enzymology 101:347-362 (Wu et al., eds, 1983).

Any of the known procedures for introducing foreign nucleotide sequences into host cells may be used. These include the use of calcium phosphate transfection, polybrene, protoplast fusion, electroporation, nucleofection, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the Cas9 variant.

The present methods can also include modifying gDNA by introducing purified Cas9 protein with a gRNA into cells as a ribonuclear protein (RNP) complex, as well as introducing a gRNA plus mRNA encoding the Cas9 protein. The gRNA can be synthetic gRNA or a nucleic acid (e.g., in an expression vector) encoding the guide RNA.

The present invention also includes the vectors and cells comprising the vectors.

EXAMPLES

The invention is further described in the following examples, which do not limit the scope of the invention described in the claims.

Methods

Bacterial-Based Positive Selection Assay for Evolving SpCas9 Variants

Competent *E. coli* BW25141(λDE3)[23] containing a positive selection plasmid (with embedded target site) were transformed with Cas9/sgRNA-encoding plasmids. Following a 60-minute recovery in SOB media, transformations were plated on LB plates containing either chloramphenicol (non-selective) or chloramphenicol+10 mM arabinose (selective).

To identify additional positions that might be critical for genome wide target specificity, a bacterial selection system previously used to study properties of homing endonucleases (hereafter referred to as the positive selection) (Chen & Zhao, Nucleic Acids Res 33, e154 (2005); Doyon et al., J Am Chem Soc 128, 2477-2484 (2006)) was adapted.

In the present adaptation of this system, Cas9-mediated cleavage of a positive selection plasmid encoding an inducible toxic gene enables cell survival, due to subsequent degradation and loss of the linearized plasmid. After establishing that SpCas9 can function in the positive selection system, both wild-type and the variants were tested for their ability to cleave a selection plasmid harboring a target site selected from the known human genome. These variants were introduced into bacteria with a positive selection plasmid containing a target site and plated on selective medium. Cleavage of the positive selection plasmid was estimated by calculating the survival frequency: colonies on selective plates/colonies on non-selective plates (see FIG. 1, 5-6).

A subset of plasmids used in this study (sequences shown below)

| Name | Addgene ID | Description |
|---|---|---|
| JDS246 | 43861 | CMV-T7-humanSpCas9-NLS-3xFLAG |
| VP12 | pending | CMV-T7-humanSpCas9-HF1(N497A, R661A, Q695A, Q926A)-NLS-3xFLAG |
| MSP2135 | pending | CMV-T7-humanSpCas9-HF2(N497A, R661A, Q695A, Q926A, D1135E)-NLS-3xFLAG |
| MSP2133 | pending | CMV-T7-humanSpCas9-HF4(Y450A, N497A, R661A, Q695A, Q926A)-NLS-3xFLAG |
| MSP469 | 65771 | CMV-T7-humanSpCas9-VQR(D1135V, R1335Q, T1337R)-NLS-3xFLAG |
| MSP2440 | pending | CMV-T7-humanSpCas9-VQR-HF1(N497A, R661A, Q695A, Q926A, D1135V, R1335Q, T1337R)-NLS-3xFLAG |
| BPK2797 | pending | CMV-T7-humanSpCas9-VRQR(D1135V, G1218R, R1335Q, T1337R)-NLS-3xFLAG |
| MSP2443 | pending | CMV-T7-humanSpCas9-VRQR-HF1(N497A, R661A, Q695A, Q926A, D1135V, G1218R, R1335Q, T1337R)-NLS-3xFLAG |
| BPK1520 | 65777 | U6-BsmBIcassette-Sp-sgRNA |

Human Cell Culture and Transfection

U2OS.EGFP cells harboring a single integrated copy of a constitutively expressed EGFP-PEST reporter gene' were cultured in Advanced DMEM media (Life Technologies) supplemented with 10% FBS, 2 mM GlutaMax (Life Technologies), penicillin/streptomycin, and 400 µg/ml of G418 at 37° C. with 5% $CO_2$. Cells were co-transfected with 750 ng of Cas9 plasmid and 250 ng of sgRNA plasmid (unless otherwise noted) using the DN-100 program of a Lonza 4D-nucleofector according to the manufacturer's protocols. Cas9 plasmid transfected together with an empty U6 promoter plasmid was used as a negative control for all human cell experiments. (see FIGS. 2, 7-10).

Human Cell EGFP Disruption Assay

EGFP disruption experiments were performed as previously described[16]. Transfected cells were analyzed for EGFP expression ~52 hours post-transfection using a Fortessa flow cytometer (BD Biosciences). Background EGFP loss was gated at approximately 2.5% for all experiments (see FIGS. 2, 7).

T7E1 Assay, Targeted Deep-Sequencing, and GUIDE-Seq to Quantify Nuclease-Induced Mutation Rates T7E1 assays were performed as previously described for human cells (Kleinstiver, B. P. et al., Nature 523, 481-485 (2015)). For U2OS.EGFP human cells, genomic DNA was extracted from transfected cells ~72 hours post-transfection using the Agencourt DNAdvance Genomic DNA Isolation Kit (Beckman Coulter Genomics). Roughly 200 ng of purified PCR product was denatured, annealed, and digested with T7E1 (New England BioLabs). Mutagenesis frequencies were quantified using a Qiaxcel capillary electrophoresis instrument (QIagen), as previously described for human cells (Kleinstiver et al., Nature 523, 481-485 (2015); Reyon et al., Nat Biotechnol 30, 460-465 (2012)).

GUIDE-seq experiments were performed as previously described (Tsai et al., Nat Biotechnol 33, 187-197 (2015)). Briefly, phosphorylated, phosphorothioate-modified double-stranded oligodeoxynucleotides (dsODNs) were transfected into U2OS cells with Cas9 nuclease along with Cas9 and sgRNA expression plasmids, as described above. dsODN-specific amplification, high-throughput sequencing, and mapping were performed to identify genomic intervals containing DSB activity. For wild-type versus double or quadruple mutant variant experiments, off-target read counts were normalized to the on-target read counts to correct for sequencing depth differences between samples. The normalized ratios for wild-type and variant SpCas9 were then compared to calculate the fold-change in activity at off-target sites. To determine whether wild-type and SpCas9 variant samples for GUIDE-seq had similar oligo tag integration rates at the intended target site, restriction fragment length polymorphism (RFLP) assays were performed by amplifying the intended target loci with Phusion Hot-Start Flex from 100 ng of genomic DNA (isolated as described above). Roughly 150 ng of PCR product was digested with 20 U of NdeI (New England BioLabs) for 3 hours at 37° C. prior to clean-up using the Agencourt Ampure XP kit. RFLP results were quantified using a Qiaxcel capillary electrophoresis instrument (QIagen) to approximate oligo tag integration rates. T7E1 assays were performed for a similar purpose, as described above.

Example 1

One potential solution to address targeting specificity of CRISPR-Cas9 RNA guided gene editing would be to engineer Cas9 variants with novel mutations.

Based on these earlier results, it was hypothesized (without wishing to be bound by theory) that the specificity of CRISPR-Cas9 nucleases might be significantly increased by reducing the non-specific binding affinity of Cas9 for DNA, mediated by the binding to the phosphate groups on the DNA or hydrophobic or base stacking interactions with the DNA. This approach would have the advantage of not decreasing the length of the target site recognized by the gRNA/Cas9 complex, as in the previously described truncated gRNA approach. It was reasoned that non-specific binding affinity of Cas9 for DNA might be reduced by mutating amino acid residues that contact phosphate groups on the target DNA.

An analogous approach has been used to create variants of non-Cas9 nucleases such as TALENs (see, for example, Guilinger et al., Nat. Methods. 11: 429 (2014)).

In an initial test of the hypothesis, the present inventors attempted to engineer a reduced affinity variant of the widely used S. pyogenes Cas9 (SpCas9) by introducing individual alanine substitutions into various residues in SpCas9 that might be expected to interact with phosphates on the DNA backbone. An E. coli-based screening assay was used to assess the activities of these variants (Kleinstiver et al., Nature. 2015 Jul. 23; 523(7561):481-5). In this bacterial system, cell survival depended on cleavage (and subsequent destruction) of a selection plasmid containing a gene for the toxic gyrase poison ccdB and a 23 base pair sequence targeted by a gRNA and SpCas9. Results of this experiment identified residues that retained or lost activity (Table 1).

TABLE 1

Activities of single alanine substitution mutants of Cas9 as assessed in the bacterial cell-based system shown in FIG. 1.

| mutation | % survival | mutation | % survival | mutation | % survival |
|---|---|---|---|---|---|
| R63A | 84.2 | Q926A | 53.3 | K1158A | 46.5 |
| R66A | 0 | K1107A | 47.4 | K1185A | 19.3 |
| R70A | 0 | E1108A | 40.0 | K1200A | 24.5 |
| R74A | 0 | S1109A | 96.6 | S1216A | 100.4 |
| R78A | 56.4 | K1113A | 51.8 | Q1221A | 98.8 |
| R165A | 68.9 | R1114A | 47.3 | K1289A | 55.2 |
| R403A | 85.2 | S1116A | 73.8 | R1298A | 28.6 |
| N407A | 97.2 | K1118A | 48.7 | K1300A | 59.8 |
| N497A | 72.6 | D1135A | 67.2 | K1325A | 52.3 |
| K510A | 79.0 | S1136A | 69.2 | R1333A | 0 |
| Y515A | 34.1 | K1151A | 0 | K1334A | 87.5 |
| R661A | 75.0 | K1153A | 76.6 | R1335A | 0 |
| Q695A | 69.8 | K1155A | 44.6 | T1337A | 64.6 |

Survival percentages between 50-100% usually indicated robust cleavage, whereas 0% survival indicated that the enzyme has been functionally compromised. Additional mutations that were assayed in bacteria (but are not shown in the table above) include: R69A, R71A, Y72A, R75A, K76A, N77A, R115A, H160A, K163A, L169A, T404A, F405A, R447A, I448A, Y450A, S460A, M495A, M694A, H698A, Y1013A, V1015A, R1122A, K1123A, and K1124A. With the exception of R69A and F405A (which had <5% survival in bacteria), all of these additional single mutations appeared to have little effect on the on-target activity of SpCas9 (>70% survival in the bacterial screen).

15 different SpCas9 variants bearing all possible single, double, triple and quadruple combinations of the N497A, R661A, Q695A, and Q926A mutations were constructed to test whether contacts made by these residues might be dispensable for on-target activity (FIG. 1b). For these experiments, a previously described human cell-based assay was used in which cleavage and induction of insertion or deletion mutations (indels) by non-homologous end-joining (NHEJ)-mediated repair within a single integrated EGFP reporter gene leads to loss of cell fluorescence (Reyon, D. et al., Nat Biotechnol. 30, 460-465, 2012). Using a EGFP-targeted sgRNA previously shown to efficiently disrupt EGFP expression in human cells when paired with wild-type SpCas9 (Fu, Y. et al., Nat Biotechnol 31, 822-826 (2013), all 15 SpCas9 variants possessed EGFP disruption activities comparable to that of wild-type SpCas9 (FIG. 1b, grey bars). Thus, substitution of one or all of these residues did not reduce on-target cleavage efficiency of SpCas9 with this EGFP-targeted sgRNA.

Next, experiments were performed to assess the relative activities of all 15 SpCas9 variants at mismatched target sites. To do this, the EGFP disruption assay was repeated with derivatives of the EGFP-targeted sgRNA used in the previous experiment that contain pairs of substituted bases at positions 13 and 14, 15 and 16, 17 and 18, and 18 and 19 (numbering starting with 1 for the most PAM-proximal base and ending with 20 for the most PAM-distal base; FIG. 1b). This analysis revealed that one of the triple mutants (R661A/Q695A/Q926A) and the quadruple mutant (N497A/R661A/Q695A/Q926A) both showed levels of EGFP disruption equivalent to that of background with all four of the mismatched sgRNAs (FIG. 1b, colored bars). Notably, among the 15 variants, those possessing the lowest activities with the mismatched sgRNAs all harbored the Q695A and Q926A mutations. Based on these results and similar data from an experiment using a sgRNA for another EGFP target site, the quadruple mutant (N497A/R661A/Q695A/Q926A) was chosen for additional analysis and designated it as SpCas9-HF1 (for high-fidelity variant #1).

On-Target Activities of SpCas9-HF1

Figure 1E:
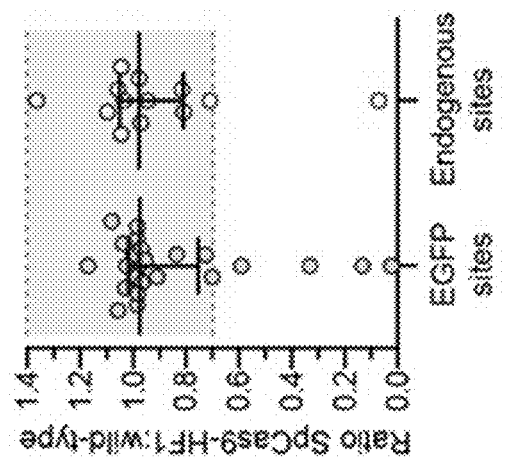
Figure 1D:
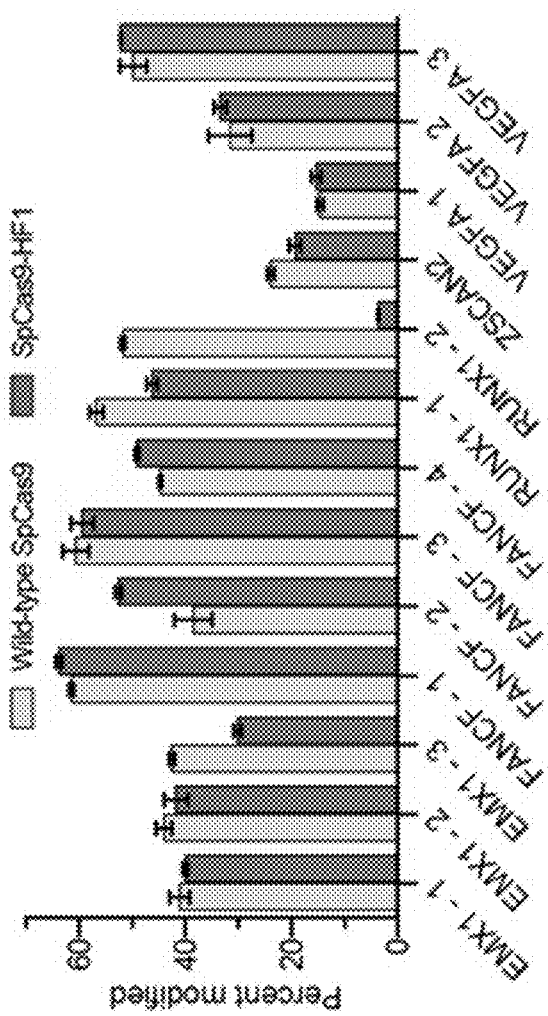

To determine how robustly SpCas9-HF1 functions at a larger number of on-target sites, direct comparisons were performed between this variant and wild-type SpCas9 using additional sgRNAs. In total, 37 different sgRNAs were tested: 24 targeted to EGFP (assayed with the EGFP disruption assay) and 13 targeted to endogenous human gene targets (assayed using the T7 Endonuclease I (T7EI) mismatch assay). 20 of the 24 sgRNAs tested with the EGFP disruption assay (FIG. 1c) and 12 of the 13 sgRNAs tested on endogenous human gene sites (FIG. 1d) showed activities with SpCas9-HF1 that were at least 70% as active as wild-type SpCas9 with the same sgRNA (FIG. 1e). Indeed, SpCas9-HF1 showed highly comparable activities (90-140%) to wild-type SpCas9 with the vast majority of sgRNAs (FIG. 1e). Three of the 37 sgRNAs tested showed essentially no activity with SpCas9-HF1 and examination of these target sites did not suggest any obvious differences in the characteristics of these sequences compared to those for which high activities were seen (Table 3). Overall, SpCas9-HF1 possessed comparable activities (greater than 70% of wild-type SpCas9 activities) for 86% (32/37) of the sgRNAs tested.

TABLE 3

List of sgRNA targets

| Prep Name | Name | Spacer length (nt) | Spacer Sequence | SEQ ID NO: | Sequence with extended PAM | SEQ ID NO: |
|---|---|---|---|---|---|---|
| | | | S. pyogenes sgRNAs | | | |
| | | | EGFP | | | |
| FYF1 320 | NGG site 1 | 20 | GGGCACGGGC AGCTTGCCGG | 9. | GGGCACGGGCAGCTTGC CGGTGGT | 10. |

TABLE 3-continued

List of sgRNA targets

| Prep Name | Name | Spacer length (nt) | Spacer Sequence | SEQ ID NO: | Sequence with extended PAM | SEQ ID NO: |
|---|---|---|---|---|---|---|
| FYF1 641 | NGG site 1 | 18 | GCACGGGCAGCTTGCCGG | 11. | GCACGGGCAGCTTGCCG GTGGT | 12. |
| CK10 12 | NGG site 1-13&14 | 20 | GGGCACccGCAGCTTGCCGG | 13. | GGGCACccGCAGCTTGC CGGTGGT | 14. |
| FYF1 429 | NGG site 1-15&16 | 20 | GGGCtgGGGCAGCTTGCCGG | 15. | GGGCtgGGGCAGCTTGC CGGTGGT | 16. |
| FYF1 430 | NGG site 1-17&18 | 20 | GGcgACGGGCAGCTTGCCGG | 17. | GGcgACGGGCAGCTTGC CGGTGGT | 18. |
| FYF1 347 | NGG site 1-18&19 | 20 | GccCACGGGCAGCTTGCCGG | 19. | GccCACGGGCAGCTTGC CGGTGGT | 20. |
| BPK1 345 | NGG site 2 | 20 | GTCGCCCTCGAACTTCACCT | 21. | GTCGCCCTCGAACTTCA CCTCGGC | 22. |
| BPK1 350 | NGG site 3 | 20 | GTAGGTCAGGGTGGTCACGA | 23. | GTAGGTCAGGGTGGTCA CGAGGGT | 24. |
| BPK1 353 | NGG site 4 | 20 | GGCGAGGGCGATGCCACCTA | 25. | GGCGAGGGCGATGCCA CCTACGGC | 26. |
| MSP7 92 | NGG site 5 | 20 | GGTCGCCACCATGGTGAGCA | 27. | GGTCGCCACCATGGTGA GCAAGGG | 28. |
| MSP7 95 | NGG site 6 | 20 | GGTCAGGGTGGTCACGAGGG | 29. | GGTCAGGGTGGTCACGA GGGTGGG | 30. |
| FYF1 328 | NGG site 7 | 20 | GGTGGTGCAGATGAACTTCA | 31. | GGTGGTGCAGATGAACT TCAGGGT | 32. |
| JAF1 001 | NGG site 7 | 17 | GGTGCAGATGAACTTCA | 33. | GGTGCAGATGAACTTCA GGGT | 34. |
| BPK1 365 | NGG site 8 | 20 | GTTGGGGTCTTTGCTCAGGG | 35. | GTTGGGGTCTTTGCTCA GGGCGGA | 36. |
| MSP7 94 | NGG site 9 | 20 | GGTGGTCACGAGGGTGGGCC | 37. | GGTGGTCACGAGGGTGG GCCAGGG | 38. |
| FYF1 327 | NGG site 10 | 20 | GATGCCGTTCTTCTGCTTGT | 39. | GATGCCGTTCTTCTGCTT GTCGGC | 40. |
| JAF9 97 | NGG site 10 | 17 | GCCGTTCTTCTGCTTGT | 41. | GCCGTTCTTCTGCTTGTC GGC | 42. |
| BPK1 347 | NGG site 11 | 20 | GTCGCCACCATGGTGAGCAA | 43. | GTCGCCACCATGGTGAG CAAGGGC | 44. |
| BPK1 369 | NGG site 12 | 20 | GCACTGCACGCCGTAGGTCA | 45. | GCACTGCACGCCGTAGG TCAGGGT | 46. |
| MSP2 545 | NGG site 13 | 20 | GTGAACCGCATCGAGCTGAA | 47. | GTGAACCGCATCGAGCT GAAGGGC | 48. |
| MSP2 546 | NGG site 14 | 20 | GAAGGGCATCGACTTCAAGG | 49. | GAAGGGCATCGACTTCA AGGAGGA | 50. |
| MSP2 547 | NGG site 15 | 20 | GCTTCATGTGGTCGGGGTAG | 51. | GCTTCATGTGGTCGGGG TAGCGGC | 52. |
| MSP2 548 | NGG site 16 | 20 | GCTGAAGCACTGCACGCCGT | 53. | GCTGAAGCACTGCACGC CGTAGGT | 54. |
| MSP2 549 | NGG site 17 | 20 | GCCGTCGTCCTTGAAGAAGA | 55. | GCCGTCGTCCTTGAAGA AGATGGT | 56. |

TABLE 3-continued

List of sgRNA targets

| Prep Name | Name | Spacer length (nt) | Spacer Sequence | SEQ ID NO: | Sequence with extended PAM | SEQ ID NO: |
|---|---|---|---|---|---|---|
| MSP2 550 | NGG site 18 | 20 | GACCAGGATGGGCACCACCC | 57. | GACCAGGATGGGCACCACCCCGGT | 58. |
| MSP2 551 | NGG site 19 | 20 | GACGTAGCCTTCGGGCATGG | 59. | GACGTAGCCTTCGGGCATGGCGGA | 60. |
| MSP2 553 | NGG site 20 | 20 | GAAGTTCGAGGGCGACACCC | 61. | GAAGTTCGAGGGCGACACCCTGGT | 62. |
| MSP2 554 | NGG site 21 | 20 | GAGCTGGACGGCGACGTAAA | 63. | GAGCTGGACGGCGACGTAAACGGC | 64. |
| MSP2 555 | NGG site 22 | 20 | GGCATCGCCCTCGCCCTCGC | 65. | GGCATCGCCCTCGCCCTCGCCGGA | 66. |
| MSP2 556 | NGG site 23 | 20 | GGCCACAAGTTCAGCGTGTC | 67. | GGCCACAAGTTCAGCGTGTCCGGC | 68. |
| FYF1 331 | NGG site 24 | 20 | GGGCGAGGAGCTGTTCACCG | 69. | GGGCGAGGAGCTGTTCACCGGGGT | 70. |
| FYF1 560 | NGG site 24 | 18 | GCGAGGAGCTGTTCACCG | 71. | GCGAGGAGCTGTTCACCGGGGT | 72. |
| BPK1 348 | NGG site 25-no 5' G | 20 | CCTCGAACTTCACCTCGGCG | 73. | CCTCGAACTTCACCTCGGCGCGGG | 74. |
| BPK1 349 | NGG site 25-mm 5' G | 20 | GCTCGAACTTCACCTCGGCG | 75. | GCTCGAACTTCACCTCGGCGCGGG | 76. |
| BPK1 351 | NGG site 26-no 5' G | 20 | CAACTACAAGACCCGCGCCG | 77. | CAACTACAAGACCCGCGCCGAGGT | 78. |
| BPK1 352 | NGG site 26-mm 5' G | 20 | GAACTACAAGACCCGCGCCG | 79. | GAACTACAAGACCCGCGCCGAGGT | 80. |
| BPK1 373 | NGG site 27-no 5' G | 20 | CGCTCCTGGACGTAGCCTTC | 81. | CGCTCCTGGACGTAGCCTTCGGGC | 82. |
| BPK1 375 | NGG site 27-mm 5' G | 20 | GGCTCCTGGACGTAGCCTTC | 83. | CGCTCCTGGACGTAGCCTTCGGGC | 84. |
| BPK1 377 | NGG site 28-no 5' G | 20 | AGGGCGAGGAGCTGTTCACC | 85. | AGGGCGAGGAGCTGTTCACCGGGG | 86. |
| BPK1 361 | NGG site 28-mm 5' G | 20 | GGGGCGAGGAGCTGTTCACC | 87. | GGGGCGAGGAGCTGTTCACCGGGG | 88. |
| BPK1 468 | NGAA site 1 | 20 | GTTCGAGGGCGACACCCTGG | 89. | GTTCGAGGGCGACACCCTGGTGAA | 90. |
| MSP8 07 | NGAA site 2 | 20 | GTTCACCAGGGTGTCGCCCT | 91. | GTTCACCAGGGTGTCGCCCTCGAA | 92. |
| MSP1 70 | NGAC site 1 | 20 | GCCCACCCTCGTGACCACCC | 93. | GCCCACCCTCGTGACCACCCCTGAC | 94. |
| MSP7 90 | NGAC site 2 | 20 | GCCCTTGCTCACCATGGTGG | 95. | GCCCTTGCTCACCATGGTGGCGAC | 96. |
| MSP1 71 | NGAT site 1 | 20 | GTCGCCGTCCAGCTCGACCA | 97. | GTCGCCGTCCAGCTCGACCACCAGGAT | 98. |
| MSP1 69 | NGAT site 2 | 20 | GTGTCCGGCGAGGGCGAGGG | 99. | GTGTCCGGCGAGGGCGAGGGCGAT | 100. |

TABLE 3-continued

List of sgRNA targets

| Prep Name | Name | Spacer length (nt) | Spacer Sequence | SEQ ID NO: | Sequence with extended PAM | SEQ ID NO: |
|---|---|---|---|---|---|---|
| MSP1 68 | NGAG site 1 | 20 | GGGGTGGTGCCCATCCTGGT | 101. | GGGGTGGTGCCCATCCTGGTCGAG | 102. |
| MSP3 66 | NGAG site 2 | 20 | GCCACCATGGTGAGCAAGGG | 103. | GCCACCATGGTGAGCAAGGGCGAG | 104. |

Endogenous genes

EMX1

| FYF1 548 | NGG site 1 | 20 | GAGTCCGAGCAGAAGAAGAA | 105. | GAGTCCGAGCAGAAGAAGAAGGGC | 106. |
| MSP8 09 | NGG site 2 | 20 | GTCACCTCCAATGACTAGGG | 107. | GTCACCTCCAATGACTAGGGTGGG | 108. |
| VC47 5 | NGG site 3 | 20 | GGGAAGACTGAGGCTACATA | 109. | GGGAAGACTGAGGCTACATAGGGT | 110. |
| MSP8 14 *1 | NGA site 1 | 20 | GCCACGAAGCAGGCCAATGG | 111. | GCCACGAAGCAGGCCAATGGGGAG | 112. |

FANCF

| DR34 8 | NGG site 1 | 20 | GGAATCCCTTCTGCAGCACC | 113. | GGAATCCCTTCTGCAGCACCTGGA | 114. |
| MSP8 15 | NGG site 2 | 20 | GCTGCAGAAGGGATTCCATG | 115. | GCTGCAGAAGGGATTCCATGAGGT | 116. |
| MSP8 16 | NGG site 3 | 20 | GGCGGCTGCACAACCAGTGG | 117. | GGCGGCTGCACAACCAGTGGAGGC | 118. |
| MSP8 17 | NGG site 4 | 20 | GCTCCAGAGCCGTGCGAATG | 119. | GCTCCAGAGCCGTGCGAATGGGGC | 120. |
| MSP8 18 *2 | NGA site 1 | 20 | GAATCCCTTCTGCAGCACCT | 121. | GAATCCCTTCTGCAGCACCTGGAT | 122. |
| MSP8 20 *3 | NGA site 2 | 20 | GCGGCGGCTGCACAACCAGT | 123. | GCGGCGGCTGCACAACCAGTGGAG | 124. |
| MSP8 85 *4 | NGA site 3 | 20 | GGTTGTGCAGCCGCCGCTCC | 125. | GGTTGTGCAGCCGCCGCTCCAGAG | 126. |

RUNX1

| MSP8 22 | NGG site 1 | 20 | GCATTTTCAGGAGGAAGCGA | 127. | GCATTTTCAGGAGGAAGCGATGGC | 128. |
| MSP8 25 | NGG site 2 | 20 | GGGAGAAGAAAGAGAGATGT | 129. | GGGAGAAGAAAGAGAGATGTAGGG | 130. |
| MSP8 26 *5 | NGA site 1 | 20 | GGTGCATTTTCAGGAGGAAG | 131. | GGTGCATTTTCAGGAGGAAGCGAT | 132. |
| MSP8 28 *6 | NGA site 2 | 20 | GAGATGTAGGGCTAGAGGGG | 133. | GAGATGTAGGGCTAGAGGGGTGAG | 134. |
| MSP1 725 | NGAA site 1 | 20 | GGTATCCAGCAGAGGGGAGA | 135. | GGTATCCAGCAGAGGGGAGAAGAA | 136. |
| MSP1 726 | NGAA site 2 | 20 | GAGGCATCTCTGCACCGAGG | 137. | GAGGCATCTCTGCACCGAGGTGAA | 138. |
| MSP1 728 | NGAC site 1 | 20 | GAGGGGTGAGGCTGAAACAG | 139. | GAGGGGTGAGGCTGAAACAGTGAC | 140. |
| MSP1 730 | NGAC site 2 | 20 | GAGCAAAAGTAGATATTACA | 141. | GAGCAAAAGTAGATATTACAAGAC | 142. |
| MSP1 732 | NGAT site 1 | 20 | GGAATTCAAACTGAGGCATA | 143. | GGAATTCAAACTGAGGCATATGAT | 144. |

TABLE 3-continued

List of sgRNA targets

| Prep Name | Name | Spacer length (nt) | Spacer Sequence | SEQ ID NO: | Sequence with extended PAM | SEQ ID NO: |
|---|---|---|---|---|---|---|
| MSP8 29 | NGAT site 2 | 20 | GCAGAGGGGA GAAGAAAGAG | 145. | GCAGAGGGGAGAAGAA AGAGAGAT | 146. |
| MSP1 734 | NGAG site 1 | 20 | GCACCGAGGC ATCTCTGCAC | 147. | GCACCGAGGCATCTCTG CACCGAG | 148. |
| MSP8 28 | NGAG site 2 | 20 | GAGATGTAGG GCTAGAGGGG | 149. | GAGATGTAGGGCTAGA GGGGTGAG | 150. |

ZSCAN2

| Prep Name | Name | Spacer length (nt) | Spacer Sequence | SEQ ID NO: | Sequence with extended PAM | SEQ ID NO: |
|---|---|---|---|---|---|---|
| NN67 5 | NGG site | 20 | GTGCGGCAAG AGCTTCAGCC | 151. | GTGCGGCAAGAGCTTC AGCCGGGG | 152. |

VEGFA

| Prep Name | Name | Spacer length (nt) | Spacer Sequence | SEQ ID NO: | Sequence with extended PAM | SEQ ID NO: |
|---|---|---|---|---|---|---|
| VC29 7 | NGG site 1 | 20 | GGGTGGGGGG AGTTTGCTCC | 153. | GGGTGGGGGGAGTTTG CTCCTGGA | 154. |
| VC29 9 | NGG site 2 | 20 | GACCCCCTCC ACCCCGCCTC | 155. | GACCCCCTCCACCCCGC CTCCGGG | 156. |
| VC22 8 | NGG site 3 | 20 | GGTGAGTGAG TGTGTGCGTG | 157. | GGTGAGTGAGTGTGTG CGTGTGGG | 158. |
| BPK1 846 *7 | NGA site 1 | 20 | GCGAGCAGCG TCTTCGAGAG | 159. | GCGAGCAGCGTCTTCG AGAGTGAG | 160. |

ZNF629

| Prep Name | Name | Spacer length (nt) | Spacer Sequence | SEQ ID NO: | Sequence with extended PAM | SEQ ID NO: |
|---|---|---|---|---|---|---|
| NN67 5 *8 | NGA site | 20 | GTGCGGCAAG AGCTTCAGCC | 161. | GTGCGGCAAGAGCTTC AGCCAGAG | 162. |

*1, NGA EMX1 site 4 from Kleinstiver et al., Nature 2015
*2, NGA FANCF site 1 from Kleinstiver et al., Nature 2015
*3, NGA FANCF site 3 from Kleinstiver et al., Nature 2015
*4, NGA FANCF site 4 from Kleinstiver et al., Nature 2015
*5, NGA RUNX1 site 1 from Kleinstiver et al., Nature 2015
*6, NGA RUNX1 site 3 from Kleinstiver et al., Nature 2015
*7, NGA VEGFA site 1 from Kleinstiver et al., Nature 2015
*8, NGA ZNF629 site from Kleinstiver et al., Nature 2015

Genome-Wide Specificity of SpCas9-HF1

Figure 2A:
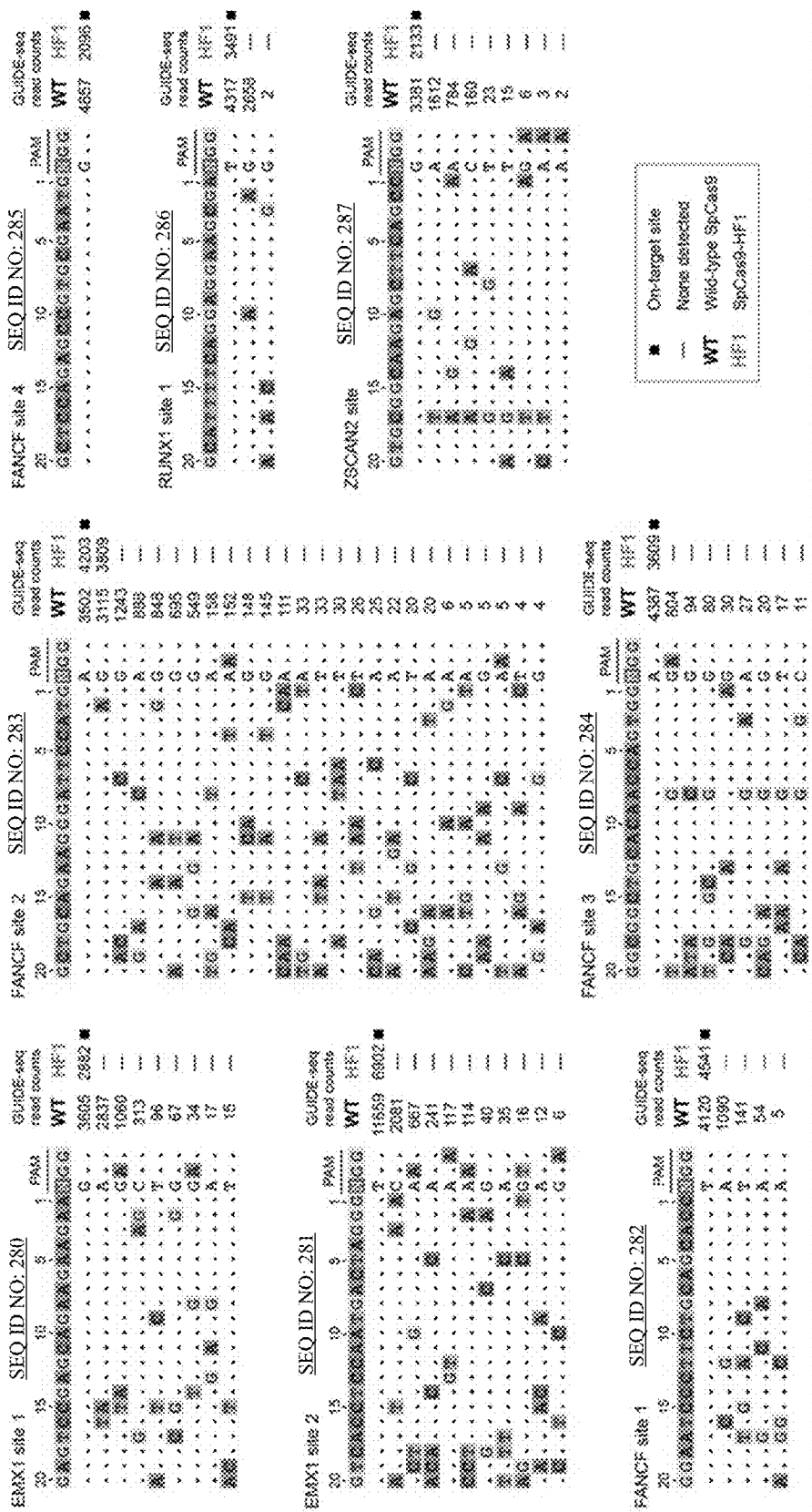

To test whether SpCas9-HF1 exhibited reduced off-target effects in human cells, the genome-wide unbiased identification of double-stranded breaks enabled by sequencing (GUIDE-seq) method was used. GUIDE-seq uses integration of a short double-stranded oligodeoxynucleotide (dsODN) tag into double-strand breaks to enable amplification and sequencing of adjacent genomic sequence, with the number of tag integrations at any given site providing a quantitative measure of cleavage efficiency (Tsai, S. Q. et al, Nat Biotechnol 33, 187-197 (2015)). GUIDE-seq was used to compare the spectrum of off-target effects induced by wild-type SpCas9 and SpCas9-HF1 using eight different sgRNAs targeted to various sites in the endogenous human EMX1, FANCF, RUNX1, and ZSCAN2 genes. The sequences targeted by these sgRNAs are unique and have variable numbers of predicted mismatched sites in the reference human genome (Table 2). Assessment of on-target dsODN tag integration (by restriction fragment length polymorphism (RFLP) assay) and indel formation (by T7EI assay) for the eight sgRNAs revealed comparable on-target activities with wild-type SpCas9 and SpCas9-HF1 (FIGS. 7a and 7b, respectively). GUIDE-seq experiments showed that seven of the eight sgRNAs induced cleavage at multiple genome-wide off-target sites (ranging from 2 to 25 per sgRNA) with wild-type SpCas9, whereas the eighth sgRNA (for FANCF site 4) did not produce any detectable off-target sites (FIGS. 2a and 2b). However, six of the seven sgRNAs that induced indels with wild-type SpCas9 showed a strikingly complete absence of GUIDE-seq detectable off-target events with SpCas9-HF1 (FIGS. 2a and 2b); and the remaining seventh sgRNA (for FANCF site 2) induced only a single detectable genome-wide off-target cleavage event, at a site harboring one mismatch within the protospacer seed sequence (FIG. 2a). Collectively, the off-target sites that were not detected when using SpCas9-HF1 harbored one to six mismatches in the protospacer and/or PAM sequence (FIG. 2c). As with wild-type SpCas9, the eighth sgRNA (for FANCF site 4) did not yield any detectable off-target cleavage events when tested with SpCas9-HF1 (FIG. 2a).

Figure 3B:
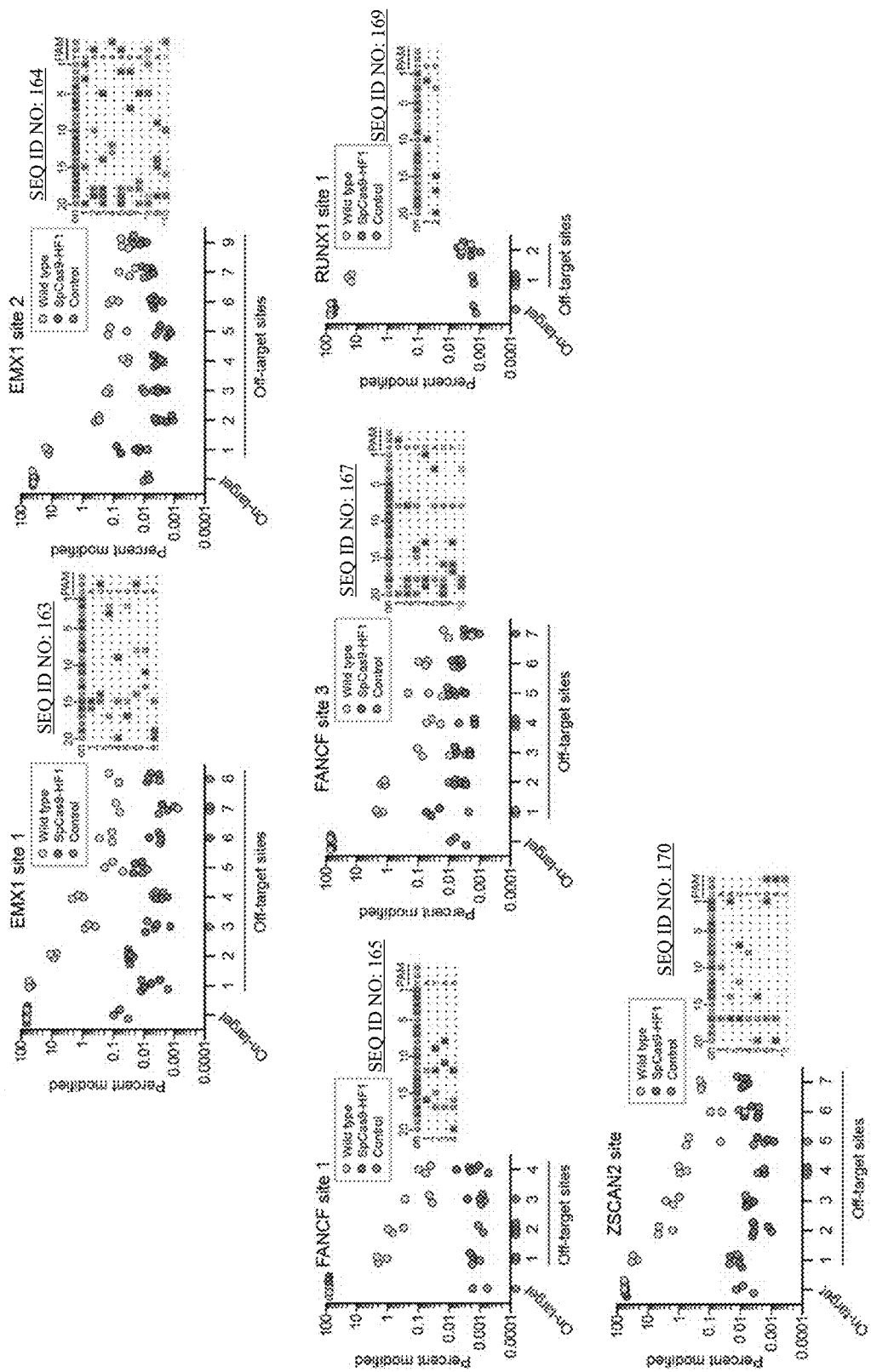
Figure 3C:
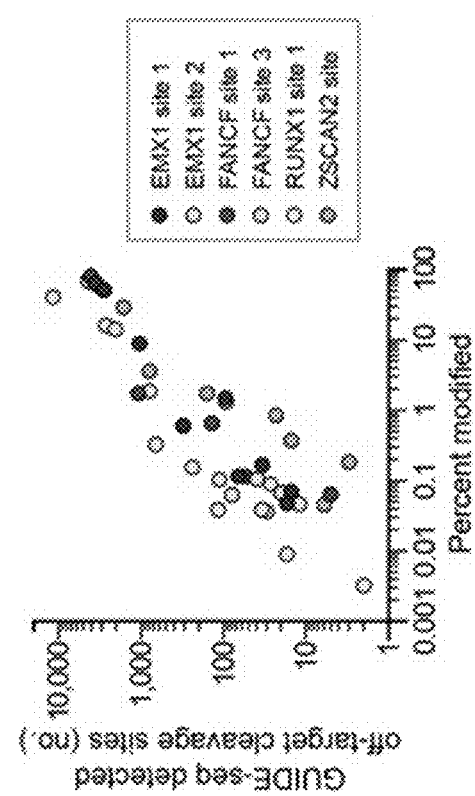

To confirm the GUIDE-seq findings, targeted amplicon sequencing was used to more directly measure the frequencies of NHEJ-mediated indel mutations induced by wild-type SpCas9 and SpCas9-HF1. For these experiments, human cells were transfected only with sgRNA- and Cas9-encoding plasmids (i.e., without the GUIDE-seq tag). Next-generation sequencing was then used to examine 36 of the 40 off-target sites that had been identified with wild-type SpCas9 for six sgRNAs in the GUIDE-seq experiments (four of the 40 sites could not be examined because they could not be specifically amplified from genomic DNA). These deep sequencing experiments showed that: (1) wild-type SpCas9 and SpCas9-HF1 induced comparable frequencies of indels at each of the six sgRNA on-target sites (FIGS. 3a and 3b); (2) wild-type SpCas9, as expected showed statistically significant evidence of indel mutations at 35 of the 36 off-target sites (FIG. 3b) at frequencies that correlated well with GUIDE-seq read counts for these same sites (FIG. 3c); and (3) the frequencies of indels induced by SpCas9-HF1 at 34 of the 36 off-target sites were indistinguishable from the background level of indels observed in samples from control transfections (FIG. 3b). For the two off-target sites that appeared to have statistically significant mutation frequencies with SpCas9-HF1 relative to the negative control, the mean frequencies of indels were 0.049% and 0.037%, levels at which it is difficult to determine whether these are due to sequencing/PCR error or are bona fide nuclease-induced indels. Based on these results, it was concluded that SpCas9-HF1 can completely or nearly completely reduce off-target mutations that occur across a range of different frequencies with wild-type SpCas9 to undetectable levels.

Figure 4A:
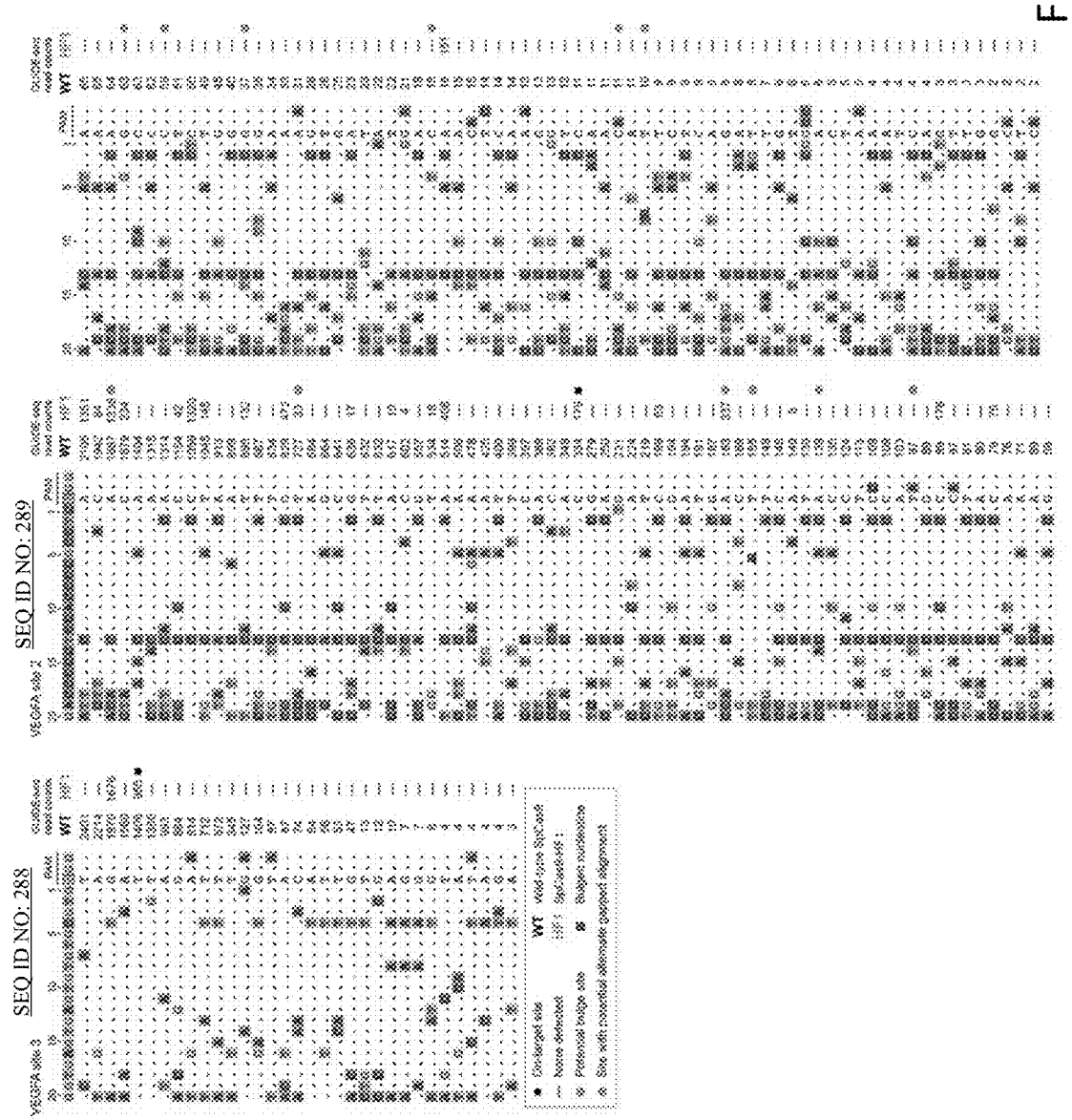
Figure 8:
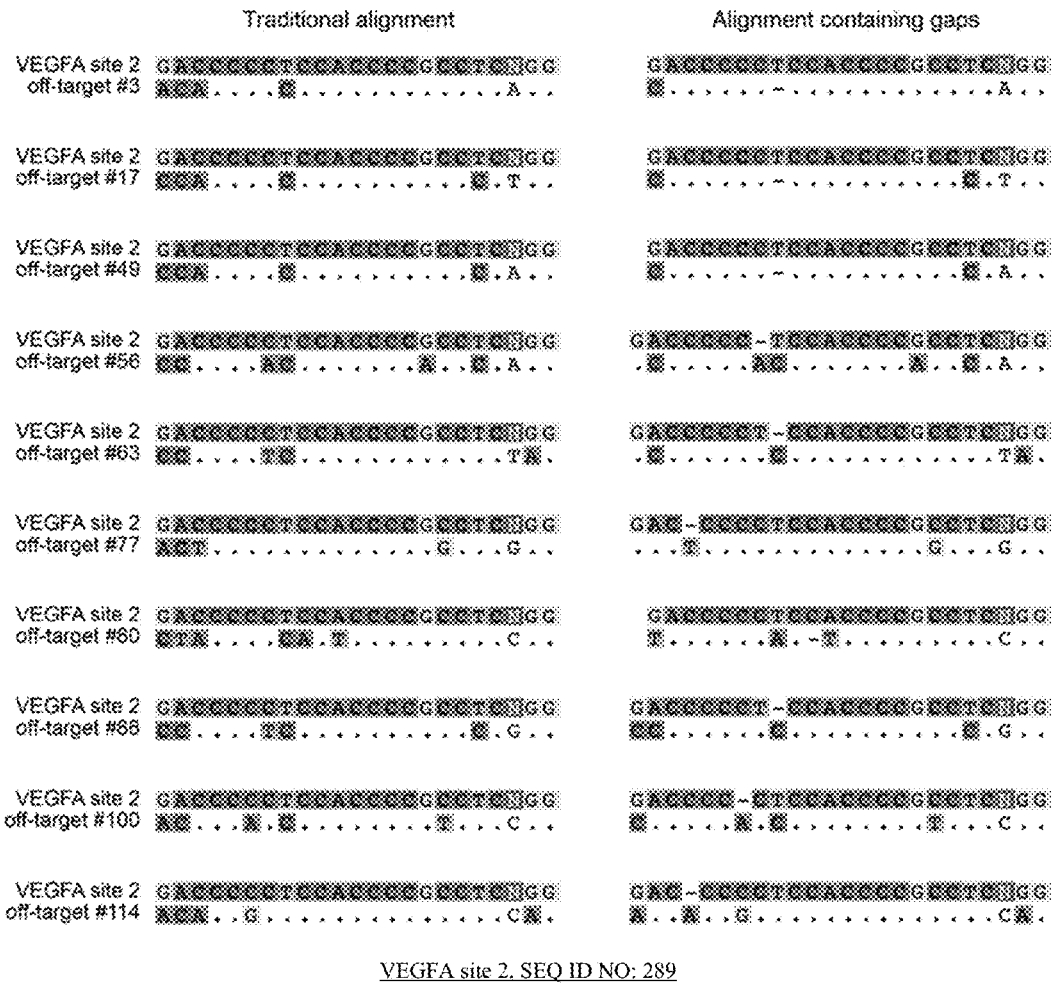
FIG. 8|Potential alternate alignments for VEGFA site 2 off-target sites. Ten VEGFA site 2 (SEQ ID NO: 289) off-target sites identified by GUIDE-seq (left) that may potentially be recognized as off-target sites that contain single nucleotide gaps (Lin et al., Nucleic Acids Res 42, 7473-7485 (2014))) (right), aligned using Geneious (Kearse et al., Bioinformatics 28, 1647-1649 (2012)) version 8.1.6.

Next the capability of SpCas9-HF1 to reduce genome-wide off-target effects of sgRNAs that target atypical homopolymeric or repetitive sequences was assessed. Although many now try to avoid on-target sites with these characteristics due to their relative lack of orthogonality to the genome, it was desirable to explore whether SpCas9-HF1 might reduce off-target indels even for these challenging targets. Therefore, previously characterized sgRNAs (Fu, Y. et al., Nat Biotechnol 31, Tsai, S. Q. et al., Nat Biotechnol 33, 187-197 (2015)) were used that target either a cytosine-rich homopolymeric sequence or a sequence containing multiple TG repeats in the human VEGFA gene (VEGFA site 2 and VEGFA site 3, respectively) (Table 2). In control experiments, each of these sgRNAs induced comparable levels of GUIDE-seq ds ODN tag incorporation (FIG. 7c) and indel mutations (FIG. 7d) with both wild-type SpCas9 and SpCas9-HF1, demonstrating that SpCas9-HF1 was not impaired in on-target activity with either of these sgRNAs. Importantly, GUIDE-seq experiments revealed that SpCas9-HF1 was highly effective at reducing off-target sites of these sgRNAs, with 123/144 sites for VEGFA site 2 and 31/32 sites for VEGFA site 3 not detected (FIGS. 4a and 4b). Examination of these off-target sites not detected with SpCas9-HF1 showed that they each possessed a range of total mismatches within their protospacer and PAM sequences: 2 to 7 mismatches for the VEGFA site 2 sgRNA and 1 to 4 mismatches for the VEGFA site 3 sgRNA (FIG. 4c); also, nine of these off-targets for VEGFA site 2 may have a potential bulged base (Lin, Y. et al., Nucleic Acids Res 42, 7473-7485 (2014).at the sgRNA-DNA interface (FIG. 4a and FIG. 8). The sites that were not detected with SpCas9-HF1 possessed 2 to 6 mismatches for the VEGFA site 2 sgRNA and 2 mismatches in the single site for the VEGFA site 3 sgRNA (FIG. 4c), with three off-target sites for VEGFA site 2 sgRNA again having a potential bulge (FIG. 8). Collectively, these results demonstrated that SpCas9-HF1 can be highly effective at reducing off-target effects of sgRNAs targeted to simple repeat sequences and can also have substantial impacts on sgRNAs targeted to homopolymeric sequences.

TABLE 2

Summary of potential mismatched sites in the reference human genome for the ten sgRNAs examined by GUIDE-seq

| site | spacer with PAM | mismatches to on-target site* | | | | | | |
|---|---|---|---|---|---|---|---|---|
| | | 1 | 2 | 3 | 4 | 5 | 6 | total |
| EMX1-1 | GAGTCCGAGCAGAAGAAGAAGGG (SEQ ID NO: 163) | 0 | 1 | 18 | 273 | 2318 | 15831 | 18441 |
| EMX1-2 | GTCACCTCCAATGACTAGGGTGG (SEQ ID NO: 164) | 0 | 0 | 3 | 68 | 780 | 6102 | 6953 |
| FANCF-1 | GGAATCCCTTCTGCAGCACCTGG (SEQ ID NO: 165) | 0 | 1 | 18 | 288 | 1475 | 9611 | 11393 |
| FANCF-2 | GCTGCAGAAGGGATTCCATGAGG (SEQ ID NO: 166) | 1 | 1 | 29 | 235 | 2000 | 13047 | 15313 |
| FANCF-3 | GGCGGCTGCACAACCAGTGGAGG (SEQ ID NO: 167) | 0 | 0 | 11 | 79 | 874 | 6651 | 7615 |
| FANCF-4 | GCTCCAGAGCCGTGCGAATGGGG (SEQ ID NO: 168) | 0 | 0 | 6 | 59 | 639 | 5078 | 5782 |
| RUNX1-1 | GCATTTTCAGGAGGAAGCGATGG (SEQ ID NO: 169) | 0 | 2 | 6 | 189 | 1644 | 11546 | 13387 |
| ZSCAN2 | GTGCGGCAAGAGCTTCAGCCGGG (SEQ ID NO: 170) | 0 | 3 | 12 | 127 | 1146 | 10687 | 11975 |
| VEGFA2 | GACCCCCTCCACCCCGCCTCCGG (SEQ ID NO: 171) | 0 | 2 | 35 | 456 | 3905 | 17576 | 21974 |
| VEGFA3 | GGTGAGTGAGTGTGTGCGTGTGG (SEQ ID NO: 172) | 1 | 17 | 383 | 6089 | 13536 | 35901 | 55927 |

*determined using Cas-OFFinder (Bae et al., Bioinformatics 30, 1473-1475 (2014))

TABLE 4

Oligonucleotides used in the study

| | sequence | SEQ ID NO: |
|---|---|---|
| description of T7E1 primers | | |
| forward primer to amplify EMX1 in U2OS human cells | GGAGCAGCTGGTCAGAGGGG | 173. |
| reverse primer to amplify EMX1 in U2OS human cells | CCATAGGGAAGGGGGACACTGG | 174. |
| forward primer to amplify FANCF in U2OS human cells | GGGCCGGGAAAGAGTTGCTG | 175. |
| reverse primer to amplify FANCF in U2OS human cells | GCCCTACATCTGCTCTCCCTCC | 176. |
| forward primer to amplify RUNX1 in U2OS human cells | CCAGCACAACTTACTCGCACTTGAC | 177. |
| reverse primer to amplify RUNX1 in U2OS human cells | CATCACCAACCCACAGCCAAGG | 178. |
| forward primer to amplify VEGFA in U2OS human cells | TCCAGATGGCACATTGTCAG | 179. |
| reverse primer to amplify VEGFA in U2OS human cells | AGGGAGCAGGAAAGTGAGGT | 180. |
| forward primer to amplify VEGFA (NGG site 2) in U2OS human cells | CGAGGAAGAGAGAGACGGGGTC | 181. |
| reverse primer to amplify VEGFA (NGG site 2) in U2OS human cells | CTCCAATGCACCCAAGACAGCAG | 182. |
| forward primer to amplify ZSCAN2 in U2OS human cells | AGTGTGGGGTGTGTGGGAAG | 183. |
| reverse primer to amplify ZSCAN2 in U2OS human cells | GCAAGGGAAGACTCTGGCA | 184. |
| forward primer to amplify ZNF629 in U2OS human cells | TACGAGTGCCTAGAGTGCG | 185. |
| reverse primer to amplify ZNF629 in U2OS human cells | GCAGATGTAGGTCTTGGAGGAC | 186. |
| description of deep sequencing primers | | |
| forward primer to amplify EMX1-1 on-target | GGAGCAGCTGGTCAGAGGGG | 187. |
| reverse primer to amplify EMX1-1 on-target | CGATGTCCTCCCCATTGGCCTG | 188. |
| forward primer to amplify EMX1-1-GUIDE_seq-OT#1 | GTGGGGAGATTTGCATCTGTGGAGG | 189. |
| reverse primer to amplify EMX1-1-GUIDE_seq-OT#1 | GCTTTTATACCATCTTGGGGTTACAG | 190. |
| forward primer to amplify EMX1-1-GUIDE_seq-OT#2 | CAATGTGCTTCAACCCATCACGGC | 191. |
| reverse primer to amplify EMX1-1-GUIDE_seq-OT#2 | CCATGAATTTGTGATGGATGCAGTCTG | 192. |
| forward primer to amplify EMX1-1-GUIDE_seq-OT#3 | GAGAAGGAGGTGCAGGAGCTAGAC | 193. |
| reverse primer to amplify EMX1-1-GUIDE_seq-OT#3 | CATCCCGACCTTCATCCCTCCTGG | 194. |
| forward primer to amplify EMX1-1-GUIDE_seq-OT#4 | GTAGTTCTGACATTCCTCCTGAGGG | 195. |

TABLE 4-continued

Oligonucleotides used in the study

| | sequence | SEQ ID NO: |
|---|---|---|
| reverse primer to amplify EMX1-1-GUIDE_seq-OT#4 | TCAAACAAGGTGCAGATACAGCA | 196. |
| forward primer to amplify EMX1-1-GUIDE_seq-OT#5 | CAGGGTCGCTCAGTCTGTGTGG | 197. |
| reverse primer to amplify EMX1-1-GUIDE_seq-OT#5 | CCAGCGCACCATTCACTCCACCTG | 198. |
| forward primer to amplify EMX1-1-GUIDE_seq-OT#6 | GGCTGAAGAGGAAGACCAGACTCAG | 199. |
| reverse primer to amplify EMX1-1-GUIDE_seq-OT#6 | GGCCCCTCTGAATTCAATTCTCTGC | 200. |
| forward primer to amplify EMX1-1-GUIDE_seq-OT#7 | CCACAGCGAGGAGTGACAGCC | 201. |
| reverse primer to amplify EMX1-1-GUIDE_seq-OT#7 | CCAAGTCTTTCCTAACTCGACCTTGG | 202. |
| forward primer to amplify EMX1-1-GUIDE_seq-OT#8 | CCCTAGGCCCACACCAGCAATG | 203. |
| reverse primer to amplify EMX1-1-GUIDE_seq-OT#8 | GGGATGGGAATGGGAATGTGAGGC | 204. |
| forward primer to amplify EMX1-2 on- target | GCCCAGGTGAAGGTGTGGTTCC | 205. |
| reverse primer to amplify EMX1-2 on- target | CCAAAGCCTGGCCAGGGAGTG | 206. |
| forward primer to amplify EMX1-2-GUIDE_seq-OT#1 | AGGCAAAGATCTAGGACCTGGATGG | 207. |
| reverse primer to amplify EMX1-2-GUIDE_seq-OT#1 | CCATCTGAGTCAGCCAGCCTTGTC | 208. |
| forward primer to amplify EMX1-2-GUIDE_seq-OT#2 | GGTTCCCTCCCTTCTGAGCCC | 209. |
| reverse primer to amplify EMX1-2-GUIDE_seq-OT#2 | GGATAGGAATGAAGACCCCCTCTCC | 210. |
| forward primer to amplify EMX1-2-GUIDE_seq-OT#3 | GGACTGGCTGGCTGTGTGTTTTGAG | 211. |
| reverse primer to amplify EMX1-2-GUIDE_seq-OT#3 | CTTATCCAGGGCTACCTCATTGCC | 212. |
| forward primer to amplify EMX1-2-GUIDE_seq-OT#4 | GCTGCTGCTGCTTTGATCACTCCTG | 213. |
| reverse primer to amplify EMX1-2-GUIDE_seq-OT#4 | CTCCTTAAACCCTCAGAAGCTGGC | 214. |
| forward primer to amplify EMX1-2-GUIDE_seq-OT#5 | GCACTGTCAGCTGATCCTACAGG | 215. |
| reverse primer to amplify EMX1-2-GUIDE_seq-OT#5 | ACGTTGGAACAGTCGAGCTGTAGC | 216. |
| forward primer to amplify EMX1-2-GUIDE_seq-OT#6 | TGTGCATAACTCATGTTGGCAAACT | 217. |
| reverse primer to amplify EMX1-2-GUIDE_seq-OT#6 | TCCACAACTACCCTCAGCTGGAG | 218. |
| forward primer to amplify EMX1-2-GUIDE_seq-OT#7 | CCACTGACAATTCACTCAACCCTGC | 219. |
| reverse primer to amplify EMX1-2-GUIDE_seq-OT#7 | AGGCAGACCAGTTATTTGGCAGTC | 220. |

TABLE 4-continued

Oligonucleotides used in the study

| | sequence | SEQ ID NO: |
|---|---|---|
| forward primer to amplify EMX1-2-GUIDE_seq-OT#9 | ACAGGCGCAGTTCACTGAGAAG | 221. |
| reverse primer to amplify EMX1-2-GUIDE_seq-OT#9 | GGGTAGGCTGACTTTGGGCTCC | 222. |
| forward primer to amplify FANCF-1 on-target | GCCCTCTTGCCTCCACTGGTTG | 223. |
| reverse primer to amplify FANCF-1 on-target | CGCGGATGTTCCAATCAGTACGC | 224. |
| forward primer to amplify FANCF-1-GUIDE_seq-OT#1 | GCGGGCAGTGGCGTCTTAGTCG | 225. |
| reverse primer to amplify FANCF-1-GUIDE_seq-OT#1 | CCCTGGGTTTGGTTGGCTGCTC | 226. |
| forward primer to amplify FANCF-1-GUIDE_seq-OT#2 | CTCCTTGCCGCCCAGCCGGTC | 227. |
| reverse primer to amplify FANCF-1-GUIDE_seq-OT#2 | CACTGGGGAAGAGGCGAGGACAC | 228. |
| forward primer to amplify FANCF-1-GUIDE_seq-OT#3 | CCAGTGTTTCCCATCCCCAACAC | 229. |
| reverse primer to amplify FANCF-1-GUIDE_seq-OT#3 | GAATGGATCCCCCCCTAGAGCTC | 230. |
| forward primer to amplify FANCF-1-GUIDE_seq-OT#4 | CAGGCCCACAGGTCCTTCTGGA | 231. |
| reverse primer to amplify FANCF-1-GUIDE_seq-OT#4 | CCACACGGAAGGCTGACCACG | 232. |
| forward primer to amplify FANCF-3 on-target | GCGCAGAGAGAGCAGGACGTC | 233. |
| reverse primer to amplify FANCF-3 on-target | GCACCTCATGGAATCCCTTCTGC | 234. |
| forward primer to amplify FANCF-3-GUIDE_seq-OT#1 | CAAGTGATGCGACTTCCAACCTC | 235. |
| reverse primer to amplify FANCF-3-GUIDE_seq-OT#1 | CCCTCAGAGTTCAGCTTAAAAGACC | 236. |
| forward primer to amplify FANCF-3-GUIDE_seq-OT#2 | TGCTTCTCATCCACTCTAGACTGCT | 237. |
| reverse primer to amplify FANCF-3-GUIDE_seq-OT#2 | CACCAACCAGCCATGTGCCATG | 238. |
| forward primer to amplify FANCF-3-GUIDE_seq-OT#3 | CTGCCTGTGCTCCTCGATGGTG | 239. |
| reverse primer to amplify FANCF-3-GUIDE_seq-OT#3 | GGGTTCAAAGCTCATCTGCCCC | 240. |
| forward primer to amplify FANCF-3-GUIDE_seq-OT#4 | GCATGTGCCTTGAGATTGCCTGG | 241. |
| reverse primer to amplify FANCF-3-GUIDE_seq-OT#4 | GACATTCAGAGAAGCGACCATGTGG | 242. |
| forward primer to amplify FANCF-3-GUIDE_seq-OT#5 | CCATCTTCCCCTTTGGCCCACAG | 243. |
| reverse primer to amplify FANCF-3-GUIDE_seq-OT#5 | CCCCAAAAGTGGCCAAGAGCCTGAG | 244. |
| forward primer to amplify FANCF-3-GUIDE_seq-OT#6 | GTTCTCCAAAGGAAGAGAGGGGAATG | 245. |

TABLE 4-continued

Oligonucleotides used in the study

| | sequence | SEQ ID NO: |
|---|---|---|
| reverse primer to amplify FANCF-3-GUIDE_seq-OT#6 | GGTGCTGTGTCCTCATGCATCC | 246. |
| forward primer to amplify FANCF-3-GUIDE_seq-OT#7 | CGGCTTGCCTAGGGTCGTTGAG | 247. |
| reverse primer to amplify FANCF-3-GUIDE_seq-OT#7 | CCTTCAGGGGCTCTTCCAGGTC | 248. |
| forward primer to amplify RUNX1-1 on-target | GGGAACTGGCAGGCACCGAGG | 249. |
| reverse primer to amplify RUNX1-1 on-target | GGGTGAGGCTGAAACAGTGACC | 250. |
| forward primer to amplify RUNX1-1-GUIDE_seq-OT#1 | GGGAGGATGTTGGTTTTAGGGAACTG | 251. |
| reverse primer to amplify RUNX1-1-GUIDE_seq-OT#1 | TCCAATCACTACATGCCATTTTGAAGA | 252. |
| forward primer to amplify RUNX1-1-GUIDE_seq-OT#2 | CCACCCTCTTCCTTTGATCCTCCC | 253. |
| reverse primer to amplify RUNX1-1-GUIDE_seq-OT#2 | TCCTCCCTACTCCTTCACCCAGG | 254. |
| forward primer to amplify ZSCAN2 on-target | GAGTGCCTGACATGTGGGGAGAG | 255. |
| reverse primer to amplify ZSCAN2 on-target | TCCAGCTAAAGCCTTTCCCACAC | 256. |
| forward primer to amplify ZSCAN2-GUIDE_seq-OT#1 | GAACTCTCTGATGCACCTGAAGGCTG | 257. |
| reverse primer to amplify ZSCAN2-GUIDE_seq-OT#1 | ACCGTATCAGTGTGATGCATGTGGT | 258. |
| forward primer to amplify ZSCAN2-GUIDE_seq-OT#2 | TGGGTTTAATCATGTGTTCTGCACTATG | 259. |
| reverse primer to amplify ZSCAN2-GUIDE_seq-OT#2 | CCCATCTTCCATTCTGCCCTCCAC | 260. |
| forward primer to amplify ZSCAN2-GUIDE_seq-OT#3 | CAGCTAGTCCATTTGTTCTCAGACTGTG | 261. |
| reverse primer to amplify ZSCAN2-GUIDE_seq-OT#3 | GGCCAACATTGTGAAACCCTGTCTC | 262. |
| forward primer to amplify ZSCAN2-GUIDE_seq-OT#4 | CCAGGGACCTGTGCTTGGGTTC | 263. |
| reverse primer to amplify ZSCAN2-GUIDE_seq-OT#4 | CACCCCATGACCTGGCACAAGTG | 264. |
| forward primer to amplify ZSCAN2-GUIDE_seq-OT#5 | AAGTGTTCCTCAGAATGCCAGCCC | 265. |
| reverse primer to amplify ZSCAN2-GUIDE_seq-OT#5 | CAGGAGTGCAGTTGTGTTGGGAG | 266. |
| forward primer to amplify ZSCAN2-GUIDE_seq-OT#6 | CTGATGAAGCACCAGAGAACCCACC | 267. |
| reverse primer to amplify ZSCAN2-GUIDE_seq-OT#6 | CACACCTGGCACCCATATGGC | 268. |
| forward primer to amplify ZSCAN2-GUIDE_seq-OT#7 | GATCCACACTGGTGAGAAGCCTTAC | 269. |
| reverse primer to amplify ZSCAN2-GUIDE_seq-OT#7 | CTTCCCACACTCACAGCAGATGTAGG | 270. |

Refining the Specificity of SpCas9-HF1

Figure 9:
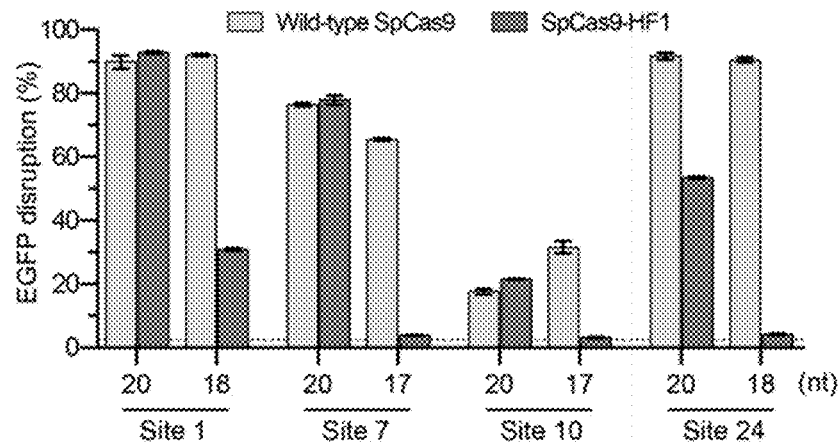
FIG. 9|Activities of wild-type SpCas9 and SpCas9-HF1 with truncated sgRNAs14. EGFP disruption activities of wild-type SpCas9 and SpCas9-HF1 using full-length or truncated sgRNAs targeted to four sites in EGFP. Error bars represent s.e.m. for n=3; mean level of background EGFP loss in control experiments is represented by the red dashed line FIG. 10|Wild-type SpCas9 and SpCas9-HF1 activities with sgRNAs bearing 5'-mismatched guanine bases. EGFP disruption activities of wild-type SpCas9 and SpCas9-HF1 with sgRNAs targeted to four different sites. For each target site, sgRNAs either contain the matched non-guanine 5'-base or a 5'-guanine that is intentionally mismatched.
Figure 10:
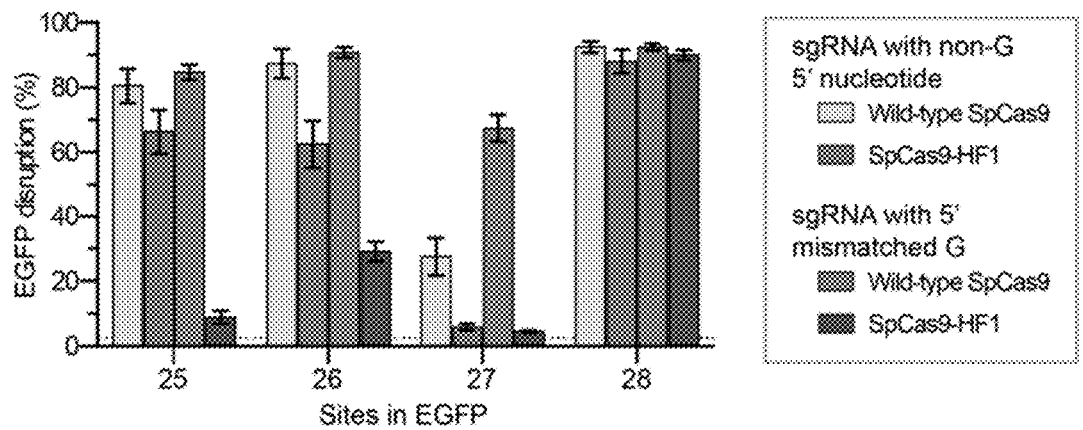

Previously described methods such as truncated gRNAs (Fu, Y. et al., Nat Biotechnol 32, 279-284 (2014)) and the SpCas9-D1135E variant (Kleinstiver, B. P. et al., Nature 523, 481-485 (2015)) can partially reduce SpCas9 off-target effects, and the present inventors wondered whether these might be combined with SpCas9-HF1 to further improve its genome-wide specificity. Testing of SpCas9-HF1 with matched full-length and truncated sgRNAs targeted to four sites in the human cell-based EGFP disruption assay revealed that shortening sgRNA complementarity length substantially impaired on-target activities (FIG. 9). By contrast, SpCas9-HF1 with an additional D1135E mutation (a variant referred to herein as SpCas9-HF2) retained 70% or more activity of wild-type SpCas9 with six of eight sgRNAs tested using a human cell-based EGFP disruption assay (FIGS. 5a and 5b). SpCas9-HF3 and SpCas9-HF4 variants were also created harboring L169A or Y450A mutations, respectively, at positions whose side chains mediated hydrophobic non-specific interactions with the target DNA on its PAM proximal end (Nishimasu, H. et al., Cell 156, 935-949 (2014); Jiang, F., et al., Science 348, 1477-1481 (2015)). SpCas9-HF3 and SpCas9-HF4 retained 70% or more of the activities observed with wild-type SpCas9 with the same six out of eight EGFP-targeted sgRNAs (FIGS. 5a and 5b).

To determine whether SpCas9-HF2, -HF3, and -HF4 could reduce indel frequencies at two off-target sites (for the FANCF site 2 and VEGFA site 3 sgRNAs) that were resistant to SpCas9-HF1, further experiments were performed. For the FANCF site 2 off-target, which bears a single mismatch in the seed sequence of the protospacer, SpCas9-HF4 reduced indel mutation frequencies to near background level as judged by T7EI assay while also beneficially increasing on-target activity (FIG. 5c), resulting in the greatest increase in specificity among the three variants (FIG. 5d). For the VEGFA site 3 off-target site, which bears two protospacer mismatches (one in the seed sequence and one at the nucleotide most distal from the PAM sequence), SpCas9-HF2 showed the greatest reduction in indel formation while showing only modest effects on on-target mutation efficiency (FIG. 5c), leading to the greatest increase in specificity among the three variants tested (FIG. 5d). Taken together, these results demonstrate the potential for reducing off-target effects that are resistant to SpCas9-HF1 by introducing additional mutations at other residues that mediate non-specific DNA contacts or that may alter PAM recognition.

Figure 5E:
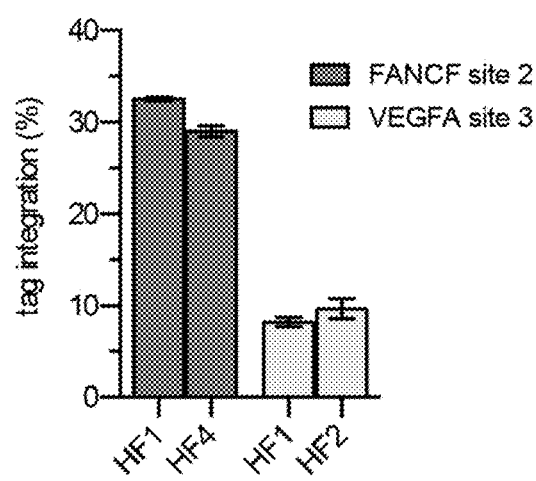
FIGS. 5E-F|Genome-wide specificities of SpCas9-HF1, -HF2, and -HF4 with sgRNAs that have off-target sites resistant to the effects of SpCas9-HF1. E, Mean GUIDE-seq tag integration at the intended on-target site for GUIDE-seq experiments in panel F. SpCas9-HF1=N497A/R661A/Q695A/Q926A; HF2=HF1+D1135E; HF4=HF1+Y450A. Error bars represent s.e.m. for n=3. F, GUIDE-seq identified off-target sites of SpCas9-HF1, -HF2, or -HF4 with either the FANCF site 2 (SEQ ID NO: 283) or VEGFA site 3 (SEQ ID NO: 288) sgRNAs. Read counts represent a measure of cleavage frequency at a given site; mismatched positions within the spacer or PAM are highlighted in color. The fold-improvement in off-target discrimination was calculated by normalizing the off-target read counts for an SpCas9-HF variant to the read counts at the on-target site prior to comparison between SpCas9-HF variants.
Figure 5F:
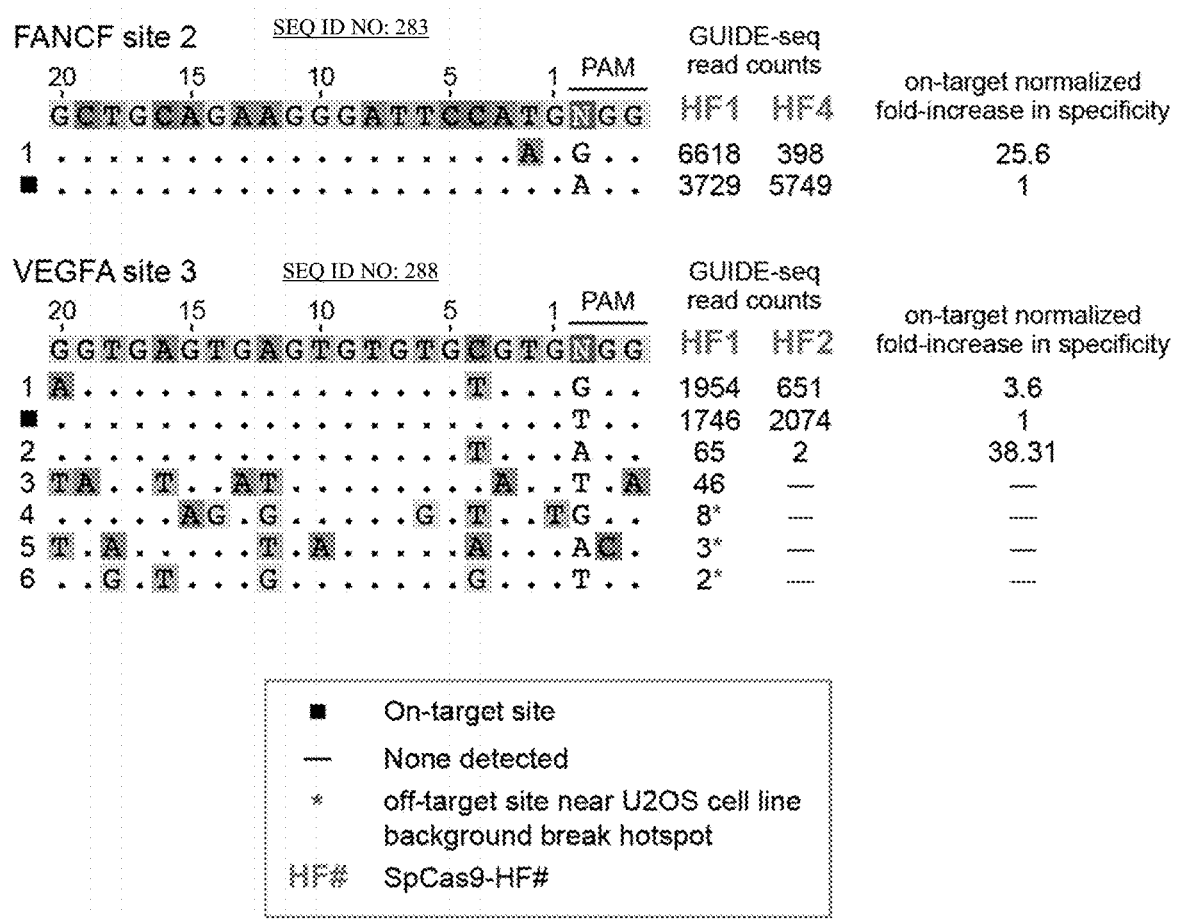

To generalize the T7E1 assay findings described above that show SpCas9-HF4 and SpCas9-HF2 have improved discrimination relative to SpCas9-HF1 against off-targets of the FANCF site 2 and VEGFA site 3 sgRNAs, respectively, the genome-wide specificities of these variants were examined using GUIDE-seq. Using an RFLP assay, it was determined that SpCas9-HF4 and SpCas9-HF2 had similar on-target activities to SpCas9-HF1, as assayed by GUIDE-seq tag integration rates (FIG. 5E). When analyzing the GUIDE-seq data, no new off-target sites were identified for SpCas9-HF2 or SpCas9-HF4 (FIG. 5F). Compared to SpCas9-HF1, off-target activities at all sites were either rendered undetectable by GUIDE-seq or substantially decreased. Relative to SpCas9-HF1, SpCas9-HF4 had nearly 26-fold better specificity against the single FANCF site 2 off-target site that remained recalcitrant to the specificity improvements of SpCas9-HF1 (FIG. 5F). SpCas9-HF2 had nearly 4-fold improved specificity relative to SpCas9-HF1 for the high-frequency VEGFA site 3 off-target, while also dramatically reducing (>38-fold) or eliminating GUIDE-seq detectable events at other low-frequency off-target sites. Of note, the genomic position of 3 of these low frequency sites identified for SpCas9-HF1 are adjacent to previously characterized background U2OS cell breakpoint hotspots. Collectively, these results suggest that the SpCas9-HF2 and SpCas9-HF4 variants can improve the genome-wide specificity of SpCas9-HF1.

SpCas9-HF1 robustly and consistently reduced off-target mutations when using sgRNAs designed against standard, non-repetitive target sequences. The two off-target sites that were most resistant to SpCas9-HF1 have only one and two mismatches in the protospacer. Together, these observations suggest that off-target mutations might be minimized to undetectable levels by using SpCas9-HF1 and targeting non-repetitive sequences that do not have closely related sites bearing one or two mismatches elsewhere in the genome (something that can be easily accomplished using existing publicly available software programs (Bae, S., et al, Bioinformatics 30, 1473-1475 (2014)). One parameter that users should keep in mind is that SpCas9-HF1 may not be compatible with the common practice of using a G at the 5' end of the gRNA that is mismatched to the protospacer sequence. Testing of four sgRNAs bearing a 5' G mismatched to its target site showed three of the four had diminished activities with SpCas9-HF1 compared to wild-type SpCas9 (FIG. 10), perhaps reflecting the ability of SpCas9-HF1 to better discriminate a partially matched site.

Figure 11:
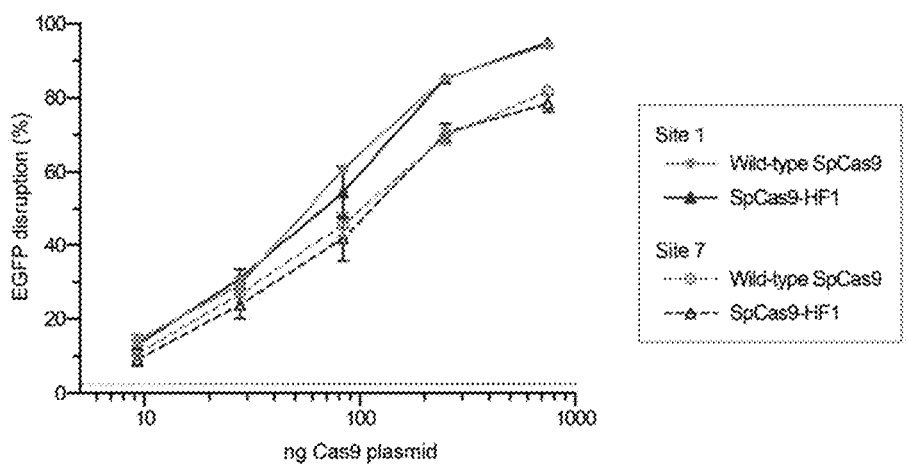
FIG. 11|Titrating the amount of wild-type SpCas9 and SpCas9-HF1 expression plasmids. Human cell EGFP disruption activities from transfections with varying amounts of wild-type and SpCas9-HF1 expression plasmids. For all transfections, the amount of sgRNA-containing plasmid was fixed at 250 ng. Two sgRNAs targeting separate sites were used; Error bars represent s.e.m. for n=3; mean level of background EGFP loss in negative controls is represented by the red dashed line.

Further biochemical work can confirm or clarify the precise mechanism by which SpCas9-HF1 achieves its high genome-wide specificity. It does not appear that the four mutations introduced alter the stability or steady-state expression level of SpCas9 in the cell, because titration experiments with decreasing concentrations of expression plasmids suggested that wild-type SpCas9 and SpCas9-HF1 behaved comparably as their concentrations are lowered (FIG. 11). Instead, the simplest mechanistic explanation is that these mutations decreased the energetics of interaction between the Cas9-sgRNA and the target DNA, with the energy of the complex at a level just sufficient to retain on-target activity but lowered it enough to make off-target site cleavage inefficient or non-existent. This mechanism is consistent with the non-specific interactions observed between the residues mutated and the target DNA phosphate backbone in structural data (Nishimasu, H. et al., Cell 156, 935-949 (2014); Anders, C et. Al., Nature 513, 569-573 (2014)). A somewhat similar mechanism has been proposed to explain the increased specificities of transcription activator-like effector nucleases bearing substitutions at positively charged residues (Guilinger, J. P. et al., Nat Methods 11, 429-435 (2014)).

Figures 12A, 12B:
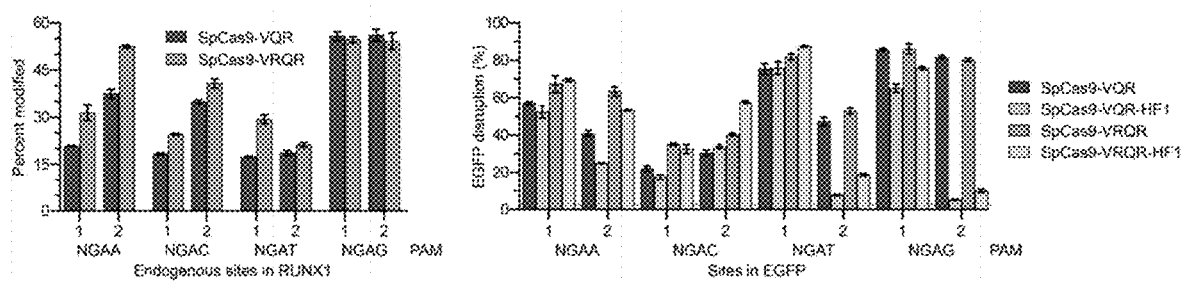

It was possible that SpCas9-HF1 might also be combined with other mutations that have been shown to alter Cas9 function. For example, an SpCas9 mutant bearing three amino acid substitutions (D1135V/R1335Q/T1337R, also known as the SpCas9-VQR variant), recognizes sites with NGAN PAMs (with relative efficiencies for NGAG>NGAT=NGAA>NGAC) (Kleinstiver, B. P. et al, Nature 523, 481-485 (2015)) and a recently identified quadruple SpCas9 mutant (D1135V/G1218R/R1335Q/T1337R, referred to as the SpCas9-VRQR variant) has improved activities relative to the VQR variant on sites with NGAH (H=A, C, or T) PAMs (FIG. 12a). Introduction of the four mutations (N497A/R661A/Q695A/Q926A) from SpCas9-HF1 into SpCas9-VQR and SpCas9-VRQR created SpCas9-VQR-HF1 and SpCas9-VRQR-HF1, respectively. Both HF versions of these nucleases showed on-target activities comparable (i.e., 70% or more) to their non-HF counterparts with five of eight sgRNAs targeted to the EGFP reporter gene and with seven of eight sgRNAs targeted to endogenous human gene sites (FIGS. 12b-12d).

More broadly, these results illuminate a general strategy for the engineering of additional high-fidelity variants of CRISPR-associated nucleases. Adding additional mutations at non-specific DNA contacting residues further reduced some of the very small number of residual off-target sites that persist with SpCas9-HF1. Thus, variants such as SpCas9-HF2, SpCas9-HF3, SpCas9-HF4, and others can be utilized in a customized fashion depending on the nature of the off-target sequences. Furthermore, success with engineering high-fidelity variants of SpCas9 suggests that the approach of mutating non-specific DNA contacts can be extended to other naturally occurring and engineered Cas9 orthologues (Ran, F. A. et al., Nature 520, 186-191 (2015), Esvelt, K. M. et al., Nat Methods 10, 1116-1121 (2013); Hou, Z. et al., Proc Natl Acad Sci USA (2013); Fonfara, I. et al., Nucleic Acids Res 42, 2577-2590 (2014); Kleinstiver, B. P. et al, Nat Biotechnol (2015) as well as newer CRISPR-associated nucleases (Zetsche, B. et al., Cell 163, 759-771 (2015); Shmakov, S. et al., Molecular Cell 60, 385-397) that are being discovered and characterized with increasing frequency.

Example 2

Described herein are SpCas9 variants with alanine substitutions in residues that contact the target strand DNA, including N497A, Q695A, R661A, and Q926A. Beyond these residues, the present inventors sought to determine whether the specificity of these variants, e.g., the SpCas9-HF1 variant (N497A/R661A/Q695A/Q926A), might be further improved by adding substitutions in positively-charged SpCas9 residues that appear to make contacts with the non-target DNA strand: R780, K810, R832, K848, K855, K968, R976, H982, K1003, K1014, K1047, and/or R1060 (see Slaymaker et al., Science. 2016 Jan. 1; 351(6268):84-8).

The activities of wild-type SpCas9 derivatives bearing single alanine substitutions at these positions and combinations thereof were initially tested using the EGFP disruption assay with a perfectly matched sgRNA designed to a site in the EGFP gene (to assess on-target activities) and the same sgRNA bearing intentional mismatches at positions 11 and 12 with position 1 being the most PAM-proximal base (to assess activities at mismatched sites, as would be found at off-target sites) (FIG. 13A). (Note that the derivatives bearing the triple substitutions K810A/K1003A/R1060A or K848A/K1003A/R1060A are the same as recently described variants known as eSpCas9(1.0) and eSpCas9(1.1), respectively; see ref 1). As expected, wild-type SpCas9 had robust on-target and mismatched-target activities. As a control, we also tested SpCas9-HF1 in this experiment and found that it maintained on-target activity while reducing mismatched-target activity as expected (FIG. 13A). All of the wild-type SpCas9 derivatives bearing one or more alanine substitutions at positions that might potentially contact the non-target DNA strand showed on-target activities comparable to wild-type SpCas9 (FIG. 13A). Interestingly, some of these derivatives also showed reduced cleavage with the mismatched 11/12 sgRNA relative to the activity observed with wild-type SpCas9, suggesting that a subset of the substitutions in these derivatives confer enhanced specificity against this mismatched site relative to wild-type SpCas9 (FIG. 13A). However, none of these single substitutions or combinations of substitutions were sufficient to completely eliminate activities observed the 11/12 mismatched sgRNA. When we tested wild-type SpCas9, SpCas9-HF1, and these same wild-type SpCas9 derivatives using an additional sgRNA bearing mismatches at positions 9 and 10 (FIG. 13B), only minimal changes in mismatched-target activities were observed for most derivatives. Again, this demonstrated that single, double, or even triple substitutions (equivalent to the previously described eSpCas9(1.0) and (1.1) variants) at these potential non-target strand contacting residues are insufficient to eliminate activities at imperfectly matched DNA sites. Collectively, these data demonstrate that the wild-type SpCas9 variants retain on-target activity with a matched sgRNA and that the substitutions contained in these derivatives on their own (in the context of wild-type SpCas9) are not sufficient to eliminate nuclease activities on two different mismatched DNA sites (FIGS. 13A and 13B).

Figure 14A:
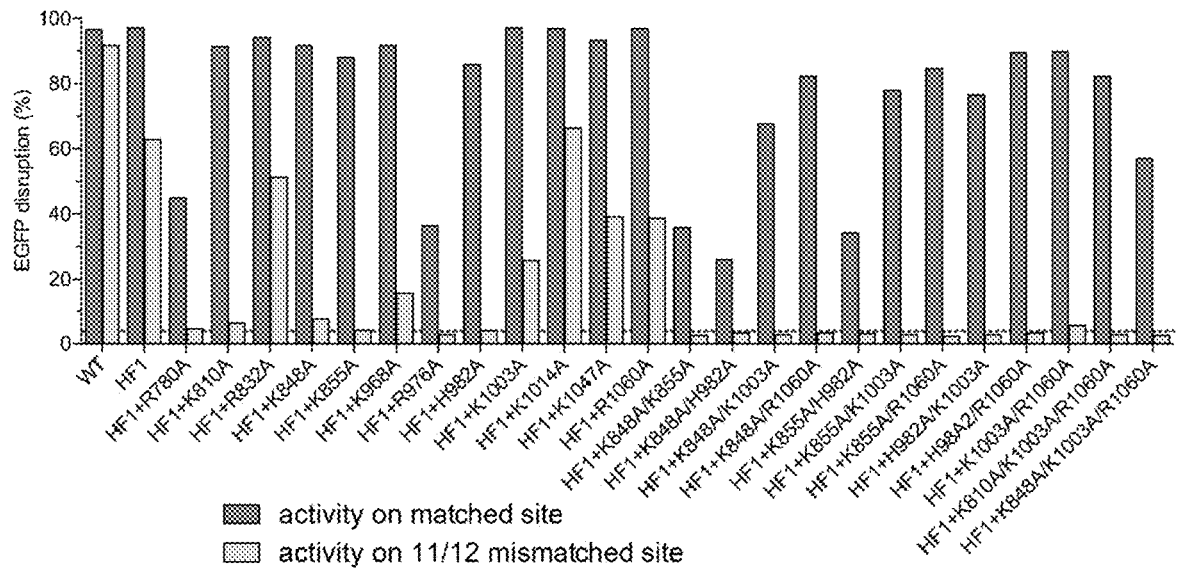
FIGS. 14A-B|Activity of wild-type SpCas9, SpCas9-HF1, and SpCas9-HF1 derivatives bearing one or more alanine substitutions at positions that can potentially contact the non-target DNA strand. A and B, Nucleases were assessed using the EGFP disruption assay, with an sgRNA that is perfectly matched to a site in the EGFP gene as well as an sgRNA that is intentionally mismatched at positions 11 and 12 (panel A) or positions 9 and 10 (panel B). Mismatched positions are numbered with position 20 being the most PAM-distal position; the red dashed line represents background levels of EGFP disruption; HF1=SpCas9 with N497A/R661A/Q695A/Q926A substitutions.
Figure 14B:
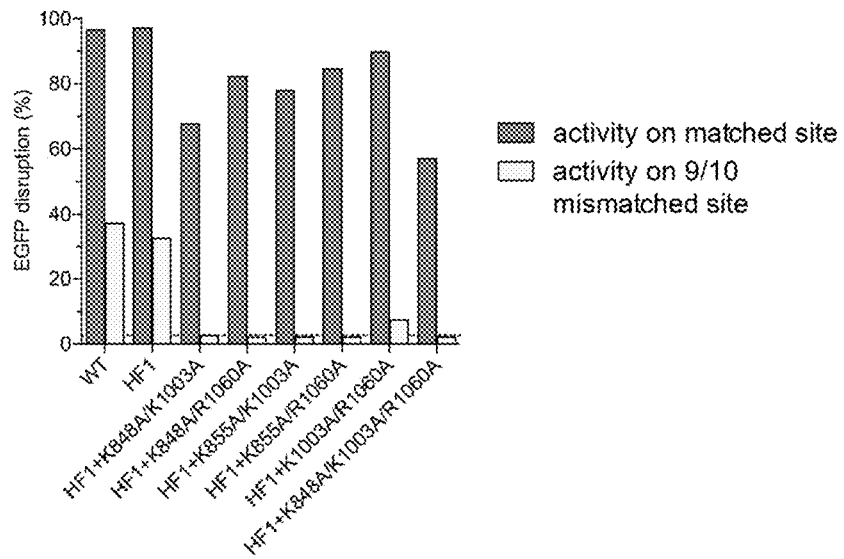

Given these results, it was hypothesized that SpCas9-HF1 derivatives bearing one or more additional amino acid substitutions at residues that might contact the non-target DNA strand might further improve specificity relative to the parental SpCas9-HF1 protein. Therefore, various SpCas9-HF1-derivatives bearing combinations of single, double, or triple alanine substitutions were tested in the human cell-based EGFP disruption assay using a perfectly matched sgRNA (to test on-target activities) and the same sgRNA bearing mismatches at positions 11 and 12 (to assess activities at a mismatched target site, as would be found for off-target sites). These sgRNAs are the same ones that were used for FIGS. 13A-B. This experiment revealed most of the SpCas9-HF1-derivative variants we tested showed comparable on-target activities to those observed with both wild-type SpCas9 and SpCas9-HF1 (FIG. 14A). With the 11/12 mismatched sgRNA, some of the SpCas9-HF1 derivatives tested (such as SpCas9-HF1+R832A and SpCas9-HF1+K1014A) did not show an appreciable change in cleavage with the mismatched sgRNA. However, importantly, most of the SpCas9-HF1 derivatives had substantially lower activity with the 11/12 mismatched sgRNA than what was observed with SpCas9-HF1, eSpCas9(1.0), or eSpCas9(1.1), suggesting that certain combinations of these new variants have reduced mismatched-target activities and thus improved specificities (FIG. 14A). Of the 16 SpCas9-HF1 derivatives that reduced mismatched-target activities with the 11/12 mismatched sgRNA to near background levels, 9 appeared to have only minimal effects on on-target activity (assessed using the perfectly matched sgRNA; FIG. 14A). Additional testing of a subset of these SpCas9-HF1 derivatives in the EGFP disruption assay using an sgRNA intentionally mismatched at positions 9 and 10 (FIG. 14B) also revealed that these variants possessed lower activities with this mismatched sgRNA than what was observed either with SpCas9-HF1 (FIG. 14b), with eSpCas9(1.1) (FIG. 13A), or with the same substitutions added to wild-type SpCas9 nuclease (FIG. 13B). Importantly, five variants showed background level off-target activity in this assay with the 9/10 mismatched sgRNA.

Figure 15:
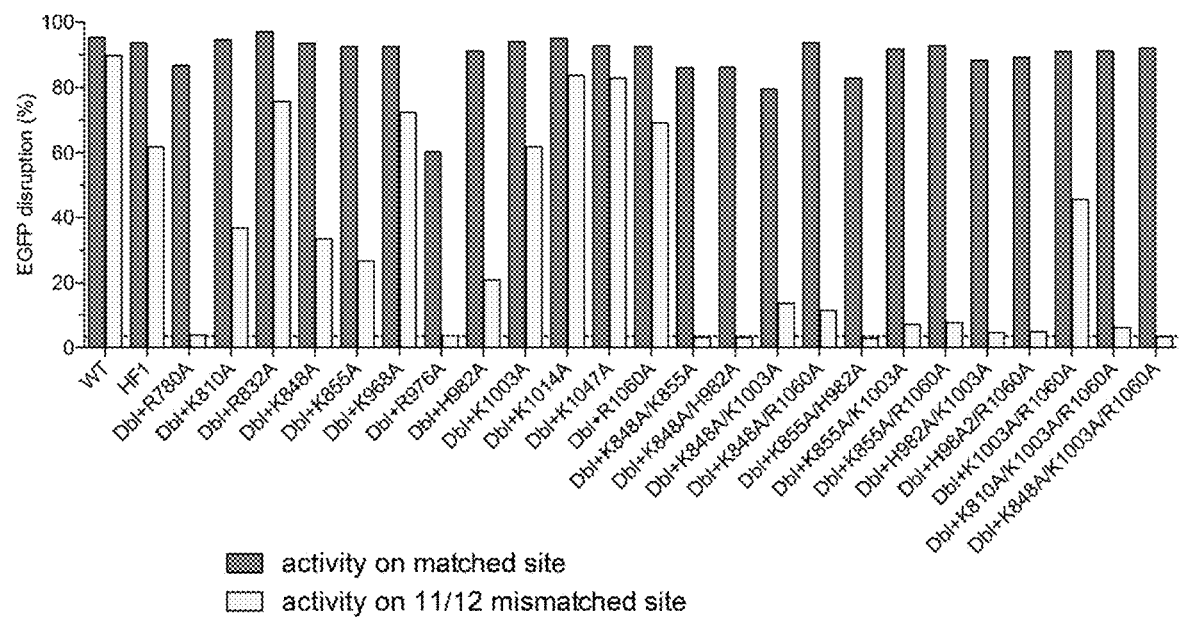
FIG. 15|Activity of wild-type SpCas9, SpCas9-HF1, and SpCas9(Q695A/Q926A) derivatives bearing one or more alanine substitutions at positions that can potentially contact the non-target DNA strand. Nucleases were assessed using the EGFP disruption assay, with an sgRNA that is perfectly matched to a site in the EGFP gene as well as an sgRNA that is intentionally mismatched at positions 11 and 12. Mismatched positions are numbered with position 20 being the most PAM-distal position; the red dashed line represents background levels of EGFP disruption; HF1=SpCas9 with N497A/R661A/Q695A/Q926A substitutions; Db1=SpCas9 with Q695A/Q926A substitutions.

Next, whether these alanine substitutions of the non-target strand could be combined with the SpCas9 variant that contains only the Q695A and Q926A substitutions from our SpCas9-HF1 variant (here "double" variant) was tested. Because many of the HF1 derivatives tested above showed an observable (and undesirable) decrease in on-target activity, it was hypothesized that combining only the two most important substitutions from SpCas9-HF1 (Q695A and Q926A; see FIG. 1B) with one or more non-target strand contacting substitutions might rescue on-target activity but still maintain the gains in specificity observed when these substitutions were added to the SpCas9-HF1 variant. Therefore, various SpCas9(Q695A/Q926A) derivatives bearing combinations of single, double, or triple alanine substitutions at potential non-target DNA strand interacting positions were tested in the human cell-based EGFP disruption assay using the same perfectly matched sgRNA targeted to EGFP described above (to test on-target activities) and the same sgRNA bearing mismatches at positions 11 and 12 (to assess activities at a mismatched target site, as would be found for off-target sites) that were used for FIGS. 13A-B. This experiment revealed most of the SpCas9(Q695A/Q926A) derivative variants tested showed comparable on-target activities to those observed with both wild-type SpCas9 and SpCas9-HF1 (FIG. 15). Importantly, many of the SpCas9-HF1 derivatives had substantially lower activity with the 11/12 mismatched sgRNA compared with what was observed with SpCas9-HF1, eSpCas9(1.0), or eSpCas9(1.1) suggesting that certain combinations of these new variants have reduced mismatched-target activities and thus improved specificities (FIG. 15). Of the 13 SpCas9(Q695A/Q926A) derivatives that reduced mismatched-target activities with the 11/12 mismatched sgRNA to near background levels, only 1 appeared to have a substantial effect on on-target activity (assessed using the perfectly matched sgRNA; FIG. 15).

Overall, these data demonstrate that the addition of one, two, or three alanine substitutions to SpCas9-HF1 or SpCas9 (Q695A/Q926A) at positions that might contact the non-target DNA strand can lead to new variants with improved abilities to discriminate against mismatched off-target sites (relative to to their parental clones or the recently described eSpCas9(1.0) or (1.1). Importantly, these same substitutions in the context of wild-type SpCas9 do not appear to provide any substantial specificity benefit.

Figure 16:
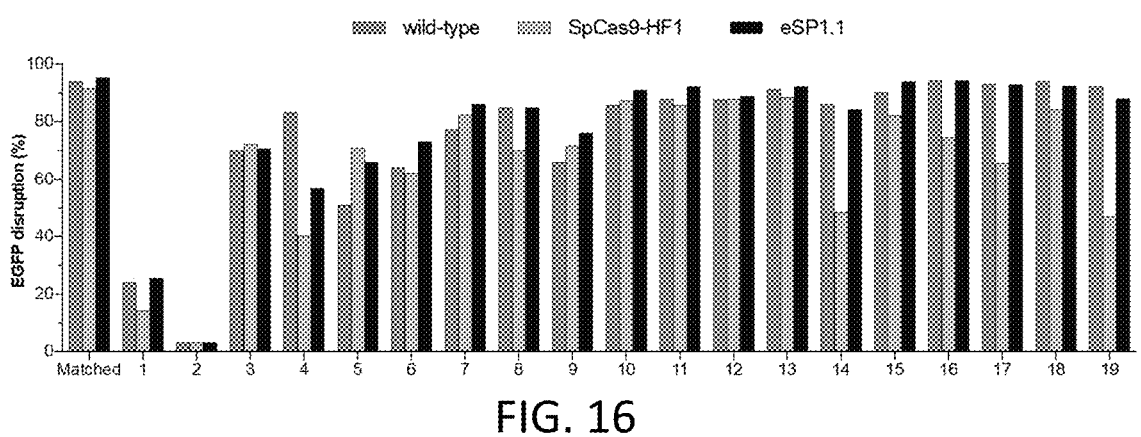
FIG. 16|Activities of wild-type SpCas9, SpCas9-HF1, and eSpCas9-1.1 using a matched sgRNA and sgRNAs with single mismatches at each position in the spacer. Nucleases were assessed using the EGFP disruption assay, with an sgRNA that is perfectly matched to a site in the EGFP gene ("matched") as well as sgRNAs that are intentionally mismatched at the positions indicated. Mismatched positions are numbered with position 20 being the most PAM-distal position. SpCas9-HF1=N497A/R661A/Q695A/Q926A, and eSP1.1=K848A/K1003A/R1060A.

To better define and compare the tolerances of SpCas9-HF1 and eSpCas9-1.1 to mismatches at the sgRNA-target DNA complementarity interface, their activities were examined using sgRNAs containing single mismatches at all possible positions in the spacer complementarity region. Both the SpCas9-HF1 and eSPCas9-1.1 variants had similar activities on most singly mismatched sgRNAs when compared to wild-type SpCas9, with a few exceptions where SpCas9-HF1 outperformed eSpCas9-1.1 (FIG. 16).

Figure 17A:
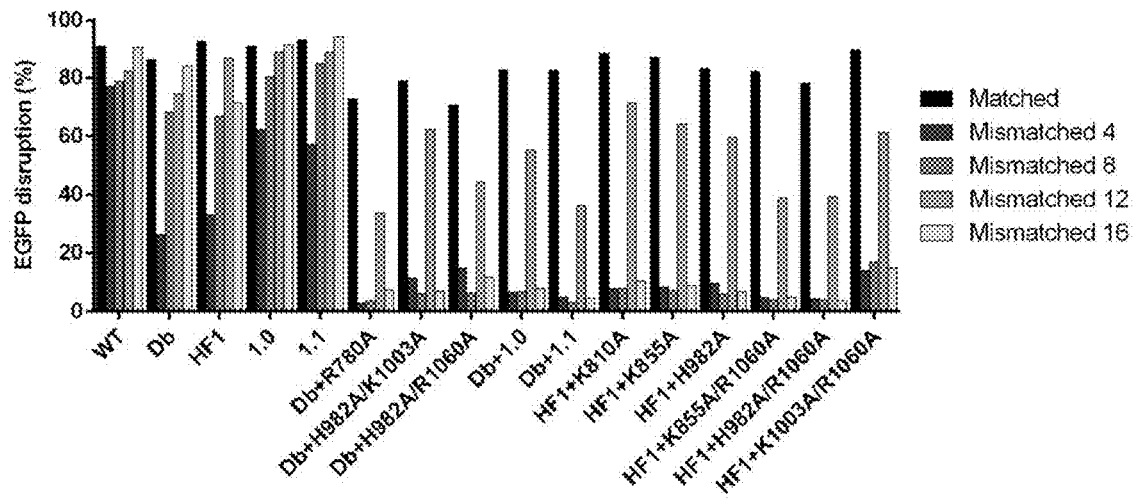
FIGS. 17A-B|Activities of wild-type SpCas9 and variants using a matched sgRNA and sgRNAs with single mismatches at various positions in the spacer. (A) The activities of SpCas9 nucleases containing combinations of alanine substitutions (directed to positions that may potentially contact the target or non-target DNA strands) were assessed using the EGFP disruption assay, with an sgRNA that is perfectly matched to a site in the EGFP gene ("matched") as well as sgRNAs that are intentionally mismatched at the indicated spacer positions. (B) A subset of these nucleases from (a) were tested using the remainder of all possible singly mismatched sgRNAs for the matched on-target site. Mismatched positions are numbered with position 20 being the most PAM-distal position. mm=mismatch, WT=wild-type, Db=Q695A/Q926A, HF1=N497A/R661A/Q695A/Q926A, 1.0=K810A/K1003A/R1060A, and 1.1=K848A/K1003A/R1060A.
Figure 17B:
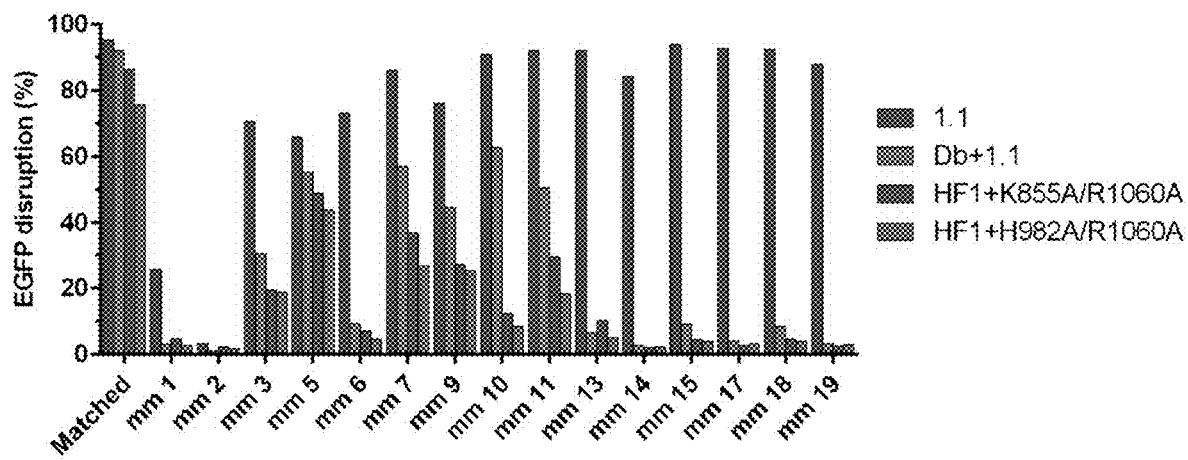
Figure 18:
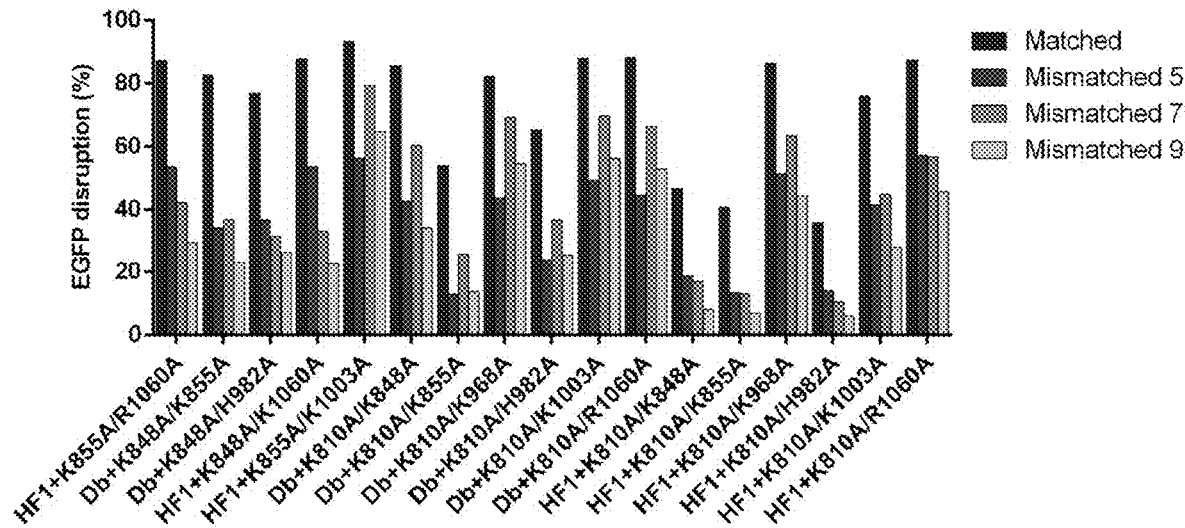
FIG. 18|Activities of wild-type SpCas9 and variants using a matched sgRNA and sgRNAs with mismatches at various individual positions in the spacer. The activities of SpCas9 nucleases containing combinations of alanine substitutions (directed to positions that may potentially contact the target or non-target DNA strands), were assessed using the EGFP disruption assay with an sgRNA that is perfectly matched to a site in the EGFP gene ("matched") as well as sgRNAs that are intentionally mismatched at the indicated positions. Db=Q695A/Q926A, HF1=N497A/R661A/Q695A/Q926A.

Next we tested the single nucleotide mismatch tolerance of some variants containing combinations of amino acid substitutions from either the double mutant (Db=Q695A/Q926A), SpCas9-HF1 (N497A/R661A/Q695A/Q926A), eSpCas9-1.0 (1.0=K810A/K1003A/R1060A), or eSpCas9-1.1(1.1=K848A/K1003A/R1060A) with additional alanine substitutions in residues that contact the target strand DNA or that potentially contact the non-target strand DNA (FIGS. 17A-B). On-target activity was assessed using a perfectly matched sgRNA, while single nucleotide mismatch tolerance was assessed using sgRNAs bearing such mismatches at positions 4, 8, 12, or 16 in the spacer sequence (FIG. 17A). A number of these variants maintained on-target activity with substantial reductions in activities observed with the mismatched sgRNAs. Three of these variants (Q695A/K848A/Q926A/K1003A/R1060A, N497A/R661A/Q695A/K855A/Q926A/R1060A, and N497A/R661A/Q695A/Q926A/H982A/R1060A) were further tested with the remaining single mismatch sgRNAs (containing mismatches at positions 1-3, 5-7, 9-11, 13-15, and 17-20). These variants demonstrated a more robust intolerance to single nucleotide substitutions in the sgRNA compared with eSp-Cas9-1.1, demonstrating the improved specificity profile of these new variants (FIG. 17B). Additional variant nucleases containing alternative combinations of amino acid substitutions were tested using sgRNAs containing mismatches at positions 5, 7, and 9 in the spacer (these particular mismatched sgRNAs were used because earlier variants appeared to tolerate mismatches at these positions) (FIG. 18). A number of these nucleases had improved specificities against the mismatched sites, with only marginal reductions in on-target activities (FIG. 18).

Figure 19A:
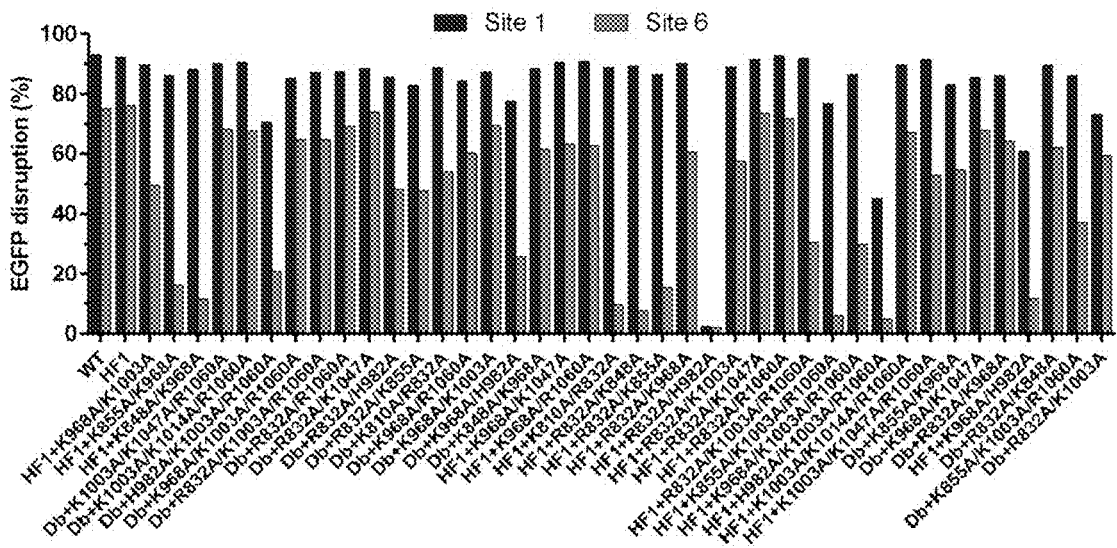
FIGS. 19A-B|Activities of wild-type SpCas9 and variants using a matched sgRNA and sgRNAs with mismatches at various individual positions in the spacer. (A) The on-target activities of SpCas9 nucleases containing combinations of alanine substitutions (directed to positions that may potentially contact the target or non-target DNA strands), were assessed using the EGFP disruption assay with two sgRNAs that are perfectly matched to a site in the EGFP gene. (B) A subset of these nucleases from (a) were tested with sgRNAs containing mismatches at positions 12, 14, 16, or 18 (of sgRNA 'site 1') in their spacer sequence to determine whether intolerance to mismatches was imparted by these substitutions. Db=Q695A/Q926A, HF1=N497A/R661A/Q695A/Q926A.
Figure 19B:
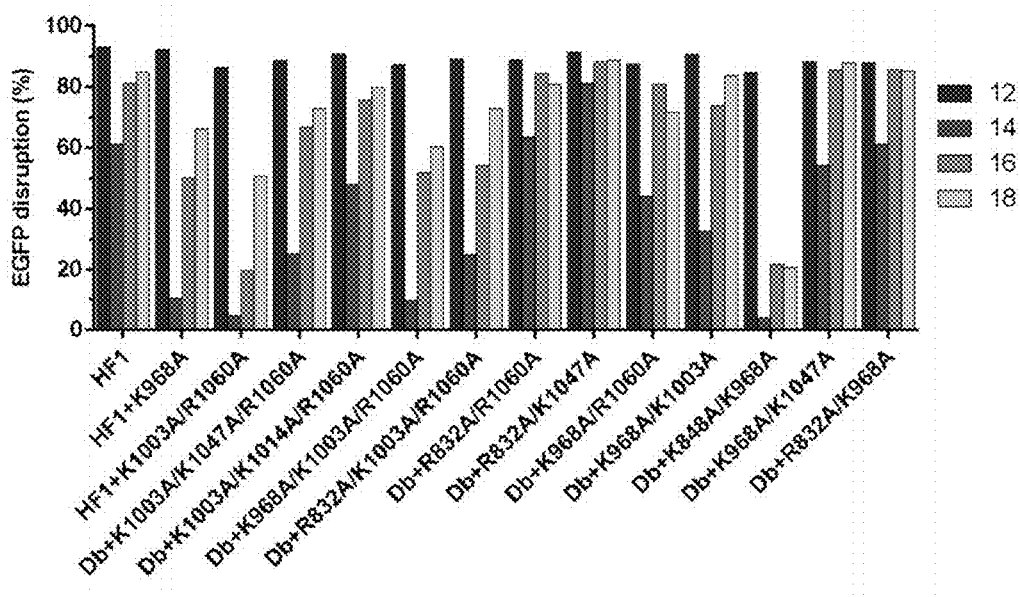

To further determine whether additional combinations of mutations could convey specificity improvements, a greatly expanded panel of nuclease variants with two additional matched sgRNAs was tested to examine on-target activity in our EGFP disruption activity (FIG. 19A). A number of these variants maintained robust on-target activities, suggesting that they may be useful for generating further mprovements to specificity (FIG. 19B). A number of these variants were tested with sgRNAs containing single substitutions at positions 12, 14, 16, or 18 to determine whether specificity improvements were observed and were found to exhibit greater intolerance to single nucleotide mismatches at these positions (FIG. 19B).

Example 3

Taking an analogous strategy with *Staphylococcus aureus* Cas9 (SaCas9) as we had done with SpCas9, experiments were performed to improve the specificity of SaCas9 by introducing alanine substitutions in residues that are known to contact the target DNA strand (FIG. 20 and FIG. 21A), residues that may contact the non-target DNA (ongoing experiments), and residues that we have previously shown can influence PAM specificity (FIG. 21B). Residues that may contact the target strand DNA backbone include: Y211, Y212, W229, Y230, R245, T392, N419, L446, Y651, and R654; residues that may contact the non-target strand DNA include: Q848, N492, Q495, R497, N498, R499, Q500, K518, K523, K525, H557, R561, K572, R634, R654, G655, N658, S662, N668, R686, K692, R694, H700, K751; and residues that contact the PAM include: E782, D786, T787, Y789, T882, K886, N888, A889, L909, K929, N985, N986, R991, and R1015. In a preliminary experiment, single alanine substitutions (or some combinations thereof) in either target strand DNA contacting residues or PAM contacting residues (FIGS. 21A and B, respectively) had variable effects on on-target EGFP disruption activity (using a perfectly matched sgRNA) and were unable to eliminate off-target cleavage (when using an sgRNA mismatched at positions 11 and 12). Interestingly, SpCas9 mutations in the HF1 were unable to completely abolish off-target activity with a similarly mismatched target/sgRNA pair, suggesting that variants containing combinations of target strand/non-target strand substitutions may be necessary to improve specificity at such sites (as we observed with SpCas9).

Figure 22B:
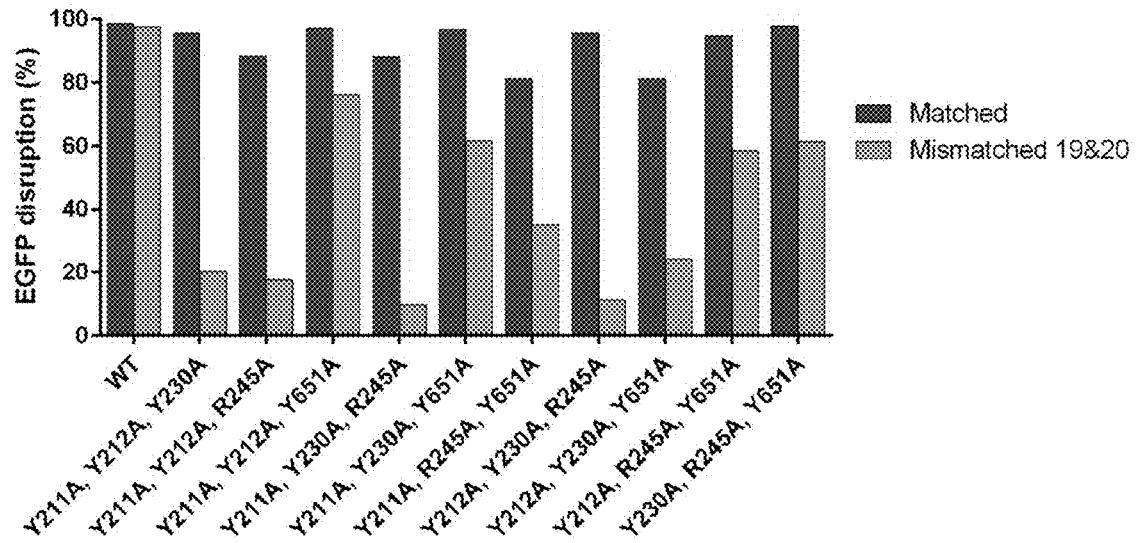

To further assess the strategy of mutating potential target strand DNA contacts to improve SaCas9 specificity, the potential of single, double, triple, and quadruple combinations of mutations to tolerate mismatches at positions 19 and 20 in an sgRNA was examined (FIGS. 22A and B). These combinations revealed that alanine substitutions at Y230 and R245, when combined with other substitutions, can increase specificity as judged by the capability to better discriminate against mismatched sites.

Figure 23:
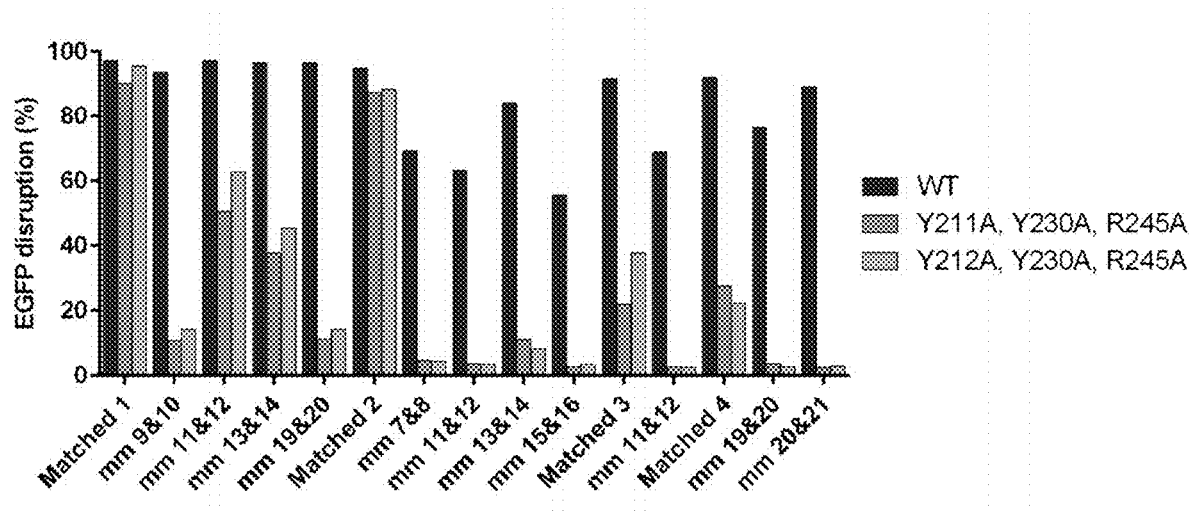
FIG. 23|Activities of wild-type (WT) SaCas9 and SaCas9 variants bearing triple combinations of alanine substitutions at residues that may potentially contact the target DNA strand. Nucleases were assessed using the EGFP disruption assay. Four different sgRNAs were used (matched #1-4), with each of the four target sites also being tested with mismatched sgRNAs known to be efficiently used by wild-type SaCas9. Mismatched sgRNAs for each site are shown to the right of each matched sgRNA (for example, the only mismatched sgRNA for matched site 3 is mm 11 & 12). Mismatched positions are numbered with position 21 being the most PAM-distal position; mm, mismatch.

Next the on-target gene disruption activities of two of these triple alanine substitution variants (Y211A/Y230A/R245A and Y212A/Y230A/R245A) were examined at 4 on-target sites in EGFP (matched sites #1-4; FIG. 23). These variants maintained robust on-target activities for matched sites 1 and 2 but showed approximately 60-70% loss of on-target activity with matched sites 3 and 4. Both of these triple alanine substitution variants dramatically improved specificity relative to wild-type SaCas9 as judged by using sgRNAs bearing double mismatches at various positions in the spacers of target sites 1-4 (FIG. 23).

Figure 24A:
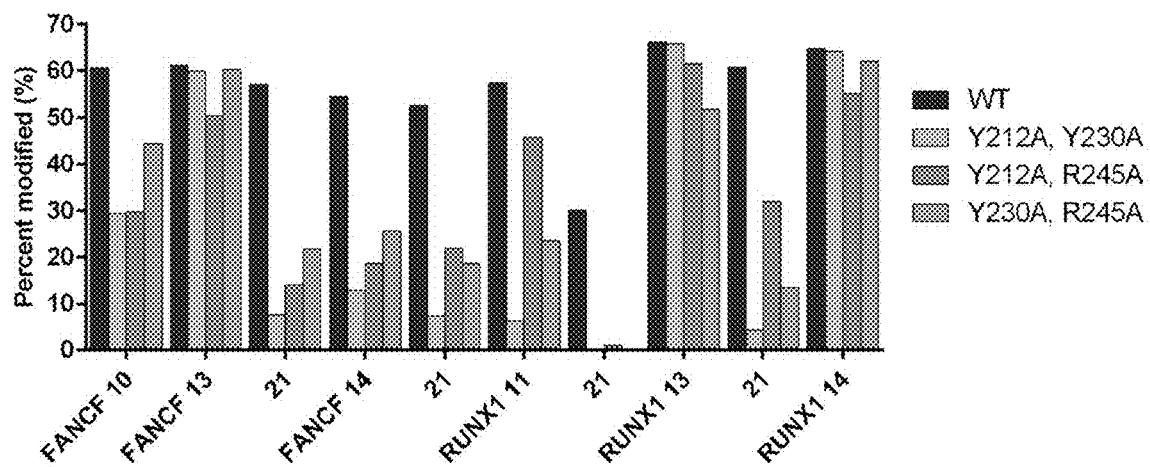
FIGS. 24A-B|Activities of wild-type (WT) SaCas9 and SaCas9 derivatives bearing one or more alanine substitutions at residues that may potentially contact the target DNA strand. A and B, SaCas9 variants bearing double (A) or triple (B) combinations substitutions were assessed against matched and singly mismatched endogenous human gene target sites using the T7E1 assay. Matched 'on-target' sites are named according to their gene target site sgRNA number from Kleinstiver et al., Nature Biotechnology 2015. Mismatched sgRNAs are numbered with the mismatch occurring at position 21, the most PAM-distal position; mismatched sgRNAs are derived from the matched on-target site that is listed to the left of the mismatched sgRNA.
Figure 24B:
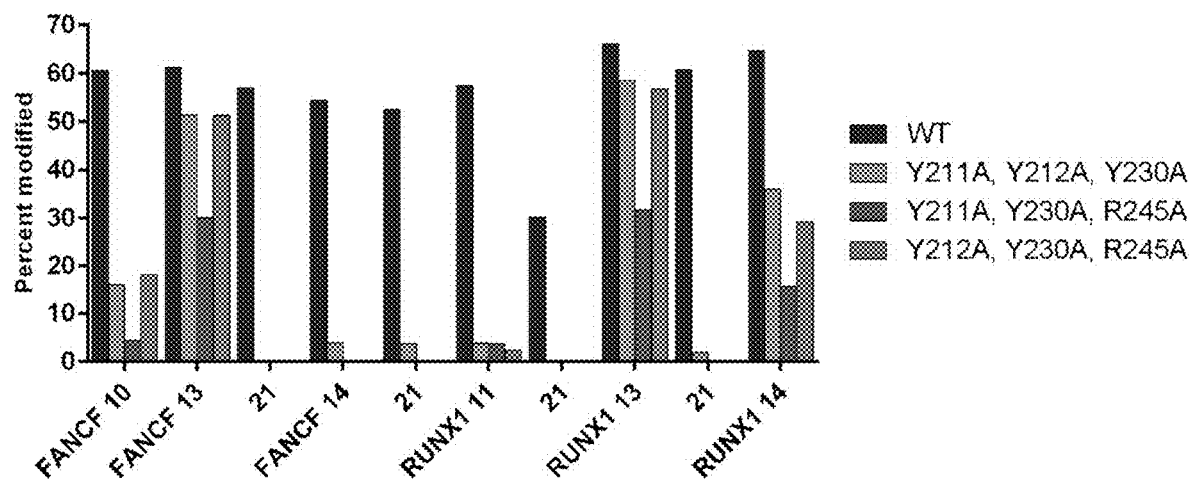

SaCas9 variants bearing double and triple combinations (FIGS. 24A and B, respectively) of these alanine substitutions were tested on six endogenous sites for on target activities and improvements in specificity assessed using an sgRNA containing a single mismatch at position 21 (the most PAM distal position expected to be a challenging mismatch to discriminate against). In some cases, on-target activities with the matched sgRNA were maintained with the variants while 'off-target' activities with the sgRNA mismatched at position 21 were eliminated (FIGS. 24A and B). In other cases, marginal to complete loss of activity was observed with the matched sgRNA.

REFERENCES

1. Sander, J. D. & Joung, J. K. CRISPR-Cas systems for editing, regulating and targeting genomes. Nat Biotechnol 32, 347-355 (2014).
2. Hsu, P. D., Lander, E. S. & Zhang, F. Development and applications of CRISPR-Cas9 for genome engineering. Cell 157, 1262-1278 (2014).
3. Doudna, J. A. & Charpentier, E. Genome editing. The new frontier of genome engineering with CRISPR-Cas9. Science 346, 1258096 (2014).
4. Barrangou, R. & May, A. P. Unraveling the potential of CRISPR-Cas9 for gene therapy. Expert Opin Biol Ther 15, 311-314 (2015).
5. Jinek, M. et al. A programmable dual-RNA-guided DNA endonuclease in adaptive bacterial immunity. Science 337, 816-821 (2012).
6. Sternberg, S. H., Redding, S., Jinek, M., Greene, E. C. & Doudna, J. A. DNA interrogation by the CRISPR RNA-guided endonuclease Cas9. Nature 507, 62-67 (2014).
7. Hsu, P. D. et al. DNA targeting specificity of RNA-guided Cas9 nucleases. Nat Biotechnol 31, 827-832 (2013).
8. Tsai, S. Q. et al. GUIDE-seq enables genome-wide profiling of off-target cleavage by CRISPR-Cas nucleases. Nat Biotechnol 33, 187-197 (2015).
9. Hou, Z. et al. Efficient genome engineering in human pluripotent stem cells using Cas9 from *Neisseria meningitidis*. Proc Natl Acad Sci USA (2013).
10. Fonfara, I. et al. Phylogeny of Cas9 determines functional exchangeability of dual-RNA and Cas9 among orthologous type II CRISPR-Cas systems. Nucleic Acids Res 42, 2577-2590 (2014).
11. Esvelt, K. M. et al. Orthogonal Cas9 proteins for RNA-guided gene regulation and editing. Nat Methods 10, 1116-1121 (2013).
12. Cong, L. et al. Multiplex genome engineering using CRISPR/Cas systems. Science 339, 819-823 (2013).
13. Horvath, P. et al. Diversity, activity, and evolution of CRISPR loci in *Streptococcus thermophilus*. J Bacteriol 190, 1401-1412 (2008).
14. Anders, C., Niewoehner, O., Duerst, A. & Jinek, M. Structural basis of PAM-dependent target DNA recognition by the Cas9 endonuclease. Nature 513, 569-573 (2014).
15. Reyon, D. et al. FLASH assembly of TALENs for high-throughput genome editing. Nat Biotechnol 30, 460-465 (2012).
16. Fu, Y. et al. High-frequency off-target mutagenesis induced by CRISPR-Cas nucleases in human cells. Nat Biotechnol 31, 822-826 (2013).
17. Chen, Z. & Zhao, H. A highly sensitive selection method for directed evolution of homing endonucleases. Nucleic Acids Res 33, e154 (2005).
18. Doyon, J. B., Pattanayak, V., Meyer, C. B. & Liu, D. R. Directed evolution and substrate specificity profile of homing endonuclease I-SceI. J Am Chem Soc 128, 2477-2484 (2006).
19. Jiang, W., Bikard, D., Cox, D., Zhang, F. & Marraffini, L. A. RNA-guided editing of bacterial genomes using CRISPR-Cas systems. Nat Biotechnol 31, 233-239 (2013).
20. Mali, P. et al. RNA-guided human genome engineering via Cas9. Science 339, 823-826 (2013).
21. Hwang, W. Y. et al. Efficient genome editing in zebrafish using a CRISPR-Cas system. Nat Biotechnol 31, 227-229 (2013).
22. Chylinski, K., Le Rhun, A. & Charpentier, E. The tracrRNA and Cas9 families of type II CRISPR-Cas immunity systems. RNA Biol 10, 726-737 (2013).
23. Kleinstiver, B. P., Fernandes, A. D., Gloor, G. B. & Edgell, D. R. A unified genetic, computational and experimental framework identifies functionally relevant residues of the homing endonuclease I-BmoI. Nucleic Acids Res 38, 2411-2427 (2010).
24. Gagnon, J. A. et al. Efficient mutagenesis by Cas9 protein-mediated oligonucleotide insertion and large-scale assessment of single-guide RNAs. PLoS One 9, e98186 (2014).

Sequences

```
JDS246: CMV-T7-humanSpCas9-NLS-3xFLAG
Human codon optimized S. pyogenes Cas9 in normal font, NLS double
underlined, 3xFLAG tag in bold:
                                                       SEQ ID NO: 271
ATGGATAAAAAGTATTCTATTGGTTTAGACATCGGCACTAATTCCGTTGGATGGGCTGTCATAACCGAT

GAATACAAAGTACCTTCAAAGAAATTTAAGGTGTTGGGGAACACAGACCGTCATTCGATTAAAAAGAAT

CTTATCGGTGCCCTCCTATTCGATAGTGGCGAAACGGCAGAGGCGACTCGCCTGAAACGAACCGCTCGG

AGAAGGTATACACGTCGCAAGAACCGAATATGTTACTTACAAGAAATTTTTAGCAATGAGATGGCCAAA

GTTGACGATTCTTTCTTTCACCGTTTGGAAGAGTCCTTCCTTGTCGAAGAGGACAAGAAACATGAACGG

CACCCCATCTTTGGAAACATAGTAGATGAGGTGGCATATCATGAAAAGTACCCAACGATTTATCACCTC
```

-continued
```
AGAAAAAAGCTAGTTGACTCAACTGATAAAGCGGACCTGAGGTTAATCTACTTGGCTCTTGCCCATATG
ATAAAGTTCCGTGGGCACTTTCTCATTGAGGGTGATCTAAATCCGGACAACTCGGATGTCGACAAACTG
TTCATCCAGTTAGTACAAACCTATAATCAGTTGTTTGAAGAGAACCCTATAAATGCAAGTGGCGTGGAT
GCGAAGGCTATTCTTAGCGCCCGCCTCTCTAAATCCCGACGGCTAGAAAACCTGATCGCACAATTACCC
GGAGAGAAGAAAAATGGGTTGTTCGGTAACCTTATAGCGCTCTCACTAGGCCTGACACCAAATTTTAAG
TCGAACTTCGACTTAGCTGAAGATGCCAAATTGCAGCTTAGTAAGGACACGTACGATGACGATCTCGAC
AATCTACTGGCACAAATTGGAGATCAGTATGCGGACTTATTTTTGGCTGCCAAAAACCTTAGCGATGCA
ATCCTCCTATCTGACATACTGAGAGTTAATACTGAGATTACCAAGGCGCCGTTATCCGCTTCAATGATC
AAAAGGTACGATGAACATCACCAAGACTTGACACTTCTCAAGGCCCTAGTCCGTCAGCAACTGCCTGAG
AAATATAAGGAAATATTCTTTGATCAGTCGAAAAACGGGTACGCAGGTTATATTGACGGCGGAGCGAGT
CAAGAGGAATTCTACAAGTTTATCAAACCCATATTAGAGAAGATGGATGGGACGGAAGAGTTGCTTGTA
AAACTCAATCGCGAAGATCTACTGCGAAAGCAGCGGACTTTCGACAACGGTAGCATTCCACATCAAATC
CACTTAGGCGAATTGCATGCTATACTTAGAAGGCAGGAGGATTTTTATCCGTTCCTCAAAGACAATCGT
GAAAAGATTGAGAAAATCCTAACCTTTCGCATACCTTACTATGTGGGACCCCTGGCCCGAGGGAACTCT
CGGTTCGCATGGATGACAAGAAAGTCCGAAGAAACGATTACTCCATGGAATTTTGAGGAAGTTGTCGAT
AAAGGTGCGTCAGCTCAATCGTTCATCGAGAGGATGACCAACTTTGACAAGAATTTACCGAACGAAAAA
GTATTGCCTAAGCACAGTTTACTTTACGAGTATTTCACAGTGTACAATGAACTCACGAAAGTTAAGTAT
GTCACTGAGGGCATGCGTAAACCCGCCTTTCTAAGCGGAGAACAGAAGAAAGCAATAGTAGATCTGTTA
TTCAAGACCAACCGCAAAGTGACAGTTAAGCAATTGAAAGAGGACTACTTTAAGAAAATTGAATGCTTC
GATTCTGTCGAGATCTCCGGGGTAGAAGATCGATTTAATGCGTCACTTGGTACGTATCATGACCTCCTA
AAGATAATTAAAGATAAGGACTTCCTGGATAACGAAGAGAATGAAGATATCTTAGAAGATATAGTGTTG
ACTCTTACCCTCTTTGAAGATCGGGAAATGATTGAGGAAAGACTAAAAACATACGCTCACCTGTTCGAC
GATAAGGTTATGAAACAGTTAAAGAGGCGTCGCTATACGGGCTGGGACGATTGTCGCGGAAACTTATC
AACGGGATAAGAGACAAGCAAAGTGGTAAAACTATTCTCGATTTTCTAAAGAGCGACGGCTTCGCCAAT
AGGAACTTTATGCAGCTGATCCATGATGACTCTTTAACCTTCAAAGAGGATATACAAAAGGCACAGGTT
TCCGGACAAGGGGACTCATTGCACGAACATATTGCGAATCTTGCTGGTTCGCCAGCCATCAAAAAGGGC
ATACTCCAGACAGTCAAAGTAGTGGATGAGCTAGTTAAGGTCATGGGACGTCACAAACCGGAAAACATT
GTAATCGAGATGGCACGCGAAAATCAAACGACTCAGAAGGGGCAAAAAAACAGTCGAGAGCGGATGAAG
AGAATAGAAGAGGGTATTAAAGAACTGGGCAGCCAGATCTTAAAGGAGCATCCTGTGGAAAATACCCAA
TTGCAGAACGAGAAACTTTACCTCTATTACCTACAAAATGGAAGGGACATGTATGTTGATCAGGAACTG
GACATAAACCGTTTATCTGATTACGACGTCGATCACATTGTACCCCAATCCTTTTTGAAGGACGATTCA
ATCGACAATAAAGTGCTTACACGCTCGGATAAGAACCGAGGGAAAAGTGACAATGTTCCAAGCGAGGAA
GTCGTAAAGAAAATGAAGAACTATTGGCGGCAGCTCCTAAATGCGAAACTGATAACGCAAAGAAAGTTC
GATAACTTAACTAAAGCTGAGAGGGGTGGCTTGTCTGAACTTGACAAGGCCGGATTTATTAAACGTCAG
CTCGTGGAAACCCGCCAAATCACAAAGCATGTTGCACAGATACTAGATTCCGAATGAATACGAAATAC
GACGAGAACGATAAGCTGATTCGGGAAGTCAAAGTAATCACTTTAAAGTCAAAATTGGTGTCGGACTTC
AGAAAGGATTTTCAATTCTATAAAGTTAGGGAGATAAATAACTACCACCATGCGCACGACGCTTATCTT
AATGCCGTCGTAGGGACCGCACTCATTAAGAAATACCCGAAGCTAGAAAGTGAGTTTGTGTATGGTGAT
TACAAAGTTTATGACGTCCGTAAGATGATCGCGAAAAGCGAACAGGAGATAGGCAAGGCTACAGCCAAA
TACTTCTTTTATTCTAACATTATGAATTTCTTTAAGACGGAAATCACTCTGGCAAACGGAGAGATACGC
AAACGACCTTTAATTGAAACCAATGGGGAGACAGGTGAAATCGTATGGGATAAGGGCCGGGACTTCGCG
```

-continued

```
ACGGTGAGAAAAGTTTTGTCCATGCCCCAAGTCAACATAGTAAAGAAAACTGAGGTGCAGACCGGAGGG

TTTTCAAAGGAATCGATTCTTCCAAAAAGGAATAGTGATAAGCTCATCGCTCGTAAAAAGGACTGGGAC

CCGAAAAAGTACGGTGGCTTCGATAGCCCTACAGTTGCCTATTCTGTCCTAGTAGTGGCAAAAGTTGAG

AAGGGAAAATCCAAGAAACTGAAGTCAGTCAAAGAATTATTGGGGATAACGATTATGGAGCGCTCGTCT

TTTGAAAAGAACCCCATCGACTTCCTTGAGGCGAAAGGTTACAAGGAAGTAAAAAAGGATCTCATAATT

AAACTACCAAAGTATAGTCTGTTTGAGTTAGAAAATGGCCGAAAACGGATGTTGGCTAGCGCCGGAGAG

CTTCAAAGGGGAACGAACTCGCACTACCGTCTAAATACGTGAATTTCCTGTATTTAGCGTCCCATTAC

GAGAAGTTGAAAGGTTCACCTGAAGATAACGAACAGAAGCAACTTTTTGTTGAGCAGCACAAACATTAT

CTCGACGAAATCATAGAGCAAATTTCGGAATTCAGTAAGAGAGTCATCCTAGCTGATGCCAATCTGGAC

AAAGTATTAAGCGCATACAACAAGCACAGGGATAAACCCATACGTGAGCAGGCGGAAAATATTATCCAT

TTGTTTACTCTTACCAACCTCGGCGCTCCAGCCGCATTCAAGTATTTTGACACAACGATAGATCGCAAA

CGATACACTTCTACCAAGGAGGTGCTAGACGCGACACTGATTCACCAATCCATCACGGGATTATATGAA

ACTCGGATAGATTTGTCACAGCTTGGGGGTGACGGATCCCCAAGAAGAAGAGGAAAGTCTCGAGCGAC

TACAAAGACCATGACGGTGATTATAAAGATCATGACATCGATTACAAGGATGACGATGACAAGTGA
```

VP12: CMV-T7-humanSpCas9-HF1 (N497A, R661A, Q695A, Q926A)-NLS-3xFLAG
Human codon optimized *S. pyogenes* Cas9 in normal font, modified codons in lower case, NLS double underlined, 3xFLAG tag in bold:

SEQ ID NO: 272

```
ATGGATAAAAAGTATTCTATTGGTTTAGACATCGGCACTAATTCCGTTGGATGGGCTGTCATAACCGAT

GAATACAAAGTACCTTCAAAGAAATTTAAGGTGTTGGGGAACACAGACCGTCATTCGATTAAAAAGAAT

CTTATCGGTGCCCTCCTATTCGATAGTGGCGAAACGGCAGAGGCGACTCGCCTGAAACGAACCGCTCGG

AGAAGGTATACACGTCGCAAGAACCGAATATGTTACTTACAAGAAATTTTTAGCAATGAGATGGCCAAA

GTTGACGATTCTTTCTTTCACCGTTTGGAAGAGTCCTTCCTTGTCGAAGAGGACAAGAAACATGAACGG

CACCCCATCTTTGGAAACATAGTAGATGAGGTGGCATATCATGAAAAGTACCCAACGATTTATCACCTC

AGAAAAAAGCTAGTTGACTCAACTGATAAAGCGGACCTGAGGTTAATCTACTTGGCTCTTGCCCATATG

ATAAAGTTCCGTGGGCACTTTCTCATTGAGGGTGATCTAAATCCGGACAACTCGGATGTCGACAAACTG

TTCATCCAGTTAGTACAAACCTATAATCAGTTGTTTGAAGAGAACCCTATAAATGCAAGTGGCGTGGAT

GCGAAGGCTATTCTTAGCGCCCGCCTCTCTAAATCCCGACGGCTAGAAAACCTGATCGCACAATTACCC

GGAGAGAAGAAAAATGGGTTGTTCGGTAACCTTATAGCGCTCTCACTAGGCCTGACACCAAATTTTAAG

TCGAACTTCGACTTAGCTGAAGATGCCAAATTGCAGCTTAGTAAGGACACGTACGATGACGATCTCGAC

AATCTACTGGCACAAATTGGAGATCAGTATGCGGACTTATTTTTGGCTGCCAAAAACCTTAGCGATGCA

ATCCTCCTATCTGACATACTGAGAGTTAATACTGAGATTACCAAGGCGCCGTTATCCGCTTCAATGATC

AAAAGGTACGATGAACATCACCAAGACTTGACACTTCTCAAGGCCCTAGTCCGTCAGCAACTGCCTGAG

AAATATAAGGAAATATTCTTTGATCAGTCGAAAAACGGGTACGCAGGTTATATTGACGGCGGAGCGAGT

CAAGAGGAATTCTACAAGTTTATCAAACCCATATTAGAGAAGATGGATGGGACGGAAGAGTTGCTTGTA

AAACTCAATCGCGAAGATCTACTGCGAAAGCAGCGGACTTTCGACAACGGTAGCATTCCACATCAAATC

CACTTAGGCGAATTGCATGCTATACTTAGAAGGCAGGAGGATTTTTATCCGTTCCTCAAAGACAATCGT

GAAAAGATTGAGAAATCCTAACCTTTCGCATACCTTACTATGTGGGACCCCTGGCCCGAGGGAACTCT

CGGTTCGCATGGATGACAAGAAAGTCCGAAGAAACGATTACTCCCTGGAATTTTGAGGAAGTTGTCGAT

AAAGGTGCGTCAGCTCAATCGTTCATCGAGAGGATGACCgccTTTGACAAGAATTTACCGAACGAAAAA

GTATTGCCTAAGCACAGTTTACTTTACGAGTATTTCACAGTGTACAATGAACTCACGAAAGTTAAGTAT

GTCACTGAGGGCATGCGTAAACCCGCCTTTCTAAGCGGAGAACAGAAGAAAGCAATAGTAGATCTGTTA
```

-continued

```
TTCAAGACCAACCGCAAAGTGACAGTTAAGCAATTGAAAGAGGACTACTTTAAGAAAATTGAATGCTTC
GATTCTGTCGAGATCTCCGGGGTAGAAGATCGATTTAATGCGTCACTTGGTACGTATCATGACCTCCTA
AAGATAATTAAAGATAAGGACTTCCTGGATAACGAAGAGAATGAAGATATCTTAGAAGATATAGTGTTG
ACTCTTACCCTCTTTGAAGATCGGGAAATGATTGAGGPAAGACTAAAAACATACGCTCACCTGTTCGAC
GATAAGGTTATGAAACAGTTAAAGAGGCGTCGCTATACGGGCTGGGGAgccTTGTCGCGGAAACTTATC
AACGGGATAAGAGACAAGCAAAGTGGTAAAACTATTCTCGATTTTCTAAAGAGCGACGGCTTCGCCAAT
AGGAACTTTATGgccCTGATCCATGATGACTCTTTAACCTTCAAAGAGGATATACAAAAGGCACAGGTT
TCCGGACAAGGGGACTCATTGCACGAACATATTGCGAATCTTGCTGGTTCGCCAGCCATCAAAAAGGGC
ATACTCCAGACAGTCAAAGTAGTGGATGAGCTAGTTAAGGTCATGGGACGTCACAAACCGGAAAACATT
GTAATCGAGATGGCACGCGAAAATCAAACGACTCAGAAGGGGCAAAAAAACAGTCGAGAGCGGATGAAG
AGAATAGAAGAGGGTATTAAAGAACTGGGCAGCCAGATCTTAAAGGAGCATCCTGTGGAAAATACCCAA
TTGCAGAACGAGAAACTTTACCTCTATTACCTACAAAATGGAAGGGACATGTATGTTGATCAGGAACTG
GACATAAACCGTTTATCTGATTACGACGTCGATCACATTGTACCCCAATCCTTTTTGAAGGACGATTCA
ATCGACAATAAAGTGCTTACACGCTCGGATAAGAACCGAGGGAAAAGTGACAATGTTCCAAGCGAGGAA
GTCGTAAAGAAAATGAAGAACTATTGGCGGCAGCTCCTAAATGCGAAACTGATAACGCAAAGAAAGTTC
GATAACTTAACTAAAGCTGAGAGGGGTGGCTTGTCTGAACTTGACAAGGCCGGATTTATTAAACGTCAG
CTCGTGGAAACCCGCgccATCACAAAGCATGTTGCGCAGATACTAGATTCCGAATGAATACGAAATAC
GACGAGAACGATAAGCTGATTCGGGAAGTCAAAGTAATCACTTTAAAGTCAAAATTGGTGTCGGACTTC
AGAAAGGATTTTCAATTCTATAAAGTTAGGGAGATAAATAACTACCACCATGCGCACGACGCTTATCTT
AATGCCGTCGTAGGGACCGCACTCATTAAGAAATACCCGAAGCTAGAAAGTGAGTTTGTGTATGGTGAT
TACAAAGTTTATGACGTCCGTAAGATGATCGCGAAAAGCGAACAGGAGATAGGCAAGGCTACAGCCAAA
TACTTCTTTTATTCTAACATTATGAATTTCTTTAAGACGGAAATCACTCTGGCAAACGGAGAGATACGC
AAACGACCTTTAATTGAAACCAATGGGGAGACAGGTGAAATCGTATGGGATAAGGGCCGGGACTTCGCG
ACGGTGAGAAAAGTTTTGTCCATGCCCCAAGTCAACATAGTAAAGAAAACTGAGGTGCAGACCGGAGGG
TTTTCAAAGGAATCGATTCTTCCAAAAAGGAATAGTGATAAGCTCATCGCTCGTAAAAAGGACTGGGAC
CCGAAAAAGTACGGTGGCTTCGATAGCCCTACAGTTGCCTATTCTGTCCTAGTAGTGGCAAAAGTTGAG
AAGGGAAAATCCAAGAAACTGAAGTCAGTCAAAGAATTATTGGGGATAACGATTATGGAGCGCTCGTCT
TTTGAAAAGAACCCCATCGACTTCCTTGAGGCGAAAGGTTACAAGGAAGTAAAAAAGGATCTCATAATT
AAACTACCAAAGTATAGTCTGTTTGAGTTAGAAAATGGCCGAAAACGGATGTTGGCTAGCGCCGGAGAG
CTTCAAAAGGGGAACGAACTCGCACTACCGTCTAAATACGTGAATTTCCTGTATTTAGCGTCCCATTAC
GAGAAGTTGAAAGGTTCACCTGAAGATAACGAACAGAAGCAACTTTTTGTTGAGCAGCACAAACATTAT
CTCGACGAAATCATAGAGCAAATTTCGGAATTCAGTAAGAGAGTCATCCTAGCTGATGCCAATCTGGAC
AAAGTATTAAGCGCATACAACAAGCACAGGGATAAACCCATACGTGAGCAGGCGGAAAATATTATCCAT
TTGTTTACTCTTACCAACCTCGGCGCTCCAGCCGCATTCAAGTATTTTGACACAACGATAGATCGCAAA
CGATACACTTCTACCAAGGAGGTGCTAGACGCGACACTGATTCACCAATCCATCACGGGATTATATGAA
ACTCGGATAGATTTGTCACAGCTTGGGGGTGACGGATCCCCCAAGAAGAAGAGGAAAGTCTCGAGC**GAC
TACAAAGACCATGACGGTGATTATAAAGATCATGACATCGATTACAAGGATGACGATGACAAG**TGA
```

-continued

MSP2135: CMV-T7-humanSpCas9-HF2 (N497A, R661A, Q695A, Q926A, D1135E)-NLS-3xFLAG
Human codon optimized *S. pyogenes* Cas9 in normal font, modified codons in lower case, NLS <u>double underlined</u>, 3xFLAG tag in bold:
SEQ ID NO: 273

ATGGATAAAAAGTATTCTATTGGTTTAGACATCGGCACTAATTCCGTTGGATGGGCTGTCATAACCGAT

GAATACAAAGTACCTTCAAAGAAATTTAAGGTGTTGGGGAACACAGACCGTCATTCGATTAAAAAGAAT

CTTATCGGTGCCCTCCTATTCGATAGTGGCGAAACGGCAGAGGCGACTCGCCTGAAACGAACCGCTCGG

AGAAGGTATACACGTCGCAAGAACCGAATATGTTACTTACAAGAAATTTTTAGCAATGAGATGGCCAAA

GTTGACGATTCTTTCTTTCACCGTTTGGAAGAGTCCTTCCTTGTCGAAGAGGACAAGAAACATGAACGG

CACCCCATCTTTGGAAACATAGTAGATGAGGTGGCATATCATGAAAAGTACCCAACGATTTATCACCTC

AGAAAAAAGCTAGTTGACTCAACTGATAAAGCGGACCTGAGGTTAATCTACTTGGCTCTTGCCCATATG

ATAAAGTTCCGTGGGCACTTTCTCATTGAGGGTGATCTAAATCCGGACAACTCGGATGTCGACAAACTG

TTCATCCAGTTAGTACAAACCTATAATCAGTTGTTTGAAGAGAACCCTATAAATGCAAGTGGCGTGGAT

GCGAAGGCTATTCTTAGCGCCCGCCTCTCTAAATCCCGACGGCTAGAAAACCTGATCGCACAATTACCC

GGAGAGAAGAAAAATGGGTTGTTCGGTAACCTTATAGCGCTCTCACTAGGCCTGACACCAAATTTTAAG

TCGAACTTCGACTTAGCTGAAGATGCCAAATTGCAGCTTAGTAAGGACACGTACGATGACGATCTCGAC

AATCTACTGGCACAAATTGGAGATCAGTATGCGGACTTATTTTTGGCTGCCAAAAACCTTAGCGATGCA

ATCCTCCTATCTGACATACTGAGAGTTAATACTGAGATTACCAAGGCGCCGTTATCCGCTTCAATGATC

AAAAGGTACGATGAACATCACCAAGACTTGACACTTCTCAAGGCCCTAGTCCGTCAGCAACTGCCTGAG

AAATATAAGGAAATATTCTTTGATCAGTCGAAAAACGGGTACGCAGGTTATATTGACGGCGGAGCGAGT

CAAGAGGAATTCTACAAGTTTATCAAACCCATATTAGAGAAGATGGATGGGACGGAAGAGTTGCTTGTA

AAACTCAATCGCGAAGATCTACTGCGAAAGCAGCGGACTTTCGACAACGGTAGCATTCCACATCAAATC

CACTTAGGCGAATTGCATGCTATACTTAGAAGGCAGGAGGATTTTTATCCGTTCCTCAAAGACAATCGT

GAAAAGATTGAGAAAATCCTAACCTTTCGCATACCTTACTATGTGGGACCCCTGGCCCGAGGGAACTCT

CGGTTCGCATGGATGACAAGAAAGTCCGAAGAAACGATTACTCCCTGGAATTTTGAGGAAGTTGTCGAT

AAAGGTGCGTCAGCTCAATCGTTCATCGAGAGGATGACCgccTTTGACAAGAATTTACCGAACGAAAAA

GTATTGCCTAAGCACAGTTTACTTTACGAGTATTTCACAGTGTACAATGAACTCACGAAAGTTAAGTAT

GTCACTGAGGGCATGCGTAAACCCGCCTTTCTAAGCGGAGAACAGAAGAAAGCAATAGTAGATCTGTTA

TTCAAGACCAACCGCAAAGTGACAGTTAAGCAATTGAAAGAGGACTACTTTAAGAAAATTGAATGCTTC

GATTCTGTCGAGATCTCCGGGGTAGAAGATCGATTTAATGCGTCACTTGGTACGTATCATGACCTCCTA

AAGATAATTAAAGATAAGGACTTCCTGGATAACGAAGAGAATGAAGATATCTTAGAAGATATAGTGTTG

ACTCTTACCCTCTTTGAAGATCGGGAAATGATTGAGGPAAGACTAAAAACATACGCTCACCTGTTCGAC

GATAAGGTTATGAAACAGTTAAAGAGGCGTCGCTATACGGGCTGGGGAgccTTGTCGCGGAAACTTATC

AACGGGATAAGAGACAAGCAAAGTGGTAAAACTATTCTCGATTTTCTAAAGAGCGACGGCTTCGCCAAT

AGGAACTTTATGgccCTGATCCATGATGACTCTTTAACCTTCAAAGAGGATATACAAAAGGCACAGGTT

TCCGGACAAGGGGACTCATTGCACGAACATATTGCGAATCTTGCTGGTTCGCCAGCCATCAAAAGGGC

ATACTCCAGACAGTCAAAGTAGTGGATGAGCTAGTTAAGGTCATGGGACGTCACAAACCGGAAACATT

GTAATCGAGATGGCACGCGAAAATCAAACGACTCAGAAGGGGCAAAAAAACAGTCGAGAGCGGATGAAG

AGAATAGAAGAGGGTATTAAAGAACTGGGCAGCCAGATCTTAAAGGAGCATCCTGTGGAAAATACCCAA

TTGCAGAACGAGAAACTTTACCTCTATTACCTACAAAATGGAAGGGACATGTATGTTGATCAGGAACTG

GACATAAACCGTTTATCTGATTACGACGTCGATCACATTGTACCCCAATCCTTTTTGAAGGACGATTCA

ATCGACAATAAAGTGCTTACACGCTCGGATAAGAACCGAGGGAAAAGTGACAATGTTCCAAGCGAGGAA

```
GTCGTAAAGAAAATGAAGAACTATTGGCGGCAGCTCCTAAATGCGAAACTGATAACGCAAAGAAAGTTC

GATAACTTAACTAAAGCTGAGAGGGGTGGCTTGTCTGAACTTGACAAGGCCGGATTTATTAAACGTCAG

CTCGTGGAAACCCGCgccATCACAAAGCATGTTGCGCAGATACTAGATTCCCGAATGAATACGAAATAC

GACGAGAACGATAAGCTGATTCGGGAAGTCAAAGTAATCACTTTAAAGTCAAAATTGGTGTCGGACTTC

AGAAAGGATTTTCAATTCTATAAAGTTAGGGAGATAAATAACTACCACCATGCGCACGACGCTTATCTT

AATGCCGTCGTAGGGACCGCACTCATTAAGAAATACCCGAAGCTAGAAAGTGAGTTTGTGTATGGTGAT

TACAAAGTTTATGACGTCCGTAAGATGATCGCGAAAAGCGAACAGGAGATAGGCAAGGCTACAGCCAAA

TACTTCTTTTATTCTAACATTATGAATTTCTTTAAGACGGAAATCACTCTGGCAAACGGAGAGATACGC

AAACGACCTTTAATTGAAACCAATGGGGAGACAGGTGAAATCGTATGGGATAAGGGCCGGGACTTCGCG

ACGGTGAGAAAGTTTTGTCCATGCCCCAAGTCAACATAGTAAAGAAACTGAGGTGCAGACCGGAGGG

TTTTCAAAGGAATCGATTCTTCCAAAAAGGAATAGTGATAAGCTCATCGCTCGTAAAAAGGACTGGGAC

CCGAAAAAGTACGGTGGCTTCgagAGCCCTACAGTTGCCTATTCTGTCCTAGTAGTGGCAAAAGTTGAG

AAGGGAAAATCCAAGAAACTGAAGTCAGTCAAAGAATTATTGGGGATAACGATTATGGAGCGCTCGTCT

TTTGAAAAGAACCCCATCGACTTCCTTGAGGCGAAAGGTTACAAGGAAGTAAAAAAGGATCTCATAATT

AAACTACCAAAGTATAGTCTGTTTGAGTTAGAAAATGGCCGAAAACGGATGTTGGCTAGCGCCGGAGAG

CTTCAAAAGGGGAACGAACTCGCACTACCGTCTAAATACGTGAATTTCCTGTATTTAGCGTCCCATTAC

GAGAAGTTGAAAGGTTCACCTGAAGATAACGAACAGAAGCAACTTTTTGTTGAGCAGCACAAACATTAT

CTCGACGAAATCATAGAGCAAATTTCGGAATTCAGTAAGAGAGTCATCCTAGCTGATGCCAATCTGGAC

AAAGTATTAAGCGCATACAACAAGCACAGGGATAAACCCATACGTGAGCAGGCGGAAAATATTATCCAT

TTGTTTACTCTTACCAACCTCGGCGCTCCAGCCGCATTCAAGTATTTTGACACAACGATAGATCGCAAA

CGATACACTTCTACCAAGGAGGTGCTAGACGCGACACTGATTCACCAATCCATCACGGGATTATATGAA

ACTCGGATAGATTTGTCACAGCTTGGGGGTGACGGATCCCCCAAGAAGAAGAGGAAAGTCTCGAGCGAC

TACAAAGACCATGACGGTGATTATAAAGATCATGACATCGATTACAAGGATGACGATGACAAGTGA

MSP2133: CMV-T7-humanSpCas9-HF4 (Y450A, N497A, R661A,
Q695A, Q926A)-NLS-3xFLAG
Human codon optimized S. pyogenes Cas9 in normal font, modified
codons in lower case, NLS double underlined, 3xFLAG tag in bold:
                                             SEQ ID NO: 274
ATGGATAAAAAGTATTCTATTGGTTTAGACATCGGCACTAATTCCGTTGGATGGGCTGTCATAACCGAT

GAATACAAAGTACCTTCAAAGAAATTTAAGGTGTTGGGGAACACAGACCGTCATTCGATTAAAAAGAAT

CTTATCGGTGCCCTCCTATTCGATAGTGGCGAAACGGCAGAGGCGACTCGCCTGAAACGAACCGCTCGG

AGAAGGTATACACGTCGCAAGAACCGAATATGTTACTTACAAGAAATTTTTAGCAATGAGATGGCCAAA

GTTGACGATTCTTTCTTTCACCGTTTGGAAGAGTCCTTCCTTGTCGAAGAGGACAAGAAACATGAACGG

CACCCCATCTTTGGAAACATAGTAGATGAGGTGGCATATCATGAAAGTACCCAACGATTTATCACCTC

AGAAAAAGCTAGTTGACTCAACTGATAAAGCGGACCTGAGGTTAATCTACTTGGCTCTTGCCCATATG

ATAAAGTTCCGTGGGCACTTTCTCATTGAGGGTGATCTAAATCCGGACAACTCGGATGTCGACAAACTG

TTCATCCAGTTAGTACAAACCTATAATCAGTTGTTTGAAGAGAACCCTATAAATGCAAGTGGCGTGGAT

GCGAAGGCTATTCTTAGCGCCCGCCTCTCTAAATCCCGACGGCTAGAAACCTGATCGCACAATTACCC

GGAGAGAAGAAAAATGGGTTGTTCGGTAACCTTATAGCGCTCTCACTAGGCCTGACACCAAATTTTAAG

TCGAACTTCGACTTAGCTGAAGATGCCAAATTGCAGCTTAGTAAGGACACGTACGATGACGATCTCGAC

AATCTACTGGCACAAATTGGAGATCAGTATGCGGACTTATTTTGGCTGCCAAAAACCTTAGCGATGCA

ATCCTCCTATCTGACATACTGAGAGTTAATACTGAGATTACCAAGGCGCCGTTATCCGCTTCAATGATC

AAAAGGTACGATGAACATCACCAAGACTTGACACTTCTCAAGGCCCTAGTCCGTCAGCAACTGCCTGAG
```

-continued

```
AAATATAAGGAAATATTCTTTGATCAGTCGAAAAACGGGTACGCAGGTTATATTGACGGCGGAGCGAGT
CAAGAGGAATTCTACAAGTTTATCAAACCCATATTAGAGAAGATGGATGGGACGGAAGAGTTGCTTGTA
AAACTCAATCGCGAAGATCTACTGCGAAAGCAGCGGACTTTCGACAACGGTAGCATTCCACATCAAATC
CACTTAGGCGAATTGCATGCTATACTTAGAAGGCAGGAGGATTTTTATCCGTTCCTCAAAGACAATCGT
GAAAAGATTGAGAAAATCCTAACCTTTCGCATACCTgccTATGTGGGACCCCTGGCCCGAGGGAACTCT
CGGTTCGCATGGATGACAAGAAAGTCCGAAGAAACGATTACTCCCTGGAATTTTGAGGAAGTTGTCGAT
AAAGGTGCGTCAGCTCAATCGTTCATCGAGAGGATGACCgccTTTGACAAGAATTTACCGAACGAAAAA
GTATTGCCTAAGCACAGTTTACTTTACGAGTATTTCACAGTGTACAATGAACTCACGAAAGTTAAGTAT
GTCACTGAGGGCATGCGTAAACCCGCCTTTCTAAGCGGAGAACAGAAGAAAGCAATAGTAGATCTGTTA
TTCAAGACCAACCGCAAAGTGACAGTTAAGCAATTGAAAGAGGACTACTTTAAGAAAATTGAATGCTTC
GATTCTGTCGAGATCTCCGGGGTAGAAGATCGATTTAATGCGTCACTTGGTACGTATCATGACCTCCTA
AAGATAATTAAAGATAAGGACTTCCTGGATAACGAAGAGAATGAAGATATCTTAGAAGATATAGTGTTG
ACTCTTACCCTCTTTGAAGATCGGGAAATGATTGAGGPAAGACTAAAAACATACGCTCACCTGTTCGAC
GATAAGGTTATGAAACAGTTAAAGAGGCGTCGCTATACGGGCTGGGGAgccTTGTCGCGGAAACTTATC
AACGGGATAAGAGACAAGCAAAGTGGTAAAACTATTCTCGATTTTCTAAAGAGCGACGGCTTCGCCAAT
AGGAACTTTATGgccCTGATCCATGATGACTCTTTAACCTTCAAAGAGGATATACAAAAGGCACAGGTT
TCCGGACAAGGGGACTCATTGCACGAACATATTGCGAATCTTGCTGGTTCGCCAGCCATCAAAAAGGGC
ATACTCCAGACAGTCAAAGTAGTGGATGAGCTAGTTAAGGTCATGGGACGTCACAAACCGGAAAACATT
GTAATCGAGATGGCACGCGAAAATCAAACGACTCAGAAGGGGCAAAAAAACAGTCGAGAGCGGATGAAG
AGAATAGAAGAGGGTATTAAAGAACTGGGCAGCCAGATCTTAAAGGAGCATCCTGTGGAAAATACCCAA
TTGCAGAACGAGAAACTTTACCTCTATTACCTACAAAATGGAAGGGACATGTATGTTGATCAGGAACTG
GACATAAACCGTTTATCTGATTACGACGTCGATCACATTGTACCCCAATCCTTTTTGAAGGACGATTCA
ATCGACAATAAAGTGCTTACACGCTCGGATAAGAACCGAGGGAAAAGTGACAATGTTCCAAGCGAGGAA
GTCGTAAAGAAAATGAAGAACTATTGGCGGCAGCTCCTAAATGCGAAACTGATAACGCAAAGAAAGTTC
GATAACTTAACTAAAGCTGAGAGGGGTGGCTTGTCTGAACTTGACAAGGCCGGATTTATTAAACGTCAG
CTCGTGGAAACCCGCgccATCACAAAGCATGTTGCGCAGATACTAGATTCCCGAATGAATACGAAATAC
GACGAGAACGATAAGCTGATTCGGGAAGTCAAAGTAATCACTTTAAAGTCAAAATTGGTGTCGGACTTC
AGAAAGGATTTTCAATTCTATAAAGTTAGGGAGATAAATAACTACCACCATGCGCACGACGCTTATCTT
AATGCCGTCGTAGGGACCGCACTCATTAAGAAATACCCGAAGCTAGAAAGTGAGTTTGTGTATGGTGAT
TACAAAGTTTATGACGTCCGTAAGATGATCGCGAAAAGCGAACAGGAGATAGGCAAGGCTACAGCCAAA
TACTTCTTTTATTCTAACATTATGAATTTCTTTAAGACGGAAATCACTCTGGCAAACGGAGAGATACGC
AAACGACCTTTAATTGAAACCAATGGGGAGACAGGTGAAATCGTATGGGATAAGGGCCGGGACTTCGCG
ACGGTGAGAAAAGTTTTGTCCATGCCCCAAGTCAACATAGTAAAGAAACTGAGGTGCAGACCGGAGGG
TTTTCAAAGGAATCGATTCTTCCAAAAAGGAATAGTGATAAGCTCATCGCTCGTAAAAAGGACTGGGAC
CCGAAAAAGTACGGTGGCTTCGATAGCCCTACAGTTGCCTATTCTGTCCTAGTAGTGGCAAAAGTTGAG
AAGGGAAAATCCAAGAAACTGAAGTCAGTCAAAGAATTATTGGGGATAACGATTATGGAGCGCTCGTCT
TTTGAAAAGAACCCCATCGACTTCCTTGAGGCGAAAGGTTACAAGGAAGTAAAAAAGGATCTCATAATT
AAACTACCAAAGTATAGTCTGTTTGAGTTAGAAAATGGCCGAAAACGGATGTTGGCTAGCGCCGGAGAG
CTTCAAAAGGGGAACGAACTCGCACTACCGTCTAAATACGTGAATTTCCTGTATTTAGCGTCCCATTAC
GAGAAGTTGAAAGGTTCACCTGAAGATAACGAACAGAAGCAACTTTTTGTTGAGCAGCACAAACATTAT
CTCGACGAAATCATAGAGCAAATTTCGGAATTCAGTAAGAGAGTCATCCTAGCTGATGCCAATCTGGAC
```

-continued

```
AAAGTATTAAGCGCATACAACAAGCACAGGGATAAACCCATACGTGAGCAGGCGGAAAATATTATCCAT

TTGTTTACTCTTACCAACCTCGGCGCTCCAGCCGCATTCAAGTATTTTGACACAACGATAGATCGCAAA

CGATACACTTCTACCAAGGAGGTGCTAGACGCGACACTGATTCACCAATCCATCACGGGATTATATGAA

ACTCGGATAGATTTGTCACAGCTTGGGGGTGACGGATCCCCCAAGAAGAAGAGGAAAGTCTCGAGCGAC

TACAAAGACCATGACGGTGATTATAAAGATCATGACATCGATTACAAGGATGACGATGACAAGTGA
```

MSP469: CMV-T7-humanSpCas9-VQR (D1135V, R1335Q, T1337R)-NLS-3xFLAG
Human codon optimized *S. pyogenes* Cas9 in normal font, modified codons in lower case, NLS double underlined, 3xFLAG tag in bold:

SEQ ID NO: 275

```
ATGGATAAAAAGTATTCTATTGGTTTAGACATCGGCACTAATTCCGTTGGATGGGCTGTCATAACCGAT

GAATACAAAGTACCTTCAAAGAAATTTAAGGTGTTGGGGAACACAGACCGTCATTCGATTAAAAAGAAT

CTTATCGGTGCCCTCCTATTCGATAGTGGCGAAACGGCAGAGGCGACTCGCCTGAAACGAACCGCTCGG

AGAAGGTATACACGTCGCAAGAACCGAATATGTTACTTACAAGAAATTTTTAGCAATGAGATGGCCAAA

GTTGACGATTCTTTCTTTCACCGTTTGGAAGAGTCCTTCCTTGTCGAAGAGGACAAGAAACATGAACGG

CACCCCATCTTTGGAAACATAGTAGATGAGGTGGCATATCATGAAAAGTACCCAACGATTTATCACCTC

AGAAAAAAGCTAGTTGACTCAACTGATAAAGCGGACCTGAGGTTAATCTACTTGGCTCTTGCCCATATG

ATAAAGTTCCGTGGGCACTTTCTCATTGAGGGTGATCTAAATCCGGACAACTCGGATGTCGACAAACTG

TTCATCCAGTTAGTACAAACCTATAATCAGTTGTTTGAAGAGAACCCTATAAATGCAAGTGGCGTGGAT

GCGAAGGCTATTCTTAGCGCCCGCCTCTCTAAATCCCGACGGCTAGAAAACCTGATCGCACAATTACCC

GGAGAGAAGAAAAATGGGTTGTTCGGTAACCTTATAGCGCTCTCACTAGGCCTGACACCAAATTTTAAG

TCGAACTTCGACTTAGCTGAAGATGCCAAATTGCAGCTTAGTAAGGACACGTACGATGACGATCTCGAC

AATCTACTGGCACAAATTGGAGATCAGTATGCGGACTTATTTTTGGCTGCCAAAAACCTTAGCGATGCA

ATCCTCCTATCTGACATACTGAGAGTTAATACTGAGATTACCAAGGCGCCGTTATCCGCTTCAATGATC

AAAAGGTACGATGAACATCACCAAGACTTGACACTTCTCAAGGCCCTAGTCCGTCAGCAACTGCCTGAG

AAATATAAGGAAATATTCTTTGATCAGTCGAAAAACGGGTACGCAGGTTATATTGACGGCGGAGCGAGT

CAAGAGGAATTCTACAAGTTTATCAAACCCATATTAGAGAAGATGGATGGGACGGAAGAGTTGCTTGTA

AAACTCAATCGCGAAGATCTACTGCGAAAGCAGCGGACTTTCGACAACGGTAGCATTCCACATCAAATC

CACTTAGGCGAATTGCATGCTATACTTAGAAGGCAGGAGGATTTTTATCCGTTCCTCAAAGACAATCGT

GAAAAGATTGAGAAATCCTAACCTTTCGCATACCTTACTATGTGGGACCCCTGGCCCGAGGGAACTCT

CGGTTCGCATGGATGACAAGAAAGTCCGAAGAAACGATTACTCCATGGAATTTTGAGGAAGTTGTCGAT

AAAGGTGCGTCAGCTCAATCGTTCATCGAGAGGATGACCAACTTTGACAAGAATTTACCGAACGAAAAA

GTATTGCCTAAGCACAGTTTACTTTACGAGTATTTCACAGTGTACAATGAACTCACGAAAGTTAAGTAT

GTCACTGAGGGCATGCGTAAACCCGCCTTTCTAAGCGGAGAACAGAAGAAAGCAATAGTAGATCTGTTA

TTCAAGACCAACCGCAAAGTGACAGTTAAGCAATTGAAAGAGGACTACTTTAAGAAAATTGAATGCTTC

GATTCTGTCGAGATCTCCGGGGTAGAAGATCGATTTAATGCGTCACTTGGTACGTATCATGACCTCCTA

AAGATAATTAAAGATAAGGACTTCCTGGATAACGAAGAGAATGAAGATATCTTAGAAGATATAGTGTTG

ACTCTTACCCTCTTTGAAGATCGGGAAATGATTGAGGPAAGACTAAAAACATACGCTCACCTGTTCGAC

GATAAGGTTATGAAACAGTTAAAGAGGCGTCGCTATACGGGCTGGGGACGATTGTCGCGGAAACTTATC

AACGGGATAAGAGACAAGCAAAGTGGTAAAACTATTCTCGATTTTCTAAAGAGCGACGGCTTCGCCAAT

AGGAACTTTATGCAGCTGATCCATGATGACTCTTTAACCTTCAAAGAGGATATACAAAAGGCACAGGTT

TCCGGACAAGGGGACTCATTGCACGAACATATTGCGAATCTTGCTGGTTCGCCAGCCATCAAAAAGGGC

ATACTCCAGACAGTCAAAGTAGTGGATGAGCTAGTTAAGGTCATGGGACGTCACAAACCGGAAAACATT
```

-continued

```
GTAATCGAGATGGCACGCGAAAATCAAACGACTCAGAAGGGGCAAAAAACAGTCGAGAGCGGATGAAG
AGAATAGAAGAGGGTATTAAAGAACTGGGCAGCCAGATCTTAAAGGAGCATCCTGTGGAAAATACCCAA
TTGCAGAACGAGAAACTTTACCTCTATTACCTACAAAATGGAAGGGACATGTATGTTGATCAGGAACTG
GACATAAACCGTTTATCTGATTACGACGTCGATCACATTGTACCCCAATCCTTTTTGAAGGACGATTCA
ATCGACAATAAAGTGCTTACACGCTCGGATAAGAACCGAGGGAAAAGTGACAATGTTCCAAGCGAGGAA
GTCGTAAAGAAAATGAAGAACTATTGGCGGCAGCTCCTAAATGCGAAACTGATAACGCAAAGAAAGTTC
GATAACTTAACTAAAGCTGAGAGGGGTGGCTTGTCTGAACTTGACAAGGCCGGATTTATTAAACGTCAG
CTCGTGGAAACCCGCCAAATCACAAAGCATGTTGCACAGATACTAGATTCCCGAATGAATACGAAATAC
GACGAGAACGATAAGCTGATTCGGGAAGTCAAAGTAATCACTTTAAAGTCAAAATTGGTGTCGGACTTC
AGAAAGGATTTTCAATTCTATAAAGTTAGGGAGATAAATAACTACCACCATGCGCACGACGCTTATCTT
AATGCCGTCGTAGGGACCGCACTCATTAAGAAATACCCGAAGCTAGAAGTGAGTTTGTGTATGGTGAT
TACAAAGTTTATGACGTCCGTAAGATGATCGCGAAAAGCGAACAGGAGATAGGCAAGGCTACAGCCAAA
TACTTCTTTTATTCTAACATTATGAATTTCTTTAAGACGGAAATCACTCTGGCAAACGGAGAGATACGC
AAACGACCTTTAATTGAAACCAATGGGGAGACAGGTGAAATCGTATGGGATAAGGGCCGGGACTTCGCG
ACGGTGAGAAAAGTTTTGTCCATGCCCCAAGTCAACATAGTAAAGAAAACTGAGGTGCAGACCGGAGGG
TTTTCAAAGGAATCGATTCTTCCAAAAAGGAATAGTGATAAGCTCATCGCTCGTAAAAAGGACTGGGAC
CCGAAAAAGTACGGTGGCTTCgtgAGCCCTACAGTTGCCTATTCTGTCCTAGTAGTGGCAAAAGTTGAG
AAGGGAAAATCCAAGAAACTGAAGTCAGTCAAAGAATTATTGGGGATAACGATTATGGAGCGCTCGTCT
TTTGAAAAGAACCCCATCGACTTCCTTGAGGCGAAAGGTTACAAGGAAGTAAAAAAGGATCTCATAATT
AAACTACCAAAGTATAGTCTGTTTGAGTTAGAAAATGGCCGAAAACGGATGTTGGCTAGCGCCGGAGAG
CTTCAAAAGGGGAACGAACTCGCACTACCGTCTAAATACGTGAATTTCCTGTATTTAGCGTCCCATTAC
GAGAAGTTGAAAGGTTCACCTGAAGATAACGAACAGAAGCAACTTTTTGTTGAGCAGCACAAACATTAT
CTCGACGAAATCATAGAGCAAATTTCGGAATTCAGTAAGAGAGTCATCCTAGCTGATGCCAATCTGGAC
AAAGTATTAAGCGCATACAACAAGCACAGGGATAAACCCATACGTGAGCAGGCGGAAAATATTATCCAT
TTGTTTACTCTTACCAACCTCGGCGCTCCAGCCGCATTCAAGTATTTTGACACAACGATAGATCGCAAA
cagTACagaTCTACCAAGGAGGTGCTAGACGCGACACTGATTCACCAATCCATCACGGGATTATATGAA
ACTCGGATAGATTTGTCACAGCTTGGGGGTGACGGATCCCCCAAGAAGAAGAGGAAAGTCTCGAGCGAC
TACAAAGACCATGACGGTGATTATAAAGATCATGACATCGATTACAAGGATGACGATGACAAGTGA
```

MSP2440: CMV-T7-humanSpCas9-VQR-HF1 (N497A, R661A, Q695A, Q926A, D1135V, R1335Q, T1337R)-NLS-3xFLAG
Human codon optimized *S. pyogenes* Cas9 in normal font, modified codons in lower case, NLS double underlined, 3xFLAG tag in bold:

SEQ ID NO: 276

```
ATGGATAAAAAGTATTCTATTGGTTTAGACATCGGCACTAATTCCGTTGGATGGGCTGTCATAACCGAT
GAATACAAAGTACCTTCAAAGAAATTTAAGGTGTTGGGGAACACAGACCGTCATTCGATTAAAAAGAAT
CTTATCGGTGCCCTCCTATTCGATAGTGGCGAAACGGCAGAGGCGACTCGCCTGAAACGAACCGCTCGG
AGAAGGTATACACGTCGCAAGAACCGAATATGTTACTTACAAGAAATTTTTAGCAATGAGATGGCCAAA
GTTGACGATTCTTTCTTTCACCGTTTGGAAGAGTCCTTCCTTGTCGAAGAGGACAAGAAACATGAACGG
CACCCCATCTTTGGAAACATAGTAGATGAGGTGGCATATCATGAAAAGTACCCAACGATTTATCACCTC
AGAAAAAAGCTAGTTGACTCAACTGATAAAGCGGACCTGAGGTTAATCTACTTGGCTCTTGCCCATATG
ATAAAGTTCCGTGGGCACTTTCTCATTGAGGGTGATCTAAATCCGGACAACTCGGATGTCGACAAACTG
TTCATCCAGTTAGTACAAACCTATAATCAGTTGTTTGAAGAGAACCCTATAAATGCAAGTGGCGTGGAT
GCGAAGGCTATTCTTAGCGCCCGCCTCTCTAAATCCCGACGGCTAGAAAACCTGATCGCACAATTACCC
```

-continued

```
GGAGAGAAGAAAAATGGGTTGTTCGGTAACCTTATAGCGCTCTCACTAGGCCTGACACCAAATTTTAAG
TCGAACTTCGACTTAGCTGAAGATGCCAAATTGCAGCTTAGTAAGGACACGTACGATGACGATCTCGAC
AATCTACTGGCACAAATTGGAGATCAGTATGCGGACTTATTTTTGGCTGCCAAAAACCTTAGCGATGCA
ATCCTCCTATCTGACATACTGAGAGTTAATACTGAGATTACCAAGGCGCCGTTATCCGCTTCAATGATC
AAAAGGTACGATGAACATCACCAAGACTTGACACTTCTCAAGGCCCTAGTCCGTCAGCAACTGCCTGAG
AAATATAAGGAAATATTCTTTGATCAGTCGAAAAACGGGTACGCAGGTTATATTGACGGCGGAGCGAGT
CAAGAGGAATTCTACAAGTTTATCAAACCCATATTAGAGAAGATGGATGGGACGGAAGAGTTGCTTGTA
AAACTCAATCGCGAAGATCTACTGCGAAAGCAGCGGACTTTCGACAACGGTAGCATTCCACATCAAATC
CACTTAGGCGAATTGCATGCTATACTTAGAAGGCAGGAGGATTTTTATCCGTTCCTCAAAGACAATCGT
GAAAAGATTGAGAAAATCCTAACCTTTCGCATACCTTACTATGTGGGACCCCTGGCCCGAGGGAACTCT
CGGTTCGCATGGATGACAAGAAAGTCCGAAGAAACGATTACTCCCTGGAATTTTGAGGAAGTTGTCGAT
AAAGGTGCGTCAGCTCAATCGTTCATCGAGAGGATGACCgccTTTGACAAGAATTTACCGAACGAAAAA
GTATTGCCTAAGCACAGTTTACTTTACGAGTATTTCACAGTGTACAATGAACTCACGAAAGTTAAGTAT
GTCACTGAGGGCATGCGTAAACCCGCCTTTCTAAGCGGAGAACAGAAGAAAGCAATAGTAGATCTGTTA
TTCAAGACCAACCGCAAAGTGACAGTTAAGCAATTGAAAGAGGACTACTTTAAGAAAATTGAATGCTTC
GATTCTGTCGAGATCTCCGGGGTAGAAGATCGATTTAATGCGTCACTTGGTACGTATCATGACCTCCTA
AAGATAATTAAAGATAAGGACTTCCTGGATAACGAAGAGAATGAAGATATCTTAGAAGATATAGTGTTG
ACTCTTACCCTCTTTGAAGATCGGGAAATGATTGAGGAAAGACTAAAAACATACGCTCACCTGTTCGAC
GATAAGGTTATGAAACAGTTAAAGAGGCGTCGCTATACGGGCTGGGGAgccTTGTCGCGGAAACTTATC
AACGGGATAAGAGACAAGCAAAGTGGTAAAACTATTCTCGATTTTCTAAAGAGCGACGGCTTCGCCAAT
AGGAACTTTATGgccCTGATCCATGATGACTCTTTAACCTTCAAAGAGGATATACAAAAGGCACAGGTT
TCCGGACAAGGGGACTCATTGCACGAACATATTGCGAATCTTGCTGGTTCGCCAGCCATCAAAAAGGGC
ATACTCCAGACAGTCAAAGTAGTGGATGAGCTAGTTAAGGTCATGGGACGTCACAAACCGGAAAACATT
GTAATCGAGATGGCACGCGAAAATCAAACGACTCAGAAGGGGCAAAAAAACAGTCGAGAGCGGATGAAG
AGAATAGAAGAGGGTATTAAAGAACTGGGCAGCCAGATCTTAAAGGAGCATCCTGTGGAAAATACCCAA
TTGCAGAACGAGAAACTTTACCTCTATTACCTACAAAATGGAAGGGACATGTATGTTGATCAGGAACTG
GACATAAACCGTTTATCTGATTACGACGTCGATCACATTGTACCCCAATCCTTTTTGAAGGACGATTCA
ATCGACAATAAAGTGCTTACACGCTCGGATAAGAACCGAGGGAAAAGTGACAATGTTCCAAGCGAGGAA
GTCGTAAAGAAAATGAAGAACTATTGGCGGCAGCTCCTAAATGCGAAACTGATAACGCAAAGAAAGTTC
GATAACTTAACTAAAGCTGAGAGGGGTGGCTTGTCTGAACTTGACAAGGCCGGATTTATTAAACGTCAG
CTCGTGGAAACCCGCgccATCACAAAGCATGTTGCGCAGATACTAGATTCCCGAATGAATACGAAATAC
GACGAGAACGATAAGCTGATTCGGGAAGTCAAAGTAATCACTTTAAAGTCAAAATTGGTGTCGGACTTC
AGAAAGGATTTTCAATTCTATAAAGTTAGGGAGATAAATAACTACCACCATGCGCACGACGCTTATCTT
AATGCCGTCGTAGGGACCGCACTCATTAAGAAATACCCGAAGCTAGAAAGTGAGTTTGTGTATGGTGAT
TACAAAGTTTATGACGTCCGTAAGATGATCGCGAAAAGCGAACAGGAGATAGGCAAGGCTACAGCCAAA
TACTTCTTTTATTCTAACATTATGAATTTCTTTAAGACGGAAATCACTCTGGCAAACGGAGAGATACGC
AAACGACCTTTAATTGAAACCAATGGGGAGACAGGTGAAATCGTATGGGATAAGGGCCGGGACTTCGCG
ACGGTGAGAAAAGTTTTGTCCATGCCCCAAGTCAACATAGTAAAGAAAACTGAGGTGCAGACCGGAGGG
TTTTCAAAGGAATCGATTCTTCCAAAAAGGAATAGTGATAAGCTCATCGCTCGTAAAAAGGACTGGGAC
CCGAAAAAGTACGGTGGCTTCgtgAGCCCTACAGTTGCCTATTCTGTCCTAGTAGTGGCAAAAGTTGAG
```

AAGGGAAAATCCAAGAAACTGAAGTCAGTCAAAGAATTATTGGGGATAACGATTATGGAGCGCTCGTCT

TTTGAAAAGAACCCCATCGACTTCCTTGAGGCGAAAGGTTACAAGGAAGTAAAAAAGGATCTCATAATT

AAACTACCAAAGTATAGTCTGTTTGAGTTAGAAAATGGCCGAAAACGGATGTTGGCTAGCGCCGGAGAG

CTTCAAAAGGGGAACGAACTCGCACTACCGTCTAAATACGTGAATTTCCTGTATTTAGCGTCCCATTAC

GAGAAGTTGAAAGGTTCACCTGAAGATAACGAACAGAAGCAACTTTTTGTTGAGCAGCACAAACATTAT

CTCGACGAAATCATAGAGCAAATTTCGGAATTCAGTAAGAGAGTCATCCTAGCTGATGCCAATCTGGAC

AAAGTATTAAGCGCATACAACAAGCACAGGGATAAACCCATACGTGAGCAGGCGGAAAATATTATCCAT

TTGTTTACTCTTACCAACCTCGGCGCTCCAGCCGCATTCAAGTATTTTGACACAACGATAGATCGCAAA cagTACagaTCTACCAAGGAGGTGCTAGACGCGACACTGATTCACCAATCCATCACGGGATTATATGAA ACTCGGATAGATTTGTCACAGCTTGGGGGTGACGGATCC<u>CCCAAGAAGAAGAGGAAAGTC</u>TCGAGCGAC

TACAAAGACCATGACGGTGATTATAAAGATCATGACATCGATTACAAGGATGACGATGACAAGTGA

BPK2797: CMV-T7-humanSpCas9-VRQR (D1135V, G1218R,
R1335Q, T1337R)-NLS-3xFLAG
Human codon optimized *S. pyogenes* Cas9 in normal font, modified
codons in lower case, NLS <u>double underlined</u>, 3xFLAG tag in bold:
SEQ ID NO: 277

ATGGATAAAAAGTATTCTATTGGTTTAGACATCGGCACTAATTCCGTTGGATGGGCTGTCATAACCGAT

GAATACAAAGTACCTTCAAAGAAATTTAAGGTGTTGGGGAACACAGACCGTCATTCGATTAAAAAGAAT

CTTATCGGTGCCCTCCTATTCGATAGTGGCGAAACGGCAGAGGCGACTCGCCTGAAACGAACCGCTCGG

AGAAGGTATACACGTCGCAAGAACCGAATATGTTACTTACAAGAAATTTTTAGCAATGAGATGGCCAAA

GTTGACGATTCTTTCTTTCACCGTTTGGAAGAGTCCTTCCTTGTCGAAGAGGACAAGAAACATGAACGG

CACCCCATCTTTGGAAACATAGTAGATGAGGTGGCATATCATGAAAAGTACCCAACGATTTATCACCTC

AGAAAAAAGCTAGTTGACTCAACTGATAAAGCGGACCTGAGGTTAATCTACTTGGCTCTTGCCCATATG

ATAAAGTTCCGTGGGCACTTTCTCATTGAGGGTGATCTAAATCCGGACAACTCGGATGTCGACAAACTG

TTCATCCAGTTAGTACAAACCTATAATCAGTTGTTTGAAGAGAACCCTATAAATGCAAGTGGCGTGGAT

GCGAAGGCTATTCTTAGCGCCCGCCTCTCTAAATCCCGACGGCTAGAAAACCTGATCGCACAATTACCC

GGAGAGAAGAAAAATGGGTTGTTCGGTAACCTTATAGCGCTCTCACTAGGCCTGACACCAAATTTTAAG

TCGAACTTCGACTTAGCTGAAGATGCCAAATTGCAGCTTAGTAAGGACACGTACGATGACGATCTCGAC

AATCTACTGGCACAAATTGGAGATCAGTATGCGGACTTATTTTTGGCTGCCAAAAACCTTAGCGATGCA

ATCCTCCTATCTGACATACTGAGAGTTAATACTGAGATTACCAAGGCGCCGTTATCCGCTTCAATGATC

AAAAGGTACGATGAACATCACCAAGACTTGACACTTCTCAAGGCCCTAGTCCGTCAGCAACTGCCTGAG

AAATATAAGGAAATATTCTTTGATCAGTCGAAAAACGGGTACGCAGGTTATATTGACGGCGGAGCGAGT

CAAGAGGAATTCTACAAGTTTATCAAACCCATATTAGAGAAGATGGATGGGACGGAAGAGTTGCTTGTA

AAACTCAATCGCGAAGATCTACTGCGAAAGCAGCGGACTTTCGACAACGGTAGCATTCCACATCAAATC

CACTTAGGCGAATTGCATGCTATACTTAGAAGGCAGGAGGATTTTTATCCGTTCCTCAAAGACAATCGT

GAAAAGATTGAGAAAATCCTAACCTTTCGCATACCTTACTATGTGGGACCCCTGGCCCGAGGGAACTCT

CGGTTCGCATGGATGACAAGAAAGTCCGAAGAAACGATTACTCCATGGAATTTTGAGGAAGTTGTCGAT

AAAGGTGCGTCAGCTCAATCGTTCATCGAGAGGATGACCAACTTTGACAAGAATTTACCGAACGAAAAA

GTATTGCCTAAGCACAGTTTACTTTACGAGTATTTCACAGTGTACAATGAACTCACGAAAGTTAAGTAT

GTCACTGAGGGCATGCGTAAACCCGCCTTTCTAAGCGGAGAACAGAAGAAAGCAATAGTAGATCTGTTA

TTCAAGACCAACCGCAAAGTGACAGTTAAGCAATTGAAAGAGGACTACTTTAAGAAAATTGAATGCTTC

GATTCTGTCGAGATCTCCGGGGTAGAAGATCGATTTAATGCGTCACTTGGTACGTATCATGACCTCCTA

AAGATAATTAAAGATAAGGACTTCCTGGATAACGAAGAGAATGAAGATATCTTAGAAGATATAGTGTTG

-continued

```
ACTCTTACCCTCTTTGAAGATCGGGAAATGATTGAGGAAAGACTAAAAACATACGCTCACCTGTTCGAC

GATAAGGTTATGAAACAGTTAAAGAGGCGTCGCTATACGGGCTGGGGACGATTGTCGCGGAAACTTATC

AACGGGATAAGAGACAAGCAAAGTGGTAAAACTATTCTCGATTTTCTAAAGAGCGACGGCTTCGCCAAT

AGGAACTTTATGCAGCTGATCCATGATGACTCTTTAACCTTCAAAGAGGATATACAAAAGGCACAGGTT

TCCGGACAAGGGGACTCATTGCACGAACATATTGCGAATCTTGCTGGTTCGCCAGCCATCAAAAAGGGC

ATACTCCAGACAGTCAAAGTAGTGGATGAGCTAGTTAAGGTCATGGGACGTCACAAACCGGAAAACATT

GTAATCGAGATGGCACGCGAAAATCAAACGACTCAGAAGGGGCAAAAAAACAGTCGAGAGCGGATGAAG

AGAATAGAAGAGGGTATTAAAGAACTGGGCAGCCAGATCTTAAAGGAGCATCCTGTGGAAAATACCCAA

TTGCAGAACGAGAAACTTTACCTCTATTACCTACAAAATGGAAGGGACATGTATGTTGATCAGGAACTG

GACATAAACCGTTTATCTGATTACGACGTCGATCACATTGTACCCCAATCCTTTTTGAAGGACGATTCA

ATCGACAATAAAGTGCTTACACGCTCGGATAAGAACCGAGGGAAAAGTGACAATGTTCCAAGCGAGGAA

GTCGTAAAGAAAATGAAGAACTATTGGCGGCAGCTCCTAAATGCGAAACTGATAACGCAAAGAAAGTTC

GATAACTTAACTAAAGCTGAGAGGGGTGGCTTGTCTGAACTTGACAAGGCCGGATTTATTAAACGTCAG

CTCGTGGAAACCCGCCAAATCACAAAGCATGTTGCACAGATACTAGATTCCCGAATGAATACGAAATAC

GACGAGAACGATAAGCTGATTCGGGAAGTCAAAGTAATCACTTTAAAGTCAAAATTGGTGTCGGACTTC

AGAAAGGATTTTCAATTCTATAAAGTTAGGGAGATAAATAACTACCACCATGCGCACGACGCTTATCTT

AATGCCGTCGTAGGGACCGCACTCATTAAGAAATACCCGAAGCTAGAAAGTGAGTTTGTGTATGGTGAT

TACAAAGTTTATGACGTCCGTAAGATGATCGCGAAAAGCGAACAGGAGATAGGCAAGGCTACAGCCAAA

TACTTCTTTTATTCTAACATTATGAATTTCTTTAAGACGGAAATCACTCTGGCAAACGGAGAGATACGC

AAACGACCTTTAATTGAAACCAATGGGGAGACAGGTGAAATCGTATGGGATAAGGGCCGGGACTTCGCG

ACGGTGAGAAAAGTTTTGTCCATGCCCCAAGTCAACATAGTAAAGAAAACTGAGGTGCAGACCGGAGGG

TTTTCAAAGGAATCGATTCTTCCAAAAAGGAATAGTGATAAGCTCATCGCTCGTAAAAAGGACTGGGAC

CCGAAAAAGTACGGTGGCTTCgtgAGCCCTACAGTTGCCTATTCTGTCCTAGTAGTGGCAAAAGTTGAG

AAGGGAAAATCCAAGAAACTGAAGTCAGTCAAAGAATTATTGGGGATAACGATTATGGAGCGCTCGTCT

TTTGAAAAGAACCCCATCGACTTCCTTGAGGCGAAAGGTTACAAGGAAGTAAAAAAGGATCTCATAATT

AAACTACCAAAGTATAGTCTGTTTGAGTTAGAAAATGGCCGAAAACGGATGTTGGCTAGCGCCagaGAG

CTTCAAAAGGGGAACGAACTCGCACTACCGTCTAAATACGTGAATTTCCTGTATTTAGCGTCCCATTAC

GAGAAGTTGAAAGGTTCACCTGAAGATAACGAACAGAAGCAACTTTTTGTTGAGCAGCACAAACATTAT

CTCGACGAAATCATAGAGCAAATTTCGGAATTCAGTAAGAGAGTCATCCTAGCTGATGCCAATCTGGAC

AAAGTATTAAGCGCATACAACAAGCACAGGGATAAACCCATACGTGAGCAGGCGGAAAATATTATCCAT

TTGTTTACTCTTACCAACCTCGGCGCTCCAGCCGCATTCAAGTATTTTGACACAACGATAGATCGCAAA cagTACagaTCTACCAAGGAGGTGCTAGACGCGACACTGATTCACCAATCCATCACGGGATTATATGAA

ACTCGGATAGATTTGTCACAGCTTGGGGGTGACGGATCCCCCAAGAAGAAGAGGAAAGTCTCGAGCGAC

TACAAAGACCATGACGGTGATTATAAAGATCATGACATCGATTACAAGGATGACGATGACAAGTGA
```

MSP2443: CMV-T7-humanSpCas9-VRQR-HF1 (N497A, R661A,
Q695A, Q926A, D1135V, G1218R, R1335Q, T1337R)-NLS-3xFLAG
Human codon optimized *S. pyogenes* Cas9 in normal font, modified
codons in lower case, NLS double underlined, 3xFLAG tag in bold:

SEQ ID NO: 278

```
ATGGATAAAAAGTATTCTATTGGTTTAGACATCGGCACTAATTCCGTTGGATGGGCTGTCATAACCGAT

GAATACAAAGTACCTTCAAAGAAATTTAAGGTGTTGGGGAACACAGACCGTCATTCGATTAAAAAGAAT

CTTATCGGTGCCCTCCTATTCGATAGTGGCGAAACGGCAGAGGCGACTCGCCTGAAACGAACCGCTCGG

AGAAGGTATACACGTCGCAAGAACCGAATATGTTACTTACAAGAAATTTTTAGCAATGAGATGGCCAAA
```

```
GTTGACGATTCTTTCTTTCACCGTTTGGAAGAGTCCTTCCTTGTCGAAGAGGACAAGAAACATGAACGG
CACCCCATCTTTGGAAACATAGTAGATGAGGTGGCATATCATGAAAAGTACCCAACGATTTATCACCTC
AGAAAAAAGCTAGTTGACTCAACTGATAAAGCGGACCTGAGGTTAATCTACTTGGCTCTTGCCCATATG
ATAAAGTTCCGTGGGCACTTTCTCATTGAGGGTGATCTAAATCCGGACAACTCGGATGTCGACAAACTG
TTCATCCAGTTAGTACAAACCTATAATCAGTTGTTTGAAGAGAACCCTATAAATGCAAGTGGCGTGGAT
GCGAAGGCTATTCTTAGCGCCCGCCTCTCTAAATCCCGACGGCTAGAAAACCTGATCGCACAATTACCC
GGAGAGAAGAAAAATGGGTTGTTCGGTAACCTTATAGCGCTCTCACTAGGCCTGACACCAAATTTTAAG
TCGAACTTCGACTTAGCTGAAGATGCCAAATTGCAGCTTAGTAAGGACACGTACGATGACGATCTCGAC
AATCTACTGGCACAAATTGGAGATCAGTATGCGGACTTATTTTTGGCTGCCAAAAACCTTAGCGATGCA
ATCCTCCTATCTGACATACTGAGAGTTAATACTGAGATTACCAAGGCGCCGTTATCCGCTTCAATGATC
AAAAGGTACGATGAACATCACCAAGACTTGACACTTCTCAAGGCCCTAGTCCGTCAGCAACTGCCTGAG
AAATATAAGGAAATATTCTTTGATCAGTCGAAAAACGGGTACGCAGGTTATATTGACGGCGGAGCGAGT
CAAGAGGAATTCTACAAGTTTATCAAACCCATATTAGAGAAGATGGATGGGACGGAAGAGTTGCTTGTA
AAACTCAATCGCGAAGATCTACTGCGAAAGCAGCGGACTTTCGACAACGGTAGCATTCCACATCAAATC
CACTTAGGCGAATTGCATGCTATACTTAGAAGGCAGGAGGATTTTTATCCGTTCCTCAAAGACAATCGT
GAAAAGATTGAGAAAATCCTAACCTTTCGCATACCTTACTATGTGGGACCCCTGGCCCGAGGGAACTCT
CGGTTCGCATGGATGACAAGAAAGTCCGAAGAAACGATTACTCCCTGGAATTTTGAGGAAGTTGTCGAT
AAAGGTGCGTCAGCTCAATCGTTCATCGAGAGGATGACCgccTTTGACAAGAATTTACCGAACGAAAAA
GTATTGCCTAAGCACAGTTTACTTTACGAGTATTTCACAGTGTACAATGAACTCACGAAAGTTAAGTAT
GTCACTGAGGGCATGCGTAAACCCGCCTTTCTAAGCGGAGAACAGAAGAAAGCAATAGTAGATCTGTTA
TTCAAGACCAACCGCAAAGTGACAGTTAAGCAATTGAAAGAGGACTACTTTAAGAAAATTGAATGCTTC
GATTCTGTCGAGATCTCCGGGGTAGAAGATCGATTTAATGCGTCACTTGGTACGTATCATGACCTCCTA
AAGATAATTAAAGATAAGGACTTCCTGGATAACGAAGAGAATGAAGATATCTTAGAAGATATAGTGTTG
ACTCTTACCCTCTTTGAAGATCGGGAAATGATTGAGGPAAGACTAAAAACATACGCTCACCTGTTCGAC
GATAAGGTTATGAAACAGTTAAAGAGGCGTCGCTATACGGGCTGGGGAgccTTGTCGCGGAAACTTATC
AACGGGATAAGAGACAAGCAAAGTGGTAAAACTATTCTCGATTTTCTAAAGAGCGACGGCTTCGCCAAT
AGGAACTTTATGgccCTGATCCATGATGACTCTTTAACCTTCAAAGAGGATATACAAAAGGCACAGGTT
TCCGGACAAGGGGACTCATTGCACGAACATATTGCGAATCTTGCTGGTTCGCCAGCCATCAAAAAGGGC
ATACTCCAGACAGTCAAAGTAGTGGATGAGCTAGTTAAGGTCATGGGACGTCACAAACCGGAAAACATT
GTAATCGAGATGGCACGCGAAAATCAAACGACTCAGAAGGGGCAAAAAAACAGTCGAGAGCGGATGAAG
AGAATAGAAGAGGGTATTAAAGAACTGGGCAGCCAGATCTTAAAGGAGCATCCTGTGGAAAATACCCAA
TTGCAGAACGAGAAACTTTACCTCTATTACCTACAAAATGGAAGGGACATGTATGTTGATCAGGAACTG
GACATAAACCGTTTATCTGATTACGACGTCGATCACATTGTACCCCAATCCTTTTTGAAGGACGATTCA
ATCGACAATAAAGTGCTTACACGCTCGGATAAGAACCGAGGGAAAAGTGACAATGTTCCAAGCGAGGAA
GTCGTAAAGAAAATGAAGAACTATTGGCGGCAGCTCCTAAATGCGAAACTGATAACGCAAAGAAAGTTC
GATAACTTAACTAAAGCTGAGAGGGGTGGCTTGTCTGAACTTGACAAGGCCGGATTTATTAAACGTCAG
CTCGTGGAAACCCGCgccATCACAAAGCATGTTGCGCAGATACTAGATTCCCGAATGAATACGAAATAC
GACGAGAACGATAAGCTGATTCGGGAAGTCAAAGTAATCACTTTAAAGTCAAAATTGGTGTCGGACTTC
AGAAAGGATTTTCAATTCTATAAAGTTAGGGAGATAAATAACTACCACCATGCGCACGACGCTTATCTT
AATGCCGTCGTAGGGACCGCACTCATTAAGAAATACCCGAAGCTAGAAAGTGAGTTTGTGTATGGTGAT
TACAAAGTTTATGACGTCCGTAAGATGATCGCGAAAAGCGAACAGGAGATAGGCAAGGCTACAGCCAAA
```

-continued

```
TACTTCTTTTATTCTAACATTATGAATTTCTTTAAGACGGAAATCACTCTGGCAAACGGAGAGATACGC

AAACGACCTTTAATTGAAACCAATGGGGAGACAGGTGAAATCGTATGGGATAAGGGCCGGGACTTCGCG

ACGGTGAGAAAAGTTTTGTCCATGCCCCAAGTCAACATAGTAAAGAAAACTGAGGTGCAGACCGGAGGG

TTTTCAAAGGAATCGATTCTTCCAAAAAGGAATAGTGATAAGCTCATCGCTCGTAAAAAGGACTGGGAC

CCGAAAAAGTACGGTGGCTTCgtgAGCCCTACAGTTGCCTATTCTGTCCTAGTAGTGGCAAAAGTTGAG

AAGGGAAAATCCAAGAAACTGAAGTCAGTCAAAGAATTATTGGGGATAACGATTATGGAGCGCTCGTCT

TTTGAAAAGAACCCCATCGACTTCCTTGAGGCGAAAGGTTACAAGGAAGTAAAAAAGGATCTCATAATT

AAACTACCAAAGTATAGTCTGTTTGAGTTAGAAAATGGCCGAAAACGGATGTTGGCTAGCGCCagaGAG

CTTCAAAAGGGGAACGAACTCGCACTACCGTCTAAATACGTGAATTTCCTGTATTTAGCGTCCCATTAC

GAGAAGTTGAAAGGTTCACCTGAAGATAACGAACAGAAGCAACTTTTTGTTGAGCAGCACAAACATTAT

CTCGACGAAATCATAGAGCAAATTTCGGAATTCAGTAAGAGAGTCATCCTAGCTGATGCCAATCTGGAC

AAAGTATTAAGCGCATACAACAAGCACAGGGATAAACCCATACGTGAGCAGGCGGAAAATATTATCCAT

TTGTTTACTCTTACCAACCTCGGCGCTCCAGCCGCATTCAAGTATTTTGACACAACGATAGATCGCAAA cagTACagaTCTACCAAGGAGGTGCTAGACGCGACACTGATTCACCAATCCATCACGGGATTATATGAA

ACTCGGATAGATTTGTCACAGCTTGGGGGTGACGGATCCCCCAAGAAGAAGAGGAAAGTCTCGAGCGAC

TACAAAGACCATGACGGTGATTATAAAGATCATGACATCGATTACAAGGATGACGATGACAAGTGA
```

BPK1520: U6-BsmBIcassette-Sp-sgRNA
U6 promoter in normal font, BsmBI sites *italicised*, S. pyogenes sgRNA
in lower case, U6 terminator double underlined:;

SEQ ID NO: 279

```
TGTACAAAAAAGCAGGCTTTAAAGGAACCAATTCAGTCGACTGGATCCGGTACCAAGGTCGGGCAGGAA

GAGGGCCTATTTCCCATGATTCCTTCATATTTGCATATACGATACAAGGCTGTTAGAGAGATAATTAGA

ATTAATTTGACTGTAAACACAAAGATATTAGTACAAAATACGTGACGTAGAAAGTAATAATTTCTTGGG

TAGTTTGCAGTTTTAAAATTATGTTTTAAAATGGACTATCATATGCTTACCGTAACTTGAAAGTATTTC

GATTTCTTGGCTTTATATATCTTGTGGAAAGGACGAAACACCGGAGACGATTAATGCGTCTCCgtttta gagctagaaatagcaagttaaaataaggctagtccgttatcaacttgaaaaagtggcaccgagtcggtg cttttttt
```

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated *Staphylococcus aureus* Cas9 (SaCas9) protein, comprising an amino acid sequence that has at least 90% sequence identity to SEQ ID NO:2, with mutations at N419A/R654A, Y211A/R654A, Y211A/Y212A, Y211A/Y230A, Y211A/R245A, Y212A/Y230A, Y212A/R245A, Y230A/R245A, W229A/R654A, Y211A/Y212A/Y230A, Y211A/Y212A/R245A, Y211A/Y212A/Y651A, Y211A/Y230A/R245A, Y211A/Y230A/Y651A, Y211A/R245A/Y651A, Y211A/R245A/R654A, Y211A/R245AN419A, Y211A/N419A/R654A, Y212A/Y230A/R245A, Y212A/Y230A/Y651A, Y212A/R245A/Y651A, Y230A/R245A/Y651A, R245A/N419A/R654A, T392A/N419A/R654A, R245A/T392A/N419A/R654A, Y211A/R245A/N419A/R654A, W229A/R245A/N419A/R654A, Y211A/R245A/T392A/N419A/R654A, or Y211A/W229A/R245A/N419A/R654A.

2. The isolated protein of claim 1, wherein the amino acid sequence has at least 95% sequence identity to SEQ ID NO: 2.

3. The isolated protein of claim 1, further comprising one or more of the following mutations: E782K; K929R;

N968K; R1015H; E782K/N968K/R1015H (KKH variant); E782K/K929R/R1015H (KRH variant); or E782K/K929R/N968K/R1015H (KRKH variant).

4. The isolated protein of claim 1, further comprising mutations that decrease nuclease activity, selected from the group consisting of mutations at D10, E477, D556, H701, and D704; and one or more mutations selected from the group consisting of mutations at H557 and N580.

5. The isolated protein of claim 4, wherein the mutation at D10 is D10A or D10N, the mutation at D556 is D556A, the mutation at H557 is H557A, H557N, or H557Y and the mutation at N580 is N580A.

6. The isolated protein of claim 1, wherein the SaCas9 protein is fused to one or more of a nuclear localization sequence, cell penetrating peptide sequence, and/or an affinity tag.

7. A fusion protein comprising the isolated protein of claim 1, fused to a heterologous functional domain, with an optional intervening linker, wherein the linker does not interfere with activity of the fusion protein.

8. The fusion protein of claim 7, wherein the heterologous functional domain is a transcriptional activation domain.

9. The fusion protein of claim 8, wherein the transcriptional activation domain is from VP64 or NF-κB p65.

10. The fusion protein of claim 7, wherein the heterologous functional domain is a transcriptional silencer or transcriptional repression domain.

11. The fusion protein of claim 10, wherein the transcriptional repression domain is a Krueppel-associated box (KRAB) domain, ERF repressor domain (ERD), or mSin3A interaction domain (SID).

12. The fusion protein of claim 10, wherein the transcriptional silencer is Heterochromatin Protein 1 (HP1).

13. The fusion protein of claim 12, wherein the HP1 is HP1α or HP1β.

14. The fusion protein of claim 7, wherein the heterologous functional domain is an enzyme that modifies the methylation state of DNA.

15. The fusion protein of claim 14, wherein the enzyme that modifies the methylation state of DNA is a DNA methyltransferase (DNMT) or a Ten-Eleven-Translocation (TET) protein.

16. The fusion protein of claim 15, wherein the TET protein is TET1.

17. The fusion protein of claim 7, wherein the heterologous functional domain is an enzyme that modifies a histone subunit.

18. The fusion protein of claim 17, wherein the enzyme that modifies a histone subunit is a histone acetyltransferase (HAT), histone deacetylase (HDAC), histone methyltransferase (HMT), or histone demethylase.

19. The fusion protein of claim 7, wherein the heterologous functional domain is a biological tether.

20. The fusion protein of claim 19, wherein the biological tether is MS2, Csy4 or lambda N protein.

21. The fusion protein of claim 7, wherein the heterologous functional domain is FokI.

22. An isolated nucleic acid encoding the isolated protein of claim 1.

23. A vector comprising the isolated nucleic acid of claim 22, optionally operably linked to one or more regulatory domains.

24. The vector of claim 23, wherein the vector is a prokaryotic vector.

25. The vector of claim 24, wherein the prokaryotic vector is a plasmid or a shuttle vector.

26. The vector of claim 23, wherein the vector is an expression vector.

27. A host cell comprising the nucleic acid of claim 22.

28. A method of altering the genome or epigenome of a cell, the method comprising expressing in the cell or contacting the cell with the isolated protein of claim 1 and a guide RNA having a region complementary to a selected portion of the genome of the cell.

29. A method of altering the genome or epigenome of a cell, the method comprising expressing in the cell or contacting the cell with the isolated fusion protein of claim 7, and a guide RNA having a region complementary to a selected portion of the genome of the cell.

30. A method of altering a double stranded DNA (dsDNA) molecule, the method comprising contacting the dsDNA molecule with the isolated protein of claim 1, and a guide RNA having a region complementary to a selected portion of the dsDNA molecule.

31. The method of claim 30, wherein the dsDNA molecule is in vitro.

32. A method of altering a double stranded DNA (dsDNA) molecule, the method comprising contacting the dsDNA molecule with the fusion protein of claim 7, and a guide RNA having a region complementary to a selected portion of the dsDNA molecule.

* * * * *

UNITED STATES PATENT AND TRADEMARK OFFICE
CERTIFICATE OF CORRECTION

PATENT NO. : 10,526,591 B2  
APPLICATION NO. : 15/935299  
DATED : January 7, 2020  
INVENTOR(S) : J. Keith Joung, Benjamin Kleinstiver and Vikram Pattanayak Page 1 of 1

It is certified that error appears in the above-identified patent and that said Letters Patent is hereby corrected as shown below:

On the Title Page

Item (63) (Related U.S. Application Data), Line 2, delete "and a" and insert -- which is a --

In the Claims

In Column 217, Line 66, Claim 1, delete "Y211A/R245AN419A," and insert
-- Y211A/R245A/N419A, --

In Column 219, Line 9 (approx.), Claim 5, delete "D1OA or D1ON," and insert -- D10A or D10N, --

Signed and Sealed this  
Thirteenth Day of October, 2020

Andrei Iancu  
*Director of the United States Patent and Trademark Office*